United States Patent
Naldini et al.

(10) Patent No.: US 12,152,240 B2
(45) Date of Patent: *Nov. 26, 2024

(54) PERMANENT EPIGENETIC GENE SILENCING

(71) Applicants: Ospedale San Raffaele S.R.L., Milan (IT); Fondazione Telethon, Rome (IT)

(72) Inventors: Luigi Naldini, Milan (IT); Angelo Leone Lombardo, Milan (IT); Angelo Amabile, Milan (IT); Alessandro Migliara, Milan (IT)

(73) Assignees: Ospedale San Raffaele S.R.L., Milan (IT); Fondazione Telethon, Rome (IT)

( * ) Notice: Subject to any disclaimer, the term of this patent is extended or adjusted under 35 U.S.C. 154(b) by 0 days.

This patent is subject to a terminal disclaimer.

(21) Appl. No.: 15/521,294

(22) PCT Filed: Oct. 23, 2015

(86) PCT No.: PCT/IB2015/058202
§ 371 (c)(1),
(2) Date: Apr. 23, 2017

(87) PCT Pub. No.: WO2016/063264
PCT Pub. Date: Apr. 28, 2016

(65) Prior Publication Data
US 2019/0032049 A1    Jan. 31, 2019

(30) Foreign Application Priority Data
Oct. 24, 2014    (GB) ...................... 1418965

(51) Int. Cl.
| | |
|---|---|
| *C12N 15/113* | (2010.01) |
| *A61K 35/12* | (2015.01) |
| *A61K 38/00* | (2006.01) |
| *A61K 38/17* | (2006.01) |
| *A61K 38/45* | (2006.01) |
| *A61K 48/00* | (2006.01) |
| *C07K 14/47* | (2006.01) |
| *C12N 9/10* | (2006.01) |
| *C12N 9/22* | (2006.01) |

(52) U.S. Cl.
CPC ............ *C12N 15/113* (2013.01); *A61K 35/12* (2013.01); *A61K 38/1709* (2013.01); *A61K 38/45* (2013.01); *A61K 48/005* (2013.01); *C07K 14/4703* (2013.01); *C12N 9/1007* (2013.01); *C12N 9/22* (2013.01); *C12Y 201/01037* (2013.01); *C12Y 201/01043* (2013.01); *A61K 38/00* (2013.01); *C07K 2319/80* (2013.01); *C12N 2310/20* (2017.05); *C12N 2740/16043* (2013.01); *C12N 2800/80* (2013.01)

(58) Field of Classification Search
None
See application file for complete search history.

(56) References Cited

U.S. PATENT DOCUMENTS

| | | | |
|---|---|---|---|
| 6,919,204 B2 | 7/2005 | Wolffe et al. | |
| 8,450,107 B1 | 5/2013 | Zhang et al. | |
| 8,658,393 B2 | 2/2014 | Reik et al. | |
| 8,697,359 B1 | 4/2014 | Zhang | |
| 8,795,965 B2 | 8/2014 | Zhang | |
| 8,865,406 B2 | 10/2014 | Zhang et al. | |
| 8,871,445 B2 | 10/2014 | Cong et al. | |
| 8,889,356 B2 | 11/2014 | Zhang | |
| 8,895,308 B1 | 11/2014 | Zhang et al. | |
| 8,906,616 B2 | 12/2014 | Zhang et al. | |
| 8,932,814 B2 | 1/2015 | Cong et al. | |
| 8,993,233 B2 | 3/2015 | Zhang et al. | |
| 8,999,641 B2 | 4/2015 | Zhang et al. | |
| 9,139,628 B2 | 9/2015 | Minzuk et al. | |
| 9,267,135 B2 | 2/2016 | Church et al. | |
| 9,322,006 B2 | 4/2016 | Liu et al. | |

(Continued)

FOREIGN PATENT DOCUMENTS

| | | |
|---|---|---|
| EP | 3209783 B1 | 11/2021 |
| JP | 2010-515448 A | 5/2010 |

(Continued)

OTHER PUBLICATIONS

Gowher et al. Mechanism of Stimulation of Catalytic Activity of Dnmt3A and Dnmt3B DNA-(Cytosine-C5)-methyltransferases By Dnmt3L. The Journal of Biological Chemistry, 2005. 280(14):13341-13348.*

Schultz et al. SETDB1: A Novel KAP-1-Associated Histone H3, Lysine 9-Specific Methyltransferase that Contributes to HP1-Mediated Silencing of Euchromatic Genes By KRAB Zinc-Finger Proteins. Genes & Development, 2002. 16:919-932.*

Aiuti A et al., Gene Therapy for Immunodeficiency due to Adenosine Deaminase Deficiency, New England Journal Medicine, 2009, vol. 360, pp. 447-458.

Aiuti A et al., Lentiviral hematopoietic stem cell gene therapy in patients with Wiskott-Aldrich syndrome, Science, 2013, vol. 341, No. 6148, pp. 1233151.

(Continued)

*Primary Examiner* — Christopher M Babic
*Assistant Examiner* — Kimberly A Aron
(74) *Attorney, Agent, or Firm* — Wolf, Greenfield & Sacks, P.C.

(57) ABSTRACT

A product comprising two or more artificial transcription repressors (ATRs), or polynucleotides encoding therefor, selected from groups (a), (b), (c) or (d): (a) an ATR comprising a DNA-binding domain operably linked to a KRAB domain or homologue thereof; (b) an ATR comprising a DNA-binding domain operably linked to a DNMT3A, DNMT3B or DNMT1 domain or homologue thereof; (c) an ATR comprising a DNA-binding domain operably linked to a DNMT3L domain or homologue thereof; and (d) an ATR comprising a DNA-binding domain operably linked to a SETDB1 domain or homologue thereof, wherein at least two of the ATRs are selected from different groups (a), (b), (c) or (d).

24 Claims, 20 Drawing Sheets

Specification includes a Sequence Listing.

(56) References Cited

U.S. PATENT DOCUMENTS

| | | | |
|---|---|---|---|
| 9,526,784 | B2 | 12/2016 | Liu et al. |
| 9,771,601 | B2 | 9/2017 | May et al. |
| 9,840,713 | B2 | 12/2017 | Zhang |
| 9,850,500 | B2 | 12/2017 | Yun et al. |
| 10,266,850 | B2 | 4/2019 | Doudna et al. |
| 10,323,073 | B2 | 6/2019 | Tremblay et al. |
| 10,329,587 | B2 | 6/2019 | Church et al. |
| 10,378,027 | B2 | 8/2019 | Joung et al. |
| 10,443,076 | B2 | 10/2019 | Doudna et al. |
| 10,525,082 | B2 | 1/2020 | Crane et al. |
| 10,570,378 | B2 | 2/2020 | Ji et al. |
| 10,583,201 | B2 | 3/2020 | Chen et al. |
| 10,612,044 | B2 | 4/2020 | Hatada et al. |
| 10,676,726 | B2 | 6/2020 | Gersbach et al. |
| 10,676,735 | B2 | 6/2020 | Gersbach et al. |
| 10,704,060 | B2 | 7/2020 | Gersbach et al. |
| 2002/0160940 | A1 | 10/2002 | Case et al. |
| 2002/0188103 | A1 | 12/2002 | Bestor |
| 2004/0204345 | A1 | 10/2004 | Case et al. |
| 2007/0059795 | A1 | 3/2007 | Moore et al. |
| 2007/0192880 | A1* | 8/2007 | Muyan .......... C12N 15/62 800/14 |
| 2009/0023153 | A1* | 1/2009 | Wolffe .......... C12N 15/63 435/6.12 |
| 2011/0306559 | A1 | 12/2011 | Forsayeth et al. |
| 2012/0207744 | A1* | 8/2012 | Mendlein .......... C12N 5/0696 424/130.1 |
| 2014/0377868 | A1 | 12/2014 | Joung et al. |
| 2015/0191744 | A1 | 7/2015 | Wolfe et al. |
| 2015/0247150 | A1 | 9/2015 | Zhang et al. |
| 2016/0201089 | A1 | 7/2016 | Gersbach et al. |
| 2016/0298135 | A1 | 10/2016 | Chen et al. |
| 2017/0191082 | A1 | 7/2017 | Chen et al. |
| 2017/0204407 | A1 | 7/2017 | Gilbert et al. |
| 2017/0219596 | A1 | 8/2017 | Tanenbaum et al. |
| 2017/0233762 | A1 | 8/2017 | Zalatan et al. |
| 2018/0273976 | A1 | 9/2018 | Ümit et al. |
| 2019/0032049 | A1 | 1/2019 | Naldini et al. |
| 2019/0376090 | A1 | 12/2019 | Joung et al. |
| 2020/0071730 | A1 | 3/2020 | Joung et al. |

FOREIGN PATENT DOCUMENTS

| | | |
|---|---|---|
| JP | 2013-543381 A | 12/2013 |
| WO | WO1998005635 A1 | 2/1998 |
| WO | WO1998007859 A2 | 2/1998 |
| WO | WO1998009985 A2 | 3/1998 |
| WO | WO1999041397 A1 | 8/1999 |
| WO | WO2001079518 A2 | 10/2001 |
| WO | WO 2003/072788 A1 | 9/2003 |
| WO | WO2008084219 A1 | 7/2008 |
| WO | WO2011016840 A2 | 2/2011 |
| WO | WO2012045082 A2 | 4/2012 |
| WO | WO2013093489 A2 | 6/2013 |
| WO | WO2013130824 A1 | 9/2013 |
| WO | WO2013138650 A1 | 9/2013 |
| WO | WO2013141680 A1 | 9/2013 |
| WO | WO2013176772 A1 | 11/2013 |
| WO | WO2014065596 A1 | 5/2014 |
| WO | WO2014089290 A1 | 6/2014 |
| WO | WO2014099744 A1 | 6/2014 |

OTHER PUBLICATIONS

Altschul J et al., Basic Local Alignment Search Tool, (1990) J. Mol. Biol. 403-410.
Amabile A et al., "Permanetn Epigenetic Silencing of Human Genes with Artificial Transcriptional Repressors", 18 ASGCT Annual Meeting, May 16, 2015, XP055245901.
Amendola, M. et al., Coordinate dual-gene transgenesis by lentiviral vectors carrying synthetic bidirectional promoters (2005) Nat. Biotechnol. 23: 108-116.
Andreani, M. et al. Quantitatively different red cell/nucleated cell chimerism in patients . . . (2011) Haematologica 96: 128-133.
Ausubel F M et al. (1999) Short Protocols in Molecular Biology, Ch. 18.
Ausubel F M et al. (1999) Short Protocols in Molecular Biology, pp. 7-58 to 7-60.
Ausubel, F.M. et al. (1995 and periodic supplements) Current Protocols in Molecular Biology, Ch. 9, 13 and 16, John Wiley & Sons.
Ayyanathan K et al., "Regulated recruitment of HP1 to a euchromatic gene induces mitotically heritable, epigenetic gene silencing . . . " Genes Devel., Jul. 17, 2003, 17:1855-69.
Bauer, D.E. et al. An erythroid enhancer of BCL 11A subject to genetic variation determines fetal hemoglobin level (2013) Science 342: 253-7.
Bauer, D.E. et al. Update on fetal hemoglobin gene regulation in hemoglobinopathies (2011) Curr. Opin. Pediatr. 23: 1-8.
Biffi A et al., Lentiviral hematopoietic stem cell gene therapy benefits metachromatic leukodystrophy, Science, 2013, vol. 341, pp. 1233158.
Broude Eugenia V et al., "P21 (CDKN1A) is a Negative regulator of p53 stability", Cell Cycle, Jun. 1, 2007, vol. 6. No. 12, pp. 1468-1471 XP009152430.
Cai, Y. et al. Targeted genome editing by lentiviral protein transduction of zinc-finger and TAL-effector nucleases (2014) Elife 3: e01911.
Carroll, D. (2014) Genome engineering with targetable nucleases, Annu. Rev. Biochem. 83: 409-439.
Cartier, N. et al., Hematopoietic Stem Cell Gene Therapy with a Lentiviral Vector in X-linked Adrenoleukodystrophy, (2009) Science 326: 818-823.
Cavazzana-Calvo, M. et al. Transfusion independence and HMGA2 activation after gene therapy of human β-thalassaemia (2010) Nature 467: 318-322.
Chen, T. et al. Chromatin modifiers and remodellers: regulators of cellular differentiation (2014) Nat. Rev. Genet. 15: 93-106.
Ciccia, A. et al. The DNA damage response: making it safe to play with knives (2010) Mol. Cell 40: 179-204.
Davidson, B. L. et al. Current prospects for RNA interference-based therapies (2011) Nat. Rev. Genet. 12: 329-340.
De Groote, M.L. et al. Epigenetic Editing: targeted rewriting of epigenetic marks to modulate expression of selected target genes (2012) Nucleic Acids Res. 40: 10596-613.
Deuschle U et al., Tetracycline-reversible silencing of eukaryotic promoters, Molecular and Cellular Biology, 1995, vol. 15, No. 4, pp. 1907.
Devereux J et al., A comprehensive set of sequence analysis programs for the VAX (1984) Nucleic Acids Res. 12: 387.
DiGiusto, D.L. et al. Development of hematopoletic stem cell based gene therapy for HIV-1 infection . . . , (2013) Viruses 5: 2898-919.
DiGiusto, D.L. et al. RNA-based gene therapy for HIV with lentiviral vector-modified CD34(+) cells in patients undergoing transplant . . . (2010) Sci. Transl. Med. 2: 36ra43.
Esvelt K M et al. Orthogonal Cas9 proteins for RNA-guided gene regulation and editing (2013) Nat. Methods 10: 1116-1121.
Feschotte, C. et al. Endogenous viruses: insights into viral evolution and impact on host biology (2012) Nat. Rev. Genet. 13: 283-296.
Gait, M.J. (1984) Oligonucleotide Synthesis: A Practical Approach, IRL Press.
Gaj T et al., ZFN, TALEN and CRISPR/Cas-based methods for genome engineering, Trends Biotechnol., 2013, vol. 31, pp. 397-405.
Gaj, T. et al. Targeted gene knockout by direct delivery of zinc-finger nuclease proteins (2012) Nat. Methods 9: 805-807.
Galarneau, G. et al. Fine-mapping at three loci known to affect fetal hemoglobinj levels explains additional genetic variation, (2010) Nat. Genet. 42: 1049-51.
Gossen, M. et al. (1992) Tight control of gene expression in mammalian cells by tetracycline-responsive promoters, Proc. Natl. Acad. Sci. USA 89: 5547-5551.
Groner, A.C. et al. (2010) KRAB-zinc finger proteins and KAP1 can mediate long-range transcriptional repression through heterochromatin spreading, PLoS Genet. 6(3): e1000869.

(56) References Cited

OTHER PUBLICATIONS

Hacein-Bey-Abina S et al., Efficacy of Gene Therapy for X-Linked Severe Combined Immunodeficiency, New England Journal Medicine, 2010, vol. 363, No. 4, pp. 355-364.
Hathaway, N.A. et al. Dynamics and memory of heterochromatin in living cell (2012) Cell 149: 1447-1460.
Huntley, S. et al. A comprehensive catalog of human KRAB-associated zinc finger genes . . . (2006) Genome Res. 16: 669-77.
Hutter, G. et al. Long-term control of HIV by CCR5 Delta32/Delta32 stem-cell transplantation (2009) N. Engl. J. Med. 360: 692-8.
Issa, J.P. et al. Azacitidine (2005) Nat. Rev. Drug Discov. Suppl. S6-7.
Iyengar, S. et al. KAP1 protein: an enigmatic master regulator of the genome (2011) J. Biol. Chem. 286: 26267-76.
Jeltsch A et al., "Application of DNA methyltransferases in targeted DNA methylation", Applied Microbiology and Biotechnology, 2007, vol. 75, No. 6, p. 1233-1240 XP019513780.
Jones, P.A. Functions of DNA methylation: islands, start sites, gene bodies and beyond (2012) Nat. Rev. Genet. 13: 484-492.
Kay, M.A. State-of-the-art gene-based therapies: the road ahead (2011) Nat. Rev. Genet. 12: 316-328.
Kim et al., "Zinc-fingers and homeoboxes 1 (ZHX1) binds DNA methyltransferase (DNMT) 3B . . . ", Biochem. Biophys. Res. Comm., Feb. 24, 2007, vol. 355, No. 2, pp. 318-323.
Konermann, S. et al. Optical control of mammalian endogenous transcription and epigenetic states (2013) Nature 500: 472-476.
Kuehnel F et al., "Tumor-specific adenoviral gene therapy . . . ", Cancer Gene Therapy, Jan. 1, 2004, vol. 11, No. 1 pp. 28-40 XP002372745.
Law, J.A. et al. Establishing, maintaining and modifying DNA methylation patterns in plants and animals (2010) Nat. Rev. Genet. 11: 204-220.
Leung, D.C. et al. Silencing of endogenous retroviruses: when and why do histone marks predominate? (2012) Trends Biochem. Sci. 37: 127-33.
Li F et al., "Chimeric DNA methyltransferases target DNA methylation . . . ", Nucleic Acids Research, Dec. 7, 2006, vol. 35, No. 1, pp. 100-112 XP055246015.
Li Hongwei et al., "The histone methyltransferase SETDB1 and the DNA methyltransferase DNMT3A interact directly . . . ", J. Biol. Chem. vol. 281 No. 28 pp. 19489-19500 XP002544945.
Lilley, D.M., and Dahlberg, J.E. (1992) Methods in Enzymology: DNA Structures Part A: Synthesis and Physical Analysis of DNA, Academic Press.
Liu, R. et al. Homozygous defect in HIV-1 coreceptor accounts for resistance of some multiply-exposed individuals to HIV-1 infection (1996) Cell 86: 367-77.
Lombardo A et al., Site-specific integration and tailoring of cassette design for sustainable gene transfer, Nat Methods, 2011, vol. 8 pp. 861-869.
Maetzig T et al., Retroviral protein transfer: falling apart to make an impact, Current Gene Ther, 2012, vol. 12, pp. 389-409.
McBride, J.L. et al. Preclinical safety of RNAi-mediated HTT suppression in the rhesus macaque as a potential therapy for Huntington's disease (2011) Mol. Ther. 19: 2152-62.
Mendenhall, E.M. et al. Locus-specific editing of histone modifications at endogenous enhancers (2013) Nat. Biotechnol. 31: 1133-1136.
Naldini, L. Ex vivo gene transfer and correction for cell-based therapies (2011) Nat. Rev. Genet. 12: 301-315.
Ooi, S.K. et al. DNMT3L connects unmethylated lysine 4 of histone H3 to de novo methylation of DNA (2007) Nature 448: 714-7.
Platt, O.S. et al. Mortality in sickle cell disease (1994) N. Engl. J. Med. 330(23): 1639-1644.
Polak, J.M., and McGee, J.O'D. (1990) In Situ Hybridization: Principles and Practice, Oxford University Press.
Probst, A.V. et al. Epigenetic inheritance during the cell cycle (2009) Nat. Rev. Mol. Cell Biol. 10: 192-206.
Qi, L.S. et al. Repurposing CRISPR as an RNA-guided platform for sequence-specific control of gene expression (2013) Cell 152: 1173-1183.
Ramachandran, P.S. et al. Recent advances in RNA interference therapeutics for CNS diseases (2013) Neurotherapeutics 10: 473-485.
Reik, W. Stability and flexibility of epigenetic gene regulation in mammalian development (2007) Nature 447: 425-432.
Rivenbark A G et al., Epigenetic reprogramming of cancer cells via targeted DNA methylation, Epigenetics, 2012, vol. 7 No. 4 pp. 350-360.
Roe, B., Crabtree, J., and Kahn, A. (1996) DNA Isolation and Sequencing: Essential Techniques, John Wiley & Sons.
Sambrook, J., Fritsch, E.F., and Maniatis, T. (1989) Molecular Cloning: A Laboratory Manual, 2nd Edition, Cold Spring Harbor Laboratory Press.
Sander, J.D. et al. CRISPR-Cas systems for editing, regulating and targeting genomes (2014) Nat. Biotechnol. 32: 347-355.
Sankaran, V.G. et al. Human Fetal Hemoglobin Expression is regulated by the developmental stage-specific repressor BCL11A (2008) Science 322: 1839-42.
Schwartz, Y.B. et al. A new world of Polycombs: unexpected partnerships and emerging functions (2013) Nat. Rev. Genet. 14: 853-864.
Sera, T. Zinc-finger-based artificial transcription factors and their applications (2009) Adv. Drug Deliv. Rev. 61: 513-526.
Silva, G. et al. Meganucleases and other tools for targeted genome engineering: perspectives and challenges for gene therapy (2011) Cur. Gene Ther. 11: 11-27.
Smith, Z.D. et al. DNA methylation: roles in mammalian development (2013) Nat. Rev. Genet. 14: 204-20.
Stamatoyannopoulos, G. Control of globin gene expression during development and erythroid differentiation, (2005) Exp. Hematol. 33(3): 259-271.
Szulc, J. et al. A versatile tool for conditional gene expression and knockdown (2006) Nat. Methods 3(2): 109-116.
Tatusova T et al., BLAST 2 Sequences, a new tool for comparing protein and nucleotide sequences, FEMS Microbiol. Lett., 1999, 174: 247-250.
Tatusova T et al., Erratum to "BLAST 2 Sequences, A new tool for comparing protein and nucleotide sequences"; FEMS Microbiol. Lett. (1999) 177: 187-188.
Two bright new faces in gene therapy, Nat. Biotechnol. (1996) 14(5): 556.
Uda, M. et al. Genome-wide association study shows BCL 11A associated with persistent fetal hemoglobin . . . (2008) Acad. Sci. USA 105: 1620-1625.
Urrutia R, "KRAB-containing zinc-finger repressor proteins", Genome Biology, Sep. 23, 2003, Genome Biology, vol. 4 No. 10, p. 231 XP055245881.
Van der Oost et al. Unraveling the structural and mechanistic basis of CRISPR-Cas systems (2014) Nat. Rev. Microbiol. 12: 479-492.
Wang H et al., Tightly regulated gene expression in human hematopoietic stem cells after transduction . . . , Exp Hematol., 2008, vol. 36, No. 7, pp. 823-831.
Weatherall, D.J. The role of the inherited disorders of hemoglobin . . . (2013) Annu. Rev. Genomics Hum. Genet. 14: 1-24.
Wilber, A. et al. Therapeutic levels of fetal hemoglobin in erythroid progeny of β-thalassemic CD34+ cells . . . (2011) Blood 117: 2817-26.
Wiznerowicz M et al., The Krüppel-associated Box Repressor Domain Can Trigger de Novo Promoter Methylation . . . , J Biol Chem, 2007, vol. 282, pp. 34535-34541.
Xu, J. et al. Correction of sickle cell disease in adult mice by intererence with fetal hemoglobin silencing (2011) Science 334: 993-6.
Younan, P. et al. Genetically modified hematopoietic stem cell transplantation for HIV-1-infected patients: can we achieve a cure? (2014) Mol. Ther. 22: 257-264.
Zhang, F. et al. Efficient construction of sequence-specific TAL effectors for modulating mammalian transcription (2011) Nat. Biotechnol. 29: 149-53.

(56) References Cited

OTHER PUBLICATIONS

Zhao X. et al., Intracellular delivery of artifical transcription factors fused to the protein transduction domain of HIV-1 Tat, Prot. Expr. Purif., Jul. 1, 2013, 90:27-33.
Amabile et al., Inheritable Silencing of Endogenous Genes by Hit-and-Run Targeted Epigenetic Editing; Cell 167:219-232; 2016.
Zhang et al., Dissecting the Roles of miR-302/367 Cluster in Cellular Reprogramming using TALE-based Repressor and TALEN, Stem Cell Reports, 2013, vol. 1, pp. 218-225.
Kearns et al., Cas9 effector-mediated regulation of transcription and differentiation in human pluripotent stem cells, Development, 2014, vol. 141, pp. 219-222.
Kocak, Daniel Dewran, Synthetic Transcription Factors and their Effects on Endogenous . . . Cells, Thesis submitted for Master of Science degree, Duke University, 2013, pp. 1-29.
Li et al,. The Histone Methyltransferase SETDB1 and the DNA Methyltransferase DNMT3A . . . promoters silenced in cancer cells, J. Biol. Chem., 2006, vol. 281, p. 19489-19500.
Siddique et al., Targeted Methylation and Gene Silencing of VEGF in Human Cells by Using a Designed Dnmt3a-Dnmt3L Single . . . ; J. Mol. Biol. 425:479-91 (2013); Epub Dec. 4, 2012.
Gilbert et al., CRISPR-Mediated Modular RNA-Guided Regulation of Transcription in Eukaryotes; Cell 154:442-451; 2013.
Gilbert et al., Genome-Scale CRISPR-Mediated Control of Gene Repression and Activation; Cell 159:647-661; 2014.
Larson et al., CRISPR interference (CRISPRi) for sequence-specific control of gene expression; Nat. Protocols 8:2180-2196; 2013.
Lupo et al., KRAB-Zinc Finger Proteins: A Repressor Family Displaying Multiple Biological Functions; Curr. Genom. 14:268-278; 2013.
Mandegar et al., CRISPR Interference Efficiently Induces Specific and Reversible Gene Silencing in Human iPSCs; Cell Stem Cell 18:541-553; 2016.
Quenneville et al., In Embryonic Stem Cells, ZFP57/KAP1 Recognize a Methylated Hexanucleotide to Affect Chromatin and DNA Methylation . . .; Molec. Cell 44:3610372; 2011.
Opposition filed by Mr. H. Ulrich Dorries against European Patent No. EP 3209783, mailed Aug. 29, 2022. 28 pages.
Opposition filed by James Poole Limited against European Patent No. EP 3209783, mailed Aug. 30, 2022. 29 pages.
Patentee's Letter dated Dec. 18, 2017. 5 pages. D20, submitted in Opposition of European Patent No. EP 3209783 on Nov. 4, 2022.
Patentee's Letter dated Aug. 12, 2019. 4 pages. D24, submitted in Opposition of European Patent No. EP 3209783 on Nov. 4, 2022.
[No Author Listed], Cell lines in the In Vitro Screen. NIH Division of Cancer Treatment & Diagnosis Aug. 5, 2015. 5 pages. D16, submitted in Opposition of European Patent No. EP 3209783 on Nov. 4, 2022.
[No Author Listed], SEQ ID No. 8 of the Patent and the DNMT3A sequence disclosed in Li et al., Nucleic Acids Res. 2007;35(1):100-12. Retrieved from www.ebi.ac.uk on Jul. 14, 2022. 2 pages. D17, submitted in Opposition of European Patent No. EP 3209783 on Nov. 4, 2022.
Amabile et al., Inheritable Silencing of Endogenous Genes by Hit-and-Run Targeted Epigenetic Editing. Cell. Sep. 22, 2016;167(1):219-232.e14. doi: 10.1016/j.cell.2016.09.006. D15, submitted in Opposition of European Patent No. EP 3209783 on Nov. 4, 2022.
Ayyanathan et al., Regulated recruitment of HP1 to a euchromatic gene induces mitotically heritable, epigenetic gene silencing: a mammalian cell culture model of gene variegation. Genes Dev. Aug. 1, 2003;17(15):1855-69. doi: 10.1101/gad.1102803. Epub Jul. 17, 2003. D3, submitted in Opposition of European Patent No. EP 3209783 on Nov. 4, 2022.
Broude et al., p21 (CDKN1A) is a negative regulator of p53 stability. Cell Cycle. Jun. 15, 2007;6(12):1468-71. Epub Apr. 12, 2007. D5, submitted in Opposition of European Patent No. EP 3209783 on Nov. 4, 2022.
Kabadi et al., Engineering synthetic TALE and CRISPR/Cas9 transcription factors for regulating gene expression. Methods. Sep. 2014;69(2):188-97. doi: 10.1016/j.ymeth.2014.06.014. Epub Jul. 8, 2014. D21, submitted in Opposition of European Patent No. EP 3209783 on Nov. 4, 2022.
Kim et al., Zinc-fingers and homeoboxes 1 (ZHX1) binds DNA methyltransferase (DNMT) 3B to enhance DNMT3B-mediated transcriptional repression. Biochem Biophys Res Commun. Apr. 6, 2007;355(2):318-23. doi: 10.1016/j.bbrc.2007.01.187. Epub Feb. 8, 2007. D8, submitted in Opposition of European Patent No. EP 3209783 on Nov. 4, 2022.
Kocak, Synthetic Transcription Factors and their Effects on Endogenous DNA Methylation in Human Cells. Duke University Thesis. Submitted 2013. 35 pages. D18, submitted in Opposition of European Patent No. EP 3209783 on Nov. 4, 2022.
Kühnel et al., Tumor-specific adenoviral gene therapy: transcriptional repression of gene expression by utilizing p53-signal transduction pathways. Cancer Gene Ther. Jan. 2004;11(1):28-40. doi: 10.1038/sj.cgt.7700632. D6, submitted in Opposition of European Patent No. EP 3209783 on Nov. 4, 2022.
Li et al., Chimeric DNA methyltransferases target DNA methylation to specific DNA sequences and repress expression of target genes. Nucleic Acids Res. 2007;35(1):100-12. doi: 10.1093/nar/gkl1035. Epub Dec. 6, 2006. D7, submitted in Opposition of European Patent No. EP 3209783 on Nov. 4, 2022.
Li et al., The histone methyltransferase SETDB1 and the DNA methyltransferase DNMT3A interact directly and localize to promoters silenced in cancer cells. J Biol Chem. Jul. 14, 2006;281(28):19489-500. doi: 10.1074/jbc.M513249200. Epub May 8, 2006. D1, submitted in Opposition of European Patent No. EP 3209783 on Nov. 4, 2022.
Ma et al., Targeted gene suppression by inducing de novo DNA methylation in the gene promoter. Epigenetics Chromatin. Aug. 18, 2014;7:20. doi: 10.1186/1756-8935-7-20. D12, submitted in Opposition of European Patent No. EP 3209783 on Nov. 4, 2022.
Murphy et al., The Transcriptional Repressive Activity of KRAB Zinc Finger Proteins Does Not Correlate with Their Ability to Recruit TRIM28. PLoS One. Sep. 22, 2016;11(9):e0163555. doi: 10.1371/journal.pone.0163555. D23, submitted in Opposition of European Patent No. EP 3209783 on Nov. 4, 2022.
Rivenbark et al., Epigenetic reprogramming of cancer cells via targeted DNA methylation. Epigenetics. Apr. 2012;7(4):350-60. doi: 10.4161/epi.19507. Epub Apr. 1, 2012. D11, submitted in Opposition of European Patent No. EP 3209783 on Nov. 4, 2022.
Schultz et al., SETDB1: a novel KAP-1-associated histone H3, lysine 9-specific methyltransferase that contributes to HP1-mediated silencing of euchromatic genes by KRAB zinc-finger proteins. Genes Dev. Apr. 15, 2002;16(8):919-32. doi: 10.1101/gad.973302. D22, submitted in Opposition of European Patent No. EP 3209783 on Nov. 4, 2022.
Siddique et al., Targeted methylation and gene silencing of VEGF-A in human cells by using a designed Dnmt3a-Dnmt3L single-chain fusion protein with increased DNA methylation activity. J Mol Biol. Feb. 8, 2013;425(3):479-91 and Supplemental Information. doi: 10.1016/j.jmb.2012.11.038. Epub Dec. 4, 2012. D10, submitted in Opposition of European Patent No. EP 3209783 on Nov. 4, 2022.
Zhao et al., Intracellular delivery of artificial transcription factors fused to the protein transduction domain of HIV-1 Tat. Protein Expr Purif. Jul. 2013;90(1):27-33. doi: 10.1016/j.pep.2013.04.007. Epub May 3, 2013. D4, submitted in Opposition of European Patent No. EP 3209783 on Nov. 4, 2022.
[No Author Listed], Figures 1-20 in color from EP Patent No. 3209783. D25, submitted in Opposition of European Patent No. EP 3209783 on May 28, 2024. 20 pages.
Abaandou et al., Affecting HEK293 Cell Growth and Production Performance by Modifying the Expression of Specific Genes. Cells. Jul. 2, 2021;10(7):1667. doi: 10.3390/cells10071667. D40, submitted in Opposition of European Patent No. EP 3209783 on May 28, 2024.
Alerasool et al., An efficient KRAB domain for CRISPRi applications in human cells. Nat Methods. Nov. 2020;17(11):1093-1096. doi: 10.1038/s41592-020-0966-x. Epub Oct. 5, 2020. D30, submitted in Opposition of European Patent No. EP 3209783 on May 28, 2024.

(56) References Cited

OTHER PUBLICATIONS

Braliou et al., The v-ErbA oncoprotein quenches the activity of an erythroid-specific enhancer. Oncogene. Feb. 15, 2001;20(7):775-87. doi: 10.1038/sj.onc.1204159. D28, submitted in Opposition of European Patent No. EP 3209783 on May 28, 2024.
Cano-Rodriguez et al., Epigenetic Editing: On the Verge of Reprogramming Gene Expression at Will. Curr Genet Med Rep. 2016;4(4):170-179. doi: 10.1007/s40142-016-0104-3. Epub Oct. 1, 2016. D41, submitted in Opposition of European Patent No. EP 3209783 on May 28, 2024.
Cortés-Mancera et al., Gene-Targeted DNA Methylation: Towards Long-Lasting Reprogramming of Gene Expression? Adv Exp Med Biol. 2022;1389:515-533. doi: 10.1007/978-3-031-11454-0_18. D27, submitted in Opposition of European Patent No. EP 3209783 on May 28, 2024.
CV of Professor Dr. A. Jeltsch. D37a, submitted in Opposition of European Patent No. EP 3209783 on May 28, 2024. 4 pages.
Das et al., Tet-On Systems For Doxycycline-inducible Gene Expression. Curr Gene Ther. 2016;16(3):156-67. doi: 10.2174/1566523216666160524144041. D43, submitted in Opposition of European Patent No. EP 3209783 on May 28, 2024.
Evidence that Luo et al., Nucleic Acids Res. 2015;43(1):674-81 was published online on Oct. 17, 2014. D39a, submitted in Opposition of European Patent No. EP 3209783 on May 28, 2024. 2 pages.
Expert Declaration of Professor Dr. Albert Jeltsch dated Oct. 2, 2023. D37, submitted in Opposition of European Patent No. EP 3209783 on May 28, 2024. 3 pages.
Fuks, DNA methylation and histone modifications: teaming up to silence genes. Curr Opin Genet Dev. Oct. 2005;15(5):490-5. doi: 10.1016/j.gde.2005.08.002. D34, submitted in Opposition of European Patent No. EP 3209783 on May 28, 2024.
Hochstrasser et al., CasA mediates Cas3-catalyzed target degradation during CRISPR RNA-guided interference. Proc Natl Acad Sci U S A. May 6, 2014;111(18):6618-23. doi: 10.1073/pnas.1405079111. Epub Apr. 18, 2014. D36, submitted in Opposition of European Patent No. EP 3209783 on May 28, 2024.
Kao et al., Ectopic DNMT3L triggers assembly of a repressive complex for retroviral silencing in somatic cells. J Virol. Sep. 2014;88(18):10680-95. doi: 10.1128/JVI.01176-14. Epub Jul. 2, 2014. D33, submitted in Opposition of European Patent No. EP 3209783 on May 28, 2024.
Kungulovski et al., Targeted epigenome editing of an endogenous locus with chromatin modifiers is not stably maintained. Epigenetics Chromatin. Mar. 18, 20158;8:12. doi: 10.1186/s13072-015-0002-z.
List of Publication of Professor Dr. Jeltsch. Aug. 2023. D37b, submitted in Opposition of European Patent No. EP 3209783 on May 28, 2024. 17 pages.
LUO Repurposing endogenous type I CRISPR-Cas systems for programmable gene repression. Nucleic Acids Res. Jan. 2015;43(1):674-81. doi: 10.1093/nar/gku971. Epub Oct. 17, 2014. D39, submitted in Opposition of European Patent No. EP 3209783 on May 28, 2024.
Moussa et al., Here to stay: Writing lasting epigenetic memories. Cell. Apr. 29, 2021;184(9):2281-2283. doi: 10.1016/j.cell.2021.04.007. D29, submitted in Opposition of European Patent No. EP 3209783 on May 28, 2024.
Nakamura et al., Durable CRISPR-Based Epigenetic Silencing. Biodesign Research. Jul. 1, 2021;2021:9815820. doi: 10.34133/2021/9815820. 8 pages.
O'Geen et al., Determinants of heritable gene silencing for KRAB-dCas9 + DNMT3 and Ezh2-dCas9 + DNMT3 hit-and-run epigenome editing. Nucleic Acids Res. Apr. 8, 2022;50(6):3239-3253. doi: 10.1093/nar/gkac123. D32, submitted in Opposition of European Patent No. EP 3209783 on May 28, 2024.
Orth et al., Structural basis of gene regulation by the tetracycline inducible Tet repressor-operator system. Nat Struct Biol. Mar. 2000;7(3):215-9. doi: 10.1038/73324. D42, submitted in Opposition of European Patent No. EP 3209783 on May 28, 2024.
Policarpi et al., Epigenetic editing: Dissecting chromatin function in context. Bioessays. May 2021;43(5):e2000316. doi: 10.1002/bies.202000316. Epub Mar. 16, 2021. D26, submitted in Opposition of European Patent No. EP 3209783 on May 28, 2024.
Second Expert Declaration of Professor Dr. Albert Jeltsch dated Dec. 13, 2023. D38, submitted in Opposition of European Patent No. EP 3209783 on May 28, 2024. 6 pages.
Stepper, CRISPR-Cas9 fusions for synthetic epigenetics. Thesis. 2020. Institut für Biochemie und Technische Biochemie der Universität Stuttgart. D44, submitted in Opposition of European Patent No. EP 3209783 on May 28, 2024. 152 pages.
Summons to Attend Oral Proceeding in Opposition against European Patent No. EP 3209783, Preliminary Opinion of Opposition Division, and Consolidated List of Cited Documents, mailed May 28, 2024. 17 pages.
Tycko et al., High-Throughput Discovery and Characterization of Human Transcriptional Effectors. Cell. Dec. 23, 2020; 183(7):2020-2035.e16. doi: 10.1016/j.cell.2020.11.024. Epub Dec. 15, 2020. D31, submitted in Opposition of European Patent No. EP 3209783 on May 28, 2024.

* cited by examiner

A

B

A

Reporter – LV randomly distributed into the genome

B

C

D

A

B

Liquid Culture

C

Colonies

A

B

A

T cells purification from buffycoat and stimulation with αCD3/CD28 beads

Beads removal

Flow cytometry analysis

Electroporation of ATRs-encoding mRNA

B

C

PERMANENT EPIGENETIC GENE SILENCING

FIELD OF THE INVENTION

The present invention relates to gene silencing and/or epigenetic editing. More specifically, the present invention relates to improved methods for silencing a gene of interest or for editing the epigenetic state of a genetic element of interest, including during gene therapy applications.

BACKGROUND TO THE INVENTION

Gene therapy involves the incorporation of genetic material into a cell to treat or prevent disease. The genetic material may supplement defective genes with functional copies of those genes, inactivate improperly functioning genes or introduce new therapeutic genes to a cell.

A classic example of gene therapy is gene replacement, where a DNA sequence that encodes a functional, therapeutic gene is used to replace a dysfunctional gene (Naldini, L. (2011) *Nat. Rev. Genet.* 12:301-15; Kay, M. A. (2011) *Nat. Rev. Genet.* 12:316-28; Biffi, A. et al. (2013) *Science* 341: 1233158; Aiuti, A. et al. (2013) *Science* 341:1233151; Aiuti, A. et al. (2009) *N. Engl. J. Med.* 360:447-58). However, there are several inherited diseases where the goal of gene therapy is to silence rather than replace gene function. Paradigmatic examples include Huntington's disease, most types of Spinocerebellar ataxias and some collagenopathies. Furthermore, gene silencing is emerging as a promising strategy to treat certain infectious diseases (Younan, P. et al. (2014) *Mol. Ther.* 22:257-64), by inactivating either pathogen-associated gene products or host genes that are necessary for the pathogen life cycle.

For example, silencing of the chemokine (C-C motif) receptor type 5 (CCR5) gene, one of two cellular co-receptors required for HIV entry into T cells, has received significant attention. This is because a natural deletion in CCR5 confers resistance to infection by CCR5-tropic HIV strains without causing overt pathological effects (Liu, R. et al. (1996) *Cell* 86:367-77; Hutter, G. et al. (2009) *N. Engl. J. Med.* 360:692-8).

In addition, it has recently been proposed that the haemoglobinopathies (Weatherall, D. J. (2013) *Annu. Rev. Genomics Hum. Genet.* 14:1-24), the most common inherited recessive disorders of the haematopoietic system and major targets for therapeutic gene replacement, can also be amenable to therapeutic gene silencing. This intriguing concept stems from our increasing understanding of the mechanisms that orchestrate the foetal to adult haemoglobin switch during development (Stamatoyannopoulos, G. (2005) *Exp. Hematol.* 33:259-71; Bauer, D. E. et al. (2011) *Curr. Opin. Pediatr.* 23:1-8) and by extensive clinical evidence showing that persistent expression of the foetal haemoglobin (HbF) significantly ameliorates morbidity and mortality of Sickle Cell Disease (SCD; Platt, O. S. et al. (1994) *N. Engl. J. Med.* 330:1639-44) and β-thalassemia (β-Thal; Andreani, M. et al. (2011) *Haematologica* 96:128-33) patients. In particular, genome-wide association studies performed on patients affected by the hereditary persistence of HbF revealed that the transcription factor B-cell lymphoma/leukaemia 11A (BCL11A) is a major regulator of the haemoglobin switch (Sankaran, V. G. et al. (2008) *Science* 322:1839-42; Uda, M. et al. (2008) *Proc. Natl. Acad. Sci. USA* 105:1620-5; Galarneau, G. et al. (2010) *Nat. Genet.* 42:1049-51) and that inactivating mutations in this gene result in increased HbF expression (Wilber, A. et al. (2011) *Blood* 117:2817-26; Xu, J. et al. (2011) *Science* 334:993-6). Moreover, an erythroid-specific enhancer within the second intron of BCL11A has recently been identified (Bauer, D. E. et al. (2013) *Science* 342:253-7). Genetic inactivation of this regulatory element impairs BCL11A expression specifically in erythroid precursors, resulting in HbF reactivation, while it preserves the activity of this protein necessary for proper B-cell ontogeny (Canver, M. C. et al. (2015) Nature September 16 doi: 10.1038/nature 15521 [Epub ahead of print]; Vierstra, J. et al. (2015) *Nat. Methods* 12:927-30).

To date, two main targeting technologies have been used to silence gene expression: RNA interference (RNAi; Davidson, B. L. et al. (2011) *Nat. Rev. Genet.* 12:329-40) with single short hairpin RNA (shRNA); and gene targeting with artificial nucleases (AN; Carroll, D. (2014) *Annu. Rev. Biochem.* 83:409-39). RNAi exploits the endogenous microRNA (miRNA) pathway to downregulate expression of the target transcript that is complementary to the shRNA (Davidson, B. L. et al. (2011) *Nat. Rev. Genet.* 12:329-40). The AN approach exploits the error-prone nature of the non-homologous end joining DNA repair process to permanently disrupt the coding frame of the AN-target gene (Ciccia, A. et al. (2010) *Mol. Cell* 40:179-204).

Although promising pre-clinical and clinical data have been obtained using these technologies (DiGiusto, D. L. et al. (2013) *Viruses* 5:2898-919; DiGiusto, D. L. et al. (2010) *Sci. Transl. Med.* 2: 36ra43; Ramachandran, P. S. et al. (2013) *Neurotherapeutics* 10:473-85; McBride, J. L. et al. (2011) *Mol. Ther.* 19:2152-62), partial depletion of gene expression with shRNA and the low efficiency by which homozygous disruption occurs in diploid mammalian cells may jeopardise efficacy of these treatments. These disadvantages are particularly relevant in those applications where residual levels of gene activity are sufficient for biological function.

Furthermore, safe exploitation of these technologies requires solving issues with: a) off-target gene silencing; b) altering the transcriptional profile of the cell by interfering with the endogenous miRNA pathway; and c) altering the cell cycle progression or triggering apoptosis by over-activating the DNA damage response (Ciccia, A. et al. (2010) *Mol. Cell* 40:179-204). In addition, RNAi and AN are not suitable for inactivation of wide non-transcribed regulatory elements, such as promoters or enhancers.

In addition, epigenetic mechanisms have been exploited to silence gene expression. Epigenetics refers to mechanisms that convey heritable changes in the function of the genome without altering the primary DNA sequence. These changes can mediate short-term instructions that can be quickly reverted in response to exogenous stimuli (e.g. histone post-transcriptional modifications; HPTMs). Alternatively, they can constitute long-term instructions that stably contribute to cellular identity and memory (e.g. DNA methylation; Smith, Z. D. et al. (2013) *Nat. Rev. Genet.* 14:204-20). Current studies are unravelling the composition and function of the molecular complexes recruited to chromatin to induce epigenetic repressive states, and the mechanisms by which these states are indefinitely propagated throughout cell division (Cedar, H. et al. (2009) *Nat. Rev. Genet.* 10:295-304; Chen, T. et al. (2014) *Nat. Rev. Genet.* 15:93-106; Probst, A. V. et al. (2009) *Nat. Rev. Mol. Cell Biol.* 10:192-206).

A number of studies have established gene silencing using stably expressed artificial transcription repressors (ATRs) created from DNA-binding domains fused to the effector domains of chromatin remodelling enzymes (de Groote, M. L. et al. (2012) *Nucleic Acids Res.* 40:10596-613; Mendenhall, E. M. et al. (2013) *Nat. Biotechnol.* 31:1133-6; Zhang, F. et al. (2011) *Nat. Biotechnol.* 29:149-53; Konermann, S. et al. (2013) *Nature* 500:472-6; Sera, T. (2009) *Adv. Drug Deliv. Rev.* 61:513-26; Qi, L. S. et al. (2013) *Cell* 152:1173-83). However, these studies failed to demonstrate permanent epigenetic silencing in the absence of continuous expression of the ATRs, likely because of the intrinsic inability of the chosen effector domains to recreate self-propagating chromatin repressive states at the ATR-target loci.

In addition, silencing induced by artificial Krüppel-associated box (KRAB)-based repressors has been shown to be erased in somatic cells once the repressor proteins are not expressed or no longer bind to their target locus (Szulc, J. et al. (2006) *Nat. Methods* 3:109-16).

Accordingly, there remains a significant need for the development of more powerful and safer gene silencing technologies.

SUMMARY OF THE INVENTION

We have developed a novel approach for gene silencing that exploits endogenous epigenetic mechanisms. Unexpectedly, our approach conveys robust and heritable states of transcriptional repression of the desired target gene. Importantly, this allows permanent inactivation of genes of therapeutic (e.g. disease-causing) or biotechnological interest.

Because of the previous difficulties with sustaining robust gene silencing, and because long-lasting expression of artificial transcription repressors (ATRs) from integrating vectors may represent a major safety threat to the cells, we selected to use only ATRs that satisfy all of the following criteria:
1. work by combinatorial assembly of two or more different effector modules;
2. establish robust and permanent states of epigenetic repression; and
3. exert this biological function when transiently expressed in the cell.

This approach has allowed us to improve both the efficiency and safety of gene silencing, as activity of each individual ATR at off-target sites will be transient if not absent.

In one aspect, the present invention provides a product comprising two or more artificial transcription repressors (ATRs), or polynucleotides encoding therefor, selected from groups (a), (b), (c) or (d):
  (a) an ATR comprising a DNA-binding domain operably linked to a KRAB domain or homologue thereof;
  (b) an ATR comprising a DNA-binding domain operably linked to a DNMT3A, DNMT3B or DNMT1 domain or homologue thereof;
  (c) an ATR comprising a DNA-binding domain operably linked to a DNMT3L domain or homologue thereof; and
  (d) an ATR comprising a DNA-binding domain operably linked to a SETDB1 domain or homologue thereof
wherein at least two of the ATRs are selected from different groups (a), (b), (c) or (d).

In another aspect, the present invention provides a product comprising two or more artificial transcription repressors (ATRs), or polynucleotides encoding therefor, selected from groups (a), (b) or (c):
  (a) an ATR comprising a DNA-binding domain operably linked to a KRAB domain or homologue thereof;
  (b) an ATR comprising a DNA-binding domain operably linked to a DNMT3A, DNMT3B or DNMT1 domain or homologue thereof; and
  (c) an ATR comprising a DNA-binding domain operably linked to a DNMT3L domain or homologue thereof
wherein at least two of the ATRs are selected from different groups (a), (b) or (c).

In one embodiment, the product of the invention comprises the ATRs (a) and (b), or polynucleotides encoding therefor. In another embodiment, the product of the invention comprises the ATRs (a) and (c), or polynucleotides encoding therefor. In another embodiment, the product of the invention comprises the ATRs (b) and (c), or polynucleotides encoding therefor. In a preferred embodiment, the product of the invention comprises the ATRs (a), (b) and (c), or polynucleotides encoding therefor. In another embodiment, the product of the invention comprises the ATRs (a), (b) and (d), or polynucleotides encoding therefor. In another embodiment, the product of the invention comprises the ATRs (b) and (d), or polynucleotides encoding therefor. In another embodiment, the product of the invention comprises the ATRs (c) and (d), or polynucleotides encoding therefor. In another preferred embodiment, the product of the invention comprises the ATRs (b), (c) and (d), or polynucleotides encoding therefor.

The KRAB domain or homologue thereof may comprise an amino acid sequence that has at least 50%, 60%, 70%, 80%, 90%, 95%, 99% or 100% identity to SEQ ID NO: 1, 2, 3, 4, 5, 6 or 7 wherein the amino acid sequence substantially retains the natural function of the protein represented by SEQ ID NO: 1, 2, 3, 4, 5, 6, or 7.

The DNMT3A domain or homologue thereof may comprise an amino acid sequence that has at least 50%, 60%, 70%, 80%, 90%, 95%, 99% or 100% identity to SEQ ID NO: 8 wherein the amino acid sequence substantially retains the natural function of the protein represented by SEQ ID NO: 8.

The DNMT3B domain or homologue thereof may comprise an amino acid sequence that has at least 50%, 60%, 70%, 80%, 90%, 95%, 99% or 100% identity to SEQ ID NO: 9 or 36 wherein the amino acid sequence substantially retains the natural function of the protein represented by SEQ ID NO: 9 or 36.

The DNMT1 domain or homologue thereof may comprise an amino acid sequence that has at least 50%, 60%, 70%, 80%, 90%, 95%, 99% or 100% identity to SEQ ID NO: 10 wherein the amino acid sequence substantially retains the natural function of the protein represented by SEQ ID NO: 10.

The DNMT3L domain or homologue thereof may comprise an amino acid sequence that has at least 50%, 60%, 70%, 80%, 90%, 95%, 99% or 100% identity to SEQ ID NO: 11 wherein the amino acid sequence substantially retains the natural function of the protein represented by SEQ ID NO: 11.

The SETDB1 domain or homologue thereof may comprise an amino acid sequence that has at least 50%, 60%, 70%, 80%, 90%, 95%, 99% or 100% identity to SEQ ID NO: 12 or 13 wherein the amino acid sequence substantially retains the natural function of the protein represented by SEQ ID NO: 12 or 13.

In one embodiment, the DNA-binding domain of (a), (b), (c) or (d) comprises a domain independently selected from a TALE DNA-binding domain, a zinc finger domain, a tetR DNA-binding domain, a meganuclease or a CRISPR/Cas system. In a preferred embodiment, the DNA-binding domain of (a), (b), (c) or (d) comprises a TALE DNA-binding domain or a CRISPR/Cas system.

The DNA-binding domains, for example the TALE DNA-binding domains or the CRISPR/Cas system, of (a), (b), (c) or (d) may be selected or engineered to bind to different binding sites.

The DNA-binding domains may bind to binding sites within a target gene or within regulatory sequences for the target gene, for example promoter or enhancer sequences.

The DNA-binding domains may bind to binding sites within splicing sites. Splicing variants of a given gene may be regulated by DNA methylation/demethylation at splicing sites. In turn, these modifications may cause exon exclusion/inclusion in the mature transcript. This exclusion/inclusion may have therapeutic relevance, such as in the case of Duchenne Muscular Dystrophy, in which exclusion (by genetic ablation or exon skipping) from the mature mRNA of an exon bearing the most frequent disease-causing mutation has been proposed for therapy (Ousterout, D. G. et al. (2015) Mol. Ther. 23:523-32; Ousterout, D. G. et al. (2015) Nat. Commun. 6:6244; Kole, R. et al. (2015) Adv. Drug Deliv. Rev. 87:104-7; Touznik, A. et al. (2014) Expert Opin. Biol. Ther. 14:809-19).

The ATRs of the present invention may also target genetic elements which may be actively transcribed or not (e.g. sequences that control the topological arrangement, stability and replication of the genome, such as insulators, laminin-associated domains, telomeric and centromeric regions), repetitive or mobile elements. Accordingly, the present invention may relate to epigenetic editing, such as silencing/editing of a genetic element. The invention may therefore encompass the use of the products and ATRs of the invention for epigenetic editing of regulatory DNA elements, such as those described herein. Epigenetic editing of a target gene or of a genetic element may also be associated with its transcription activation or activity, respectively. The invention may also encompass the use of the products and ATRs of the invention for simultaneous epigenetic silencing of multiple target genes or regulatory DNA elements, such as those described herein.

In one embodiment, the polynucleotides encoding the two or more ATRs are in the form of a single vector or are comprised within separate vectors.

In one embodiment where two ATRs are used, polynucleotides encoding (a) and (b) may be comprised within a single vector; polynucleotides encoding (a) and (c) may be comprised within a single vector; or polynucleotides encoding (b) and (c) may be comprised within a single vector.

In another embodiment where two ATRs are used, polynucleotides encoding (a) and (d) may be comprised within a single vector; polynucleotides encoding (b) and (d) may be comprised within a single vector; or polynucleotides encoding (c) and (d) may be comprised within a single vector.

In another embodiment where two ATRs are used, polynucleotides encoding (a) and (b) may be comprised within separate vectors; polynucleotides encoding (a) and (c) may be comprised within separate vectors; or polynucleotides encoding (b) and (c) may be comprised within separate vectors.

In another embodiment where two ATRs are used, polynucleotides encoding (a) and (d) may be comprised within separate vectors; polynucleotides encoding (b) and (d) may be comprised within separate vectors; or polynucleotides encoding (c) and (d) may be comprised within separate vectors.

In one embodiment where three ATRs are used, polynucleotides encoding (a), (b) and (c) may be comprised within a single vector; polynucleotides encoding (a), (b) and (c) may be comprised within separate vectors; polynucleotides encoding (a) and (b) may be comprised within a single vector and the polynucleotide encoding (c) may be comprised within a separate vector; polynucleotides encoding (a) and (c) may be comprised within a single vector and the polynucleotide encoding (b) may be comprised within a separate vector; or polynucleotides encoding (b) and (c) may be comprised within a single vector and the polynucleotide encoding (a) may be comprised within a separate vector.

In another embodiment where three ATRs are used, polynucleotides encoding (a), (b) and (d) may be comprised within a single vector; polynucleotides encoding (a), (b) and (d) may be comprised within separate vectors; polynucleotides encoding (a) and (b) may be comprised within a single vector and the polynucleotide encoding (d) may be comprised within a separate vector; polynucleotides encoding (a) and (d) may be comprised within a single vector and the polynucleotide encoding (b) may be comprised within a separate vector; or polynucleotides encoding (b) and (d) may be comprised within a single vector and the polynucleotide encoding (a) may be comprised within a separate vector.

In another embodiment where three ATRs are used, polynucleotides encoding (b), (c) and (d) may be comprised within a single vector; polynucleotides encoding (b), (c) and (d) may be comprised within separate vectors; polynucleotides encoding (b) and (c) may be comprised within a single vector and the polynucleotide encoding (d) may be comprised within a separate vector; polynucleotides encoding (b) and (d) may be comprised within a single vector and the polynucleotide encoding (c) may be comprised within a separate vector; or polynucleotides encoding (c) and (d) may be comprised within a single vector and the polynucleotide encoding (b) may be comprised within a separate vector.

The vectors may, for example, be plasmid vectors, mRNA vectors (e.g. in vitro transcribed mRNA vectors) or viral vectors. Preferably the vectors enable transient expression of the ATRs within a cell.

As an alternative to the delivery of polynucleotides encoding ATRs to cells, the ATRs of the present invention may be delivered to cells by protein transduction. The protein transduction may, for example, be via vector delivery or by direct protein delivery.

In one embodiment, the product of the invention is in the form of a pharmaceutical composition further comprising a pharmaceutically acceptable carrier, diluent or excipient.

In one embodiment, the product of the invention further comprises a KRAB domain or homologue thereof, or polynucleotide encoding therefor, wherein the KRAB domain or homologue thereof is not operably linked to a DNA-binding domain.

In one embodiment, the product of the invention further comprises a DNMT3A, DNMT3B or DNMT1 domain or homologue thereof, or polynucleotide encoding therefor, wherein the DNMT3A, DNMT3B or DNMT1 domain or homologue thereof is not operably linked to a DNA-binding domain.

In one embodiment, the product of the invention further comprises a DNMT3L domain or homologue thereof, or polynucleotide encoding therefor, wherein the DNMT3L domain or homologue thereof is not operably linked to a DNA-binding domain.

In one embodiment, the product of the invention further comprises a SETDB1 domain or homologue thereof, or polynucleotide encoding therefor, wherein the SETDB1 domain or homologue thereof is not operably linked to a DNA-binding domain.

In another aspect, the present invention provides the product of the invention for use in therapy.

In another aspect, the present invention provides the product of the invention for use in therapy, wherein the two or more artificial transcription repressors (ATRs), or polynucleotides encoding therefor, are a combined preparation for administration to a subject simultaneously, sequentially or separately.

Herein, administration to a subject may include administration to a cell, for example during ex vivo therapy.

In another aspect, the present invention provides the use of the product of the invention for silencing a target gene. The use may, for example, be in vitro or ex vivo use. For example, a target gene may be silenced in a population of cells (e.g. a cell line or primary cells) to enhance the production of an agent (e.g. a biotherapeutic agent) by the cells, or to impart a growth advantage to the cells. Alternatively, for example, a target gene may be silenced to generate a knockout animal model for the target gene. The epigenetic approach of the present invention provides an alternative to existing methods of knocking out a gene, such as those utilising homologous recombination. Alternatively, for example, a target gene may be silenced in a plant cell.

According to the above uses, including the uses in therapy, the delivery of the two or more ATRs of the invention to a cell may silence a target gene. The delivery may be transient delivery. The delivery may be via expression of the two or more ATRs in a cell, for example expression from polynucleotides encoding the ATRs. The delivery of the two or more ATRs of the invention to a cell may also cause exon exclusion/inclusion in a mature transcript, for example through an effect on a splicing site. The delivery of the two or more ATRs of the invention to a cell may also enable silencing and/or editing of a genetic element as described herein.

In one embodiment, expression of the two or more ATRs of the invention in a cell silences a target gene. The expression may be transient expression.

In one embodiment, delivery of the two or more ATRs of the invention to a cell (e.g. by expression in the cell) permanently silences a target gene. In another embodiment, delivery of the two or more ATRs of the invention to a cell (e.g. by expression in the cell) permanently silences a target gene in the cell's progeny. For example, the cell may be a stem cell and the target gene may be silenced in the stem cell's progeny (e.g. the target gene may be silenced in cells resulting from differentiation of the stem cells).

By way of example, the cells may be derived from animals (such as mammals, e.g. humans), fungi (such as yeast) or plants. For example, the cells may be haematopoietic stem and progenitor cells, T lymphocytes, mesenchymal stem cells, fibroblasts, monocytes, epidermal or neural stem cells.

The separation of the binding sites to which the DNA-binding domains of the different ATRs are selected to bind is not particularly limited in size. For example, the DNA-binding domains of the different ATRs may be selected to bind to binding sites that are separated by about 1-100 bp, 1-50 bp, 1-30 bp, 5-30 bp, 10-30 bp or 15-30 bp. In one embodiment, the DNA-binding domains of the different ATRs are selected to bind to binding sites that are separated by 1-30 bp. Preferably, the DNA-binding domains of the different ATRs are selected to bind to binding sites that are separated by about 15-25 bp. For example, the DNA-binding domains of the different ATRs may be selected to bind to binding sites that are separated by 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 bp.

The DNA-binding domains of the different ATRs may also be selected to bind to the same binding site, for example the DNA-binding domains of the different ATRs may be selected to bind to binding sites that are separated by 0 bp. Thus, for example, the DNA-binding domains of the different ATRs may be selected to bind to binding sites that are separated by about 0-100 bp, 0-50 bp, 0-30 bp, 5-30 bp, 10-30 bp or 15-30 bp. The DNA-binding domains of the different ATRs may be selected to bind to binding sites that are separated by about 0-15 or 15-25 bp.

The directional order in which the different ATRs bind relative to the target gene is not particularly important. In one embodiment, the two or more ATRs comprise an ATR comprising a KRAB domain or homologue thereof and an ATR comprising a DNMT3A, DNMT3B or DNMT1 domain or homologue thereof, and the DNA-binding domains (e.g. TALE DNA-binding domains) of each ATR are selected such that the ATR comprising a DNMT3A, DNMT3B or DNMT1 domain or homologue thereof binds to DNA upstream of the ATR comprising a KRAB domain or homologue thereof.

In one embodiment, the DNA-binding domains are TALE DNA-binding domains or CRISPR/Cas systems.

The selection of the DNA-binding domains may comprise engineering DNA-binding domains to bind to specific, desired DNA sequences.

In another aspect, the present invention provides an artificial transcription repressor (ATR) comprising a DNA-binding domain operably linked to a KRAB domain or homologue thereof, or polynucleotide encoding therefor, for use in therapy wherein the ATR is administered to a subject simultaneously, sequentially or separately in combination with a second ATR comprising a DNA-binding domain operably linked to a DNMT3A, DNMT3B or DNMT1 domain or homologue thereof and/or a third ATR comprising a DNA-binding domain operably linked to a DNMT3L domain or homologue thereof, or polynucleotides encoding therefor.

In another aspect, the present invention provides an artificial transcription repressor (ATR) comprising a DNA-binding domain operably linked to a DNMT3A, DNMT3B or DNMT1 domain or homologue thereof, or polynucleotide encoding therefor, for use in therapy wherein the ATR is administered to a subject simultaneously, sequentially or separately in combination with a second ATR comprising a DNA-binding domain operably linked to a KRAB domain or homologue thereof and/or a third ATR comprising a DNA-binding domain operably linked to a DNMT3L domain or homologue thereof, or polynucleotides encoding therefor.

In another aspect, the present invention provides an artificial transcription repressor (ATR) comprising a DNA-binding domain operably linked to a DNMT3L domain or homologue thereof, or polynucleotide encoding therefor, for use in therapy wherein the ATR is administered to a subject simultaneously, sequentially or separately in combination with a second ATR comprising a DNA-binding domain operably linked to a KRAB domain or homologue thereof and/or a third ATR comprising a DNA-binding domain operably linked to a DNMT3A, DNMT3B or DNMT1 domain or homologue thereof, or polynucleotides encoding therefor.

In another aspect, the present invention provides an artificial transcription repressor (ATR) comprising a DNA-binding domain operably linked to a KRAB domain or homologue thereof, or polynucleotide encoding therefor, for use in therapy wherein the ATR is administered to a subject simultaneously, sequentially or separately in combination with a second ATR comprising a DNA-binding domain operably linked to a DNMT3A, DNMT3B or DNMT1 domain or homologue thereof, and/or a third ATR comprising a DNA-binding domain operably linked to a DNMT3L domain or homologue thereof, and/or a fourth ATR comprising a DNA-binding domain operably linked to a SETDB1 domain or homologue thereof, or polynucleotides encoding therefor.

In another aspect, the present invention provides an artificial transcription repressor (ATR) comprising a DNA-binding domain operably linked to a DNMT3A, DNMT3B or DNMT1 domain or homologue thereof, or polynucleotide encoding therefor, for use in therapy wherein the ATR is administered to a subject simultaneously, sequentially or separately in combination with a second ATR comprising a DNA-binding domain operably linked to a KRAB domain or homologue thereof, and/or a third ATR comprising a DNA-binding domain operably linked to a DNMT3L domain or homologue thereof, and/or a fourth ATR comprising a DNA-binding domain operably linked to a SETDB1 domain or homologue thereof, or polynucleotides encoding therefor.

In another aspect, the present invention provides an artificial transcription repressor (ATR) comprising a DNA-binding domain operably linked to a DNMT3L domain or homologue thereof, or polynucleotide encoding therefor, for use in therapy wherein the ATR is administered to a subject simultaneously, sequentially or separately in combination with a second ATR comprising a DNA-binding domain operably linked to a KRAB domain or homologue thereof, and/or a third ATR comprising a DNA-binding domain operably linked to a DNMT3A, DNMT3B or DNMT1 domain or homologue thereof, and/or a fourth ATR comprising a DNA-binding domain operably linked to a SETDB1 domain or homologue thereof, or polynucleotides encoding therefor.

In another aspect, the present invention provides an artificial transcription repressor (ATR) comprising a DNA-binding domain operably linked to a SETDB1 domain or homologue thereof, or polynucleotide encoding therefor, for use in therapy wherein the ATR is administered to a subject simultaneously, sequentially or separately in combination with a second ATR comprising a DNA-binding domain operably linked to a DNMT3A, DNMT3B or DNMT1 domain or homologue thereof, and/or a third ATR comprising a DNA-binding domain operably linked to a DNMT3L domain or homologue thereof, and/or a fourth ATR comprising a DNA-binding domain operably linked to a KRAB domain or homologue thereof, or polynucleotides encoding therefor.

In another aspect, the present invention provides a cell comprising the two or more artificial transcription repressors (ATRs) of the invention. The cell may be transfected by the polynucleotides encoding the two or more ATRs of the invention. The polynucleotides may be in the form of a single vector or may be comprised within separate vectors.

In another aspect, the present invention provides a cell wherein said cell is a descendant of a cell comprising the two or more artificial transcription repressors (ATRs) of the invention. In one embodiment, the descendant cell no longer comprises the two or more ATRs of the invention. In another aspect, the present invention provides the cell of the invention for use in therapy.

In another aspect, the present invention provides a method of gene therapy comprising transfecting a cell with the polynucleotides encoding the two or more artificial transcription repressors (ATRs) of the invention, wherein the polynucleotides are in the form of a single vector or are comprised within separate vectors.

In one embodiment, the transfection is carried out ex vivo.

In another aspect, the present invention provides a method of gene therapy comprising administering two or more artificial transcription repressors (ATRs), or polynucleotides encoding therefor, selected from groups (a), (b) or (c):
(a) an ATR comprising a DNA-binding domain operably linked to a KRAB domain or homologue thereof;
(b) an ATR comprising a DNA-binding domain operably linked to a DNMT3A, DNMT3B or DNMT1 domain or homologue thereof; and
(c) an ATR comprising a DNA-binding domain operably linked to a DNMT3L domain or homologue thereof
to a subject simultaneously, sequentially or separately wherein at least two of the ATRs are selected from different groups (a), (b) or (c). The present invention also provides a method of gene therapy comprising administering two or more artificial transcription repressors (ATRs), or polynucleotides encoding therefor, selected from groups (a), (b), (c) or (d):
(a) an ATR comprising a DNA-binding domain operably linked to a KRAB domain or homologue thereof;
(b) an ATR comprising a DNA-binding domain operably linked to a DNMT3A, DNMT3B or DNMT1 domain or homologue thereof;
(c) an ATR comprising a DNA-binding domain operably linked to a DNMT3L domain or homologue thereof; and
(d) an ATR comprising a DNA-binding domain operably linked to a SETDB1 domain or homologue thereof
to a subject simultaneously, sequentially or separately, wherein at least two of the ATRs are selected from different groups (a), (b), (c) or (d).

In another aspect, the present invention provides a kit comprising two or more artificial transcription repressors (ATRs), or polynucleotides encoding therefor, selected from groups (a), (b) or (c):
(a) an ATR comprising a DNA-binding domain operably linked to a KRAB domain or homologue thereof;
(b) an ATR comprising a DNA-binding domain operably linked to a DNMT3A, DNMT3B or DNMT1 domain or homologue thereof; and
(c) an ATR comprising a DNA-binding domain operably linked to a DNMT3L domain or homologue thereof
wherein at least two of the ATRs are selected from different groups (a), (b) or (c). The present invention also provides a kit comprising two or more artificial transcription repressors (ATRs), or polynucleotides encoding therefor, selected from groups (a), (b), (c) or (d):
(a) an ATR comprising a DNA-binding domain operably linked to a KRAB domain or homologue thereof;
(b) an ATR comprising a DNA-binding domain operably linked to a DNMT3A, DNMT3B or DNMT1 domain or homologue thereof;
(c) an ATR comprising a DNA-binding domain operably linked to a DNMT3L domain or homologue thereof; and
(d) an ATR comprising a DNA-binding domain operably linked to a SETDB1 domain or homologue thereof
wherein at least two of the ATRs are selected from different groups (a), (b), (c) or (d).

In another aspect, the present invention provides a method of silencing a target gene comprising the step of administering the two or more ATRs, or polynucleotides encoding therefor, of the invention to a cell. The method may be an in vitro method.

In another aspect, the present invention provides a product comprising an artificial transcription repressor (ATR) comprising a DNA-binding domain operably linked to a DNMT3A, DNMT3B or DNMT1 domain or homologue thereof, preferably a DNMT3A domain or homologue thereof, and an ATR comprising a DNA-binding domain operably linked to a SETDB1 domain or homologue thereof, or polynucleotides encoding therefor. The present invention also provides uses of this product, uses of this product in therapy, cells comprising this product and their descendants, methods employing this product and kits comprising this product, as described herein. This product may also further comprise an ATR comprising a DNA-binding domain operably linked to a DNMT3L or KRAB domain or homologue thereof, or polynucleotide encoding therefor.

In one embodiment, the product comprises an artificial transcription repressor (ATR) comprising a DNA-binding domain operably linked to a DNMT3A, DNMT3B or DNMT1 domain or homologue thereof, preferably a DNMT3A domain or homologue thereof, an ATR comprising a DNA-binding domain operably linked to a SETDB1 domain or homologue thereof, and an ATR comprising a DNA-binding domain operably linked to a DNMT3L domain or homologue thereof, or polynucleotides encoding therefor.

In one embodiment, the product comprises an artificial transcription repressor (ATR) comprising a DNA-binding domain operably linked to a DNMT3A, DNMT3B or DNMT1 domain or homologue thereof, preferably a DNMT3A domain or homologue thereof, an ATR comprising a DNA-binding domain operably linked to a SETDB1 domain or homologue thereof, and an ATR comprising a DNA-binding domain operably linked to a KRAB domain or homologue thereof, or polynucleotides encoding therefor.

The SETDB1 domain or homologue thereof may comprise an amino acid sequence that has at least 50%, 60%, 70%, 80%, 90%, 95%, 99% or 100% identity to SEQ ID NO: 12 or 13 wherein the amino acid sequence substantially retains the natural function of the protein represented by SEQ ID NO: 12 or 13.

In another aspect, the present invention provides an artificial transcription repressor (ATR), or a polynucleotide encoding therefor, wherein the ATR comprises a DNA-binding domain operably linked to two or more domains selected from groups (a), (b) or (c):
  (a) a KRAB domain or homologue thereof;
  (b) a DNMT3A, DNMT3B or DNMT1 domain or homologue thereof; and
  (c) a DNMT3L domain or homologue thereof
wherein at least two of the domains operably linked to the DNA-binding domain are selected from different groups (a), (b) or (c). The ATR may, for example, comprise a DNA-binding domain operably linked to a domain of group (a), a domain of group (b) and a domain of group (c). The present invention also provides an artificial transcription repressor (ATR) comprising a DNA-binding domain operably linked to two or more domains selected from groups (a), (b), (c) or (d):
  (a) a KRAB domain or homologue thereof;
  (b) a DNMT3A, DNMT3B or DNMT1 domain or homologue thereof;
  (c) a DNMT3L domain or homologue thereof; and
  (d) a SETDB1 domain or homologue thereof
wherein at least two of the domains operably linked to the DNA-binding domain are selected from different groups (a), (b), (c) or (d).

In one embodiment, the DNA-binding domain comprises a TALE DNA-binding domain, a zinc finger domain, a tetR DNA-binding domain, a meganuclease or a CRISPR/Cas system.

The present invention also provides uses of this ATR, uses of this ATR in therapy, cells comprising this ATR and their descendants, methods employing this ATR and kits comprising this ATR, as described herein.

In another aspect, the present invention provides a product comprising two or more different artificial transcription repressors (ATRs), or polynucleotides encoding therefor, wherein the two or more different ATRs individually comprise a DNA-binding domain operably linked to two or more domains selected from groups (a), (b) or (c):
  (a) a KRAB domain or homologue thereof;
  (b) a DNMT3A, DNMT3B or DNMT1 domain or homologue thereof; and
  (c) a DNMT3L domain or homologue thereof
wherein at least two of the domains operably linked to each individual DNA-binding domain are selected from different groups (a), (b) or (c). Each ATR may, for example, comprise a DNA-binding domain operably linked to a domain of group (a), a domain of group (b) and a domain of group (c). The present invention also provides a product comprising two or more different artificial transcription repressors (ATRs), or polynucleotides encoding therefor, wherein the two or more different ATRs individually comprise a DNA-binding domain operably linked to two or more domains selected from groups (a), (b), (c) or (d):
  (a) a KRAB domain or homologue thereof;
  (b) a DNMT3A, DNMT3B or DNMT1 domain or homologue thereof;
  (c) a DNMT3L domain or homologue thereof; and
  (d) a SETDB1 domain or homologue thereof
wherein at least two of the domains operably linked to each individual DNA-binding domain are selected from different groups (a), (b), (c) or (d).

In one embodiment, the DNA-binding domains of the two or more different ATRs are individually selected from the group consisting of a TALE DNA-binding domain, a zinc finger domain, a tetR DNA-binding domain, a meganuclease or a CRISPR/Cas system.

The DNA-binding domains, for example the TALE DNA-binding domains or the CRISPR/Cas system, of the two or more different ATRs may be selected or engineered to bind to different binding sites.

The DNA-binding domains may bind to binding sites within a target gene or within regulatory sequences for the target gene, for example promoter or enhancer sequences. The DNA-binding domains may bind to binding sites within splicing sites.

The present invention also provides uses of this product, uses of this product in therapy, cells comprising this product and their descendants, methods employing this product and kits comprising this product, as described herein.

In another aspect, the present invention provides a product comprising only one ATR and a separate effector protein that is not operably linked to a DNA-binding domain, or polynucleotides encoding therefor. The ATR may comprise a DNA-binding domain operably linked to an effector domain selected from: (a) a KRAB domain or homologue thereof; (b) a DNMT3A, DNMT3B or DNMT1 domain or homologue thereof; or (c) a DNMT3L domain or homologue thereof (i.e. the ATR may be as described herein). The separate effector protein that is not operably linked to a DNA-binding domain may comprise a KRAB, DNMT3A, DNMT3B, DNMT1 or DNMT3L domain or homologue thereof. The separate effector protein may be an effector domain/protein as described herein. The separate effector protein may be a full-length protein or functional fragment thereof. Preferably the separate effector protein is different to the effector domain of the ATR. Preferably the separate effector protein is of a different class to the effector domain of the ATR. Preferably the separate effector protein is selected such that it does not comprise a domain belonging to the same group (a), (b) or (c) as the effector domain that constitutes the ATR.

The separate effector protein that is not operably linked to a DNA-binding domain may also comprise a SETDB1 domain or homologue thereof.

In another aspect, the present invention provides a product comprising only one ATR and a separate effector protein that is not operably linked to a DNA-binding domain, or polynucleotides encoding therefor. The ATR may comprise a DNA-binding domain operably linked to a SETDB1 effector domain or homologue thereof (i.e. the ATR may be as described herein). The separate effector protein that is not operably linked to a DNA-binding domain may comprise a KRAB, DNMT3A, DNMT3B, DNMT1 or DNMT3L domain or homologue thereof. The separate effector protein may be an effector domain/protein as described herein. The separate effector protein may be a full-length protein or functional fragment thereof.

In one embodiment, the DNA-binding domain of the ATR is selected from the group consisting of a TALE DNA-binding domain, a zinc finger domain, a tetR DNA-binding domain, a meganuclease or a CRISPR/Cas system.

The present invention also provides uses of this product, uses of this product in therapy, cells comprising this product and their descendants, methods employing this product and kits comprising this product, as described herein.

When the product of the invention comprises only one ATR and a separate effector protein that is not operably linked to a DNA-binding domain, the polynucleotides encoding the ATR and separate effector protein may be in the form of a single vector or comprised within separate vectors.

The vectors may, for example, be plasmid vectors, mRNA vectors (e.g. in vitro transcribed mRNA vectors) or viral vectors. Preferably the vectors enable transient expression of the ATR and/or separate effector protein within a cell.

The ATR and/or separate effector protein of the present invention may also be delivered to cells by protein transduction, as described herein.

The ATRs and/or separate effector proteins of the invention, or polynucleotides encoding therefor, may be in the form of a pharmaceutical composition further comprising a pharmaceutically acceptable carrier, diluent or excipient.

In another aspect, the present invention provides the ATR of the invention, or the ATR and separate effector protein of the invention, or polynucleotides encoding therefor, for use in therapy.

In another aspect, the present invention provides the ATR and separate effector protein of the invention, or polynucleotides encoding therefor, for use in therapy, wherein the ATR and separate effector protein, or polynucleotides encoding therefor, are a combined preparation for administration to a subject simultaneously, sequentially or separately.

In another aspect, the present invention provides the ATR of the invention, or the ATR and separate effector protein of the invention, or polynucleotides encoding therefor, for silencing a target gene. The use may, for example, be in vitro or ex vivo use.

According to the above uses, including the uses in therapy, the delivery of the ATR of the invention, or the ATR and separate effector protein of the invention to a cell may silence a target gene. The delivery may be transient delivery. The delivery may be via expression of the ATR of the invention, or the ATR and separate effector protein of the invention in a cell, for example expression from polynucleotides encoding the ATR of the invention, or the ATR and separate effector protein of the invention.

In one embodiment, expression of the ATR of the invention, or the ATR and separate effector protein of the invention in a cell silences a target gene. The expression may be transient expression.

In one embodiment, delivery of the ATR of the invention, or the ATR and separate effector protein of the invention to a cell (e.g. by expression in the cell) permanently silences a target gene. In another embodiment, delivery of the ATR of the invention, or the ATR and separate effector protein of the invention to a cell (e.g. by expression in the cell) permanently silences a target gene in the cell's progeny. For example, the cell may be a stem cell and the target gene may be silenced in the stem cell's progeny (e.g. the target gene may be silenced in cells resulting from differentiation of the stem cells).

By way of example, the cells may be derived from animals (such as mammals, e.g. humans), fungi (such as yeast) or plants. For example, the cells may be haematopoietic stem and progenitor cells, T lymphocytes, mesenchymal stem cells, fibroblasts, monocytes, epidermal or neural stem cells.

In another aspect, the present invention provides an artificial transcription repressor (ATR) comprising a DNA-binding domain operably linked to a KRAB domain or homologue thereof, or polynucleotide encoding therefor, for use in therapy wherein the ATR is administered to a subject simultaneously, sequentially or separately in combination with a first separate effector protein that is not operably linked to a DNA-binding domain comprising a DNMT3A, DNMT3B or DNMT1 domain or homologue thereof and/or a second separate effector protein that is not operably linked to a DNA-binding domain comprising a DNMT3L domain or homologue thereof, or polynucleotides encoding therefor.

In another aspect, the present invention provides an artificial transcription repressor (ATR) comprising a DNA-binding domain operably linked to a DNMT3A, DNMT3B or DNMT1 domain or homologue thereof, or polynucleotide encoding therefor, for use in therapy wherein the ATR is administered to a subject simultaneously, sequentially or separately in combination with a first separate effector protein that is not operably linked to a DNA-binding domain comprising a KRAB domain or homologue thereof and/or a second separate effector protein that is not operably linked to a DNA-binding domain comprising a DNMT3L domain or homologue thereof, or polynucleotides encoding therefor.

In another aspect, the present invention provides an artificial transcription repressor (ATR) comprising a DNA-binding domain operably linked to a DNMT3L domain or homologue thereof, or polynucleotide encoding therefor, for use in therapy wherein the ATR is administered to a subject simultaneously, sequentially or separately in combination with a first separate effector protein that is not operably linked to a DNA-binding domain comprising a KRAB domain or homologue thereof and/or a second separate effector protein that is not operably linked to a DNA-binding domain comprising a DNMT3A, DNMT3B or DNMT1 domain or homologue thereof, or polynucleotides encoding therefor.

A third separate effector protein that is not operably linked to a DNA-binding domain comprising a SETDB1 domain or homologue thereof may also be used in these combinations.

In another aspect, the present invention provides an artificial transcription repressor (ATR) comprising a DNA-binding domain operably linked to a SETDB1 domain or homologue thereof, or polynucleotide encoding therefor, for use in therapy wherein the ATR is administered to a subject simultaneously, sequentially or separately in combination with a first separate effector protein that is not operably linked to a DNA-binding domain comprising a KRAB domain or homologue thereof and/or a second separate effector protein that is not operably linked to a DNA-binding domain comprising a DNMT3A, DNMT3B or DNMT1 domain or homologue thereof and/or a third separate effector protein that is not operably linked to a DNA-binding domain comprising a DNMT3L domain or homologue thereof, or polynucleotides encoding therefor.

In another aspect, the present invention provides a cell comprising the ATR of the invention, or the ATR and separate effector protein of the invention. The cell may be transfected by the polynucleotides encoding the ATR of the invention, or the ATR and separate effector protein of the invention. The polynucleotides encoding the ATR and separate effector protein of the invention may be in the form of a single vector or may be comprised within separate vectors.

In another aspect, the present invention provides a cell wherein said cell is a descendant of a cell comprising the ATR of the invention, or the ATR and separate effector protein of the invention. In one embodiment, the descendant cell no longer comprises the ATR and/or separate effector protein of the invention. In another aspect, the present invention provides the cell of the invention for use in therapy.

In another aspect, the present invention provides a method of gene therapy comprising transfecting a cell with the polynucleotides encoding the ATR of the invention, or the ATR and separate effector protein of the invention. The polynucleotides encoding the ATR and separate effector protein of the invention may be in the form of a single vector or comprised within separate vectors.

In one embodiment, the transfection is carried out ex vivo.

In another aspect, the present invention provides a method of gene therapy comprising administering only one ATR and a separate effector protein that is not operably linked to a DNA-binding domain, or polynucleotides encoding therefor, to a subject simultaneously, sequentially or separately. The ATR may comprise a DNA-binding domain operably linked to an effector domain selected from: (a) a KRAB domain or homologue thereof; (b) a DNMT3A, DNMT3B or DNMT1 domain or homologue thereof; or (c) a DNMT3L domain or homologue thereof (i.e. the ATR may be as described herein). The separate effector protein that is not operably linked to a DNA-binding domain may comprise a KRAB, DNMT3A, DNMT3B, DNMT1 or DNMT3L domain or homologue thereof. The separate effector protein may be an effector domain/protein as described herein. The separate effector protein may be a full-length protein or functional fragment thereof. Preferably the separate effector protein is different to the effector domain of the ATR. Preferably the separate effector protein is of a different class to the effector domain of the ATR. Preferably the separate effector protein is selected such that it does not comprise a domain belonging to the same group (a), (b) or (c) as the effector domain that constitutes the ATR. The ATR may also comprise a DNA-binding domain operably linked to a SETDB1 effector domain or homologue thereof. The separate effector protein that is not operably linked to a DNA-binding domain may also comprise a SETDB1 domain or homologue thereof.

In another aspect, the present invention provides a kit comprising only one ATR and a separate effector protein that is not operably linked to a DNA-binding domain, or polynucleotides encoding therefor. The ATR may comprise a DNA-binding domain operably linked to an effector domain selected from: (a) a KRAB domain or homologue thereof; (b) a DNMT3A, DNMT3B or DNMT1 domain or homologue thereof; or (c) a DNMT3L domain or homologue thereof (i.e. the ATR may be as described herein). The separate effector protein that is not operably linked to a DNA-binding domain may comprise a KRAB, DNMT3A, DNMT3B, DNMT1 or DNMT3L domain or homologue thereof. The separate effector protein may be an effector domain/protein as described herein. The separate effector protein may be a full-length protein or functional fragment thereof. Preferably the separate effector protein is different to the effector domain of the ATR. Preferably the separate effector protein is of a different class to the effector domain of the ATR. Preferably the separate effector protein is selected such that it does not comprise a domain belonging to the same group (a), (b) or (c) as the effector domain that constitutes the ATR The ATR may also comprise a DNA-binding domain operably linked to a SETDB1 effector domain or homologue thereof. The separate effector protein that is not operably linked to a DNA-binding domain may also comprise a SETDB1 domain or homologue thereof.

In another aspect, the present invention provides a method of silencing a target gene comprising the step of administering the ATR of the invention, or the ATR and separate effector protein of the invention, or polynucleotides encoding therefor, to a cell. The method may be an in vitro method.

In addition, it is envisaged that the ATR or separate effector protein of the invention may comprise a SETDB1 domain or homologue thereof, when another component of the product of the invention (i.e. the ATR or separate effector protein) comprises a DNMT3A, DNMT3B or DNMT1 domain or homologue thereof.

The methods and uses of the present invention, for example methods of gene therapy or silencing a target gene, may also include a step of inactivating an endogenous gene that may counteract the activity of the ATRs or separate effector proteins of the invention. For example, the DNMT3B gene may be inactivated. The inactivation of this method step may, for example, be transient or permanent. The inactivation may, for example, be accomplished by genetic deletion, for example by using CRISPR/Cas9-based approaches, or by post-transcriptional downregulation, for example by using sh/siRNAs, or by transcriptional downregulation, for example by using an individual KRAB-based ATR targeted to the regulatory sequences of the gene of interest. Inactivating DNMT3B may be particularly preferred when three ATRs individually comprising KRAB, DNMT3A and DNMT3L domains are used.

Figure 1:
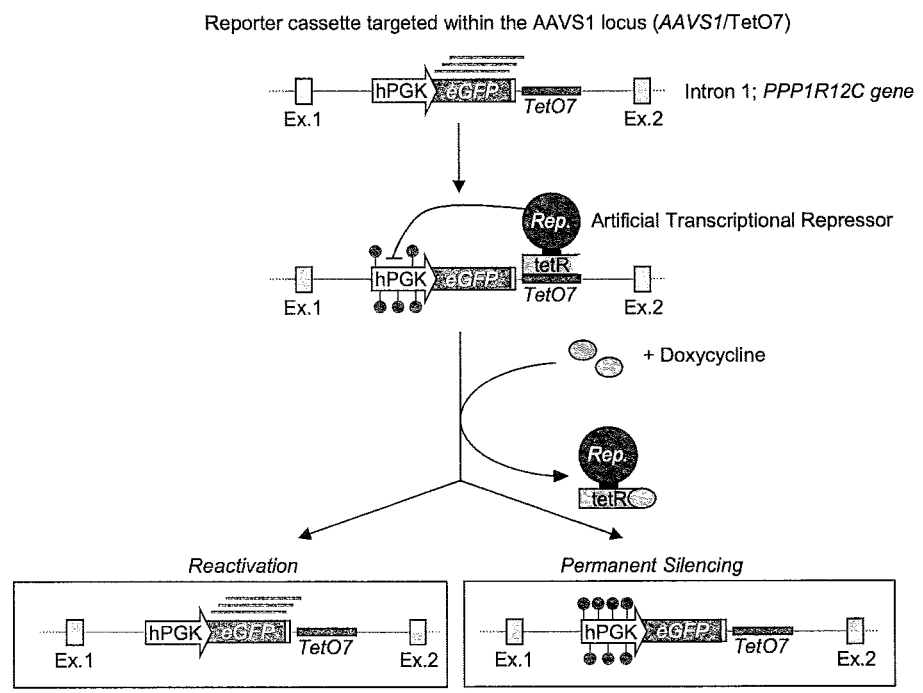
FIG. 1
Schematic detailing the experimental cell model.
An eGFP expression cassette (based on the hPGK promoter) followed by the TetO7 sequence is integrated within the first intron of the PPP1R12C gene (also known as the AAVS1 locus) of K562 cell line. Single cell derived clones containing homozygous insertion of the cassette are then transduced with a vector expressing ATRs (with candidate Repressive-Rep.—domains) and, after deposition of repressive epigenetic marks (red lollipops), the cells are treated or not with doxycycline. Maintenance of silencing or reactivation of eGFP expression is then evaluated by measuring eGFP expression.

Comparison of epigenetic silencing induced by tetR:K and tetR:D3A.

A. Schematics of the Bidirectional Lentiviral Vectors (Bid.LVs) expressing tetR:K and the marker gene mOrange (on the left) or tetR:DNMT3A and the marker gene ΔLNGFR (on the right). B. TetO7.eGFP reporter clones were transduced with the Bid.LV-tetR:K or with the Bid.LV-tetR:D3A in presence or in absence of doxycycline (right and left graphs, respectively), and analysed by flow cytometry over time to measure the percentage of eGFP-negative cells. C. Representative dot plot analysis at the indicated time-points of TetO7.eGFP reporter cell line transduced with Bid. LV-tetR:K or Bid.LV-tetR:D3A in presence or absence of doxycycline. The Mean Fluorescence Intensity (MFI) of eGFP silenced cells is compared to the MFI of untreated, wild-type cells. D. Silenced cells from the minus doxycycline conditions in (B) were sorted to purity and kept in culture with or without doxycycline to assess of eGFP reactivation. Representative dot plots of the cells in presence or absence of the drug are shown at the bottom. E. The silenced sorted cells from the conditions in (B) were treated for 7 days with AZA (1 μM) or vehicle (DMSO) and analysed for expression of eGFP (histogram on the left). Representative dot plots of vehicle and AZA treated cells are shown.

FIG. 3

TetR:D3A-induced transcriptional repression is confined to the target locus.

A. Schematic of the AAVS1 locus. The genes surrounding the reporter cassette (red arrow) are indicated. B. Histograms showing the fold changes in the expression levels of the indicated genes between eGFP-negative cells silenced with either the Bid.LV-tetR:K or the Bid.LV-tetR:D3A, and untreated cells. The relative expression level of each gene was normalised to the expression of B2M, and represented as fold change relative to the untreated cells (calibrator) (n=3).

FIG. 4

Synergistic activity of tetR:K and tetR:D3A upon their transient co-delivery.

A. The TetO7.eGFP reporter cell line was transiently transfected with plasmids encoding for tetR:K and tetD3A, either alone or in combination. The cells were analysed by flow cytometry over time and efficiency of silencing was measured as percentage of eGFP negative cells after transfection. Representative dot plot for each transfection condition are shown at the bottom of the histogram (n=3). B. Histogram showing the fold changes in the expression levels of the indicated genes between sorted eGFP-silenced cells from the mixed conditions shown in (A) and untreated cells. The relative expression level of each gene was normalised to B2M, and represented as fold change relative to the untreated cells (calibrator) (n=3). C. The eGFP-negative cells from the mixed-treated condition in (A) were sorted and then treated with AZA or DMSO (histogram showing the percentage of eGFP positive cells after 7 day from the indicated treatments; n=3). D. Similar experiment as in (A) but performed with in vitro transcribed mRNA encoding for tetR:K and tetD3A, delivered either alone or in combination. E. Histogram showing the fold changes in expression levels of the indicated genes between sorted eGFP-silenced cells from the mixed conditions shown in (D) and untreated cells (n=3).

FIG. 5

Gene silencing with the tetR:K and tetR:D3A combination is locus and cell-type independent.

A. Schematic of the TetO7 reporter LV used in the study. TetO7 sequence was cloned upstream the hPGK promoter driving the expression of the eGFP reporter transgene. B. Graph showing the kinetics of eGFP silencing (% of eGFP-negative cells by flow cytometry) in the K562 LV/TETO7 reporter cell line transfected with in vitro transcribed mRNA encoding for tetR:K and tetR:D3A, delivered either alone or in combination (n=3; data are represented as mean±S.E.M.). C-D. Graphs showing the kinetics of eGFP silencing (% of eGFP-negative cells by flow cytometry) in the U937LV/TETO7 cell line (C) or in the β-lymphoblastoid LV/TETO7 reporter cell line (D). Cells were transfected as indicated in (B) (n=1 for U937 and n=3 for B-lymphoblastoid cells).

FIG. 6

Screening of additional epigenetic effector domains for ATRs.

A. Graph showing the kinetics of eGFP silencing (% of eGFP-negative cells by flow cytometry) in the K562 LV/TETO7 reporter cell line upon transduction with lentiviral vectors expressing the indicated tetR-based ATRs (n=3). B. Graph showing the percentage of cells positive for the indicated LVs over time in culture (n=3). C. Graph showing the kinetics of eGFP silencing (% of eGFP-negative cells by flow cytometry) in the K562 LV/TETO7 reporter cell line transduced with lentiviral vectors stably expressing the indicated tetR-based ATRs, before and after doxycycline administration (n=3).

FIG. 7

Screening of additional combinations of artificial transcription repressors (ATRs) in different mammalian cells.

A-D. Graphs showing the kinetics of eGFP silencing (% of eGFP-negative cells by flow cytometry) in the K562 LV/TETO7 reporter cell line upon electroporation with individual plasmids encoding for the indicated tetR-based ATRs (A; n=3; data are represented as mean±S.E.M.), or upon electroporation with the plasmid encoding for tetR:D3A plus the plasmid encoding for one of the other tetR-based ATRs (B; n=3; data are represented as mean±S.E.M.), or upon electroporation with the plasmid encoding for tetR:K plus the plasmid encoding for one of the other tetR-based ATRs (C; n=3; data are represented as mean±S.E.M.), or upon electroporation with the plasmids encoding for tetR:D3A+tetR:K in conjunction with the plasmid encoding for one of the other tetR-based ATRs (D; n=3; data are represented as mean±S.E.M.). E. Histogram showing the efficacy of eGFP silencing 21 days post electroporation of the K562 LV/TETO7 reporter cell line with plasmids encoding for the indicated tetR-based ATRs (later time-points of A-D; n=3; data are represented as mean±S.E.M.). F. Histogram showing the efficiency eGFP silencing 30 days post electroporation of the K562 LV/TETO7 reporter cell line with plasmids encoding for the indicated tetR-based ATRs, including that based on SETDB1 (n=3; data are represented as mean±S.E.M.). G. Graph showing the kinetics of eGFP silencing of the B-lymphoblastoid LV/TETO7 reporter cell line electroporated with mRNA encoding for the indicated tetR-based ATRs (n=3; data are represented as mean±S.E.M.). H. Graph showing the kinetics of eGFP silencing of the murine NIH/3T3 LV/TETO7 reporter cell line electroporated with mRNA encoding for the indicated tetR-based ATRs (n=2; data are represented as mean±range).

FIG. 8

Gene silencing by transient co-delivery of artificial transcription repressors (ATRs) comprising custom-made DNA-binding domains (head-to-tail orientation).

A. Schematic representation of the various Artificial Tale Binding Sites. (head-to-tail).hPGK.eGFP cassettes semi-randomly integrated in the genome of K562 cells via LV transduction, differing in spacer length between the two ATRs binding sites. Two different TALE domains have been separately fused to each epigenetic effector, thus leading to two alternative co-delivery strategies differing for the D3A-K relative order of binding on the target. B. Graphs showing the silencing efficiency (% of eGFP-negative cells at 34 days post-electroporation) with respect to the spacer length, in the K→D3A (Left) and D3A→K (Right) relative ATRs order of binding on the target. C. Graphs showing the kinetics of eGFP silencing in the cell line with the 25 bp spacer (the best-performing spacer tested in the experiments shown in B) in the K→D3A (Left) and D3A→K (Right) relative ATRs order of binding on the target (n=3; data are represented as mean±S.E.M.).

FIG. 9

Gene silencing by transient co-delivery of artificial transcription repressors (ATRs) comprising custom-made DNA-binding domains (head-to-head orientation).

A. Schematic representation of the various Artificial Tale Binding Sites. (head-to-head).hPGK.eGFP cassettes semi-randomly integrated in the genome via LV transduction, differing in the spacer length between the two ATRs binding sites. Two different TALE domains have been separately fused to each epigenetic effector, thus leading to two alternative co-delivery strategies differing for the D3A-K relative order of binding on the target. B. Graphs showing silencing efficiency (i.e. % of eGFP-negative cells at 34 days post-electroporation) with respect to the spacer length, in the D3A→K (Left) and K→D3A (Right) relative ATRs order of binding on the target. C. Graphs showing the kinetics of eGFP silencing in the cell line with the 15 bp spacer (the best-performing spacer tested in the experiments shown in B) in the D3A→K (Left) and K→D3A (Right) relative ATRs order of binding on the target (n=3; data are represented as mean±S.E.M.).

FIG. 10

Gene silencing with artificial transcription repressors (ATRs) comprising more than one effector domain.

A. Schematic representation of the Artificial Tale Binding Sites (head-to-head).hPGK.eGFP cassette semi-randomly integrated in the genome of K562 cells via LV transduction bound by chimeric K:tetR:D3A ATR (Bi-Partite; BiP), where KRAB and DNMT3A domains were fused to the N- and C-terminus (respectively) of the same DNA binding domain. B. Graphs showing the kinetics of eGFP silencing in the cell line with the 25 bp spacer (the same line used in of FIG. 8B), transfected with plasmids encoding for the Bi-Partite (BiP) fusion protein, when transfected alone or in combination (n=3; data are represented as mean±S.E.M.).

FIG. 11

Permanent epigenetic silencing in human haematopoietic stem and progenitor cells (HSPCs) by using different combinations of artificial transcription repressors (ATRs).

A. Schematic time-line of the protocol used to assess efficiency of silencing in HSPCs. Briefly, on day 0, the human CD34+ cells were thawed in stimulating media with early acting cytokines and transduced at day 1 with the TetO7 reporter LV (schematic of the vector in FIG. 5A). Cells were then washed and electroporated with in vitro transcribed mRNA on day 3 from thawing. The day after, 800 cells were plated for CFC-U assays, while the remaining cells were grown in liquid culture and analysed by flow cytometry at the indicated time points. CFC-U analysis was performed 14 days after thawing. B. Graph showing the kinetic of silencing of eGFP in liquid cultured human CD34+ transfected with in vitro transcribed mRNA encoding for the indicated ATRs, delivered either alone, or in double, or triple combinations (data were normalised to the un-electroporated but LV-transduced control; n=3; data are represented as mean±S.E.M.). C. Histogram showing the percentage of eGFP-silencing in erythroid and myeloid colonies derived from the human CD34+transfected with in vitro transcribed mRNAs as indicated in (B) (n=3; data are represented as mean±S.E.M.).

FIG. 12

Permanent epigenetic silencing in human T lymphocytes by using different combinations of artificial transcription repressors (ATRs).

A. Schematic time-line of the protocol used in this study to assess efficiency of silencing in human primary T cells. Briefly, on day 0, T-cells were isolated with anti-CD3/CD28 coated beads and left in culture 3 days before transduction with the reporter TetO.LV. On day 6, the cells were transfected with in vitro transcribed mRNA encoding for the indicated ATRs, and expression of eGFP was measured by flow cytometry at the indicated time points. At 3 weeks post-transfection, cells were re-stimulated and stability of eGFP silencing was measured by flow cytometry. B. Graph showing the kinetic of eGFP-silencing in human primary T cells transfected with in vitro transcribed mRNA encoding for the indicated ATRs, which were delivered either alone, or in double, or triple combinations normalised over untreated cells (data were normalised to the un-electroporated but LV-transduced control; n=2; data are represented as mean±range).

FIG. 13

Permanent epigenetic silencing of the human 32-microglobulin (B2M) gene using artificial transcription repressor (ATR) combinations.

Figure 2:
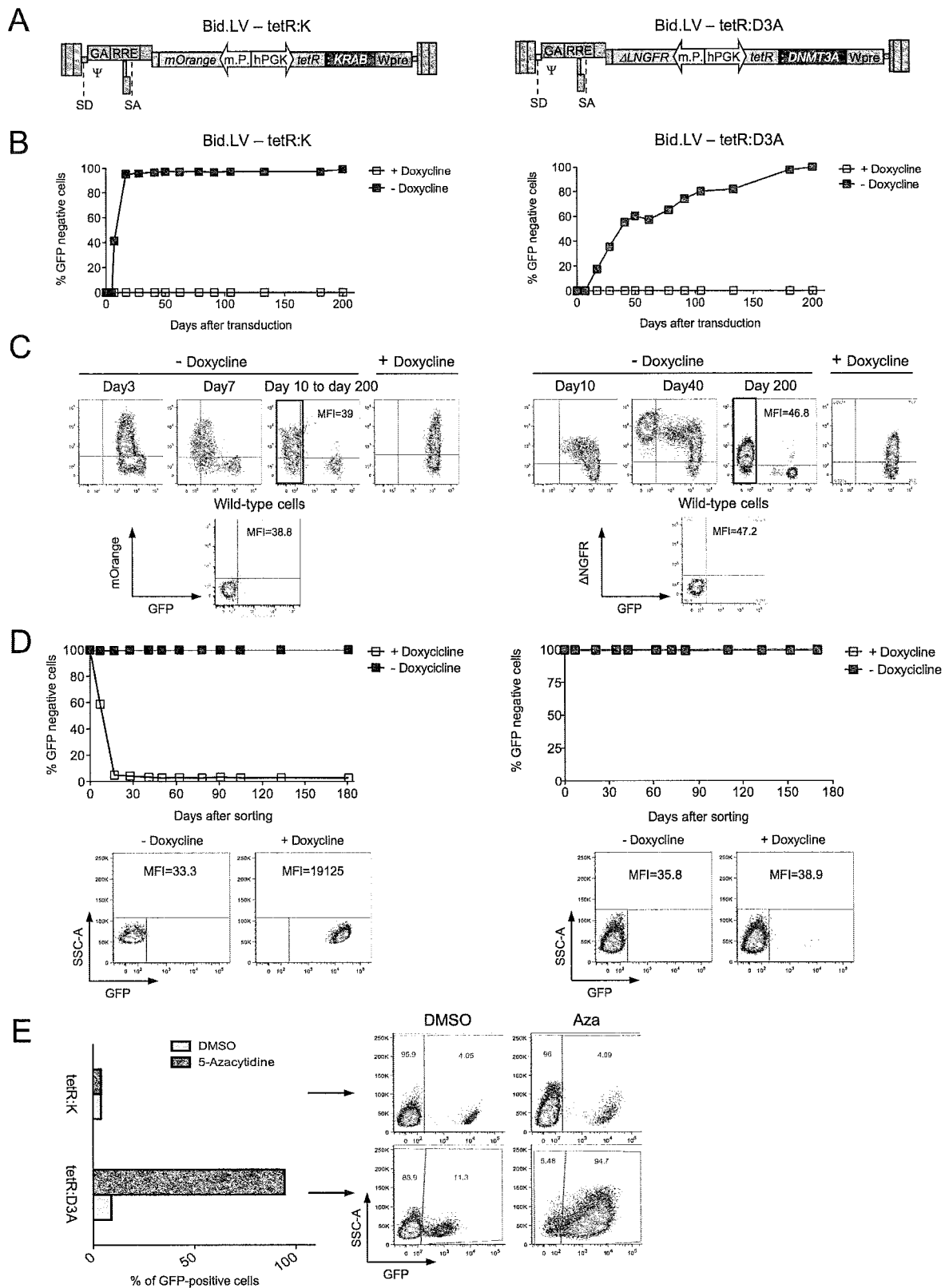
FIG. 2

A. Schematic representation of the B2M locus indicating the binding sites of the TALE-based ATRs. B. Graph showing the kinetics of B2M silencing in HEK-293T cells electroporated with plasmids encoding for the indicated TALE-based ATRs, which were delivered either alone or in combination (n=3; data are represented as mean±S.E.M.). C. Representative flow cytometry dot plots of HEK-293T cells transfected with plasmids encoding for the triple TALE:ATR combination (plot on the top), and the cell sorting strategy used to enrich for the double negative (bottom plot on the left) and the double positive (bottom plot on the right) cells. D. Histogram showing the fold change in the expression levels of the B2M gene in the sorted cells from (C) and in untreated HEK293T cells (n=3; data are represented as mean±S.E.M.). E. Schematics of the dCas9-based ATRs and of the gRNAs selected to target the CpG island located in the B2M promoter region. F. Histogram showing the silencing efficiency at day 33 post-CRISPR/dCas9-based ATRs plasmid electroporation (n=3; data are represented as mean±S.E.M.). G. The B2M silenced cells from FIG. 2C (named TALE B2M—in this panel), the B2M-silenced cells sorted from the triple-CRISPR/dCas9 based ATR combination in FIG. 2F (named TALE B2M—in this panel), and wild-type HeK-293T cells (named WT B2M+ in this panel) were exposed or not to IFN-γ, and then analysed to measure the expression levels of B2M and OAS1. Histogram showing the fold change in the expression levels of the B2M and the OAS1 gene between IFN-γ and untreated cells. The expression of the Hypoxanthine Phosphoribosyltansferase 1 (HPRT1) gene was used as normaliser (n=3; data are represented as mean±S.E.M.). H. Representative flow cytometry dot plots of the indicated HEK-293T populations either untreated (plots on the left) or at 4 days post IFN-γ treatment (plots on the right). Numbers indicate the MFI B2M.

FIG. 14

Silencing of B2-microglobulin (B2M) is associated with significant epigenetic editing of the gene.

A. Representative flow cytometry dot plots of HEK-293T cells transfected with plasmids encoding for the triple TALE:ATR combination, and the cell sorting strategy used to enrich for the double positive and double negative cells. B. ChIP analysis performed on untreated (top histogram) and silenced cells from (A) (bottom histogram) for the presence of the RNA PolII. Histogram shows the fold enrichment in RNA PolI over the input in relation to the distance of the qPCRs assays from the Transcription Start Site (TSS; set at +1) of the gene (n=3; data are represented as mean±S.E.M.). The ubiquitously transcribed AAVS1 locus was used as Positive Control (PC) for RNA PolII enrichment, while the silent CCR5 gene as a Negative Control (NC). C. Bisulfite analysis of the B2M CpG island in untreated (UT) and silenced cells. The TSS of the gene and relative position of binding site of the three TALE:ATRs (D;L;K) are indicated. D. Histogram showing the percentage of B2M positive cells at day 7 upon AZA treatment (n=3; data are represented as mean±S.E.M.). E. Top: schematic representation of the B2M locus. The CpG islands within this locus are depicted in green. Bottom: histogram showing the fold change in gene expression levels of the indicated genes between silenced and untreated cells. Genes with a Ct value ≥37 were excluded from the analysis. The relative expression level of each gene was normalized to HPRT, and represented as fold change relative to the untreated cells (calibrator).

FIG. 15

Silencing of B2-microglobulin (B2M) is effective in another human cell line.

A. Schematics (on the left) of the CRISPR/Cas9-based gene targeting strategy used to insert the tdTomato transgene under the control of the B2M promoter. Representative flow cytometry dot plots of K-562 cells pre- and post-gene targeting (upper and bottom right, respectively). B. Histogram showing the B2M silencing efficiency (i.e. dtTomato-negative cells) at day 30 post electroporation with plasmids encoding for the indicated TALE-based ATRs carrying either the wild-type (WT) or the codon-optimised effector domains (n=1). C. Graph showing the kinetics of B2M silencing (measured as % of dtTomato-negative cells) of K-562 cells electroporated with plasmids encoding for the indicated CRISPR/dCas9-based ATRs (n=1). D. Representative flow cytometry analyses of: (i) sorted tdTomato-negative cells post-transfection with in vitro transcribed mRNAs encoding for the triple TALE:ATR combination (left schematic and dot plot); (ii) the cells from (i) upon transfection with a plasmid encoding for the dCas9:Tet1 in conjunction with plasmids for the B2M gRNAs (left schematic and dot plot) (n=1).

FIG. 16

Silencing of β2-microglobulin (B2M) is effective in primary T-lymphocytes.

A. Schematics of the experimental workflow. B. Graph showing the kinetics of B2M silencing in human T-lymphocytes electroporated with mRNAs encoding for the triple TALE-based ATRs (n=1). C. Representative flow cytometry dot plots of the indicated T-lymphocytes populations 14 days post-treatment. The percentage of cells within the indicated gates and the B2M MFI are shown.

FIG. 17

Single ATR binding site is sufficient for effective silencing of the endogenous gene both with Cas9 and TALE-based ATRs.

Figure 13:
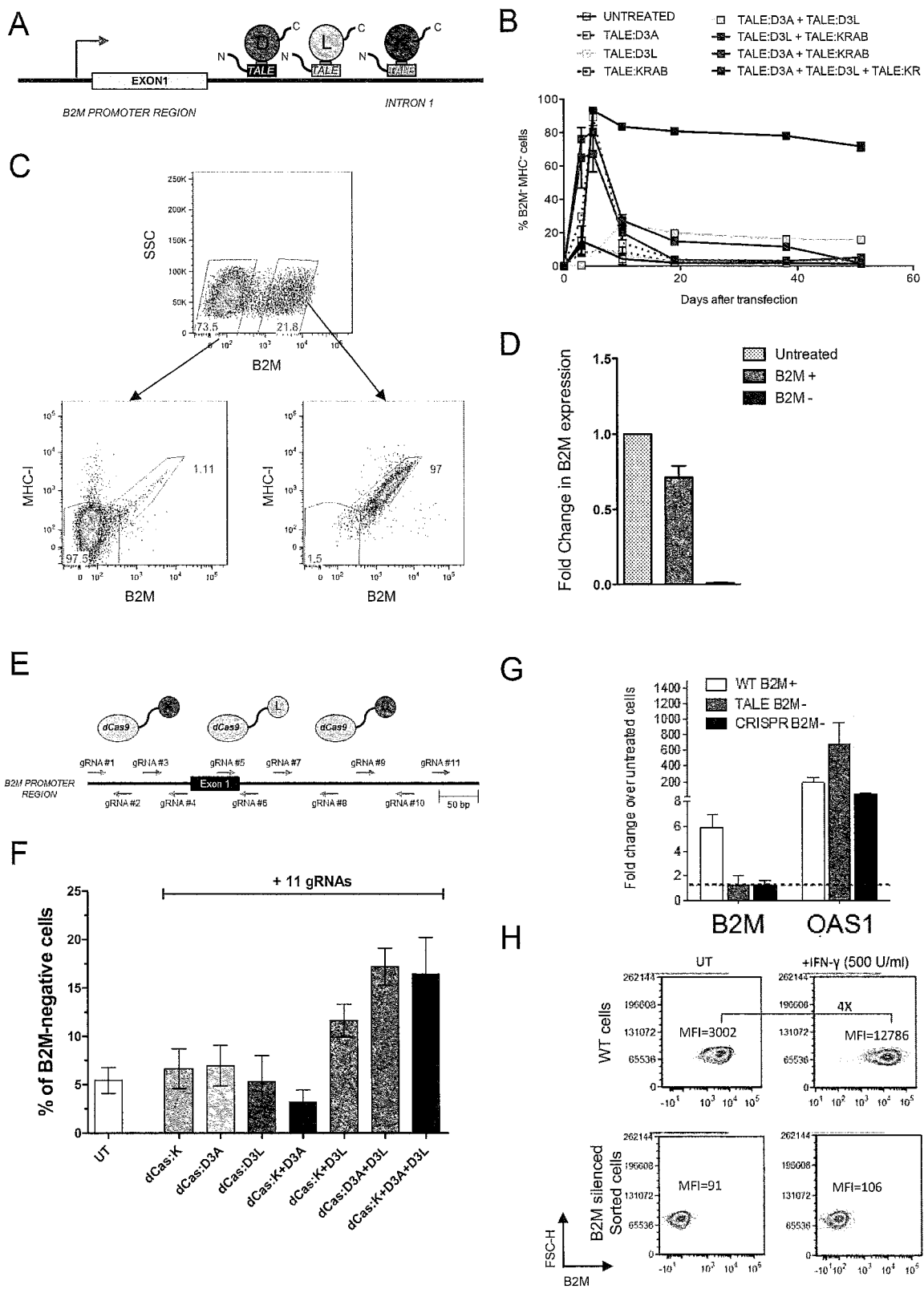

A. Top: schematic of the B2M gene indicating the relative location of the gRNAs (read arrows) selected to target the CpG island of this gene. Bottom: histogram showing the efficiency of B2M silencing (calculated as % of tdTomato-negative cells) 18 days post CRISPR/dCas9-based ATRs plasmid electroporation in the K562 B2M_tdTomato reporter cell line (n=1). B. Left: schematic of binding of TALE based-ATRs on the DNA. In the grey boxes are indicated the conditions in which each of the three different DNA binding domains (form #1 to #3; named in the figure as Repeat Variable Diresidue-RDV) are equipped with both of the three different effector domains. Bottom to this schematic is depicted the condition in which the three different RDVs are equipped each with a different effector domain, as already shown in FIG. 13A. Right: histogram showing the percentage of tdTomato-negative cells upon transfection with plasmids encoding for the indicated TALE-based ATR combinations (n=3; data are represented as mean±S.E.M.).

FIG. 18

Transient expression of an un-targeted DNMT3L improves and rescues silencing efficiency of the DNMT3A+KRAB based ATRs in refractory cell types.

A. Histogram showing the percentage of eGFP silencing of B-lymphoblastoid LV-TetO7 reporter cell line at 27 days post-transfection with in vitro transcribed mRNAs encoding for the indicated tetR-based ATRs, which were delivered in conjunction or not with either the tetR:D3L or with the un-targeted, full-length DNMT3L-encoding mRNA (n=2; data are represented as mean±range). B. Schematics of the B2M locus depicting the binding sites and the relative arrangement of the indicated TALE-based ATRs. Note that each Module can be bound by a pair of TALE-based ATRs. Moreover, for each Module, the relative order of the effector domain can be swapped. For example, for Module 1, site A can be bound by the KRAB-based ATR, while site B by DNMT3A-based ATR, or vice versa. C. Representative flow cytometry dot plots of B2M silencing in HEK-293T cells 21 days post-transfection with plasmids encoding for the indicated pairs of TALE-based ATRs (Module 1 or Module 2, shown for the two possible relative order of binding of the ATRs), which were delivered either alone (top plots row) or in combination with the un-targeted DNMT3L (bottom plots row). D. Histogram showing the percentage of B2M silencing of HEK-293T cells at 45 days post-transfection with plasmids encoding for the indicated dCas9-based ATRs and the cognate gRNAs (as those depicted in FIG. 13E), which were delivered either alone or in conjunction with the dCas9:D3L or with un-targeted, full-length DNMT3L-encoding plasmid (n=3; data are represented as mean±S.E.M.).

FIG. 19

Genetic inactivation of the DNMT3B increases the silencing efficiency of the triple ATR combination in permissive cell lines, while transient expression of an un-targeted DNMT3B rescues silencing efficiency of the DNMT3A+KRAB combination in refractory cell types.

A. Schematics of the lentiviral vectors used to conditionally express Cas9 upon doxycycline administration (left) or to express the gRNA of interest (right). B. Representative flow cytometry analyses of: i) eGFP-positive K-562 cells upon transduction with the lentiviral vector described in FIG. 5A and then sorted to near purity for eGFP-expression (left plot); ii) the cell line from (i) upon were transduction with the LV encoding for the inducible Cas9 and with the LV encoding for the DNMT3B-gRNA (ΔLNGFR was used as a marker of transduction for the latter LV; middle plot). Note that this second cell line was then exposed to doxycycline for 7 days in order to activate the Cas9 expression and disrupt the coding sequence of the endogenous DNMT3B gene; iii) the cells from (ii) upon electroporation with plasmids encoding for either the double tetR:K+tetR:D3A (top right plot) or the triple tetR:K+tetR:D3A+tetR:D3L (bottom right plot) ATRs combinations. C. Histogram showing the percentage of eGFP silenced cells at day 19 post genetic disruption of the DNMT3B gene by the CRISPR/inducibleCas9 system (n=1). These numbers were obtained by calculating the silencing efficiencies in ΔLNGFR-positive (the cells with disruption of DNMT3B; red bars) and -negative cells (wild-type K-562 cells; blue bars). D. Histogram showing the silencing efficiency (% of eGFP-negative cells) in the B-lymphoblastoid TetO7 reporter cell line at day 27 post-transfection with mRNAs encoding for the indicated tetR-based ATRs, which were delivered in conjunction or not with the mRNA encoding for the un-targeted, wild-type DNMT3B sequence (data are shown as mean of the two experiments).

FIG. 20

Permanent epigenetic silencing of additional human endogenous genes (using artificial transcription repressor (ATR) combinations.

A. Schematic (on the left) of the B-Cell Lymphoma/leukemia 11A (BCL11A) gene showing the two transcript variants of this gene. Dashed boxes highlight gene regulatory elements. In particular, the gene promoter/enhancer region at the level of the transcription start site (yellow box) with cluster of 4 different CpG islands varying in size and number of CpG residues, and the erythroid specific enhancer (red box) responsible for the lineage restricted expression of the gene within the second intron of gene. In order to study both gene promoter and erythroid specific enhancer functions, the tdTomato transgene linked to the BCL11A transcript through a 2A self-catalytic peptide was targeted within the third exon of the gene. On the right, is shown a representative dot plot of B-lymphoblastoid cells after sorting of the tdTomato-positive cells. B. Histogram showing the percentage of tdTomato-negative cells at day 32 post-transfection with the indicated dCas9-based ATRs and the corresponding pools of gRNAs (namely, 11 gRNAs for CpG105; 8 gRNAs for CpG31; 9 gRNAs for CpG38; 10 gRNAs for CpG115) targeting the indicated CpG islands of BCL11A (n=3; data are represented as mean±S.E.M.). Untreated cells, or cells transfected with the pools of gRNAs alone or with the dCas9-based ATRs alone were used as controls. C. The tdTomato reporter cell line was co-transfected with plasmids encoding for dCas9-based ATRs, either alone, or in double or triple combination, and with plasmids for a pool of 9 gRNAs targeting the CpG 38, or with plasmids for a pool of 8 gRNAs for CpG 31. Silencing efficiency was measured at 2 weeks post-transfection and is reported in the histogram (n=3; data are represented as mean±S.E.M.). D. Top: Schematics of the binding sites of TALE-based ATRs targeting CpG 31 (top left) or CpG 31 (top right) of the BCL11A promoter region, and their relative orientation of binding on the DNA (+ indicates Watson strand, while-indicates Crick strand). Bottom: the dTomato reporter cell line was transfected with plasmids encoding TALE:KRAB alone, or with the indicated combinations of triple TALE-based ATRs, as labelled on the x axis of the histograms. Silencing efficiency is reported as percentage of dTomato-negative cells. Analysis was performed at day 18 post-plasmid transfection (n=3; data are represented as mean±S.E.M.). E. Top: Schematic of the Interferon (alpha, beta and omega) Receptor 1 (IFNAR1) gene. The green box highlights a CpG island (the number of CpG residues are indicated) at the level of the gene promoter/enhancer region. Bottom: Histogram showing the fold change in the expression level of the IFNAR1 gene between cells electroporated with plasmids encoding for a pool of 13 gRNAs against the IFNAR1 CpG island plus the dCas9:K+dCas9:D3A+dCas9:D3L ATRs (18 days post treatment) and untreated cells. The relative expression level of the IFNAR1 gene was normalised to the expression of DNMT1, and represented as fold change relative to the untreated cells (calibrator) (n=1). F. Top: Schematic of the Vascular Endothelial Growth Factor A (VEGFA) gene. The green box highlights a CpG island (the number of CpG residues are indicated) at the level of the gene promoter/enhancer region. Bottom: Histogram showing the fold change in the expression level of the VEGFA gene between cells electroporated with plasmids encoding for a pool of 3 gRNAs against the VEGFA CpG island plus the dCas9:K+dCas9:D3A+dCas9:D3L ATRs (14 days post treatment) and untreated cells. The relative expression level of the VEGFA gene was normalised to the expression of DNMT1, and represented as fold change relative to the untreated cells (calibrator) (n=1).

DETAILED DESCRIPTION OF THE INVENTION

Various preferred features and embodiments of the present invention will now be described by way of non-limiting examples.

The practice of the present invention will employ, unless otherwise indicated, conventional techniques of chemistry, biochemistry, molecular biology, microbiology and immunology, which are within the capabilities of a person of ordinary skill in the art. Such techniques are explained in the literature. See, for example, Sambrook, J., Fritsch, E. F., and Maniatis, T. (1989) *Molecular Cloning: A Laboratory Manual*, 2nd Edition, Cold Spring Harbor Laboratory Press; Ausubel, F. M. et al. (1995 and periodic supplements) *Current Protocols in Molecular Biology*, Ch. 9, 13 and 16, John Wiley & Sons; Roe, B., Crabtree, J., and Kahn, A. (1996) *DNA Isolation and Sequencing: Essential Techniques*, John Wiley & Sons; Polak, J. M., and McGee, J. O'D. (1990) *In Situ Hybridization: Principles and Practice*, Oxford University Press; Gait, M. J. (1984) Oligonucleotide Synthesis: A Practical Approach, IRL Press; and Lilley, D. M., and Dahlberg, J. E. (1992) *Methods in Enzymology: DNA Structures Part A: Synthesis and Physical Analysis of DNA*, Academic Press. Each of these general texts is herein incorporated by reference.

In one aspect, the present invention provides a product comprising two or more artificial transcription repressors (ATRs), or polynucleotides encoding therefor, selected from groups (a), (b) or (c):
  (a) an ATR comprising a DNA-binding domain operably linked to a KRAB domain or homologue thereof;
  (b) an ATR comprising a DNA-binding domain operably linked to a DNMT3A, DNMT3B or DNMT1 domain or homologue thereof; and
  (c) an ATR comprising a DNA-binding domain operably linked to a DNMT3L domain or homologue thereof wherein at least two of the ATRs are selected from different groups (a), (b) or (c).

The product of the present invention may, for example, be a composition (e.g. a pharmaceutical composition) comprising two or more ATRs, or polynucleotides encoding therefor, selected from groups (a), (b) or (c): (a) an ATR comprising a DNA-binding domain operably linked to a KRAB domain or homologue thereof; (b) an ATR comprising a DNA-binding domain operably linked to a DNMT3A, DNMT3B or DNMT1 domain or homologue thereof; and (c) an ATR comprising a DNA-binding domain operably linked to a DNMT3L domain or homologue thereof, in admixture, wherein at least two of the ATRs are selected from different groups (a), (b) or (c). Alternatively, the product may, for example, be a kit comprising a preparation of two or more ATRs, or polynucleotides encoding therefor, selected from groups (a), (b) or (c): (a) an ATR comprising a DNA-binding domain operably linked to a KRAB domain or homologue thereof; (b) an ATR comprising a DNA-binding domain operably linked to a DNMT3A, DNMT3B or DNMT1 domain or homologue thereof; and (c) an ATR comprising a DNA-binding domain operably linked to a DNMT3L domain or homologue thereof, wherein at least two of the ATRs are selected from different groups (a), (b) or (c), and, optionally, instructions for the simultaneous, sequential or separate administration of the preparations to a subject in need thereof.

Artificial transcription repressors (ATRs) are agents that act to reduce the transcription of a target gene. ATRs may be chimeric proteins that are comprised of a DNA-binding domain operably linked to an effector domain (e.g. a KRAB domain, a DNMT3A, DNMT3B or DNMT1 domain or a DNMT3L domain, or homologues thereof). The DNA-binding domain enables binding of the ATR to a specific nucleic acid sequence, and may be engineered to bind to a nucleic acid sequence of choice. The effector domain may harbour a catalytic activity which enables repression of transcription of the target gene. Alternatively, or additionally, the effector domain may recruit additional agents within the cell to the target gene, which results in the repression of transcription of the target gene.

By "operably linked", it is to be understood that the individual components are linked together in a manner which enables them to carry out their function (e.g. binding to DNA, catalysing a reaction or recruiting additional agents from within a cell) substantially unhindered. For example, a DNA-binding domain may be conjugated to an effector domain, for example to form a fusion protein. Methods for conjugating polypeptides are known in the art, for example through the provision of a linker amino acid sequence connecting the polypeptides. Alternative methods of conjugating polypeptides known in the art include chemical and light-induced conjugation methods (e.g. using chemical cross-linking agents). Preferably, the DNA-binding domain and effector domain (e.g. KRAB domain, DNMT3A, DNMT3B or DNMT1 domain or DNMT3L domain, or homologue thereof) of the ATR form a fusion protein.

Effector Domains

The term "effector domain", is to be understood as referring to the part of the ATR which provides for the silencing effect on a target gene, for example by catalysing a reaction on the DNA or chromatin (e.g. methylation of DNA), or by recruiting an additional agent from within a cell, resulting in the repression of the transcription of a gene.

"Domain" is to be understood in this context as referring to a part of the ATR that harbours a certain function. The domain may be an individual domain (e.g. a catalytic domain) isolated from a natural protein or it may be an entire, full-length natural protein. Put another way, either the full-length protein or a functional fragment thereof can be used as an effector domain. Therefore, for example, "KRAB domain" refers to the part of the ATR that comprises an amino acid sequence with the function of a KRAB domain.

Chromatin remodelling enzymes that are known to be involved in the permanent epigenetic silencing of endogenous retroviruses (ERVs; Feschotte, C. et al. (2012) Nat. Rev. Genet. 13:283-96; Leung, D. C. et al. (2012) Trends Biochem. Sci. 37:127-33) may provide suitable effector domains for exploitation in the present invention.

The family of the Krüppel-associated box containing zinc finger proteins (KRAB-ZFP; Huntley, S. et al. (2006) Genome Res. 16:669-77) plays an important role in the silencing of endogenous retroviruses. These transcription factors bind to specific ERV sequences through their ZFP DNA binding domain, while they recruit the KRAB Associated Protein 1 (KAP1) with their conserved KRAB domain. KAP1 in turn binds a large number of effectors that promote the local formation of repressive chromatin (Iyengar, S. et al. (2011) J. Biol. Chem. 286:26267-76).

In the early embryonic development, KAP1 is known to recruit SET domain bifurcated 1 (SETDB1), a histone methyltransferase that deposits histone H3 lysine-9 di- and tri-methylation (H3K9me2 and H3K9me3, respectively), two histone marks associated with transcriptional repression. Concurrently, KAP1 binds to Heterochromatin Protein 1 alpha (HP1α), which reads H3K9me2 and H3K9me3 and stabilises the KAP1-containing complex. KAP1 can also interact with other well known epigenetic silencers, such as the lysine-specific histone demethylase 1 (LSD1) that inhibits transcription by removing histone H3 lysine-4 methylation, and the nucleosome remodelling and deacetylase complex (NURD), which removes acetyl groups from histones. Finally, the KAP1-containing complex contributes to the recruitment of the de novo DNA methyltransferase 3A (DNMT3A), which methylates cytosines at CpG sites (Jones, P. A. (2012) Nat. Rev. Genet. 13:484-92). Together, these data suggest a model in which, in the pre-implantation embryo, the KAP1-complex ensures ERV silencing through the concerted action of histone modifying enzymes and DNA methylation. Then, after implantation, the DNA methylation previously targeted by KRAB-ZFPs to the ERVs becomes stable (Reik, W. (2007) Nature 447:425-32), being inherited throughout mitosis and somatic cell differentiation without the need of the continuous expression of ERVs-specific KRAB-ZFPs. Contrary to embryonic stem cells, the KAP1-complex is not able to efficiently induce DNA methylation in somatic cells, being only able to deposit H3K9 methylation. However, this histone mark is not maintained without being continuously deposited at the targeted site by the KRAB-ZFPs (Hathaway, N. A. et al. (2012) Cell 149: 1447-60).

Therefore, in view of an epigenetic therapy approach based on the transient expression of ATRs in somatic cells, the KRAB-ZFPs/KAP1 machinery is expected not to be functional if employed alone. On the other hand, we consider a preferable strategy to co-deliver two distinct ATRs: one based on, for example, the KRAB domain, the initiator of the epigenetic cascade occurring at ERVs in embryonic stem cells, and the other based on, for example, DNMT3A, the final lock of this process. This approach may allow recapitulating on a pre-selected target gene those repressive chromatin states established at ERVs in the pre-implantation embryo and then permanently inherited throughout mammalian development and adult life.

An ATR of the present invention may, for example, comprise a KRAB domain. Various KRAB domains are known in the family of KRAB-ZFP proteins. For example, an ATR of the present invention may comprise the KRAB domain of human zinc finger protein 10 (ZNF10; Szulc, J. et al. (2006) *Nat. Methods* 3:109-16):

```
                                          (SEQ ID NO: 1)
ALSPQHSAVTQGSIIKNKEGMDAKSLTAWSRTLVTFKDVFVDFTREEWKL

LDTAQQIVYRNVMLENYKNLVSLGYQLTKPDVILRLEKGEEPWLVEREIH

QETHPDSETAFEIKSSV
```

Further examples of suitable KRAB domains for use in the present invention include:

```
(the KRAB domain of the ZNF350 protein;
SEQ ID NO: 2)
ITLEDVAVDFTWEEWQLLGAAQKDLYRDVMLENYSNLVAVGYQASKPDAL

FKLEQGEQLWTIEDGIHSGACS (the KRAB domain of the ZNF197 protein;
SEQ ID NO: 3)
VMFEEVSVCFTSEEWACLGPIQRALYWDVMLENYGNVTSLEWETMTENEE

VTSKPSSSQRADSHKGTSKRLQG (the KRAB domain of the RBAK protein;
SEQ ID NO: 4)
VSFKDVAVDFTQEEWQQLDPDEKITYRDVMLENYSHLVSVGYDTTKPNVI

IKLEQGEEPWIMGGEFPCQHSP (the KRAB domain of the ZKSCAN1 protein;
SEQ ID NO: 5)
VKIEDMAVSLILEEWGCQNLARRNLSRDNRQENYGSAFPQGGENRNENEE

STSKAETSEDSASRGETTGRSQKE (the KRAB domain of the KRBOX4 protein;
SEQ ID NO: 6)
LTFKDVFVDFTLEEWQQLDSAQKNLYRDVMLENYSHLVSVGYLVAKPDVI

FRLGPGEESWMADGGTPVRTCA (the KRAB domain of the ZNF274 protein;
SEQ ID NO: 7)
VTFEDVTLGFTPEEWGLLDLKQKSLYREVMLENYRNLVSVEHQLSKPDVV

SQLEEAEDFWPVERGIPQDTIP
```

An ATR of the present invention may, for example, comprise a domain of human DNA methyltransferase 3A (DNMT3A; Law, J. A. et al. (2010) Nat. Rev. Genet. 11:204-20), preferably the catalytic domain. For example, an ATR of the present invention may comprise the sequence:

```
                                          (SEQ ID NO: 8)
TYGLLRRREDWPSRLQMFFANNHDQEFDPPKVYPPVPAEKRKPIRVLSLF

DGIATGLLVLKDLGIQVDRYIASEVCEDSITVGMVRHQGKIMYVGDVRSV

TQKHIQEWGPFDLVIGGSPCNDLSIVNPARKGLYEGTGRLFFEFYRLLHD

ARPKEGDDRPFFWLFENVVAMGVSDKRDISRFLESNPVMIDAKEVSAAHR

ARYFWGNLPGMNRPLASTVNDKLELQECLEHGRIAKFSKVRTITTRSNSI

KQGKDQHFPVFMNEKEDILWCTEMERVFGFPVHYTDVSNMSRLARQRLLG

RSWSVPVIRHLFAPLKEYFACV
```

DNA methyltransferases 3B and 1 (DNMT3B and DNMT1), similarly to DNMT3A, are also responsible for the deposition and maintenance of DNA methylation, and may also be used in an ATR of the present invention. For example, an ATR of the present invention may comprise any of the sequences:

```
(the catalytic domain of human DNMT3B;
SEQ ID NO: 9)
CHGVLRRRKDWNVRLQAFFTSDTGLEYEAPKLYPAIPAARRRPIRVLSLF

DGIATGYLVLKELGIKVGKYVASEVCEESIAVGTVKHEGNIKYVNDVRNI

TKKNIEEWGPFDLVIGGSPCNDLSNVNPARKGLYEGTGRLFFEFYHLLNY

SRPKEGDDRPFFWMFENVVAMKVGDKRDISRFLECNPVMIDAIKVSAAHR

ARYFWGNLPGMNRPVIASKNDKLELQDCLEYNRIAKLKKVQTITTKSNSI

KQGKNQLFPVVMNGKEDVLWCTELERIFGFPVHYTDVSNMGRGARQKLLG

RSWSVPVIRHLFAPLKDYFACE (DNMT3B; SEQ ID NO: 36)
MVAELISEEDLEFMKGDTRHLNGEEDAGGREDSILVNGACSDQSSDSPPI

LEAIRTPEIRGRRSSSRLSKREVSSLLSYTQDLTGDGDGEDGDGSDTPVM

PKLFRETRTRSESPAVRTRNNNSVSSRERHRPSPRSTRGRQGRNHVDESP

VEFPATRSLRRRATASAGTPWPSPPSSYLTIDLTDDTEDTHGTPQSSSTP

YARLAQDSQQGGMESPQVEADSGDGDSSEYQDGKEFGIGDLVWGKIKGFS

WWPAMVVSWKATSKRQAMSGMRWVQWFGDGKFSEVSADKLVALGLFSQHF

NLATFNKLVSYRKAMYHALEKARVRAGKTFPSSPGDSLEDQLKPMLEWAH

GGFKPTGIEGLKPNNTQPENKTRRRTADDSATSDYCPAPKRLKTNCYNNG

KDRGDEDQSREQMASDVANNKSSLEDGCLSCGRKNPVSFHPLFEGGLCQT

CRDRFLELFYMYDDDGYQSYCTVCCEGRELLLCSNTSCCRCFCVECLEVL

VGTGTAAEAKLQEPWSCYMCLPQRCHGVLRRRKDWNVRLQAFFTSDTGLE

YEAPKLYPAIPAARRRPIRVLSLFDGIATGYLVLKELGIKVGKYVASEVC

EESIAVGTVKHEGNIKYVNDVRNITKKNIEEWGPFDLVIGGSPCNDLSNV

NPARKGLYEGTGRLFFEFYHLLNYSRPKEGDDRPFFWMFENVVAMKVGDK

RDISRFLECNPVMIDAIKVSAAHRARYFWGNLPGMNRPVIASKNDKLELQ

DCLEYNRIAKLKKVQTITTKSNSIKQGKNQLFPVVMNGKEDVLWCTELER

IFGFPVHYTDVSNMGRGARQKLLGRSWSVPVIRHLFAPLKDYFACE (the catalytic domain of human DNMT1;
SEQ ID NO: 10)
LRTLDVFSGCGGLSEGFHQAGISDTLWAIEMWDPAAQAFRLNNPGSTVFT

EDCNILLKLVMAGETTNSRGQRLPQKGDVEMLCGGPPCQGFSGMNRFNSR

TYSKFKNSLVVSFLSYCDYYRPRFFLLENVRNFVSFKRSMVLKLTLRCLV

RMGYQCTFGVLQAGQYGVAQTRRRAIILAAAPGEKLPLFPEPLHVFAPRA

CQLSVVVDDKKFVSNITRLSSGPFRTITVRDTMSDLPEVRNGASALEISY

NGEPQSWFQRQLRGAQYQPILRDHICKDMSALVAARMRHIPLAPGSDWRD

LPNIEVRLSDGTMARKLRYTHHDRKNGRSSSGALRGVCSCVEAGKACDPA

ARQFNTLIPWCLPHTGNRHNHWAGLYGRLEWDGFFSTTVTNPEPMGKQGR

VLHPEQHRVVSVRECARSQGFPDTYRLFGNILDKHRQVGNAVPPPLAKAI

GLEIKLCMLAKARESASAKIKEEEAAKD
```

An ATR of the present invention may, for example, comprise DNA (cytosine-5)-methyltransferase 3-like (DNMT3L), a catalytically inactive DNA methyltransferase that activates DNMT3A by binding to its catalytic domain. For example, an ATR of the present invention may comprise the sequence:

```
                                          (SEQ ID NO: 11)
MAAIPALDPEAEPSMDVILVGSSELSSSVSPGTGRDLIAYEVKANQRNIE

DICICCGSLQVHTQHPLFEGGICAPCKDKFLDALFLYDDDGYQSYCSICC

SGETLLICGNPDCTRCYCFECVDSLVGPGTSGKVHAMSNWVCYLCLPSSR

SGLLQRRRKWRSQLKAFYDRESENPLEMFETVPVWRRQPVRVLSLFEDIK

KELTSLGFLESGSDPGQLKHVVDVTDTVRKDVEEWGPFDLVYGATPPLGH

TCDRPPSWYLFQFHRLLQYARPKPGSPRPFFWMFVDNLVLNKEDLDVASR

FLEMEPVTIPDVHGGSLQNAVRVWSNIPAIRSRHWALVSEEELSLLAQNK

QSSKLAAKWPTKLVKNCFLPLREYFKYFSTELTSSL
```

An ATR of the present invention may, for example, comprise a SETDB1 domain. For example, an ATR of the present invention may comprise any of the sequences:

```
                                          (SEQ ID NO: 12)
MSSLPGCIGLDAATATVESEEIAELQQAVVEELGISMEELRHFIDEELEK

MDCVQQRKKQLAELETWVIQKESEVAHVDQLFDDASRAVTNCESLVKDFY

SKLGLQYRDSSSEDESSRPTEIIEIPDEDDDVLSIDSGDAGSRTPKDQKL

REAMAALRKSAQDVQKFMDAVNKKSSSQDLHKGTLSQMSGELSKDGDLIV

SMRILGKKRTKTWHKGTLIAIQTVGPGKKYKVKFDNKGKSLLSGNHIAYD

YHPPADKLYVGSRVVAKYKDGNQVWLYAGIVAETPNVKNKLRFLIFFDDG

YASYVTQSELYPICRPLKKTWEDIEDISCRDFIEEYVTAYPNRPMVLLKS

GQLIKTEWEGTWVVKSRVEEVDGSLVRILFLDDKRCEWIYRGSTRLEPMF

SMKTSSASALEKKQGQLRTRPNMGAVRSKGPVVQYTQDLTGTGTQFKPVE

PPQPTAPPAPPFPPAPPLSPQAGDSDLESQLAQSRKQVAKKSTSFRPGSV

GSGHSSPTSPALSENVSGGKPGINQTYRSPLGSTASAPAPSALPAPPAPP

VFHGMLERAPAEPSYRAPMEKLFYLPHVCSYTCLSRVRPMRNEQYRGKNP

LLVPLLYDFRRMTARRRVNRKMGFHVIYKTPCGLCLRTMQEIERYLFETG

CDFLFLEMFCLDPYVLVDRKFQPYKPFYYILDITYGKEDVPLSCVNEIDT

TPPPQVAYSKERIPGKGVFINTGPEFLVGCDCKDGCRDKSKCACHQLTIQ

ATACTPGGQINPNSGYQYKRLEECLPTGVYECNKRCKCDPNMCTNRLVQH

GLQVRLQLFKTQNKGWGIRCLDDIAKGSFVCIYAGKILTDDFADKEGLEM

GDEYFANLDHIESVENFKEGYESDAPCSSDSSGVDLKDQEDGNSGTEDPE

ESNDDSSDDNFCKDEDFSTSSVWRSYATRRQTRGQKENGLSETTSKDSHP

PDLGPPHIPVPPSIPVGGCNPPSSEETPKNKVASWLSCNSVSEGGFADSD

SHSSFKTNEGGEGRAGGSRMEAEKASTSGLGIKDEGDIKQAKKEDTDDRN

KMSVVTESSRNYGYNPSPVKPEGLRRPPSKTSMHQSRRLMASAQSNPDDV

LTLSSSTESEGESGTSRKPTAGQTSATAVDSDDIQTISSGSEGDDFEDKK

NMTGPMKRQVAVKSTRGFALKSTHGIAIKSTNMASVDKGESAPVRKNTRQ

FYDGEESCYIIDAKLEGNLGRYLNHSCSPNLFVQNVFVDTHDLRFPWVAF

FASKRIRAGTELTVVDYNYEVGSVEGKELLCCCGAIECRGRLL
```

```
                                          -continued
(the catalytic domain of human SETDB1;
SEQ ID NO: 13)
VGCDCKDGCRDKSKCACHQLTIQATACTPGGQINPNSGYQYKRLEECLPT

GVYECNKRCKCDPNMCTNRLVQHGLQVRLQLFKTQNKGWGIRCLDDIAKG

SFVCIYAGKILTDDFADKEGLEMGDEYFANLDHIESVENFKEGYESDAPC

SSDSSGVDLKDQEDGNSGTEDPEESNDDSSDDNFCKDEDFSTSSVWRSYA

TRRQTRGQKENGLSETTSKDSHPPDLGPPHIPVPPSIPVGGCNPPSSEET

PKNKVASWLSCNSVSEGGFADSDSHSSFKTNEGGEGRAGGSRMEAEKAST

SGLGIKDEGDIKQAKKEDTDDRNKMSVVTESSRNYGYNPSPVKPEGLRRP

PSKTSMHQSRRLMASAQSNPDDVLTLSSSTESEGESGTSRKPTAGQTSAT

AVDSDDIQTISSGSEGDDFEDKKNMTGPMKRQVAVKSTRGFALKSTHGIA

IKSTNMASVDKGESAPVRKNTRQFYDGEESCYIIDAKLEGNLGRYLNHSC

SPNLFVQNVFVDTHDLRFPWVAFFASKRIRAGTELTWDYNYEVGSVEGKE

LLCCCGAIECRGRLL
```

The ATR of the present invention may, for example, comprise an amino acid sequence that has 50%, 60%, 70%, 80%, 90%, 95%, 99% or 100% identity to SEQ ID NOs: 1, 2, 3, 4, 5, 6, 7, 8, 9, 10, 11, 12 or 13 wherein the amino acid sequence substantially retains the natural function of the protein represented by SEQ ID NOs: 1, 2, 3, 4, 5, 6, 7, 8, 9, 10, 11, 12 or 13.

The ATR of the present invention may, for example, be encoded by a polynucleotide comprising a nucleic acid sequence which encodes the protein of SEQ ID NOs: 1, 2, 3, 4, 5, 6, 7, 8, 9, 10, 11, 12 or 13, or a protein that has 50%, 60%, 70%, 80%, 90%, 95%, 99% or 100% amino acid identity to SEQ ID NOs: 1, 2, 3, 4, 5, 6, 7, 8, 9, 10, 11, 12 or 13 wherein the amino acid sequence substantially retains the natural function of the protein represented by SEQ ID NOs: 1, 2, 3, 4, 5, 6, 7, 8, 9, 10, 11, 12 or 13.

The ATR of the present invention may, for example, comprise an amino acid sequence that has at least 50%, 60%, 70%, 80%, 90%, 95%, 99% or 100% identity to SEQ ID NOs: 1, 2, 3, 4, 5, 6, 7, 8, 9, 10, 11, 12 or 13 wherein the amino acid sequence substantially retains the natural function of the protein represented by SEQ ID NOs: 1, 2, 3, 4, 5, 6, 7, 8, 9, 10, 11, 12 or 13.

The ATR of the present invention may, for example, be encoded by a polynucleotide comprising a nucleic acid sequence which encodes the protein of SEQ ID NOs: 1, 2, 3, 4, 5, 6, 7, 8, 9, 10, 11, 12 or 13, or a protein that has at least 50%, 60%, 70%, 80%, 90%, 95%, 99% or 100% amino acid identity to SEQ ID NOs: 1, 2, 3, 4, 5, 6, 7, 8, 9, 10, 11, 12 or 13 wherein the amino acid sequence substantially retains the natural function of the protein represented by SEQ ID NOs: 1, 2, 3, 4, 5, 6, 7, 8, 9, 10, 11, 12 or 13.

DNA-Binding Domains

The ATRs of the invention comprise a DNA-binding domain which binds a specific nucleic acid sequence and enables the ATR to be targeted to specific site in a polynucleotide, for example the genome of a cell. The DNA-binding domain may, for example, be protein-, DNA-, RNA- or chemical-based.

A number of suitable DNA-binding domains are known in the art, for example transcription-activator like effector (TALE) domains and zinc finger proteins (ZFPs) (Gaj, T. et al. (2013) *Trends Biotechnol.* 31:397-405).

The tetracycline-controlled repressor (tetR) DNA-binding domain, for example the *E. coli* tetR DNA-binding domain (Gossen, M. et al. (1992) *Proc. Natl. Acad. Sci. USA* 89:5547-51), may also be employed as a suitable DNA-binding domain in the ATRs of the present invention. The tetR system is particularly advantageous for use in model systems, because it allows temporal control of binding of tetR to its target nucleotide sequence, the tetracycline operon (TetO), by doxycycline (doxy) administration. This allows investigation of whether the chromatin states induced by the ATRs can be maintained after the release of the ATRs from their target locus.

In addition, methods for the engineering of DNA-binding domains to bind to desired nucleic acid sequences are known in the art.

Example sequences of suitable TALE domains include:

MGKPIPNPLLGLDSTGGMAPKKKRKVDGGVDLRTLGYSQQQQEKIKPKVR
STVAQHHEALVGHGFTHAHIVALSQHPAALGTVAVKYQDMIAALPEATHE
AIVGVGKQWSGARALEALLTVAGELRGPPLQLDTGQLLKIAKRGGVTAVE
AVHAWRNALTGAPLNLTPEQVVAIASNIGGKQALETVQRLLPVLCQAHGL
TPEQVVAIASHDGGKQALETVQRLLPVLCQAHGLTPEQVVAIASHDGGKQ
ALETVQRLLPVLCQAHGLTPEQVVAIASHDGGKQALETVQRLLPVLCQAH
GLTPEQVVAIASNIGGKQALETVQRLLPVLCQAHGLTPEQVVAIASNNGG
KQALETVQRLLPVLCQAHGLTPEQVVAIASNIGGKQALETVQRLLPVLCQ
AHGLTPEQVVAIASNGGGKQALETVQRLLPVLCQAHGLTPEQVVAIASNG
GGKQALETVQRLLPVLCQAHGLTPEQVVAIASNNGGKQALETVQRLLPVL
CQAHGLTPEQVVAIASNNGGKQALETVQRLLPVLCQAHGLTPEQVVAIAS
HDGGKQALETVQRLLPVLCQAHGLTPEQVVAIASHDGGKQALETVQRLLP
VLCQAHGLTPEQVVAIASHDGGKQALETVQRLLPVLCQAHGLTPEQVVAI
ASHDGGKQALETVQRLLPVLCQAHGLTPEQVVAIASNIGGKQALETVQRL
LPVLCQAHGLTPEQVVAIASHDGGKQALETVQRLLPVLCQAHGLTPQQWA
IASNGGGRPALESIVAQLSRPDPALAALTNDHLVALACLGGRPALDAVKK
GLPHAPALIKRTNRRIPERTSHRVA (SEQ ID NO: 14), which
targets the binding site: 5'-TACCCAGATTGGCCCC
ACT-3' (SEQ ID NO: 34)
and:
MGKPIPNPLLGLDSTGGMAPKKKRKVDGGVDLRTLGYSQQQQEKIKPKVR
STVAQHHEALVGHGFTHAHIVALSQHPAALGTVAVKYQDMIAALPEATHE
AIVGVGKQWSGARALEALLTVAGELRGPPLQLDTGQLLKIAKRGGVTAVE
AVHAWRNALTGAPLNLTPEQVVAIASNIGGKQALETVQRLLPVLCQAHGL
TPEQVVAIASHDGGKQALETVQRLLPVLCQAHGLTPEQVVAIASHDGGKQ
ALETVQRLLPVLCQAHGLTPEQVVAIASNGGGKQALETVQRLLPVLCQAH
GLTPEQVVAIASNIGGKQALETVQRLLPVLCQAHGLTPEQVVAIASNNGG
KQALETVQRLLPVLCQAHGLTPEQVVAIASNIGGKQALETVQRLLPVLCQ
AHGLTPEQVVAIASNNGGKQALETVQRLLPVLCQAHGLTPEQVVAIASNN
GGKQALETVQRLLPVLCQAHGLTPEQVVAIASNIGGKQALETVQRLLPVL
CQAHGLTPEQVVAIASNNGGKQALETVQRLLPVLCQAHGLTPEQVVAIAS
NIGGKQALETVQRLLPVLCQAHGLTPEQVVAIASNIGGKQALETVQRLLP
VLCQAHGLTPEQVVAIASNIGGKQALETVQRLLPVLCQAHGLTPEQVVAI
ASNNGGKQALETVQRLLPVLCQAHGLTPEQVVAIASNNGGKQALETVQRL
LPVLCQAHGLTPEQVVAIASNGGGKQALETVQRLLPVLCQAHGLTPQQWA
IASNGGGRPALESIVAQLSRPDPALAALTNDHLVALACLGGRPALDAVKK
GLPHAPALIKRTNRRIPERTSHRVA (SEQ ID NO: 15), which
targets the binding site: 5'-TACCTAGAGGAGAAAG
GTT-3' (SEQ ID NO: 35)

Example sequences of TALE domains that have been designed to target the promoter region of the β2-microglobulin gene include:

MGKPIPNPLLGLDSTGGMAPKKKRKVDGGVDLRTLGYSQQQQEKIKPKVR
STVAQHHEALVGHGFTHAHIVALSQHPAALGTVAVKYQDMIAALPEATHE
AIVGVGKQWSGARALEALLTVAGELRGPPLQLDTGQLLKIAKRGGVTAVE
AVHAWRNALTGAPLNLTPDQVVAIASHDGGKQALETVQRLLPVLCQDHGL
TPDQVVAIASNGGGKQALETVQRLLPVLCQDHGLTPDQVVAIASHDGGKQ
ALETVQRLLPVLCQDHGLTPDQVVAIASNGGGKQALETVQRLLPVLCQDH
GLTPDQVVAIASHDGGKQALETVQRLLPVLCQDHGLTPDQVVAIASHDGG
KQALETVQRLLPVLCQDHGLTPDQVVAIASNGGGKQALETVQRLLPVLCQ
DHGLTPDQVVAIASNIGGKQALETVQRLLPVLCQDHGLTPDQVVAIASHD
GGKQALETVQRLLPVLCQDHGLTPDQVVAIASHDGGKQALETVQRLLPVL
CQDHGLTPDQVVAIASHDGGKQALETVQRLLPVLCQDHGLTPDQVVAIAS
NGGGKQALETVQRLLPVLCQDHGLTPDQVVAIASHDGGKQALETVQRLLP
VLCQDHGLTPDQVVAIASHDGGKQALETVQRLLPVLCQDHGLTPDQVVAI
ASHDGGKQALETVQRLLPVLCQDHGLTPDQVVAIASNHGGKQALETVQRL
LPVLCQDHGLTPDQVVAIASHDGGKQALETVQRLLPVLCQDHGLTPDQVV
AIASNGGGKQALESIVAQLSRPDPALAALTNDHLVALACLGGRPALDAVK
KGLPHAPALIKRTNRRIPERTSHRVAGSGGG (SEQ ID NO:16),
which targets the binding site: 5'-TCTCTCCTACCCTCC
CGCT-3' (SEQ ID NO:17)

MGKPIPNPLLGLDSTGGMAPKKKRKVDGGVDLRTLGYSQQQQEKIKPKVR
STVAQHHEALVGHGFTHAHIVALSQHPAALGTVAVKYQDMIAALPEATHE
AIVGVGKQWSGARALEALLTVAGELRGPPLQLDTGQLLKIAKRGGVTAVE
AVHAWRNALTGAPLNLTPDQVVAIASNNGGKQALETVQRLLPVLCQDHGL
TPDQVVAIASNNGGKQALETVQRLLPVLCQDHGLTPDQVVAIASNGGGKQ
ALETVQRLLPVLCQDHGLTPDQVVAIASHDGGKQALETVQRLLPVLCQDH
GLTPDQVVAIASHDGGKQALETVQRLLPVLCQDHGLTPDQVVAIASNGGG
KQALETVQRLLPVLCQDHGLTPDQVVAIASNGGGKQALETVQRLLPVLCQ
DHGLTPDQVVAIASHDGGKQALETVQRLLPVLCQDHGLTPDQVVAIASHD
GGKQALETVQRLLPVLCQDHGLTPDQVVAIASNGGGKQALETVQRLLPVL
CQDHGLTPDQVVAIASHDGGKQALETVQRLLPVLCQDHGLTPDQVVAIAS

NGGGKQALETVQRLLPVLCQDHGLTPDQVVAIASHDGGKQALETVQRLLP

VLCQDHGLTPDQVVAIASHDGGKQALETVQRLLPVLCQDHGLTPDQVVAI

ASHDGGKQALETVQRLLPVLCQDHGLTPDQVVAIASNGGGKQALETVQRL

LPVLCQDHGLTPDQVVAIASHDGGKQALETVQRLLPVLCQDHGLTPDQVV

AIASNGGGKQALESIVAQLSRPDPALAALTNDHLVALACLGGRPALDAVK

KGLPHAPALIKRTNRRIPERTSHRVAGSGGG (SEQ ID NO: 18), which targets the binding site: 5'-TGGTCCTTCCTCTCC

CGCT-3' (SEQ ID NO: 19)

MGKPIPNPLLGLDSTGGMAPKKKRKVDGGVDLRTLGYSQQQQEKIKPKVR

STVAQHHEALVGHGFTHAHIVALSQHPAALGTVAVKYQDMIAALPEATHE

AIVGVGKQWSGARALEALLTVAGELRGPPLQLDTGQLLKIAKRGGVTAVE

AVHAWRNALTGAPLNLTPDQVVAIASHDGGKQALETVQRLLPVLCQDHGL

TPDQVVAIASNNGGKQALETVQRLLPVLCQDHGLTPDQVVAIASHDGGKQ

ALETVQRLLPVLCQDHGLTPDQVVAIASNGGGKQALETVQRLLPVLCQDH

GLTPDQVVAIASHDGGKQALETVQRLLPVLCQDHGLTPDQVVAIASHDGG

KQALETVQRLLPVLCQDHGLTPDQVVAIASNNGGKQALETVQRLLPVLCQ

DHGLTPDQVVAIASNGGGKQALETVQRLLPVLCQDHGLTPDQVVAIASNN

GGKQALETVQRLLPVLCQDHGLTPDQVVAIASNIGGKQALETVQRLLPVL

CQDHGLTPDQVVAIASHDGGKQALETVQRLLPVLCQDHGLTPDQVVAIAS

NGGGKQALETVQRLLPVLCQDHGLTPDQVVAIASNGGGKQALETVQRLLP

VLCQDHGLTPDQVVAIASHDGGKQALETVQRLLPVLCQDHGLTPDQVVAI

ASHDGGKQALETVQRLLPVLCQDHGLTPDQVVAIASHDGGKQALETVQRL

LPVLCQDHGLTPDQVVAIASNGGGKQALETVQRLLPVLCQDHGLTPDQVV

AIASNGGGKQALESIVAQLSRPDPALAALTNDHLVALACLGGRPALDAVK

KGLPHAPALIKRTNRRIPERTSHRVAGSGGG (SEQ ID NO:20), which targets the binding site: 5'-TCGCTCCGTGACTTC

CCTT-3' (SEQ ID NO:21)

Example sequences of TALE domains that have been designed to target the BCL11A gene include:

TALE BCL11A #1
MGKPIPNPLLGLDSTGGMAPKKKRKVDGGVDLRTLGYSQQQQEKIKPKVRSTVAQ

HHEALVGHGFTHAHIVALSQHPAALGTVAVKYQDMIAALPEATHEAIVGVGKQWSG

ARALEALLTVAGELRGPPLQLDTGQLLKIAKRGGVTAVEAVHAWRNALTGAPLNLTP

DQVVAIASHDGGKQALETVQRLLPVLCQDHGLTPDQVVAIASHDGGKQALETVQRL

LPVLCQDHGLTPDQVVAIASNGGGKQALETVQRLLPVLCQDHGLTPDQVVAIASNN

GGKQALETVQRLLPVLCQDHGLTPDQVVAIASNNGGKQALETVQRLLPVLCQDHGL

TPDQVVAIASNGGGKQALETVQRLLPVLCQDHGLTPDQVVAIASHDGGKQALETVQ

RLLPVLCQDHGLTPDQVVAIASHDGGKQALETVQRLLPVLCQDHGLTPDQVVAIAS

NNGGKQALETVQRLLPVLCQDHGLTPDQVVAIASHDGGKQALETVQRLLPVLCQD

HGLTPDQVVAIASHDGGKQALETVQRLLPVLCQDHGLTPDQVVAIASHDGGKQALE

TVQRLLPVLCQDHGLTPDQVVAIASHDGGKQALETVQRLLPVLCQDHGLTPDQVVA

IASHDGGKQALETVQRLLPVLCQDHGLTPDQVVAIASNIGGKQALETVQRLLPVLCQ

DHGLTPDQVVAIASNNGGKQALETVQRLLPVLCQDHGLTPDQVVAIASHDGGKQAL

ETVQRLLPVLCQDHGLTPDQVVAIASNIGGKQALESIVAQLSRPDPALAALTNDHLV

ALACLGGRPALDAVKKGLPHAPALIKRTNRRIPERTSHRVAGSGGG (SEQ ID NO:

37), which targets the binding site: 5'-TCCAAAAGCCAGTCTCACC-3'

(SEQ ID NO: 38)

TALE BCL11A #2
MGKPIPNPLLGLDSTGGMAPKKKRKVDGGVDLRTLGYSQQQQEKIKPKVRSTVAQ

HHEALVGHGFTHAHIVALSQHPAALGTVAVKYQDMIAALPEATHEAIVGVGKQWSG

ARALEALLTVAGELRGPPLQLDTGQLLKIAKRGGVTAVEAVHAWRNALTGAPLNLTP

DQVVAIASNNGGKQALETVQRLLPVLCQDHGLTPDQVVAIASHDGGKQALETVQRL

LPVLCQDHGLTPDQVVAIASHDGGKQALETVQRLLPVLCQDHGLTPDQVVAIASNN

GGKQALETVQRLLPVLCQDHGLTPDQVVAIASNIGGKQALETVQRLLPVLCQDHGL

TPDQVVAIASNNGGKQALETVQRLLPVLCQDHGLTPDQVVAIASNIGGKQALETVQ

RLLPVLCQDHGLTPDQVVAIASHDGGKQALETVQRLLPVLCQDHGLTPDQVVAIAS
HDGGKQALETVQRLLPVLCQDHGLTPDQVVAIASNGGGKQALETVQRLLPVLCQD
HGLTPDQVVAIASHDGGKQALETVQRLLPVLCQDHGLTPDQVVAIASNGGGKQALE
TVQRLLPVLCQDHGLTPDQVVAIASNGGGKQALETVQRLLPVLCQDHGLTPDQVVA
IASHDGGKQALETVQRLLPVLCQDHGLTPDQVVAIASNGGGKQALETVQRLLPVLC
QDHGLTPDQVVAIASHDGGKQALETVQRLLPVLCQDHGLTPDQVVAIASNNGGKQ
ALETVQRLLPVLCQDHGLTPDQVVAIASNIGGKQALESIVAQLSRPDPALAALTNDHL
VALACLGGRPALDAVKKGLPHAPALIKRTNRRIPERTSHRVAGSGGG (SEQ ID NO:
39), which targets the binding site: 5'-TCTCCCCGGGAATCGTTTT-3'
(SEQ ID NO: 40)

TALE BCL11A #3
MGKPIPNPLLGLDSTGGMAPKKKRKVDGGVDLRTLGYSQQQQEKIKPKVRSTVAQ
HHEALVGHGFTHAHIVALSQHPAALGTVAVKYQDMIAALPEATHEAIVGVGKQWSG
ARALEALLTVAGELRGPPLQLDTGQLLKIAKRGGVTAVEAVHAWRNALTGAPLNLTP
DQVVAIASHDGGKQALETVQRLLPVLCQDHGLTPDQVVAIASNNGGKQALETVQRL
LPVLCQDHGLTPDQVVAIASNNGGKQALETVQRLLPVLCQDHGLTPDQVVAIASHD
GGKQALETVQRLLPVLCQDHGLTPDQVVAIASNGGGKQALETVQRLLPVLCQDHG
LTPDQVVAIASNGGGKQALETVQRLLPVLCQDHGLTPDQVVAIASNGGGKQALETV
QRLLPVLCQDHGLTPDQVVAIASNNGGKQALETVQRLLPVLCQDHGLTPDQVVAIA
SHDGGKQALETVQRLLPVLCQDHGLTPDQVVAIASNIGGKQALETVQRLLPVLCQD
HGLTPDQVVAIASNIGGKQALETVQRLLPVLCQDHGLTPDQVVAIASNIGGKQALET
VQRLLPVLCQDHGLTPDQVVAIASNHGGKQALETVQRLLPVLCQDHGLTPDQVVAI
ASHDGGKQALETVQRLLPVLCQDHGLTPDQVVAIASNIGGKQALETVQRLLPVLCQ
DHGLTPDQVVAIASNGGGKQALETVQRLLPVLCQDHGLTPDQVVAIASNGGGKQAL
ETVQRLLPVLCQDHGLTPDQVVAIASNGGGKQALESIVAQLSRPDPALAALTNDHLV
ALACLGGRPALDAVKKGLPHAPALIKRTNRRIPERTSHRVAGSGGG (SEQ ID NO:
41), which targets the binding site: 5'-TCCTCCCGCTGCACACTTG-3'
(SEQ ID NO: 42)

TALE BCL11A #4
MGKPIPNPLLGLDSTGGMAPKKKRKVDGGVDLRTLGYSQQQQEKIKPKVRSTVAQ
HHEALVGHGFTHAHIVALSQHPAALGTVAVKYQDMIAALPEATHEAIVGVGKQWSG
ARALEALLTVAGELRGPPLQLDTGQLLKIAKRGGVTAVEAVHAWRNALTGAPLNLTP
DQVVAIASNNGGKQALETVQRLLPVLCQDHGLTPDQVVAIASHDGGKQALETVQRL
LPVLCQDHGLTPDQVVAIASNIGGKQALETVQRLLPVLCQDHGLTPDQVVAIASNIG
GKQALETVQRLLPVLCQDHGLTPDQVVAIASNIGGKQALETVQRLLPVLCQDHGLT
PDQVVAIASNNGGKQALETVQRLLPVLCQDHGLTPDQVVAIASHDGGKQALETVQR
LLPVLCQDHGLTPDQVVAIASHDGGKQALETVQRLLPVLCQDHGLTPDQVVAIASN
NGGKQALETVQRLLPVLCQDHGLTPDQVVAIASNIGGKQALETVQRLLPVLCQDHG
LTPDQVVAIASNNGGKQALETVQRLLPVLCQDHGLTPDQVVAIASNGGGKQALETV
QRLLPVLCQDHGLTPDQVVAIASNGGGKQALETVQRLLPVLCQDHGLTPDQVVAIA
SNGGGKQALETVQRLLPVLCQDHGLTPDQVVAIASHDGGKQALETVQRLLPVLCQ

-continued

DHGLTPDQVVAIASNIGGKQALETVQRLLPVLCQDHGLTPDQVVAIASHDGGKQAL

ETVQRLLPVLCQDHGLTPDQVVAIASHDGGKQALESIVAQLSRPDPALAALTNDHLV

ALACLGGRPALDAVKKGLPHAPALIKRTNRRIPERTSHRVAGSGGG (SEQ ID NO:

43), which targets the binding site: 5'-TAGTCATCCCCACAATAGT-3'

(SEQ ID NO: 44)

TALE BCL11A #5
MGKPIPNPLLGLDSTGGMAPKKKRKVDGGVDLRTLGYSQQQQEKIKPKVRSTVAQ

HHEALVGHGFTHAHIVALSQHPAALGTVAVKYQDMIAALPEATHEAIVGVGKQWSG

ARALEALLTVAGELRGPPLQLDTGQLLKIAKRGGVTAVEAVHAWRNALTGAPLNLTP

DQVVAIASNIGGKQALETVQRLLPVLCQDHGLTPDQVVAIASHDGGKQALETVQRLL

PVLCQDHGLTPDQVVAIASNIGGKQALETVQRLLPVLCQDHGLTPDQVVAIASNNG

GKQALETVQRLLPVLCQDHGLTPDQVVAIASNGGGKQALETVQRLLPVLCQDHGLT

PDQVVAIASNGGGKQALETVQRLLPVLCQDHGLTPDQVVAIASNNGGKQALETVQR

LLPVLCQDHGLTPDQVVAIASHDGGKQALETVQRLLPVLCQDHGLTPDQVVAIASH

DGGKQALETVQRLLPVLCQDHGLTPDQVVAIASHDGGKQALETVQRLLPVLCQDH

GLTPDQVVAIASNGGGKQALETVQRLLPVLCQDHGLTPDQVVAIASNNGGKQALET

VQRLLPVLCQDHGLTPDQVVAIASHDGGKQALETVQRLLPVLCQDHGLTPDQVVAI

ASNIGGKQALETVQRLLPVLCQDHGLTPDQVVAIASNIGGKQALETVQRLLPVLCQD

HGLTPDQVVAIASNIGGKQALETVQRLLPVLCQDHGLTPDQVVAIASNIGGKQALET

VQRLLPVLCQDHGLTPDQVVAIASNGGGKQALESIVAQLSRPDPALAALTNDHLVAL

ACLGGRPALDAVKKGLPHAPALIKRTNRRIPERTSHRVAGSGGG (SEQ ID NO: 45), which targets the binding site: 5'-TCCCGCTGCCTTTTGTGCC-3'

(SEQ ID NO: 46)

TALE BCL11A #6
MGKPIPNPLLGLDSTGGMAPKKKRKVDGGVDLRTLGYSQQQQEKIKPKVRSTVAQ

HHEALVGHGFTHAHIVALSQHPAALGTVAVKYQDMIAALPEATHEAIVGVGKQWSG

ARALEALLTVAGELRGPPLQLDTGQLLKIAKRGGVTAVEAVHAWRNALTGAPLNLTP

DQVVAIASHDGGKQALETVQRLLPVLCQDHGLTPDQVVAIASHDGGKQALETVQRL

LPVLCQDHGLTPDQVVAIASNNGGKQALETVQRLLPVLCQDHGLTPDQVVAIASHD

GGKQALETVQRLLPVLCQDHGLTPDQVVAIASHDGGKQALETVQRLLPVLCQDHGL

TPDQVVAIASHDGGKQALETVQRLLPVLCQDHGLTPDQVVAIASNGGGKQALETVQ

RLLPVLCQDHGLTPDQVVAIASNNGGKQALETVQRLLPVLCQDHGLTPDQVVAIAS

NNGGKQALETVQRLLPVLCQDHGLTPDQVVAIASNNGGKQALETVQRLLPVLCQD

HGLTPDQVVAIASNGGGKQALETVQRLLPVLCQDHGLTPDQVVAIASNIGGKQALE

TVQRLLPVLCQDHGLTPDQVVAIASHDGGKQALETVQRLLPVLCQDHGLTPDQVVA

IASNGGGKQALETVQRLLPVLCQDHGLTPDQVVAIASNGGGKQALETVQRLLPVLC

QDHGLTPDQVVAIASNGGGKQALETVQRLLPVLCQDHGLTPDQVVAIASHDGGKQ

ALETVQRLLPVLCQDHGLTPDQVVAIASNGGGKQALESIVAQLSRPDPALAALTNDH

LVALACLGGRPALDAVKKGLPHAPALIKRTNRRIPERTSHRVAGSGGG (SEQ ID

NO: 47), which targets the binding site: 5'-TCCTCGCGCTTGCCCT

CCC-3' (SEQ ID NO: 48)

TALE BCL11A #7

-continued

MGKPIPNPLLGLDSTGGMAPKKKRKVDGGVDLRTLGYSQQQQEKIKPKVRSTVAQ

HHEALVGHGFTHAHIVALSQHPAALGTVAVKYQDMIAALPEATHEAIVGVGKQWSG

ARALEALLTVAGELRGPPLQLDTGQLLKIAKRGGVTAVEAVHAWRNALTGAPLNLTP

DQVVAIASHDGGKQALETVQRLLPVLCQDHGLTPDQVVAIASNGGGKQALETVQRL

LPVLCQDHGLTPDQVVAIASHDGGKQALETVQRLLPVLCQDHGLTPDQVVAIASNG

GGKQALETVQRLLPVLCQDHGLTPDQVVAIASNGGGKQALETVQRLLPVLCQDHG

LTPDQVVAIASNNGGKQALETVQRLLPVLCQDHGLTPDQVVAIASNGGGKQALETV

QRLLPVLCQDHGLTPDQVVAIASHDGGKQALETVQRLLPVLCQDHGLTPDQVVAIA

SHDGGKQALETVQRLLPVLCQDHGLTPDQVVAIASNIGGKQALETVQRLLPVLCQD

HGLTPDQVVAIASHDGGKQALETVQRLLPVLCQDHGLTPDQVVAIASNIGGKQALET

VQRLLPVLCQDHGLTPDQVVAIASNHGGKQALETVQRLLPVLCQDHGLTPDQVVAI

ASHDGGKQALETVQRLLPVLCQDHGLTPDQVVAIASNGGGKQALETVQRLLPVLC

QDHGLTPDQVVAIASHDGGKQALETVQRLLPVLCQDHGLTPDQVVAIASNNGGKQ

ALETVQRLLPVLCQDHGLTPDQVVAIASNNGGKQALESIVAQLSRPDPALAALTNDH

LVALACLGGRPALDAVKKGLPHAPALIKRTNRRIPERTSHRVAGSGGG (SEQ ID

NO: 49), which targets the binding site: 5'-TCCCCCGGCCCTAGC

TCCT-3' (SEQ ID NO: 50)

TALE BCL11A #8
MGKPIPNPLLGLDSTGGMAPKKKRKVDGGVDLRTLGYSQQQQEKIKPKVRSTVAQ

HHEALVGHGFTHAHIVALSQHPAALGTVAVKYQDMIAALPEATHEAIVGVGKQWSG

ARALEALLTVAGELRGPPLQLDTGQLLKIAKRGGVTAVEAVHAWRNALTGAPLNLTP

DQVVAIASHDGGKQALETVQRLLPVLCQDHGLTPDQVVAIASNGGGKQALETVQRL

LPVLCQDHGLTPDQVVAIASHDGGKQALETVQRLLPVLCQDHGLTPDQVVAIASHD

GGKQALETVQRLLPVLCQDHGLTPDQVVAIASHDGGKQALETVQRLLPVLCQDHGL

TPDQVVAIASNNGGKQALETVQRLLPVLCQDHGLTPDQVVAIASHDGGKQALETVQ

RLLPVLCQDHGLTPDQVVAIASNGGGKQALETVQRLLPVLCQDHGLTPDQVVAIAS

NNGGKQALETVQRLLPVLCQDHGLTPDQVVAIASNIGGKQALETVQRLLPVLCQDH

GLTPDQVVAIASHDGGKQALETVQRLLPVLCQDHGLTPDQVVAIASNGGGKQALET

VQRLLPVLCQDHGLTPDQVVAIASNHGGKQALETVQRLLPVLCQDHGLTPDQVVAI

ASHDGGKQALETVQRLLPVLCQDHGLTPDQVVAIASNHGGKQALETVQRLLPVLCQ

DHGLTPDQVVAIASHDGGKQALETVQRLLPVLCQDHGLTPDQVVAIASHDGGKQAL

ETVQRLLPVLCQDHGLTPDQVVAIASNGGGKQALESIVAQLSRPDPALAALTNDHLV

ALACLGGRPALDAVKKGLPHAPALIKRTNRRIPERTSHRVAGSGGG (SEQ ID NO:

51), which targets the binding site: 5'-TCCTGGTCCGCCCCCAGCA-3'

(SEQ ID NO: 52)

TALE BCL11A #9
MGKPIPNPLLGLDSTGGMAPKKKRKVDGGVDLRTLGYSQQQQEKIKPKVRSTVAQ

HHEALVGHGFTHAHIVALSQHPAALGTVAVKYQDMIAALPEATHEAIVGVGKQWSG

ARALEALLTVAGELRGPPLQLDTGQLLKIAKRGGVTAVEAVHAWRNALTGAPLNLTP

DQVVAIASHDGGKQALETVQRLLPVLCQDHGLTPDQVVAIASHDGGKQALETVQRL

LPVLCQDHGLTPDQVVAIASHDGGKQALETVQRLLPVLCQDHGLTPDQVVAIASNG

GGKQALETVQRLLPVLCQDHGLTPDQVVAIASNGGGKQALETVQRLLPVLCQDHG

LTPDQVVAIASNNGGKQALETVQRLLPVLCQDHGLTPDQVVAIASHDGGKQALETV

QRLLPVLCQDHGLTPDQVVAIASNGGGKQALETVQRLLPVLCQDHGLTPDQVVAIA

SNNGGKQALETVQRLLPVLCQDHGLTPDQVVAIASHDGGKQALETVQRLLPVLCQ

DHGLTPDQVVAIASHDGGKQALETVQRLLPVLCQDHGLTPDQVVAIASNIGGKQAL

ETVQRLLPVLCQDHGLTPDQVVAIASNIGGKQALETVQRLLPVLCQDHGLTPDQVV

AIASNIGGKQALETVQRLLPVLCQDHGLTPDQVVAIASHDGGKQALETVQRLLPVLC

QDHGLTPDQVVAIASNGGGKQALETVQRLLPVLCQDHGLTPDQVVAIASNGGGKQ

ALETVQRLLPVLCQDHGLTPDQVVAIASNGGGKQALESIVAQLSRPDPALAALTNDH

LVALACLGGRPALDAVKKGLPHAPALIKRTNRRIPERTSHRVAGSGGG (SEQ ID

NO: 53), which targets the binding site: 5'-TGCCGAGACCTCTT

CTCGA-3' (SEQ ID NO: 54)

TALE BCL11A #10
MGKPIPNPLLGLDSTGGMAPKKKRKVDGGVDLRTLGYSQQQQEKIKPKVRSTVAQ

HHEALVGHGFTHAHIVALSQHPAALGTVAVKYQDMIAALPEATHEAIVGVGKQWSG

ARALEALLTVAGELRGPPLQLDTGQLLKIAKRGGVTAVEAVHAWRNALTGAPLNLTP

DQVVAIASNNGGKQALETVKRLLPVLCQDHGLTPDQVVAIASNNGGKQALETVQRL

LPVLCQDHGLTPDQVVAIASNNGGKQALETVQRLLPVLCQDHGLTPDQVVAIASHD

GGKQALETVQRLLPVLCQDHGLTPDQVVAIASHDGGKQALETVQRLLPVLCQDHGL

TPDQVVAIASHDGGKQALETVQRLLPVLCQDHGLTPDQVVAIASNGGGKQALETVQ

RLLPVLCQDHGLTPDQVVAIASHDGGKQALETVQRLLPVLCQDHGLTPDQVVAIAS

NIGGKQALETVQRLLPVLCQDHGLTPDQVVAIASHDGGKQALETVQRLLPVLCQDH

GLTPDQVVAIASNNGGKQALETVQRLLPVLCQDHGLTPDQVVAIASHDGGKQALET

VQRLLPVLCQDHGLTPDQVVAIASHDGGKQALETVQRLLPVLCQDHGLTPDQVVAI

ASNGGGKQALETVQRLLPVLCQDHGLTPDQVVAIASNGGGKQALETVQRLLPVLC

QDHGLTPDQVVAIASNGGGKQALETVQRLLPVLCQDHGLTPDQVVAIASHDGGKQ

ALETVQRLLPVLCQDHGLTPDQVVAIASNGGGKQALESIVAQLSRPDPALAALTNDH

LVALACLGGRPALDAVKKGLPHAPALIKRTNRRIPERTSHRVAGSGGG (SEQ ID

NO: 55), which targets the binding site: 5'-TCGGCTTTGCAAAGC

ATTT-3' (SEQ ID NO: 56)

TALE BCL11A #11
MGKPIPNPLLGLDSTGGMAPKKKRKVDGGVDLRTLGYSQQQQEKIKPKVRSTVAQ

HHEALVGHGFTHAHIVALSQHPAALGTVAVKYQDMIAALPEATHEAIVGVGKQWSG

ARALEALLTVAGELRGPPLQLDTGQLLKIAKRGGVTAVEAVHAWRNALTGAPLNLTP

DQVVAIASHDGGKQALETVQRLLPVLCQDHGLTPDQVVAIASNGGGKQALETVQRL

LPVLCQDHGLTPDQVVAIASHDGGKQALETVQRLLPVLCQDHGLTPDQVVAIASHD

GGKQALETVQRLLPVLCQDHGLTPDQVVAIASHDGGKQALETVQRLLPVLCQDHGL

TPDQVVAIASHDGGKQALETVQRLLPVLCQDHGLTPDQVVAIASNNGGKQALETVQ

RLLPVLCQDHGLTPDQVVAIASNNGGKQALETVQRLLPVLCQDHGLTPDQVVAIAS

NNGGKQALETVQRLLPVLCQDHGLTPDQVVAIASNIGGKQALETVQRLLPVLCQDH

GLTPDQVVAIASNIGGKQALETVQRLLPVLCQDHGLTPDQVVAIASNGGGKQALETV

QRLLPVLCQDHGLTPDQVVAIASHDGGKQALETVQRLLPVLCQDHGLTPDQVVAIA

-continued

SNNGGKQALETVQRLLPVLCQDHGLTPDQVVAIASNGGGKQALETVQRLLPVLCQ

DHGLTPDQVVAIASNGGGKQALETVQRLLPVLCQDHGLTPDQVVAIASNGGGKQAL

ETVQRLLPVLCQDHGLTPDQVVAIASNGGGKQALESIVAQLSRPDPALAALTNDHLV

ALACLGGRPALDAVKKGLPHAPALIKRTNRRIPERTSHRVAGSGGG (SEQ ID NO:

57), which targets the binding site: 5'-TGCAAAGCCGAGTTTCACC-3'

(SEQ ID NO: 58)

TALE BCL11A #12
MGKPIPNPLLGLDSTGGMAPKKKRKVDGGVDLRTLGYSQQQQEKIKPKVRSTVAQ

HHEALVGHGFTHAHIVALSQHPAALGTVAVKYQDMIAALPEATHEAIVGVGKQWSG

ARALEALLTVAGELRGPPLQLDTGQLLKIAKRGGVTAVEAVHAWRNALTGAPLNLTP

DQVVAIASHDGGKQALETVQRLLPVLCQDHGLTPDQVVAIASHDGGKQALETVQRL

LPVLCQDHGLTPDQVVAIASNIGGKQALETVQRLLPVLCQDHGLTPDQVVAIASNIG

GKQALETVQRLLPVLCQDHGLTPDQVVAIASNIGGKQALETVQRLLPVLCQDHGLT

PDQVVAIASNIGGKQALETVQRLLPVLCQDHGLTPDQVVAIASNHGGKQALETVQR

LLPVLCQDHGLTPDQVVAIASHDGGKQALETVQRLLPVLCQDHGLTPDQVVAIASH

DGGKQALETVQRLLPVLCQDHGLTPDQVVAIASNIGGKQALETVQRLLPVLCQDHG

LTPDQVVAIASNNGGKQALETVQRLLPVLCQDHGLTPDQVVAIASNGGGKQALETV

QRLLPVLCQDHGLTPDQVVAIASHDGGKQALETVQRLLPVLCQDHGLTPDQVVAIA

SNGGGKQALETVQRLLPVLCQDHGLTPDQVVAIASHDGGKQALETVQRLLPVLCQ

DHGLTPDQVVAIASNIGGKQALETVQRLLPVLCQDHGLTPDQVVAIASHDGGKQAL

ETVQRLLPVLCQDHGLTPDQVVAIASHDGGKQALESIVAQLSRPDPALAALTNDHLV

ALACLGGRPALDAVKKGLPHAPALIKRTNRRIPERTSHRVAGSGGG (SEQ ID NO:

59), which targets the binding site: 5'-TACAGTTGCCCTGCAAAAT-3'

(SEQ ID NO: 60)

TALE BCL11A #13
MGKPIPNPLLGLDSTGGMAPKKKRKVDGGVDLRTLGYSQQQQEKIKPKVRSTVAQ

HHEALVGHGFTHAHIVALSQHPAALGTVAVKYQDMIAALPEATHEAIVGVGKQWSG

ARALEALLTVAGELRGPPLQLDTGQLLKIAKRGGVTAVEAVHAWRNALTGAPLNLTP

DQVVAIASHDGGKQALETVQRLLPVLCQDHGLTPDQVVAIASHDGGKQALETVQRL

LPVLCQDHGLTPDQVVAIASNGGGKQALETVQRLLPVLCQDHGLTPDQVVAIASHD

GGKQALETVQRLLPVLCQDHGLTPDQVVAIASHDGGKQALETVQRLLPVLCQDHGL

TPDQVVAIASHDGGKQALETVQRLLPVLCQDHGLTPDQVVAIASNNGGKQALETVQ

RLLPVLCQDHGLTPDQVVAIASHDGGKQALETVQRLLPVLCQDHGLTPDQVVAIAS

NGGGKQALETVQRLLPVLCQDHGLTPDQVVAIASNNGGKQALETVQRLLPVLCQD

HGLTPDQVVAIASHDGGKQALETVQRLLPVLCQDHGLTPDQVVAIASNIGGKQALET

VQRLLPVLCQDHGLTPDQVVAIASHDGGKQALETVQRLLPVLCQDHGLTPDQVVAI

ASNIGGKQALETVQRLLPVLCQDHGLTPDQVVAIASHDGGKQALETVQRLLPVLCQ

DHGLTPDQVVAIASNGGGKQALETVQRLLPVLCQDHGLTPDQVVAIASNGGGKQAL

ETVQRLLPVLCQDHGLTPDQVVAIASNNGGKQALESIVAQLSRPDPALAALTNDHLV

ALACLGGRPALDAVKKGLPHAPALIKRTNRRIPERTSHRVAGSGGG (SEQ ID NO:

61), which targets the binding site: 5'-TCCGCCCTGGGTACTTTCT-3'

(SEQ ID NO: 62)

```
TALE BCL11A #14
MGKPIPNPLLGLDSTGGMAPKKKRKVDGGVDLRTLGYSQQQQEKIKPKVRSTVAQ

HHEALVGHGFTHAHIVALSQHPAALGTVAVKYQDMIAALPEATHEAIVGVGKQWSG

ARALEALLTVAGELRGPPLQLDTGQLLKIAKRGGVTAVEAVHAWRNALTGAPLNLTP

DQVVAIASNIGGKQALETVQRLLPVLCQDHGLTPDQVVAIASNNGGKQALETVQRLL

PVLCQDHGLTPDQVVAIASNGGGKQALETVQRLLPVLCQDHGLTPDQVVAIASHDG

GKQALETVQRLLPVLCQDHGLTPDQVVAIASNIGGKQALETVQRLLPVLCQDHGLT

PDQVVAIASNGGGKQALETVQRLLPVLCQDHGLTPDQVVAIASHDGGKQALETVQR

LLPVLCQDHGLTPDQVVAIASHDGGKQALETVQRLLPVLCQDHGLTPDQVVAIASH

DGGKQALETVQRLLPVLCQDHGLTPDQVVAIASHDGGKQALETVQRLLPVLCQDH

GLTPDQVVAIASNIGGKQALETVQRLLPVLCQDHGLTPDQVVAIASHDGGKQALETV

QRLLPVLCQDHGLTPDQVVAIASNIGGKQALETVQRLLPVLCQDHGLTPDQVVAIAS

NIGGKQALETVQRLLPVLCQDHGLTPDQVVAIASNGGGKQALETVQRLLPVLCQDH

GLTPDQVVAIASNIGGKQALETVQRLLPVLCQDHGLTPDQVVAIASNNGGKQALETV

QRLLPVLCQDHGLTPDQVVAIASNGGGKQALESIVAQLSRPDPALAALTNDHLVALA

CLGGRPALDAVKKGLPHAPALIKRTNRRIPERTSHRVAGSGGG (SEQ ID NO: 63), which targets the binding site: 5'-TCTCTTGTCCACAGCTCGG-3'

(SEQ ID NO: 64)

TALE BCL11A #15
MGKPIPNPLLGLDSTGGMAPKKKRKVDGGVDLRTLGYSQQQQEKIKPKVRSTVAQ

HHEALVGHGFTHAHIVALSQHPAALGTVAVKYQDMIAALPEATHEAIVGVGKQWSG

ARALEALLTVAGELRGPPLQLDTGQLLKIAKRGGVTAVEAVHAWRNALTGAPLNLTP

DQVVAIASHDGGKQALETVQRLLPVLCQDHGLTPDQVVAIASHDGGKQALETVQRL

LPVLCQDHGLTPDQVVAIASHDGGKQALETVQRLLPVLCQDHGLTPDQVVAIASNN

GGKQALETVQRLLPVLCQDHGLTPDQVVAIASHDGGKQALETVQRLLPVLCQDHGL

TPDQVVAIASNGGGKQALETVQRLLPVLCQDHGLTPDQVVAIASNNGGKQALETVQ

RLLPVLCQDHGLTPDQVVAIASHDGGKQALETVQRLLPVLCQDHGLTPDQVVAIAS

HDGGKQALETVQRLLPVLCQDHGLTPDQVVAIASNGGGKQALETVQRLLPVLCQD

HGLTPDQVVAIASNGGGKQALETVQRLLPVLCQDHGLTPDQVVAIASNGGGKQALE

TVQRLLPVLCQDHGLTPDQVVAIASNGGGKQALETVQRLLPVLCQDHGLTPDQVVA

IASNNGGKQALETVQRLLPVLCQDHGLTPDQVVAIASNGGGKQALETVQRLLPVLC

QDHGLTPDQVVAIASNNGGKQALETVQRLLPVLCQDHGLTPDQVVAIASHDGGKQ

ALETVQRLLPVLCQDHGLTPDQVVAIASHDGGKQALESIVAQLSRPDPALAALTNDH

LVALACLGGRPALDAVKKGLPHAPALIKRTNRRIPERTSHRVAGSGGG (SEQ ID

NO: 65), which targets the binding site: 5'-TCTCCCGCTGACTG

CGCCT-3' (SEQ ID NO: 66)

TALE BCL11A #16
MGKPIPNPLLGLDSTGGMAPKKKRKVDGGVDLRTLGYSQQQQEKIKPKVRSTVAQ

HHEALVGHGFTHAHIVALSQHPAALGTVAVKYQDMIAALPEATHEAIVGVGKQWSG

ARALEALLTVAGELRGPPLQLDTGQLLKIAKRGGVTAVEAVHAWRNALTGAPLNLTP

DQVVAIASHDGGKQALETVQRLLPVLCQDHGLTPDQVVAIASHDGGKQALETVQRL

LPVLCQDHGLTPDQVVAIASNGGGKQALETVQRLLPVLCQDHGLTPDQVVAIASHD
```

-continued

```
GGKQALETVQRLLPVLCQDHGLTPDQVVAIASNNGGKQALETVQRLLPVLCQDHGL

TPDQVVAIASHDGGKQALETVQRLLPVLCQDHGLTPDQVVAIASNNGGKQALETVQ

RLLPVLCQDHGLTPDQVVAIASHDGGKQALETVQRLLPVLCQDHGLTPDQVVAIAS

NGGGKQALETVQRLLPVLCQDHGLTPDQVVAIASNGGGKQALETVQRLLPVLCQD

HGLTPDQVVAIASNNGGKQALETVQRLLPVLCQDHGLTPDQVVAIASHDGGKQALE

TVQRLLPVLCQDHGLTPDQVVAIASHDGGKQALETVQRLLPVLCQDHGLTPDQVVA

IASHDGGKQALETVQRLLPVLCQDHGLTPDQVVAIASNGGGKQALETVQRLLPVLC

QDHGLTPDQVVAIASHDGGKQALETVQRLLPVLCQDHGLTPDQVVAIASHDGGKQ

ALETVQRLLPVLCQDHGLTPDQVVAIASHDGGKQALESIVAQLSRPDPALAALTNDH

LVALACLGGRPALDAVKKGLPHAPALIKRTNRRIPERTSHRVAGSGGG (SEQ ID

NO: 67), which targets the binding site: 5'-TCCCTTGCTGCCAAA

CTTT-3' (SEQ ID NO: 68)

TALE BCL11A #17
MGKPIPNPLLGLDSTGGMAPKKKRKVDGGVDLRTLGYSQQQQEKIKPKVRSTVAQ

HHEALVGHGFTHAHIVALSQHPAALGTVAVKYQDMIAALPEATHEAIVGVGKQWSG

ARALEALLTVAGELRGPPLQLDTGQLLKIAKRGGVTAVEAVHAWRNALTGAPLNLTP

DQVVAIASHDGGKQALETVQRLLPVLCQDHGLTPDQVVAIASHDGGKQALETVQRL

LPVLCQDHGLTPDQVVAIASHDGGKQALETVQRLLPVLCQDHGLTPDQVVAIASHD

GGKQALETVQRLLPVLCQDHGLTPDQVVAIASHDGGKQALETVQRLLPVLCQDHGL

TPDQVVAIASNNGGKQALETVQRLLPVLCQDHGLTPDQVVAIASNNGGKQALETVQ

RLLPVLCQDHGLTPDQVVAIASHDGGKQALETVQRLLPVLCQDHGLTPDQVVAIAS

HDGGKQALETVQRLLPVLCQDHGLTPDQVVAIASHDGGKQALETVQRLLPVLCQD

HGLTPDQVVAIASNGGGKQALETVQRLLPVLCQDHGLTPDQVVAIASNIGGKQALE

TVQRLLPVLCQDHGLTPDQVVAIASNNGGKQALETVQRLLPVLCQDHGLTPDQVVA

IASHDGGKQALETVQRLLPVLCQDHGLTPDQVVAIASNGGGKQALETVQRLLPVLC

QDHGLTPDQVVAIASHDGGKQALETVQRLLPVLCQDHGLTPDQVVAIASHDGGKQ

ALETVQRLLPVLCQDHGLTPDQVVAIASNGGGKQALESIVAQLSRPDPALAALTNDH

LVALACLGGRPALDAVKKGLPHAPALIKRTNRRIPERTSHRVAGSGGG (SEQ ID

NO: 69), which targets the binding site: 5'-TGGGCCCTCACGCC

TTTCT-3' (SEQ ID NO: 70)
```

Meganucleases (Silve, G. et al. (2011) *Cur. Gene Ther.* 11:11-27) and CRISPR/Cas systems (Sander, J. D. et al. (2014) *Nat. Biotechnol.* 32:347-55) may also be employed as suitable DNA-binding domains in the ATRs of the present invention.

The CRISPR/Cas system is an RNA-guided DNA binding system (van der Oost et al. (2014) *Nat. Rev. Microbiol.* 12:479-92), wherein the guide RNA (gRNA) may be selected to enable an ATR comprising a Cas9 domain to be targeted to a specific sequence. Thus, to employ the CRISPR/Cas system as a DNA-binding domain in the present invention it is to be understood that an ATR effector domain may be operably linked to a Cas9 endonuclease. Preferably, the ATR effector domain is operably linked to a Cas9 endonuclease which has been inactivated such that it substantially does not possess nuclease activity. The ATR comprising the Cas9 endonuclease may be delivered to a target cell in combination with one or more guide RNAs (gRNAs). The guide RNAs are designed to target the ATR to a target gene of interest or a regulatory element (e.g. promoter, enhancer or splicing sites) of the target gene. Methods for the design of gRNAs are known in the art. Furthermore, fully orthogonal Cas9 proteins, as well as Cas9/gRNA ribonucleoprotein complexes and modifications of the gRNA structure/composition to bind different proteins, have been recently developed to simultaneously and directionally target different effector domains to desired genomic sites of the cells (Esvelt et al. (2013) *Nat. Methods* 10:1116-21; Zetsche, B. et al. (2015) Cell pii: S0092-8674 (15) 01200-3; Dahlman, J. E. et al. (2015) Nat. Biotechnol. 2015 Oct. 5. doi: 10.1038/nbt.3390. [Epub ahead of print]; Zalatan, J. G. et al. (2015) Cell 160:339-50; Paix, A. et al. (2015) Genetics 201:47-54), and are suitable for use in the present invention.

For example, an ATR of the present invention may comprise the sequence:

```
(catalytically inactive Cas9; SEQ ID NO: 22)
MGGRRVRWEVYISRALWLTREPTAYVVLIEINTTHYRETQATGATMYPYD

VPDYASPKKKRKVEASDKKYSIGLAIGTNSVGWAVITDEYKVPSKKFKVL

GNTDRHSIKKNLIGALLFDSGETAEATRLKRTARRRYTRRKNRICYLQEI

FSNEMAKVDDSFFHRLEESFLVEEDKKHERHPIFGNIVDEVAYHEKYPTI

YHLRKKLVDSTDKADLRLIYLALAHMIKFRGHFLIEGDLNPDNSDVDKLF

IQLVQTYNQLFEENPINASGVDAKAILSARLSKSRRLENLIAQLPGEKKN

GLFGNLIALSLGLTPNFKSNFDLAEDAKLQLSKDTYDDDLDNLLAQIGDQ

YADLFLAAKNLSDAILLSDILRVNTEITKAPLSASMIKRYDEHHQDLTLL

KALVRQQLPEKYKEIFFDQSKNGYAGYIDGGASQEEFYKFIKPILEKMDG

TEELLVKLNREDLLRKQRTFDNGSIPHQIHLGELHAILRRQEDFYPFLKD

NREKIEKILTFRIPYYVGPLARGNSRFAWMTRKSEETITPWNFEEVVDKG

ASAQSFIERMTNFDKNLPNEKVLPKHSLLYEYFTVYNELTKVKYVTEGMR

KPAFLSGEQKKAIVDLLFKTNRKVTVKQLKEDYFKKIECFDSVEISGVED

RFNASLGTYHDLLKIIKDKDFLDNEENEDILEDIVLTLTLFEDREMIEER

LKTYAHLFDDKVMKQLKRRRYTGWGRLSRKLINGIRDKQSGKTILDFLKS

DGFANRNFMQLIHDDSLTFKEDIQKAQVSGQGDSLHEHIANLAGSPAIKK

GILQTVKVVDELVKVMGRHKPENIVIEMARENQTTQKGQKNSRERMKRIE

EGIKELGSQILKEHPVENTQLQNEKLYLYYLQNGRDMYVDQELDINRLSD

YDVDAIVPQSFLKDDSIDNKVLTRSDKNRGKSDNVPSEEVVKKMKNYVVR

QLLNAKLITQRKFDNLTKAERGGLSELDKAGFIKRQLVETRQITKHVAQI

LDSRMNTKYDENDKLIREVKVITLKSKLVSDFRKDFQFYKVREINNYHHA

HDAYLNAVVGTALIKKYPKLESEFVYGDYKVYDVRKMIAKSEQEIGKATA

KYFFYSNIMNFFKTEITLANGEIRKRPLIETNGETGEIVWDKGRDFATVR

KVLSMPQVNIVKKTEVQTGGFSKESILPKRNSDKLIARKKDWDPKKYGGF

DSPTVAYSVLVVAKVEKGKSKKLKSVKELLGITIMERSSFEKNPIDFLEA

KGYKEVKKDLIIKLPKYSLFELENGRKRMLASAGELQKGNELALPSKYVN

FLYLASHYEKLKGSPEDNEQKQLFVEQHKHYLDEIIEQISEFSKRVILAD

ANLDKVLSAYNKHRDKPIREQAENIIHLFTLTNLGAPAAFKYFDTTIDRK

RYTSTKEVLDATLIHQSITGLYETRIDLSQLGGDSPKKKRKVG
```

The ATR of the present invention may, for example, comprise an amino acid sequence that has 50%, 60%, 70%, 80%, 90%, 95%, 99% or 100% identity to SEQ ID NO: 22 wherein the amino acid sequence substantially retains the natural function of the protein represented by SEQ ID NO: 22.

The ATR of the present invention may, for example, be encoded by a polynucleotide comprising a nucleic acid sequence which encodes the protein of SEQ ID NO: 22, or a protein that has 50%, 60%, 70%, 80%, 90%, 95%, 99% or 100% amino acid identity to SEQ ID NO: 22 wherein the amino acid sequence substantially retains the natural function of the protein represented by SEQ ID NO: 22.

The ATR of the present invention may, for example, comprise an amino acid sequence that has at least 50%, 60%, 70%, 80%, 90%, 95%, 99% or 100% identity to SEQ ID NO: 22 wherein the amino acid sequence substantially retains the natural function of the protein represented by SEQ ID NO: 22.

The ATR of the present invention may, for example, be encoded by a polynucleotide comprising a nucleic acid sequence which encodes the protein of SEQ ID NO: 22, or a protein that has at least 50%, 60%, 70%, 80%, 90%, 95%, 99% or 100% amino acid identity to SEQ ID NO: 22 wherein the amino acid sequence substantially retains the natural function of the protein represented by SEQ ID NO: 22.

Example sequences of genomic target sites recognised by guide RNAs (gRNAs) for use in targeting the β2-microglobulin gene include:

```
gRNA #1:
                                    (SEQ ID NO: 23)
           TATAAGTGGAGGCGTCGCGC gRNA #2:
                                    (SEQ ID NO: 24)
           GCCCGAATGCTGTCAGCTTC gRNA #3:
                                    (SEQ ID NO: 25)
           TGCGTCGCTGGCTTGGAGAC gRNA #4:
                                    (SEQ ID NO: 26)
           CCAATCAGGACAAGGCCCGC gRNA #5:
                                    (SEQ ID NO: 27)
           AGGGTAGGAGAGACTCACGC gRNA #6:
                                    (SEQ ID NO: 28)
           GCGGGCCACCAAGGAGAACT gRNA #7:
                                    (SEQ ID NO: 29)
           GCTACTCTCTCTTTCTGGCC gRNA #8:
                                    (SEQ ID NO: 30)
           CTCCCGCTCTGCACCCTCTG gRNA #9:
                                    (SEQ ID NO: 31)
           TTTGGCCTACGGCGACGGGA gRNA #10:
                                    (SEQ ID NO: 32)
           GGGGCAAGTAGCGCGCGTCC gRNA #11:
                                    (SEQ ID NO: 33)
           TAGTCCAGGGCTGGATCTCG
```

Example of guide RNAs (gRNAs) for use in targeting the β2-microglobulin gene include:

```
                                    (SEQ ID NO: 149)
gRNA #1:    UAUAAGUGGAGGCGUCGCGC (SEQ ID NO: 150)
gRNA #2:    GCCCGAAUGCUGUCAGCUUC (SEQ ID NO: 151)
gRNA #3:    UGCGUCGCUGGCUUGGAGAC (SEQ ID NO: 152)
gRNA #4:    CCAAUCAGGACAAGGCCCGC
```

-continued

```
                              (SEQ ID NO: 153)
gRNA #5:       AGGGUAGGAGAGACUCACGC (SEQ ID NO: 154)
gRNA #6:       GCGGGCCACCAAGGAGAACU (SEQ ID NO: 155)
gRNA #7:       GCUACUCUCUCUUUCUGGCC (SEQ ID NO: 156)
gRNA #8:       CUCCCGCUCUGCACCCUCUG (SEQ ID NO: 157)
gRNA #9:       UUUGGCCUACGGCGACGGGA (SEQ ID NO: 158)
gRNA #10:      GGGGCAAGUAGCGCGCGUCC (SEQ ID NO: 159)
gRNA #11:      UAGUCCAGGGCUGGAUCUCG
```

All the above gRNAs may be fused to the gRNA scaffold with the following sequence:

```
                              (SEQ ID NO: 160)
GUUUAAGAGCUAUGCUGGAAACAGCAUAGCAAGUUUAAAUAAGGCUAGUC

CGUUAUCAACUUGAAAAAGUGGCACCGAGUCGGUGCU.
```

Example sequences of gRNAs targeting the BCL11A gene include:

```
gRNA #1 against CpG 105:
                              (SEQ ID NO: 71)
GCCUUUCUGCAGACGUUCCC gRNA #2 against CpG 105:
                              (SEQ ID NO: 72)
UGGGUGUGCGCCUUGGCCGG gRNA #3 against CpG 105:
                              (SEQ ID NO: 73)
CGGUGGUGAGAUGACCGCCU gRNA #4 against CpG 105:
                              (SEQ ID NO: 74)
GGAAUGUGCUCACGGCGCCG gRNA #5 against CpG 105:
                              (SEQ ID NO: 75)
GACUGCCCGCGCUUUGUCCU gRNA #6 against CpG 105:
                              (SEQ ID NO: 76)
CCAGAGUCUGGCCCCCGGAG gRNA #7 against CpG 105:
                              (SEQ ID NO: 77)
UCUGCGACCCUUAGGAGCCG gRNA #8 against CpG 105:
                              (SEQ ID NO: 78)
GAGCGCCCCGCCAAGCGACU gRNA #9 against CpG 105:
                              (SEQ ID NO: 79)
CAAGUCUCCAGGAGCCCGCG gRNA #10 against CpG 105:
                              (SEQ ID NO: 80)
CGCGGAAUCCAGCCUAAGUU gRNA #11 against CpG 105:
                              (SEQ ID NO: 81)
CCCGCUGCGGAGCUGUAACU gRNA #1 against CpG 31:
                              (SEQ ID NO: 82)
CGCUCCUGAGUCCGCGGAGU gRNA #2 against CpG 31:
                              (SEQ ID NO: 83)
CACGGCUCUCCCCGUCGCCG gRNA #3 against CpG 31:
                              (SEQ ID NO: 84)
CCGCCUUUUGUUCCGGCCAG gRNA #4 against CpG 31:
                              (SEQ ID NO: 85)
GCGCGAGGAGCCGGCACAAA gRNA #5 against CpG 31:
                              (SEQ ID NO: 86)
GCCACUUUCUCACUAUUGUG gRNA #6 against CpG 31:
                              (SEQ ID NO: 87)
GCUGCCUCUGAGGUUCGGUC gRNA #7 against CpG 31:
                              (SEQ ID NO: 88)
AAGGGCAGGAGCUAGGGCCG gRNA #8 against CpG 31:
                              (SEQ ID NO: 89)
GAGCCCGGACUGCUGCCUCC gRNA #1 against CpG 38:
                              (SEQ ID NO: 90)
GUUUACAAGCACCGCGUGUG gRNA #2 against CpG 38:
                              (SEQ ID NO: 91)
AACAGACAGAGGACCGAGCG gRNA #3 against CpG 38:
                              (SEQ ID NO: 92)
GGCGCCGGGUGGGCGAUCCG gRNA #4 against CpG 38:
                              (SEQ ID NO: 93)
GGUCGGGCAAGGCCCGGGCG gRNA #5 against CpG 38:
                              (SEQ ID NO: 94)
AAGAGGUCUCGGCAUUGUGC gRNA #6 against CpG 38:
                              (SEQ ID NO: 95)
GUUCCACAGCUUCGGGACCGCG gRNA #7 against CpG 38:
                              (SEQ ID NO: 96)
GAAAUCGGCUGGGUGAAACU gRNA #8 against CpG 38:
                              (SEQ ID NO: 97)
GCAGUGUCUCCGCGCCAGCC gRNA #9 against CpG 38:
                              (SEQ ID NO: 98)
CCUCCCCUCCCCUCCGCCCUGGG gRNA #1 against CpG 115:
                              (SEQ ID NO: 99)
UCCUCCUGUCCCGGGUUAAAGG gRNA #2 against CpG 115:
                              (SEQ ID NO: 100)
CAUCUUUUGGGACACUCUAGGCUGG gRNA #3 against CpG 115:
                              (SEQ ID NO: 101)
AAGUCAGGCCCUUCUUCGGAAGG
``` gRNA #4 against CpG 115:
(SEQ ID NO: 102)
GCAGCCUGGACUGCGCGCCCCGG gRNA #5 against CpG 115:
(SEQ ID NO: 103)
UGCCCGGCGAUUCUCGUCCG gRNA #6 against CpG 115:
(SEQ ID NO: 104)
UGAGCCAUUCGGUCGCUAGG gRNA #7 against CpG 115:
(SEQ ID NO: 105)
GGUGGUACUGAGGACCGGGA gRNA #8 against CpG 115:
(SEQ ID NO: 107)
AUUUUCUGGGUGCUCAGAGG gRNA #9 against CpG 115:
(SEQ ID NO: 108)
UGGUCUCAGCUCGCGCACGG gRNA #10 against CpG 115:
(SEQ ID NO: 109)
ACAAAGACAUACGGGUGAU Example sequences of gRNAs targeting the IFNAR1 gene include:

gRNA #1:   AGGAACGGCGCGUGCGCGGA (SEQ ID NO: 106)

gRNA #2:   AAGAGGCGGCGCGUGCGUAG (SEQ ID NO: 161)

gRNA #3:   GGGCGGUGUGACUUAGGACG (SEQ ID NO: 162)

gRNA #4:   CCAGAUGAUGGUCGUCCUCC (SEQ ID NO: 163)

gRNA #5:   GACCCUAGUGCUCGUCGCCG (SEQ ID NO: 164)

gRNA #6:   UGGGUGUUGUCCGCAGCCGC (SEQ ID NO: 165)

gRNA #7:   ACGGGGCGGCGAUGCUGUU (SEQ ID NO: 166)

gRNA #8:   GACCGAAGGUUUCCCAGACU (SEQ ID NO: 167)

gRNA #9:   GUCGGGUUUAAUCUUUGGCG (SEQ ID NO: 168)

gRNA #10:  CGCUCCCGAGGACCCGUACA (SEQ ID NO: 169)

gRNA #11:  CGGGUCCCACCCCCGUGAAA (SEQ ID NO: 170)

gRNA #12:  UCAAACUCGACACAAAGCUC (SEQ ID NO: 171)

gRNA #13:  GCGGAGCCGCGGUACUUUCC (SEQ ID NO: 172)

Example sequences of gRNAs targeting the VEGFA gene include:

gRNA #1:   GGCGCGCGCGCUAGGUGGGA (SEQ ID NO: 173)

gRNA #2:   AGAGAGGCUCACCGCCCACG (SEQ ID NO: 174)

gRNA #3:   GUACGUGCGGUGACUCCGGU (SEQ ID NO: 175)

All the above gRNAs may be fused to the gRNA scaffold with the following sequence:

(SEQ ID NO: 160)
GUUUAAGAGCUAUGCUGGAAACAGCAUAGCAAGUUUAAAUAAGGCUAGUC
CGUUAUUCAACUUGAAAAAGUGGCACCGAGUCGGUGCU.

Target Gene Repression

By "silencing a target gene", it is to be understood that the expression of the target gene is reduced to an extent sufficient to achieve a desired effect. The reduced expression may be sufficient to achieve a therapeutically relevant effect, such as the prevention or treatment of a disease. For example, a dysfunctional target gene which gives rise to a disease is preferably repressed to an extent that there is either no expression of the target gene, or the residual level of expression of the target gene is sufficiently low to ameliorate or prevent the disease state.

The reduced expression may be sufficient to enable investigations to be performed into the gene's function by studying cells reduced in or lacking that function.

Following administration of the two or more ATRs of the invention, the level of transcription or expression of the target gene may be reduced by, for example, at least 50%, 60%, 70%, 80%, 90%, 95%, 99% or 100% compared to the level of transcription or expression in the absence of the two or more ATRs.

Preferably, the two or more ATRs of the present invention have a synergistic effect in silencing a target gene. The two or more ATRs of the present invention may therefore demonstrate synergy, for example therapeutic synergy, when used as described herein.

For example, the two or more ATRs of the present invention may result in a synergistic increase in the fraction of a population of cells comprising the two or more ATRs that exhibits a silenced target gene, in comparison to a population of cells that lacks the two or more ATRs (e.g. comprises only one ATR or comprises a different combination of ATRs). Alternatively, or additionally, the two or more ATRs of the present invention may result in a synergistic increase in the duration that the target gene is silenced in a population of cells comprising the two or more ATRs, in comparison to a population of cells that lacks the two or more ATRs.

Preferably, the silencing of the target gene occurs following transient delivery or expression of the ATRs of the present invention to or in a cell.

By "transient expression", it is to be understood that the expression of the ATR is not stable over a prolonged period of time. Preferably, the polynucleotide encoding the ATR does not integrate into the host genome. More specifically, transient expression may be expression which is substantially lost within 20 weeks following introduction of the polynucleotide encoding the ATR into the cell. Preferably, expression is substantially lost within 12, 6, 4 or 2 weeks following introduction of the polynucleotide encoding the ATR into the cell.

Similarly, by "transient delivery", it is to be understood that the ATR substantially does not remain in the cell (i.e. is substantially lost by the cell) over a prolonged period of time. More specifically, transient delivery may result in the ATR being substantially lost by the cell within 20 weeks following introduction of the ATR into the cell. Preferably, the ATR is substantially lost within 12, 6, 4 or 2 weeks following introduction of the ATR into the cell.

Methods for determining the transcription of a gene, for example the target of an ATR, are known in the art. Suitable methods include reverse transcription PCR and Northern blot-based approaches. In addition to the methods for determining the transcription of a gene, methods for determining the expression of a gene are known in the art. Suitable additional methods include Western blot-based or flow cytometry approaches.

The effect of an ATR or combination of ATRs may be studied by comparing the transcription or expression of the target gene, for example a gene endogenous to a cell, in the presence and absence of the ATRs or combination of ATRs.

The effect of an ATR or combination of ATRs may also be studied using a model system wherein the expression of a reporter gene, for example a gene encoding a fluorescent protein, is monitored. Suitable methods for monitoring expression of such reporter genes include flow cytometry, fluorescence-activated cell sorting (FACS) and fluorescence microscopy.

For example, a population of cells may be transfected with a vector which harbours a reporter gene. The vector may be constructed such that the reporter gene is expressed when the vector transfects a cell. Suitable reporter genes include genes encoding fluorescent proteins, for example green, yellow, cherry, cyan or orange fluorescent proteins. In addition, the population of cells may be transfected with vectors encoding the ATRs of interest. Subsequently, the number of cells expressing and not-expressing the reporter gene, as well as the level of expression of the reporter gene may be quantified using a suitable technique, such as FACS. The level of reporter gene expression may then be compared in the presence and absence of the ATRs.

Preferably, the target gene is silenced permanently. By "permanent silencing" of a target gene, it is to be understood that transcription or expression of the target gene is reduced (e.g. reduced by 100%) compared to the level of transcription or expression in the absence of the two or more ATRs for at least 2 months, 6 months, 1 year, 2 year or the entire lifetime of the cell/organism. Preferably, a permanently silenced target gene remains silenced for the remainder of the cell's life.

Preferably the target gene remains silenced in the progeny of the cell to which the two or more ATRs of the invention has been administered (i.e. the silencing of the target gene is inherited by the cell's progeny). For example, the two or more ATRs of the invention may be administered to a stem cell (e.g. a haematopoietic stem cell) to silence a target gene in a stem cell and also in the stem cell's progeny, which may include cells that have differentiated from the stem cell.

A target gene may be silenced by using ATRs which bind to the target gene itself or to regulatory sequences for the target gene (e.g. promoter or enhancer sequences). Furthermore, alternative splicing of a target gene may be altered by using ATRs which bind to the splicing sites of the target gene itself. The ability to silence a target gene or to modulate its splicing variants by using ATRs which bind to regulatory sequences is not possible with certain other gene silencing technologies and is a particular advantage of the present invention.

Use in Therapy

In another aspect, the present invention provides the products, artificial transcription repressors (ATRs), polynucleotides and cells of the present invention for use in therapy.

The use in therapy may, for example, be a use for the treatment of β-thalassemia or sickle cell anaemia.

The use in therapy may, for example, be a use for the preparation of "universally" allogeneic transplantable cells (e.g. by the silencing of 32-microglobulin, B2M). This use may, for example, be applied to the preparation of haematopoietic stem and/or progenitor cells (HSPCs), whole organ transplantation and cancer immunotherapy.

The two or more ATRs, or polynucleotides encoding therefor, may be administered simultaneously, in combination, sequentially or separately (as part of a dosing regime).

By "simultaneously", it is to be understood that the two agents are administered concurrently, whereas the term "in combination" is used to mean they are administered, if not simultaneously, then "sequentially" within a time frame that they both are available to act therapeutically within the same time frame. Thus, administration "sequentially" may permit one agent to be administered within 5 minutes, 10 minutes or a matter of hours after the other provided the circulatory half-life of the first administered agent is such that they are both concurrently present in therapeutically effective amounts. The time delay between administration of the components will vary depending on the exact nature of the components, the interaction there-between, and their respective half-lives.

In contrast to "in combination" or "sequentially", "separately" is to be understood as meaning that the gap between administering one agent and the other agent is significant, i.e. the first administered agent may no longer be present in the bloodstream in a therapeutically effective amount when the second agent is administered.

Target Gene

Preferably, the target gene gives rise to a therapeutic effect when silenced.

By way of example, the products, artificial transcription repressors (ATRs) and polynucleotides of the present invention may be used to silence β2-microglobulin (B2M), BCL11A, KLF1, globin genes, CCR5, CXCR4, TCR genes, miR126, PDL1, CTLA4, COL1A1, viral sequences and oncogenes.

Silencing of the TCR genes, PDL1 and CTLA4 may be used to improve efficacy of cancer immunotherapy approaches.

Silencing of B2M may be used to generate allogeneic HSPCs, T-cells or mesenchymal cells to be used for transplantation.

Silencing of miR126 may be used to expand the more primitive haematopoietic stem cell pool prior to or after their infusion.

By way of example, the products, artificial transcription repressors (ATRs), polynucleotides and cells of the present invention may be used in the treatment of, for example, Huntington's disease, Spinocerebellar ataxias, collagenopathies, haemaglobinopathies and diseases caused by trinucleotide expansions. Furthermore, the product of the present invention may be used in the treatment or prevention of certain infectious diseases (e.g. CCR5-tropic HIV infections) by inactivating either pathogen-associated gene products or host genes that are necessary for the pathogen life cycle.

In addition, or in the alternative, the products, artificial transcription repressors (ATRs), polynucleotides and cells of the present invention may be useful in the treatment of the disorders listed in WO 1998/005635. For ease of reference, part of that list is now provided: cancer, inflammation or inflammatory disease, dermatological disorders, fever, cardiovascular effects, haemorrhage, coagulation and acute phase response, cachexia, anorexia, acute infection, HIV infection, shock states, graft-versus-host reactions, autoimmune disease, reperfusion injury, meningitis, migraine and aspirin-dependent anti-thrombosis; tumour growth, invasion and spread, angiogenesis, metastases, malignant, ascites and malignant pleural effusion; cerebral ischaemia, ischaemic heart disease, osteoarthritis, rheumatoid arthritis, osteoporosis, asthma, multiple sclerosis, neurodegeneration, Alzheimer's disease, atherosclerosis, stroke, vasculitis, Crohn's disease and ulcerative colitis; periodontitis, gingivitis; psoriasis, atopic dermatitis, chronic ulcers, epidermolysis bullosa; corneal ulceration, retinopathy and surgical wound healing; rhinitis, allergic conjunctivitis, eczema, anaphylaxis; restenosis, congestive heart failure, endometriosis, atherosclerosis or endosclerosis.

In addition, or in the alternative, the products, artificial transcription repressors (ATRs), polynucleotides and cells of the present invention may be useful in the treatment of the disorders listed in WO 1998/007859. For ease of reference, part of that list is now provided: cytokine and cell proliferation/differentiation activity; immunosuppressant or immunostimulant activity (e.g. for treating immune deficiency, including infection with human immune deficiency virus; regulation of lymphocyte growth; treating cancer and many autoimmune diseases, and to prevent transplant rejection or induce tumour immunity); regulation of haematopoiesis, e.g. treatment of myeloid or lymphoid diseases; promoting growth of bone, cartilage, tendon, ligament and nerve tissue, e.g. for healing wounds, treatment of burns, ulcers and periodontal disease and neurodegeneration; inhibition or activation of follicle-stimulating hormone (modulation of fertility); chemotactic/chemokinetic activity (e.g. for mobilising specific cell types to sites of injury or infection); haemostatic and thrombolytic activity (e.g. for treating haemophilia and stroke); anti-inflammatory activity (for treating e.g. septic shock or Crohn's disease); as anti-microbials; modulators of e.g. metabolism or behaviour; as analgesics; treating specific deficiency disorders; in treatment of e.g. psoriasis, in human or veterinary medicine.

In addition, or in the alternative, the products, artificial transcription repressors (ATRs), polynucleotides and cells of the present invention may be useful in the treatment of the disorders listed in WO 1998/009985. For ease of reference, part of that list is now provided: macrophage inhibitory and/or T cell inhibitory activity and thus, anti-inflammatory activity; anti-immune activity, i.e. inhibitory effects against a cellular and/or humoral immune response, including a response not associated with inflammation; inhibit the ability of macrophages and T cells to adhere to extracellular matrix components and fibronectin, as well as up-regulated fas receptor expression in T cells; inhibit unwanted immune reaction and inflammation including arthritis, including rheumatoid arthritis, inflammation associated with hypersensitivity, allergic reactions, asthma, systemic lupus erythematosus, collagen diseases and other autoimmune diseases, inflammation associated with atherosclerosis, arteriosclerosis, atherosclerotic heart disease, reperfusion injury, cardiac arrest, myocardial infarction, vascular inflammatory disorders, respiratory distress syndrome or other cardiopulmonary diseases, inflammation associated with peptic ulcer, ulcerative colitis and other diseases of the gastrointestinal tract, hepatic fibrosis, liver cirrhosis or other hepatic diseases, thyroiditis or other glandular diseases, glomerulonephritis or other renal and urologic diseases, otitis or other oto-rhino-laryngological diseases, dermatitis or other dermal diseases, periodontal diseases or other dental diseases, orchitis or epididimo-orchitis, infertility, orchidal trauma or other immune-related testicular diseases, placental dysfunction, placental insufficiency, habitual abortion, eclampsia, pre-eclampsia and other immune and/or inflammatory-related gynaecological diseases, posterior uveitis, intermediate uveitis, anterior uveitis, conjunctivitis, chorioretinitis, uveoretinitis, optic neuritis, intraocular inflammation, e.g. retinitis or cystoid macular oedema, sympathetic ophthalmia, scleritis, retinitis pigmentosa, immune and inflammatory components of degenerative fondus disease, inflammatory components of ocular trauma, ocular inflammation caused by infection, proliferative vitreo-retinopathies, acute ischaemic optic neuropathy, excessive scarring, e.g. following glaucoma filtration operation, immune and/or inflammation reaction against ocular implants and other immune and inflammatory-related ophthalmic diseases, inflammation associated with autoimmune diseases or conditions or disorders where, both in the central nervous system (CNS) or in any other organ, immune and/or inflammation suppression would be beneficial, Parkinson's disease, complication and/or side effects from treatment of Parkinson's disease, AIDS-related dementia complex HIV-related encephalopathy, Devic's disease, Sydenham chorea, Alzheimer's disease and other degenerative diseases, conditions or disorders of the CNS, inflammatory components of stokes, post-polio syndrome, immune and inflammatory components of psychiatric disorders, myelitis, encephalitis, subacute sclerosing pan-encephalitis, encephalomyelitis, acute neuropathy, subacute neuropathy, chronic neuropathy, Guillaim-Barre syndrome, Sydenham chora, myasthenia gravis, pseudo-tumour cerebri, Down's Syndrome, Huntington's disease, amyotrophic lateral sclerosis, inflammatory components of CNS compression or CNS trauma or infections of the CNS, inflammatory components of muscular atrophies and dystrophies, and immune and inflammatory related diseases, conditions or disorders of the central and peripheral nervous systems, post-traumatic inflammation, septic shock, infectious diseases, inflammatory complications or side effects of surgery, bone marrow transplantation or other transplantation complications and/or side effects, inflammatory and/or immune complications and side effects of gene therapy, e.g. due to infection with a viral carrier, or inflammation associated with AIDS, to suppress or inhibit a humoral and/or cellular immune response, to treat or ameliorate monocyte or leukocyte proliferative diseases, e.g. leukaemia, by reducing the amount of monocytes or lymphocytes, for the prevention and/or treatment of graft rejection in cases of transplantation of natural or artificial cells, tissue and organs such as cornea, bone marrow, organs, lenses, pacemakers, natural or artificial skin tissue.

Polynucleotides

Polynucleotides of the invention may comprise DNA or RNA. They may be single-stranded or double-stranded. It will be understood by a skilled person that numerous different polynucleotides can encode the same polypeptide as a result of the degeneracy of the genetic code. In addition, it is to be understood that the skilled person may, using routine techniques, make nucleotide substitutions that do not affect the polypeptide sequence encoded by the polynucleotides of the invention to reflect the codon usage of any particular host organism in which the polypeptides of the invention are to be expressed.

The polynucleotides may be modified by any method available in the art. Such modifications may be carried out in order to enhance the in vivo activity or lifespan of the polynucleotides of the invention.

Polynucleotides such as DNA polynucleotides may be produced recombinantly, synthetically or by any means available to those of skill in the art. They may also be cloned by standard techniques.

Longer polynucleotides will generally be produced using recombinant means, for example using polymerase chain reaction (PCR) cloning techniques. This will involve making a pair of primers (e.g. of about 15 to 30 nucleotides) flanking the target sequence which it is desired to clone, bringing the primers into contact with mRNA or cDNA obtained from an animal or human cell, performing a polymerase chain reaction under conditions which bring about amplification of the desired region, isolating the amplified fragment (e.g. by purifying the reaction mixture with an agarose gel) and recovering the amplified DNA. The primers may be designed to contain suitable restriction enzyme recognition sites so that the amplified DNA can be cloned into a suitable vector.

Proteins

As used herein, the term "protein" includes single-chain polypeptide molecules as well as multiple-polypeptide complexes where individual constituent polypeptides are linked by covalent or non-covalent means. As used herein, the terms "polypeptide" and "peptide" refer to a polymer in which the monomers are amino acids and are joined together through peptide or disulfide bonds.

Variants, Derivatives, Analogues, Homologues and Fragments

In addition to the specific proteins and nucleotides mentioned herein, the present invention also encompasses the use of variants, derivatives, analogues, homologues and fragments thereof.

In the context of the present invention, a variant of any given sequence is a sequence in which the specific sequence of residues (whether amino acid or nucleic acid residues) has been modified in such a manner that the polypeptide or polynucleotide in question substantially retains at least one of its endogenous functions. A variant sequence can be obtained by addition, deletion, substitution, modification, replacement and/or variation of at least one residue present in the naturally-occurring protein.

The term "derivative" as used herein, in relation to proteins or polypeptides of the present invention includes any substitution of, variation of, modification of, replacement of, deletion of and/or addition of one (or more) amino acid residues from or to the sequence providing that the resultant protein or polypeptide substantially retains at least one of its endogenous functions. The term "analogue" as used herein, in relation to polypeptides or polynucleotides includes any mimetic, that is, a chemical compound that possesses at least one of the endogenous functions of the polypeptides or polynucleotides which it mimics.

Typically, amino acid substitutions may be made, for example from 1, 2 or 3 to 10 or 20 substitutions provided that the modified sequence substantially retains the required activity or ability. Amino acid substitutions may include the use of non-naturally occurring analogues.

Proteins used in the present invention may also have deletions, insertions or substitutions of amino acid residues which produce a silent change and result in a functionally equivalent protein. Deliberate amino acid substitutions may be made on the basis of similarity in polarity, charge, solubility, hydrophobicity, hydrophilicity and/or the amphipathic nature of the residues as long as the endogenous function is retained. For example, negatively charged amino acids include aspartic acid and glutamic acid; positively charged amino acids include lysine and arginine; and amino acids with uncharged polar head groups having similar hydrophilicity values include asparagine, glutamine, serine, threonine and tyrosine.

Conservative substitutions may be made, for example according to the table below. Amino acids in the same block in the second column and preferably in the same line in the third column may be substituted for each other:

| ALIPHATIC | Non - polar | G A P |
| | | I L V |
| | Polar - uncharged | C S T M |
| | | N Q |
| | Polar - charged | D E |
| | | K R H |
| AROMATIC | | F W Y |

The term "homologue" as used herein means an entity having a certain homology with the wild type amino acid sequence and the wild type nucleotide sequence. The term "homology" can be equated with "identity".

A homologous sequence may include an amino acid sequence which may be at least 50%, 55%, 65%, 75%, 85% or 90% identical, preferably at least 95% or 97% or 99% identical to the subject sequence. Typically, the homologues will comprise the same active sites etc. as the subject amino acid sequence. Although homology can also be considered in terms of similarity (i.e. amino acid residues having similar chemical properties/functions), in the context of the present invention it is preferred to express homology in terms of sequence identity.

A homologous sequence may include a nucleotide sequence which may be at least 50%, 55%, 65%, 75%, 85% or 90% identical, preferably at least 95% or 97% or 99% identical to the subject sequence. Although homology can also be considered in terms of similarity, in the context of the present invention it is preferred to express homology in terms of sequence identity.

Preferably, reference to a sequence which has a percent identity to any one of the SEQ ID NOs detailed herein refers to a sequence which has the stated percent identity over the entire length of the SEQ ID NO referred to.

Homology comparisons can be conducted by eye or, more usually, with the aid of readily available sequence comparison programs. These commercially available computer programs can calculate percentage homology or identity between two or more sequences.

Percentage homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion in the nucleotide sequence may cause the following codons to be put out of alignment, thus potentially resulting in a large reduction in percent homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible, reflecting higher relatedness between the two compared sequences, will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package the default gap penalty for amino acid sequences is-12 for a gap and −4 for each extension.

Calculation of maximum percentage homology therefore firstly requires the production of an optimal alignment, taking into consideration gap penalties. A suitable computer program for carrying out such an alignment is the GCG Wisconsin Bestfit package (University of Wisconsin, U.S.A.; Devereux et al. (1984) *Nucleic Acids Res.* 12:387). Examples of other software that can perform sequence comparisons include, but are not limited to, the BLAST package (see Ausubel et al. (1999) *ibid*-Ch. 18), FASTA (Atschul et al. (1990) *J. Mol. Biol.* 403-410) and the GENE-WORKS suite of comparison tools. Both BLAST and FASTA are available for offline and online searching (see Ausubel et al. (1999) *ibid*, pages 7-58 to 7-60). However, for some applications, it is preferred to use the GCG Bestfit program. Another tool, called BLAST 2 Sequences is also available for comparing protein and nucleotide sequences (see *FEMS Microbiol. Lett.* (1999) 174:247-50; *FEMS Microbiol. Lett.* (1999) 177:187-8).

Although the final percentage homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see the user manual for further details). For some applications, it is preferred to use the public default values for the GCG package, or in the case of other software, the default matrix, such as BLOSUM62.

Once the software has produced an optimal alignment, it is possible to calculate percentage homology, preferably percentage sequence identity. The software typically does this as part of the sequence comparison and generates a numerical result.

"Fragments" are also variants and the term typically refers to a selected region of the polypeptide or polynucleotide that is of interest either functionally or, for example, in an assay. "Fragment" thus refers to an amino acid or nucleic acid sequence that is a portion of a full-length polypeptide or polynucleotide.

Such variants may be prepared using standard recombinant DNA techniques such as site-directed mutagenesis. Where insertions are to be made, synthetic DNA encoding the insertion together with 5' and 3' flanking regions corresponding to the naturally-occurring sequence either side of the insertion site may be made. The flanking regions will contain convenient restriction sites corresponding to sites in the naturally-occurring sequence so that the sequence may be cut with the appropriate enzyme(s) and the synthetic DNA ligated into the cut. The DNA is then expressed in accordance with the invention to make the encoded protein. These methods are only illustrative of the numerous standard techniques known in the art for manipulation of DNA sequences and other known techniques may also be used.

Codon Optimisation

The polynucleotides used in the present invention may be codon-optimised. Codon optimisation has previously been described in WO 1999/41397 and WO 2001/79518. Different cells differ in their usage of particular codons. This codon bias corresponds to a bias in the relative abundance of particular tRNAs in the cell type. By altering the codons in the sequence so that they are tailored to match with the relative abundance of corresponding tRNAs, it is possible to increase expression. By the same token, it is possible to decrease expression by deliberately choosing codons for which the corresponding tRNAs are known to be rare in the particular cell type. Thus, an additional degree of translational control is available.

Vectors

A vector is a tool that allows or facilitates the transfer of an entity from one environment to another. In accordance with the present invention, and by way of example, some vectors used in recombinant nucleic acid techniques allow entities, such as a segment of nucleic acid (e.g. a heterologous DNA segment, such as a heterologous cDNA segment), to be transferred into a target cell. The vector may serve the purpose of maintaining the heterologous nucleic acid (DNA or RNA) within the cell, facilitating the replication of the vector comprising a segment of nucleic acid, or facilitating the expression of the protein encoded by a segment of nucleic acid. Vectors may be non-viral or viral. Examples of vectors used in recombinant nucleic acid techniques include, but are not limited to, plasmids, mRNA molecules (e.g. in vitro transcribed mRNAs), chromosomes, artificial chromosomes and viruses. The vector may also be, for example, a naked nucleic acid (e.g. DNA). In its simplest form, the vector may itself be a nucleotide of interest.

The vectors used in the invention may be, for example, plasmid, mRNA or virus vectors and may include a promoter for the expression of a polynucleotide and optionally a regulator of the promoter.

Vectors comprising polynucleotides used in the invention may be introduced into cells using a variety of techniques known in the art, such as transfection, transformation and transduction. Several such techniques are known in the art, for example infection with recombinant viral vectors, such as retroviral, lentiviral (e.g. integration-defective lentiviral), adenoviral, adeno-associated viral, baculoviral and herpes simplex viral vectors; direct injection of nucleic acids and biolistic transformation.

Non-viral delivery systems include but are not limited to DNA transfection methods. Here, transfection includes a process using a non-viral vector to deliver a gene to a target cell. Typical transfection methods include electroporation, DNA biolistics, lipid-mediated transfection, compacted DNA-mediated transfection, liposomes, immunoliposomes, lipofectin, cationic agent-mediated transfection, cationic facial amphiphiles (CFAs) (Nat. Biotechnol. (1996) 14:556) and combinations thereof.

The term "transfection" is to be understood as encompassing the delivery of polynucleotides to cells by both viral and non-viral delivery.

Protein Transduction

As an alternative to the delivery of polynucleotides to cells, the products and artificial transcription repressors (ATRs) of the present invention may be delivered to cells by protein transduction.

Protein transduction may be via vector delivery (Cai, Y. et al. (2014) *Elife* 3: e01911; Maetzig, T. et al. (2012) *Curr. Gene Ther.* 12:389-409). Vector delivery involves the engineering of viral particles (e.g. lentiviral particles) to comprise the proteins to be delivered to a cell. Accordingly, when the engineered viral particles enter a cell as part of their natural life cycle, the proteins comprised in the particles are carried into the cell.

Protein transduction may be via protein delivery (Gaj, T. et al. (2012) Nat. Methods 9:805-7). Protein delivery may be achieved, for example, by utilising a vehicle (e.g. liposomes) or even by administering the protein itself directly to a cell.

Pharmaceutical Composition

The products, artificial transcription repressors (ATRs), polynucleotides and cells of the present invention may be formulated for administration to subjects with a pharmaceutically acceptable carrier, diluent or excipient. Suitable carriers and diluents include isotonic saline solutions, for example phosphate-buffered saline, and potentially contain human serum albumin.

Handling of the cell therapy products is preferably performed in compliance with FACT-JACIE International Standards for cellular therapy.

Kit

In one aspect, the present invention provides a kit comprising two or more artificial transcription repressors (ATRs), or polynucleotides encoding therefor, selected from groups (a), (b) or (c): (a) an ATR comprising a DNA-binding domain operably linked to a KRAB domain or homologue thereof; (b) an ATR comprising a DNA-binding domain operably linked to a DNMT3A, DNMT3B or DNMT1 domain or homologue thereof; and (c) an ATR comprising a DNA-binding domain operably linked to a DNMT3L domain or homologue thereof, wherein at least two of the ATRs are selected from different groups (a), (b) or (c).

The two or more ATRs, or polynucleotides encoding therefor, may be provided in suitable containers.

The kit may also include instructions for use, for example instructions for the simultaneous, sequential or separate administration of the two or more ATRs, or polynucleotides encoding therefor, to a subject in need thereof.

Method of Treatment

It is to be appreciated that all references herein to treatment include curative, palliative and prophylactic treatment; although in the context of the present invention references to preventing are more commonly associated with prophylactic treatment. The treatment of mammals, particularly humans, is preferred. Both human and veterinary treatments are within the scope of the present invention.

EXAMPLES

Example 1

With the aim of recapitulating the endogenous epigenetic mechanisms that permanently silence endogenous retroviruses (ERVs) during development, we employed the Krüppel-associated box (KRAB) domain of human zinc finger protein 10 (ZNF10; Szulc, J. et al. (2006) *Nat. Methods* 3:109-16) and the catalytic domain of human DNA methyltransferase 3A (DNMT3A; Law, J. A. et al. (2010) *Nat. Rev. Genet.* 11:204-20). The amino acid sequences of these domains are shown in Table 1.

To test the activity and stability of gene silencing induced by these two effector domains we used the tetracycline (tet) responsive system. We separately fused the two effector domains to the *E. coli* tetracycline-controlled Repressor (tetR) DNA-binding domain (Gossen, M. et al. (1992) *Proc. Natl. Acad. Sci. USA* 89:5547-51), generating the tetR:KRAB and the tetR:DNMT3A artificial transcription repressors (ATRs, hereafter referred as tetR:K and tetR:D3A, respectively). The advantage of the tetR system is that it allows temporal control of binding of tetR to its target nucleotide sequence, the tetracycline operon (TetO), by doxycycline (doxy) administration. This allows us to investigate if the chromatin states induced by the ATRs can be maintained after the release of the ATRs from their target locus.

To rapidly assess activity of the ATRs we devised an experimental cell model in which activity of the ATRs can be easily followed over time by flow cytometry analyses (FIG. 1). Specifically, we generated single cell-derived clones of K562 cells engineered to contain within the first intron of the PPP1R12C gene (Lombardo, A. et al. (2011) *Nat. Methods* 8:861-9; also known as the AAVS1 locus) homozygous insertion of an eGFP-expression cassette followed by seven tandem repeats of TetO (TetO7; FIG. 1, top schematic). Expression of the eGFP marker in this reporter construct is driven by the ubiquitously expressed human phosphoglycerate kinase (hPGK) gene promoter. This reporter cell line will hereafter be referred to as the AAVS1/TetO7 cell line.

Upon expression of the ATRs, these chimeric proteins bind to the TetO7 element through their tetR DNA binding domain, thus eventually leading to the deposition of repressive epigenetic marks over the nearby chromatin (shown as red lollipops on the hPGK promoter; FIG. 1, middle schematic). This induces transcriptional silencing of the cassette. Upon conditional release of the ATR from the TetO7 element by doxy administration, the repressive marks can be either erased or propagated to the cell progeny by the endogenous cell machinery, thereby leading to transcriptional reactivation or permanent silencing of eGFP expression, respectively (FIG. 1, bottom schematics). Major advantages in the use of such an experimental model are: i) activity of the ATRs can be rapidly and easily monitored by observing eGFP expression by flow cytometry analysis; and ii) because these clones were engineered to contain homozygous insertion of the cassette, we can study the epigenetic and transcriptional impact of silencing on the genes at and nearby the integration site without the confounding effect of the unmodified wild-type locus.

In order to assess if the new ATRs were biologically active, we delivered the tetR:K and tetR:D3A into the AAVS1/TetO7 cell line using standard integrating bidirectional lentiviral vectors (Amendola, M. et al. (2005) *Nat. Biotechnol.* 23:108-16; Bid.LV; FIG. 2A). The advantage of these vectors is that they constitutively co-express the ATRs and a marker gene (either the truncated low-affinity nerve growth factor receptor-ΔLNGFR- or monomeric orange-mOrange-) from the same promoter, thus allowing us to restrict our analysis of silencing exclusively to the cells expressing the ATRs.

In summary, by virtue of the experimental setting described, we can test if constitutive binding of candidate ATRs to the TetO7 cassette is able to deposit repressive epigenetic marks over the nearby chromatin and to induce transcriptional silencing of the reporter cassette. In this case, the subsequent conditional release of ATR binding by doxy administration allows us to discern if the artificially induced repressive marks are then erased (thereby leading to transcriptional reactivation), or propagated to the cell progeny by the endogenous machinery (thus indicating that a permanently inherited epigenetic silencing state has been established).

Upon molecular characterisation, the AAVS1/Tet07 cell line was transduced with either Bid.LV-tetR:K or Bid.LV-tetR:D3A in the presence or absence of doxy and then maintained in these culture conditions for up to 200 days. During this time, the cells were periodically analysed by flow cytometry to measure the percentage of eGFP-negative (eGFP-) cells within the Bid.LV-transduced cell populations. As shown in FIG. 2B, constitutive binding of the ATRs to the TetO7 sequence (doxy-conditions) eventually led to eGFP silencing in 100% of the transduced cells, although with different kinetics between the two ATRs. Specifically, the tetR:K transduced cells rapidly became eGFP-(FIG. 2B, left histogram) and this effect was independent of the level of transduction (FIG. 2C, left flow cytometry dot blots). On the other hand, silencing induced by tetR:D3A was significantly slower (FIG. 2B, right histogram). In this case, the cells with the higher expression level of the marker gene (likely those with higher vector copy number, VCN) were the first to be silenced (FIG. 2C, right flow cytometry dot blots), indicating the requirement of a certain level of expression of the tetR:D3A to ensure faster repression. Importantly, at later time points (~200 days), flow cytometry analyses showed that the mean fluorescence intensity (MFI) of eGFP was superimposable between silenced and wild-type (WT) K562 cells (compare MFIs in FIG. 2C), indicating complete silencing of eGFP expression. When doxy was present in the cultures (doxy+ conditions), none of the transduced cells silenced eGFP, indicating that ATR binding to the target sequence is necessary to induce silencing. Overall, these data show that both ATRs are functional although they induce silencing with different kinetics.

We then assessed if release of the ATRs from the locus would result in eGFP reactivation. To this aim, we sorted the eGFP-cells at day 21 post Bid. LVs transduction and then cultured these cells in the presence or absence of doxy for an additional 170 days. Interestingly, doxy administration resulted in two opposite outcomes according to the ATR used: silencing induced by tetR:K was rapidly (within 15 days post doxy administration) and fully erased in the whole cell population (FIG. 2D, left histogram and representative flow cytometry analyses at the bottom); while silencing induced by tetR:D3A was maintained unaltered throughout the duration of the experiment (FIG. 2D, right histogram and representative flow cytometry analyses at the bottom). This clearly indicates that, opposite to tetR:K which has to be continuously active on the locus to repress it, tetR:D3A is able to establish repressive epigenetic modifications that can be permanently propagated by the endogenous cellular machinery even in the absence of the initial stimulus. This difference can be explained by the fact that in somatic cells, the KRAB-based machinery is not able to efficiently induce DNA methylation (which can be stably propagated), and deposits only reversible epigenetic marks, such as H3K9 methylation (Hathaway, N. A. et al. (2012) Cell 149:1447-60).

Overall, these experiments clearly show that even in the absence of binding of tetR:D3A to the TetO7 element, silencing of the reporter cassette can be maintained unaltered throughout several cell generations. On the other hand, conditional release of tetR:K from the TetO7 element leads to rapid and full reactivation of eGFP expression in tetR:K transduced cells.

DNA methylation is involved in the maintenance of permanent silencing induced by tetR:D3A In order to understand if DNA methylation was necessary to maintain the repressive state induced by tetR:D3A, the eGFP-cells from the doxy-conditions in FIG. 2D were treated with either 5-Aza-2'-deoxycytidine (5-Aza) or vehicle (i.e. Dimethyl Sulfoxide, DMSO) and then analysed by flow cytometry to measure eGFP expression. 5-Aza is a cytosine analogue that after becoming incorporated into DNA is recognised by DNA methyltransferase as a substrate, establishing a covalent bond that, contrary to cytosine, is not resolved, thus blocking DNMT activity (Issa, J. P. et al. (2005) Nat. Rev. Drug Discov. Suppl. S6-7). As shown in FIG. 2E, treatment with 5-Aza resulted in full reactivation of eGFP expression. As expected, DMSO treatment did not alter silencing of eGFP, with eGFP+ cells in the culture representing contaminant cells from the cell sorting procedure.

Contrary to tetR:K, tetR:D3A-Induced Repression is Confined to the Target Locus

One of the requisites necessary for a safe epigenetic therapy approach is that silencing should not spread into the genes surrounding the desired target gene. Note that the site-specific integration of the reporter cassette into the AAVS1 locus allows us to easily analyse the impact of our silencing platform on the expression of genes embedded near the reporter cassette integration site. Thus, we compared the expression levels of the genes at and nearby the AAVS1 integration site (FIG. 3A) between the eGFP-cells from FIG. 2 and the untreated AAVS1/TetO7 cell line.

eGFP-cells transduced with tetR:K significantly down-regulated all the analysed genes (FIG. 3B, left histogram; data are represented as mean±SEM, n=3), indicating that this ATR deposits repressive marks able to spread for at least 340 kb (~170 kb on both sides of the ATR binding site). This finding is consistent with previous studies performed in other somatic cell lines and showing that tetR:K can silence promoters located several tens of kilobases away from the ATR binding sites through the long-range spreading of H3K9me3 (Groner, A. C. et al. (2010) PLoS Genet. 6: e1000869). Importantly, when analysing the eGFP-cells transduced with tetR:D3A and grown with doxy, only eGFP and, to a lesser extent, the PPP1R12C gene (hosting the reporter cassette in its first intron) showed a significant down-regulation (FIG. 3B, right histogram; data are represented as mean±SEM, n=3; *$p<0.0001$ and $p<0.001$, one-way anova and Bonferroni post-test), indicating a very localised epigenetic repression.

Figure 4:
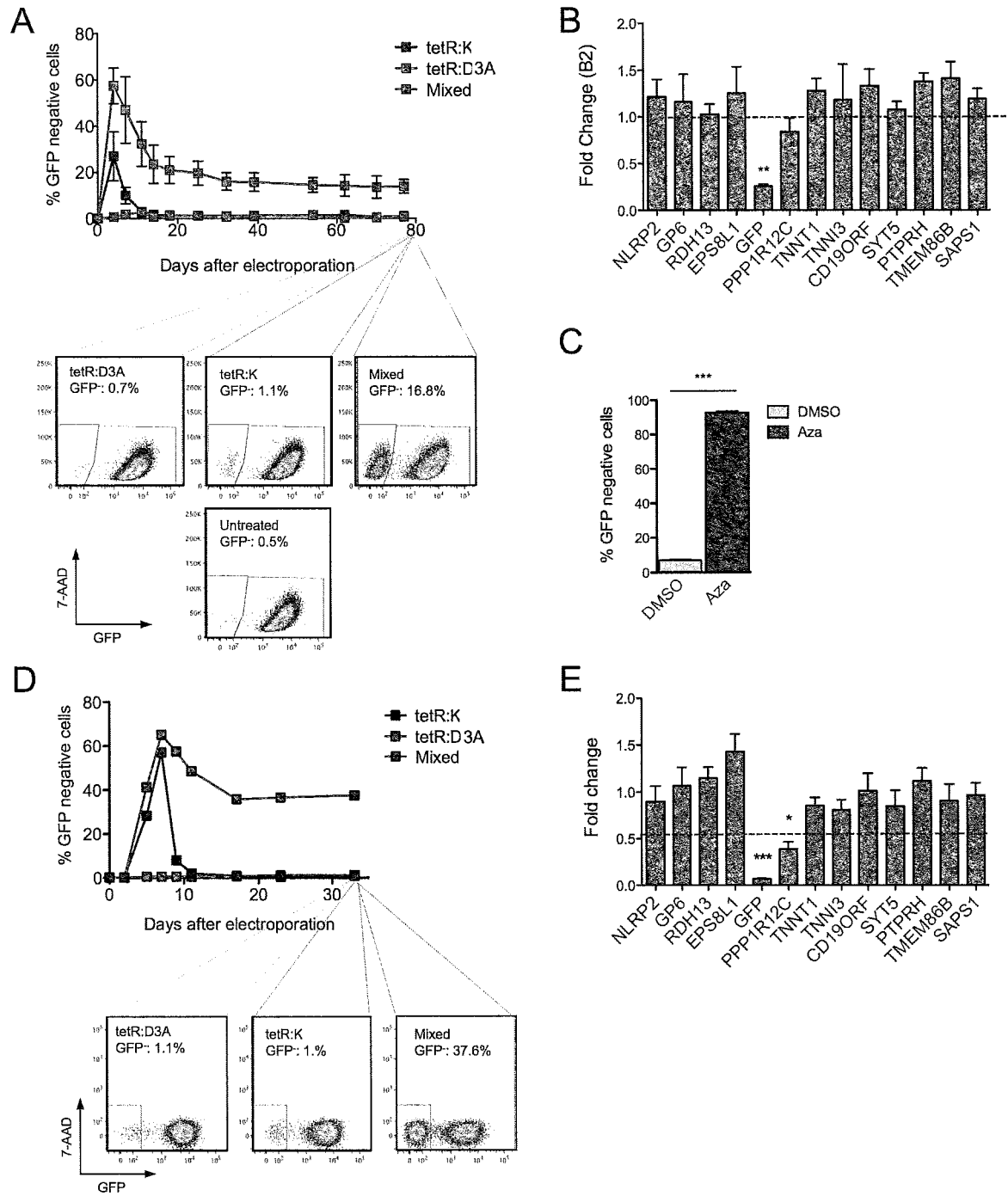

Overall, these experiments show that tetR:K induces a rapid and robust transcriptional repression, capable of long-range spreading, which however is reversible upon ATR release from the locus. On the other hand, tetR:D3A induces silencing with slower kinetics, but this transcriptional repression is sharply confined to the target locus and permanently maintained even in the absence of the initial stimulus Synergistic Activity of the ATRs Upon their Transient Co-Delivery We then asked if the transient co-delivery of these two ATRs was sufficient to induce rapid (as tetR:K) and permanent (as tetR:D3A) epigenetic silencing. To answer to this question we transfected the AAVS1/TetO7 cell line with plasmids encoding for the ATRs, either alone or in combination, and then followed eGFP expression in these cells by time course flow cytometry analysis. Representative examples of these experiments are shown in FIG. 4A, in which we report the kinetics of silencing of the eGFP-expression cassette (% of eGFP-cells; data are represented as mean±SEM, n=3) in cells transfected with the plasmids encoding for the indicated ATRs, and the corresponding flow cytometry dot plot analyses performed at termination of the experiments. From these analyses we found that: i) none of the cells transfected with the plasmid encoding for either the tetR:K or tetR:D3A became eGFP negative, although transient delivery of the tetR:K was associated with a short wave of repression that rapidly returned to control levels by day 10 post-transfection (this latter data indicates transient deposition of H3K9me3 followed by its disappearance concomitantly with the mitotic dilution of the tetR:K encoding plasmid); and ii) remarkably, up to 20% of the cells co-transfected with the plasmids encoding for the tetR:K and tetR:D3A became stably silenced. These data revealed a significant degree of synergy between the DNMT3A- and the KRAB-based repressors, and represent the first demonstration of permanent epigenetic silencing upon transient co-delivery of ATRs.

Figure 3:
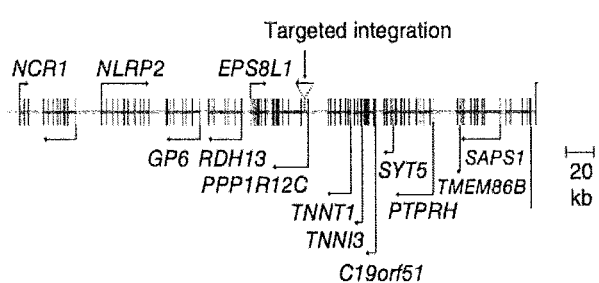
Figure 3:
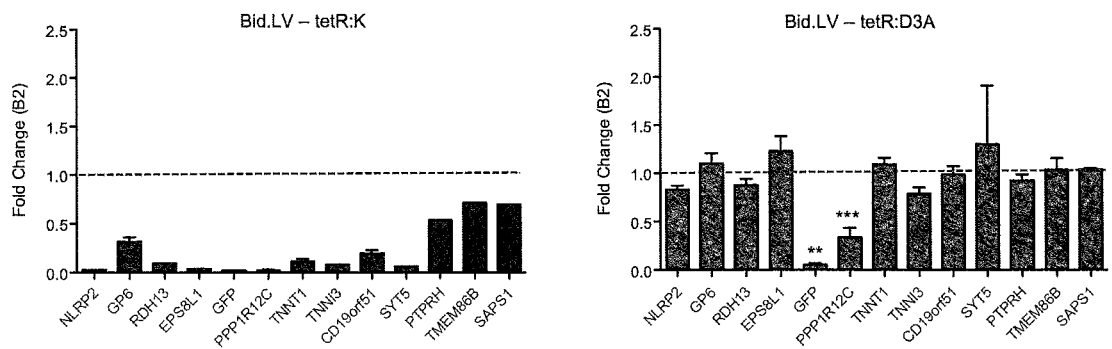

We then asked whether the silencing induced by the tetR:K/tetR:D3A combination was limited to the reporter cassette or instead spread along the AAVS1 locus, thus also affecting the genes nearby the insertion site of the reporter cassette. To answer to this question, we compared the expression profile of the genes at and nearby the AAVS1 integration site (a schematic of the locus is shown in FIG. 3A) between the eGFP-negative and the eGFP-positive populations sorted from the tetR:K/tetR:D3A treated conditions. In these analyses we found that the treatment resulted in significant silencing only of the reporter transgene (FIG. 4B; data are represented as mean±SEM, n=3; $p<0.001$, one-way anova and Bonferroni post-test). These important data indicate that the tetR:K/tetR:D3A combination deposited punctuated epigenetic silencing only at the intended target gene, highlighting the safety our approach. Finally, treatment of the eGFP-negative sorted cells from tetR:K/tetR:D3A conditions with 5-Aza completely reactivated eGFP expression in these cells (FIG. 4C; data are represented as mean±SEM, n=3; *$p<0.0001$, two-tailed unpaired t test), thus indicating that DNA methylation plays an important role in the maintenance of these epigenetic states of repression. Similar results were also found by transfecting the AAVS1/TetO7 reporter cell lines with in vitro transcribed mRNAs encoding for the ATRs (FIG. 4D). Remarkably, the extent of silencing measured in these experiments was ~2-fold higher than that measured upon plasmid transfection, likely reflecting the better tolerability and the higher expression levels achieved by mRNA transfection. Gene expression analyses showed that only eGFP and the gene lodging the eGFP-reporter cassette (i.e. PPP1R12C) were down-regulated by the treatment (FIG. 4E; data are represented as mean±SEM, n=3; ***$p<0.0001$ and *$p<0.01$, one-way anova and Bonferroni post-test).

Silencing with ATR Combinations is Locus and Cell-Type Independent

Having shown that the two ATRs are capable of inducing permanent silencing even when transiently delivered to the cells, we then asked if this effect was locus independent. Indeed, the efficacy of an epigenetic therapy approach might depend on the chromatin environment in which the target locus is embedded, with theoretically some loci being more refractory to a specific repressive mechanism than others. For example, some published evidence suggests that loci enriched in H3K4 methylation may be protected from DNA methylation (Ooi, S. K. et al. (2007) Nature 448:714-7). In line with this, endogenous epigenetic factors naturally present at the target locus or in its neighbouring regions may counteract the activity of the ATRs or restore the original physiological epigenetic profile of the target gene.

Figure 5:
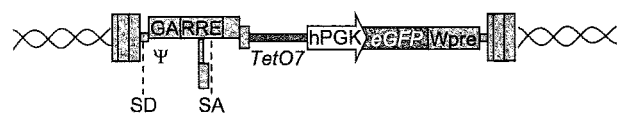
Figure 5:
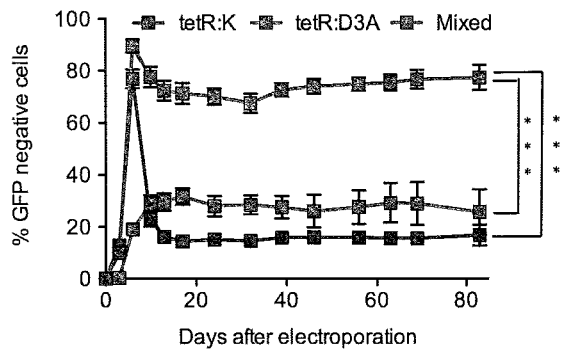
Figure 5:
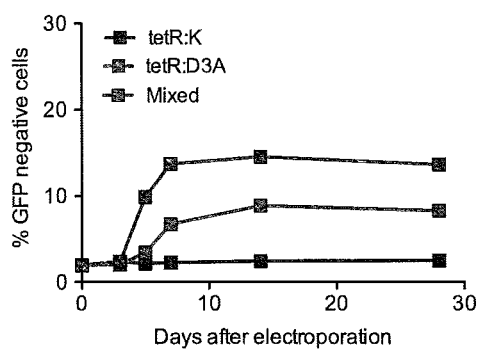
Figure 5:
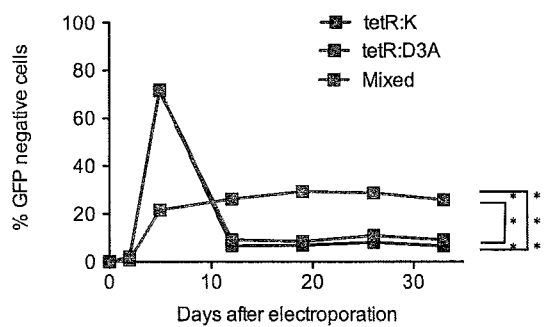

To address this question, we inserted the TetO7 sequence upstream of the hPGK promoter of an eGFP expression cassette, and then delivered this construct semi-randomly in the genome of the K562 cells by standard lentiviral vector transduction (a schematic of the provirus used is shown in FIG. 5A). We then sorted to purity the eGFP-expressing cells (hereafter referred as the TetO7.LV-reporter cell line) and transfected them with in vitro transcribed mRNAs encoding for the tetR:K or the tetR:D3A, either alone or in combination. Time-course flow cytometry analyses of these cells (FIG. 5B; data are represented as mean±SEM, n=3; ***$p<0.0001$, two-way anova and Bonferroni post-test) showed that: i) up to 32% of the cells transfected with the mRNA encoding for tetR:D3A progressively became eGFP-negative, reaching a plateau of repression in two weeks after transfection; ii) up to 80% of the cells transfected with the plasmid encoding for tetR:K rapidly became eGFP-negative but soon after most of these cells reactivated eGFP expression (contrary to the experiment performed with the AAVS1/TetO7 cell line, up to 19% of the cells remained eGFP negative); and iii) remarkably, up to 80% of the cells co-transfected with mRNAs encoding for the tetR:K/tetR:D3A became permanently silenced.

Interestingly, even if we measured comparable efficiencies of silencing between the tetR:K and the tetR:K/tetR:D3A conditions at short term post-transfection, only the combination of the two factors resulted in high levels of permanent epigenetic silencing. Similar results were also found in U937 cells with random insertion of the TetO7/eGFP cassette (FIG. 5C). Here, however, the efficiencies of silencing for all treatment conditions were lower than those obtained in K562 cells, although the overall efficiencies of transfection between these two cell types were comparable. Unexpectedly, when we performed a similar experiment in B-lymphoblastoid cells containing random insertion of the TetO7/eGFP cassette, long-term stable silencing was observed only in the conditions treated with the tetR:D3A (FIG. 5D; data are represented as mean±SEM, n=3; ***$p<0.0001$, two-way anova and Bonferroni post-test). Contrary to the results of all the above experiments, silencing induced by the combination of the ATRs was transient, displaying kinetics that were superimposable to those measured under the tetR:K-treated conditions.

Overall, these results clearly demonstrate that the two ATRs cooperate in the establishment of stable states of epigenetic repression also when their target sites are randomly distributed throughout the lentiviral vector accessible genome of different cell types, thus indicating that the silencing mechanism might be locus-independent. Yet, these studies suggest that that several cell-intrinsic factors can modulate the in vivo activity of these proteins.

Identification of Novel ATRs Able to Increase the Silencing Efficiency of Our Platform While the above data provide the first demonstration to our knowledge of permanent epigenetic silencing upon transient expression of ATRs, they also indicate that several cell-intrinsic factors can modulate the in vivo activity of these proteins. For instance, the lower level of silencing observed in the U937 cell line and the unexpected lack of silencing activity of the ATR combination found in B-lymphoblastoid cells might be explained by the absence of a cofactor(s) involved in the silencing process or by the presence of a cell-type specific repressor(s). Because of this reason, the inclusion of another ATR in our cocktail might be useful to increase the efficiency of silencing of the KRAB/DNMT3A combination, either by obviating to the absence of a cofactor, or by allowing proper function of the repressive complex even when the ATRs are present at low concentrations. Thus, we investigated whether any alternative effector domains (or combination thereof) from chromatin remodelling enzymes involved in the establishment of permanent states of epigenetic repression could be used to increase the silencing efficiency of our ATRs. To this end, by mining the literature for known interactors of the DNMT3A or KRAB-ZFPs proteins (Chen, T. et al. (2014) Nat. Rev. Genet. 15:93-106) and, more broadly, for molecules involved in the transcriptional control of cell fate specification and development (Schwartz, Y. B. et al. (2013) Nat. Rev. Genet. 14:853-64), we identified the following candidates:

Euchromatic histone-lysine N-methyltransferase 2 (EHMT2 also known as G9a): a histone methyltransferase that catalyses dimethylation of histone H3 lysine-9 and recruits several histone deacetylases;

SET domain bifurcated 1 (SETDB1): a histone methyltransferase that deposits histone H3 lysine-9 di- and tri-methylation (two histone marks associated with transcriptional repression);

Chromobox protein homolog 5 (CBX5, also known as HP1α): a component of heterochromatin that recognises and binds histone H3K9me, leading to epigenetic repression;

DNA (cytosine-5)-methyltransferase 3-like (DNMT3L): a catalytically inactive DNA methyltransferase that activates DNMT3A by binding to its catalytic domain;

Enhancer of Zeste homolog 2 (EZH2): the catalytic subunit of the polycomb repressive complex 2, which methylates lysine-9 and lysine-27 of histone H3, thus creating binding sites for the canonical polycomb repressive complex 1;

Suppressor of variegation 4-20 homolog 2 (SUV420H2): a histone methyltransferase that specifically trimethylates lysine-20 of histone H4 (a specific histone mark associated with transcriptional repression at pericentric heterochromatin); and Transducin-like enhancer protein 1 (TLE1): a chromatin-associated transcriptional co-repressor that binds to and inhibits the activity of a number of transcription factors.

We generated new ATRs containing the effector domains of these proteins and the DNA binding domain of tetR. Hereafter, the new ATRs will be referred as: tetR:SET (SETDB1); tetR:H (HP1-α); tetR:T (TLE1); tetR:GS or tetR:GL (according to the length of the effector domain cloned from G9a); tetR:ES or tetR:EL (according to length of the effector domain cloned from EZH2); tetR:D3L (DNMT3L); and tetR:SUV (SUV420H2). The amino acid sequences of the effector domains are listed in Table 1.

Figure 6:
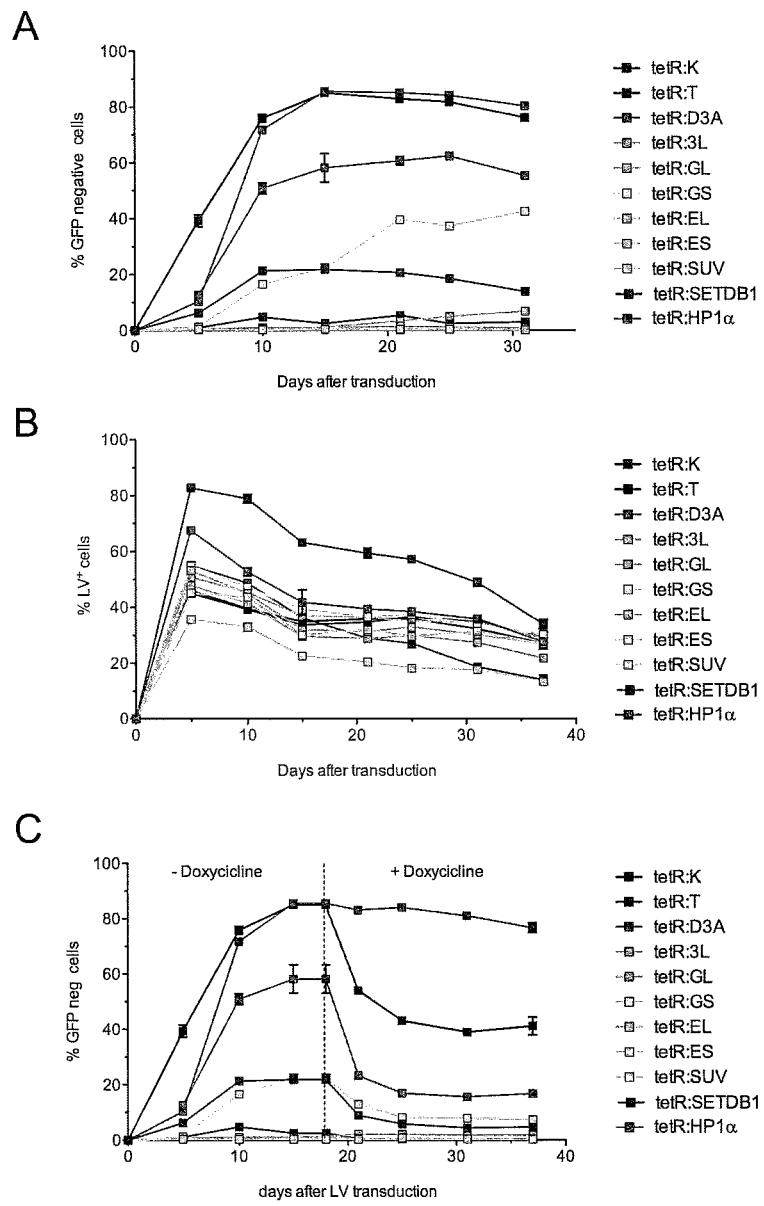

We initially tested the activity of these novel ATRs in the LV/TetO7 K562 reporter cell line by using standard integrating Bid. LV and found that, among the new ATRs, tetR:SET, tetR:GS and tetR:H efficiently induced silencing when individually and stably expressed (FIG. 6A; data are represented as mean±SEM, n=3). However, none of these ATRs reached the silencing efficiency of tetR:K and tetR:D3A. Unlike tetR:GS, tetR:GL was not efficient in this experimental setting, suggesting that inclusion of the ankyrin repeats in this longer version of G9A was negatively impacting the silencing efficiency. The inefficiency of tetR:T, tetR:SUV, tetR:ES and tetR:EL in this experimental setting may be due to the intrinsic biological inactivity of the chosen domains or to the absence in this cell line of endogenous interactors necessary for the activity of these proteins. Furthermore, we noticed a decrease in the percentage of transduced cells over time for some of the ATRs used (FIG. 6B; data are represented as mean±SEM, n=3). This data indicates a growth disadvantage of cells stably expressing the ATRs, thus strengthening the rationale of using transient delivery approaches to safely express the ATRs.

We then assessed if silencing induced by the new ATRs could be maintained even in the absence of the ATRs on the target locus. To this aim, 18 days after Bid.LV-ATR transduction, we treated the samples with doxy, and monitored eGFP expression by flow cytometry analysis (FIG. 6C; data are represented as mean±SEM, n=3). As expected, tetR:D3A-induced silencing was maintained after doxy administration. Considering the other samples, silencing was maintained only in a fraction of the originally repressed cells, which varied among the different ATRs. Particularly, tetR:K-induced silencing resulted to be more stable than the others, being maintained in up to 45.8% of the originally repressed cells. This is in contrast with that observed using the AAVS1/Tet07 K562 reporter cell line, in which 7 days post doxy administration eGFP was fully reactivated in all the transduced cells. This data indicate a role in that positioning of the TetO7 relative to the hPGK promoter and/or the epigenetic environments in which the cassette is integrated might play an important role in the maintenance of the tetR:K-induced repressive state.

Figure 7:
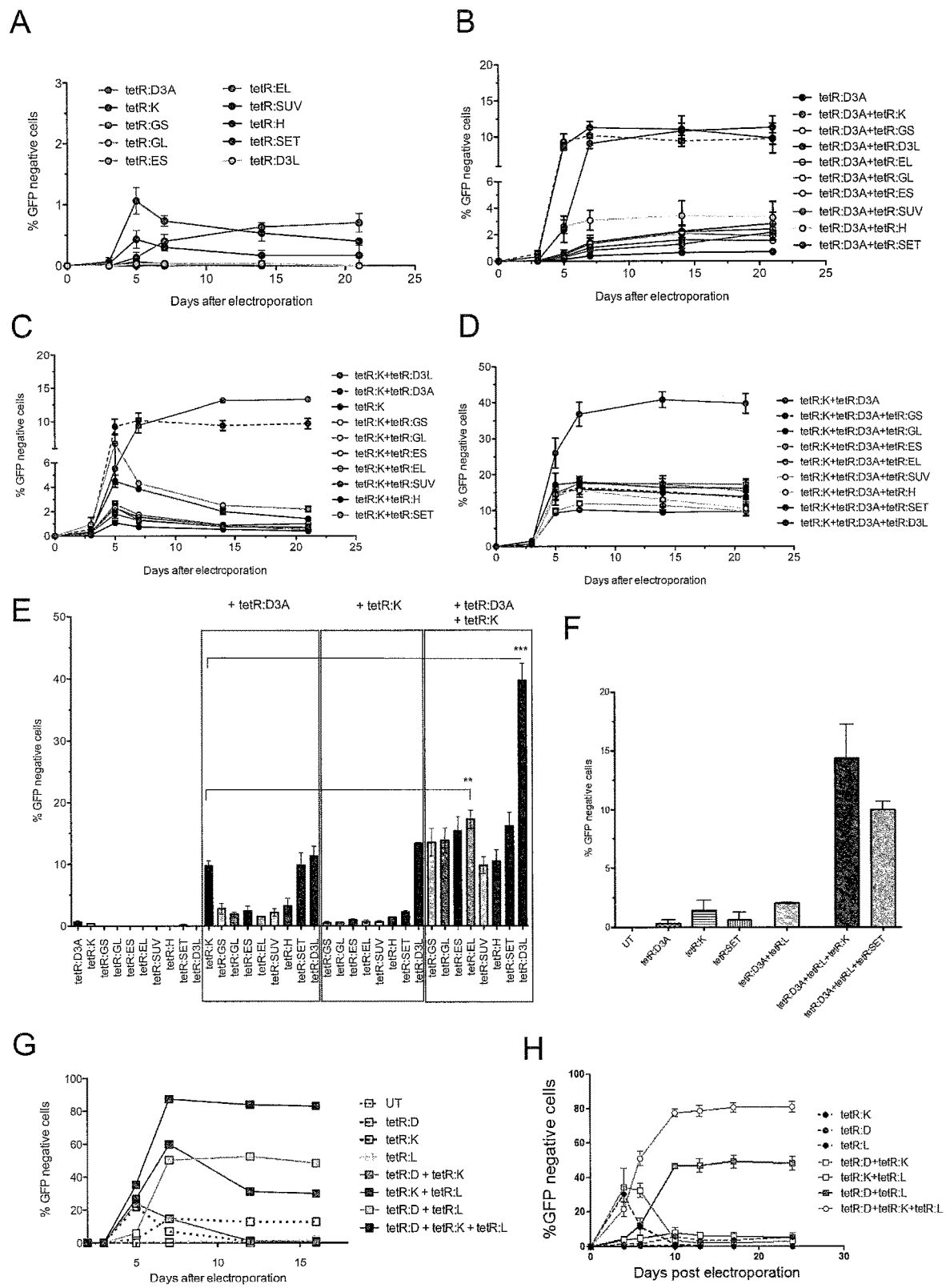

We then tested the efficiency of the ATRs upon their transient delivery in the same LV/TetO7 K562 reporter cell line. Particularly, we tested the ATRs either individually (FIG. 7A) or in combination with tetR:D3A (FIG. 7B), tetR:K (FIG. 7C) or with the tetR:K+tetR:D3A combination (FIG. 7D). To better appreciate any eventual increase in the silencing efficiency above the levels measured in positive controls, these experiments were performed using non-saturating doses of the ATR-expressing plasmids. tetR:T was not tested in this experiment, since it was not available in the same plasmid backbone as the other ATRs at the time of the experiment.

By following eGFP expression in the treated cells over time by flow cytometry, we found that when individually expressed, none of the ATRs efficiently induced silencing, with tetR:K, tetR:D3A and tetR:SET repressing only up to 1% of the cell (FIG. 7A; data are represented as mean±SEM, n=3). When combined to tetR:D3A (FIG. 7B; data are represented as mean±SEM, n=3), all the new ATRs conferred a gain in silencing efficiency. However, an efficiency similar to that measured with the tetR:K+tetR:D3A condition was achieved only when tetR:D3A was combined with either tetR:SET or tetR:D3L. Furthermore, when co-delivered with tetR:K (FIG. 7C; data are represented as mean±SEM, n=3), only tetR:D3L among the new ATRs synergised better than tetR:D3A. Finally, when adding one of the new ATRs to the tetR:K+tetR:D3A combination (FIG. 7D; data are represented as mean±SEM, n=3), most of the ATRs increased silencing efficiency, thus indicating a biological activity also for those ATRs that were not working when stably, but individually, delivered (FIG. 6A). Importantly, this experiment identified the tetR:K+tetR:D3A+tetR:D3L combination as the best-performing combination, showing a striking efficiency considering the low plasmid doses employed in these experiments. Specifically, the tetR:K+tetR:D3A+tetR:D3L combination resulted in a 4.1-fold increase in silencing efficiency compared to the tetR:K+ tetR:D3A combination (FIG. 7E; data are represented as mean±SEM, n=3; ***p<0.0001, one-way anova and Bonferroni post-test). Given the increment in silencing efficiency compared to both the tetR:D3A+tetR:D3L, tetR:K+tetR:D3A and tetR:D3L+tetR:K combinations, all the three ATRs play a relevant role in the tetR:K+tetR:D3A+tetR:D3L cocktail. Interestingly, starting from the evidence that tetR:SET was able to synergise with both tetR:D3A and tetR:D3A+tetR:K (see FIG. 7E), we reloaded a similar experiment at even lower ATR doses, and found that tetR:SET was also able to significantly synergise with the tetR:D3A+tetR:D3L combination (FIG. 7F; tetR:D3L shown as tetR:L). This data indicates that the tetR:D3A+tetR:D3L+tetR:SET combination can be a valid alternative to the tetR:D3A+tetR:D3L+tetR:K combination, even if with lower silencing efficiency.

Inclusion of tetR:D3L to the tetR:K+tetR:D3A Combination Allows Rescue of Silencing Efficiency in Refractory Cell Types We then asked if the use of the tetR:K+tetR:D3A+tetR:D3L combination was able to overcome the block observed in B-lymphoblastoid cells (see FIG. 5D). To address this question, the TetO7.LV-reporter B-lymphoblastoid cell line was transfected with in vitro transcribed mRNAs encoding for the three ATRs, either alone or in different combinations (FIG. 7G; tetR:D3A shown as tetR:D; tetR:D3L shown as tetR:L; data are represented as mean±SEM, n=3). As expected from previous experiments, tetR:K+tetR:D3A co-delivery resulted in a transient wave of silencing that was completely erased after dilution of the transfected mRNAs, resulting in the absence of eGFP negative cells. However, both tetR:D3A+tetR:D3L and tetR:D3L+tetR:K were capable of inducing high levels of silencing (50% and 60%, respectively). These levels are substantially higher than those observed in conditions in which the ATRs were delivered alone (14% for tetR:D3A, and levels comparable to untreated samples for tetR:K and tetR:D3L transfected cells). Strikingly, when the three ATRs were delivered together, most of the cells became eGFP negative (up to 80%), clearly demonstrating that the addition of one single factor to the tetR:D3A/tetR:K mix was sufficient to restore silencing induction and maintenance in previously refractory cell lines. Based on these promising results, we also asked if our silencing platform could be effective in experimentally relevant cell types derived from other organisms, such as mice. To answer this question, we first transduced the murine NIH/3T3 cell line with the TetO7.LV, sorted the cells to obtain a pure eGFP-positive population (hosting on average 1 copy of vector per cell), and finally transfected them with mRNAs encoding for the tetR-based ATRs, which were delivered individually or in combination. Remarkably, flow cytometry analysis of the treated cells showed effective and long-term silencing also in this cell model: a single administration of the tetR:D3A+tetR:D3L or of the triple ATR combination led to 45% or 80% gene silencing efficiency, respectively (FIG. 7H). On the other hand, the tetR:D3A+tetR:K combination did not work, as previously observed in B-lymphoblastoid cells.

Effective Silencing by Transient Co-Delivery of ATRs Equipped with Custom-Made DNA Binding Domains The main objective of this project was to develop an epigenetic therapy platform that can be used to silence expression of any gene of interest. Although we have already identified effector domains that when fused to the tetR synergistically cooperate to silence the promoter nearby the TetO7 element, the artificial nature of the prokaryotic TetO7/tetR system hinders therapeutic application of this technology. Moreover, the TetO7 element can accommodate with high avidity 7 tetR dimers, thus leading to stochastic homo- or hetero-dimerisation of the ATRs on this element. This occurrence may favour mutual positive interactions between repressors. For these reasons, several questions remain to be addressed in order to translate the findings obtained with the TetO7/tetR system to a situation in which each of the ATRs has single and yet independent binding site on the target gene. In particular, it is unknown whether one element (defined as a given genomic sequence containing the binding site for each of the repressors, hereafter referred as the "Silencing Element") would be sufficient to silence a gene of interest. Furthermore, the relative order and the orientation in which the two repressors are arranged on the Silencing Element, and the distance between their binding sites might represent important determinants for the activity of the repressive complex. Of note, it is impossible to define these determinants based on the literature or by empirically testing them on an endogenous gene, as it would require designing several different ATRs each with its own binding site and affinity.

To address these questions, we developed an ad hoc engineered cell model that easily reports the silencing activity of ATRs containing transcription-activator like effector (TALE; Gaj, T. et al. (2013) *Trends Biotechnol.* 31:397-405) DNA-binding domains. In this set of experiments we initially tested ATRs corresponding to the tetR:K+tetR:D3A combination.

Figure 8:
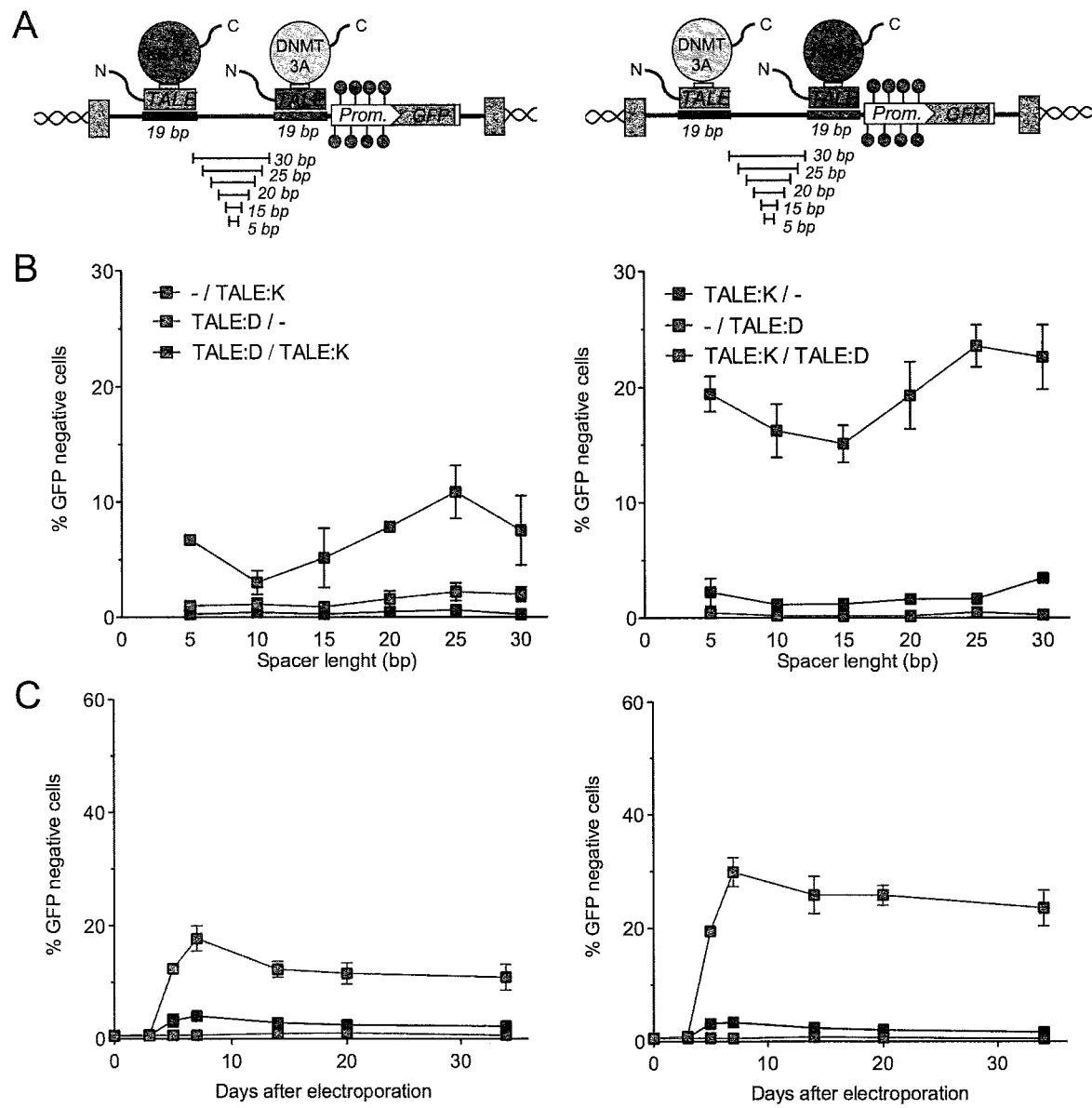

Briefly, we fused the KRAB and DNMT3A domains to the DNA binding domains of two TALEs that recognise two different genomic target sites with high efficiency (the amino acid sequences of the two TALEs are listed in Table 2). Using this approach we obtained two TALE:KRAB fusion proteins (hereafter referred as TALE:K) and two TALE:DNMT3A fusion proteins (hereafter referred as TALE:D3A) corresponding to each of the two genomic target sites. In parallel, we inserted the two TALE target sites, spaced by progressively longer nucleotide sequences (5, 10, 15, 20, 25 and 30 bp), upstream of the hPGK promoter of an eGFP expression cassette, and then delivered these constructs semi-randomly in the genome of the K562 cell line by standard lentiviral vector transduction. Of note, the target sites for the two TALEs were placed in such a way that binding of the TALE-repressors occurs in head-to-tail (H-T) configuration. A schematic representation of these vectors is shown in FIG. 8A (on the left is depicted the vector containing the binding sites for the TALE:K→TALE:D3A configuration; on the right is depicted the vector containing the binding sites for the TALE:D3A→TALE:K configuration. We then sorted to purity the eGFP expressing cells and transfected these lines with in vitro transcribed mRNAs encoding for the TALE:K or the TALE:D3A, either alone or in combination. The cells were then analysed by time-course flow cytometry to measure the extent and duration of silencing. Representative examples of these analyses can be seen in FIG. 8, in which we report the silencing efficiencies (% of eGFP-negative cells) of the indicated ATRs with respect to the length of the spacers (FIG. 8B; data are represented as mean±SEM, n=3), and the kinetics of silencing of the eGFP-expression cassette measured in the cell line with the 25 bp spacer (FIG. 8C; data are represented as mean±SEM, n=3; *p<0.0001 and p<0.001, two-way anova and Bonferroni post-test).

From these experiments we found that: i) co-delivery of TALE:D3A and TALE:K resulted in full silencing of eGFP-expression cassette in up to 25% of the treated cells; ii) the relative order of binding of the two ATRs on the target locus impacted on the overall silencing efficiency, with the TALE:D3A→TALE:K configuration performing from 2.2 to 5.4-fold better than the opposite one; iii) among the spacer lengths tested, the 25 and the 30 bp performed better than the others; and iv) individual delivery of TALE:K or TALE:D3A resulted in low (3%) or absent silencing of the eGFP-expression cassette, respectively.

Figure 9:
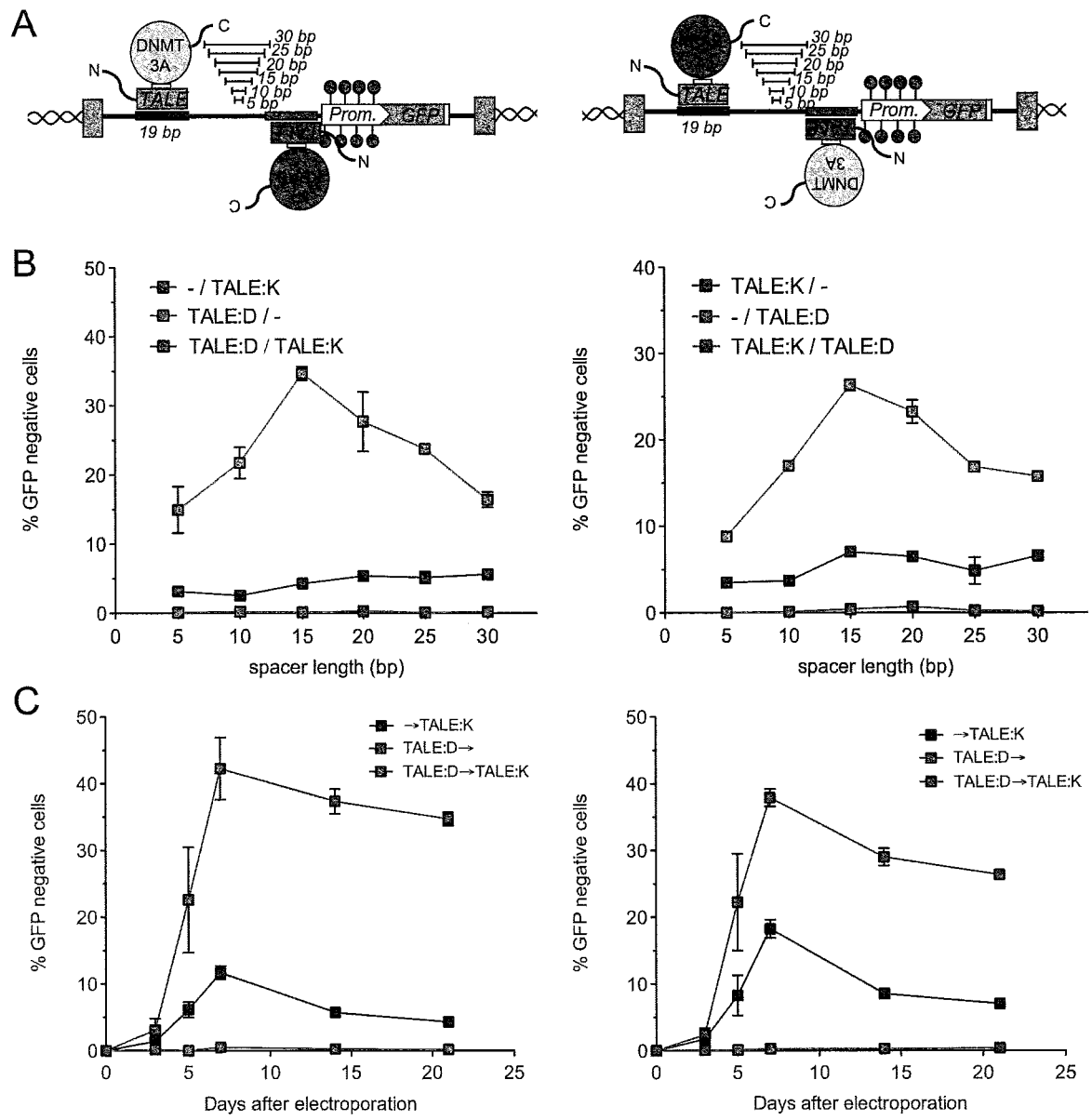

Considering the significant impact of structural variables (such as spacer length and the relative order of binding of the two ATRs on the target sequence) on the silencing efficiency, we then asked if moving to a head-to-head (H-H) configuration in which the C-termini of the two ATRs face each other could be beneficial for our strategy. To move from the head-to-tail to the head-to-head configuration, starting from the reporter cassette described in FIG. 8 we maintained the 5' TALE binding site unaltered, while we changed the orientation of the 3' TALE binding site. This simple change allowed us to use the same four ATRs employed in the previous experiments. We also generated six eGFP reporter cassettes differing in spacer length between the two TALE target sites (5, 10, 15, 20, 25 and 30 bp) and we delivered these constructs to K562 cells via lentiviral vector transduction (a schematic of these vectors is shown in FIG. 9A). Transduced cells were then sorted to obtain pure eGFP+ populations and electroporated with plasmids encoding for TALE:K or TALE:D3A, either alone or in combination. Treated cells were then analysed by time-course flow cytometry to measure the extent and duration of silencing. To stringently compare the head-to-head to the head-to-tail configuration, we included the cell line containing the 25 bp spacer and the H-T, TALE:D3A→TALE:K configuration described in FIG. 8C in this experiment. The results of these experiments indicated that: i) co-delivery of TALE:K and TALE:D3A resulted in evident synergy even in the H-H configuration, allowing long-term silencing of the reporter cassette in up to 34.7% of the treated cells (FIG. 9B; data are represented as mean±SEM, n=3); ii) individual delivery of TALE:K or TALE:D3A resulted in low (up to 7.1%) or absent permanent silencing, respectively; and iii) the relative order of binding of the two ATRs on the target locus impacted on the overall silencing efficiency, with the TALE:D3A→TALE:K configuration performing from 1.3 to 1.7 fold better than the opposite one (FIG. 9C; data are represented as mean±SEM, n=3). However, the relative order of binding seems to have a greater impact on silencing efficiency in the head-to-tail configuration than in the head-to-head configuration (compare FIG. 8 with FIG. 9). A bell-shaped trend seems to describe the impact of the tested spacer lengths on silencing efficiency of the H-H configuration, with the 15 bp spacer performing best both in the TALE:D3A→TALE:K and in the TALE:K→TALE:D3A configurations (even outperforming the 25 bp spacer in the head-to-tail experiment). However, the difference between the 15 bp head-to-head configuration and the 25 bp head-to-tail configuration was minimal (34.7% versus 26.8% long-term eGFP-cells, respectively, i.e. a 1.3-fold increase).

Overall, these data show for the first time to our knowledge the feasibility of achieving permanent epigenetic silencing of a desired target gene upon transient delivery of a combination of ATRs equipped with custom-made DNA binding domains. Moreover, from these studies we were able to define rules for the selection of TALE binding sites that can be used for the identification of Silencing Elements on a desired target gene. By targeting multiple Silencing Elements on the regulatory sequence of this gene we should be able to increase the efficiency of silencing.

Figure 10:
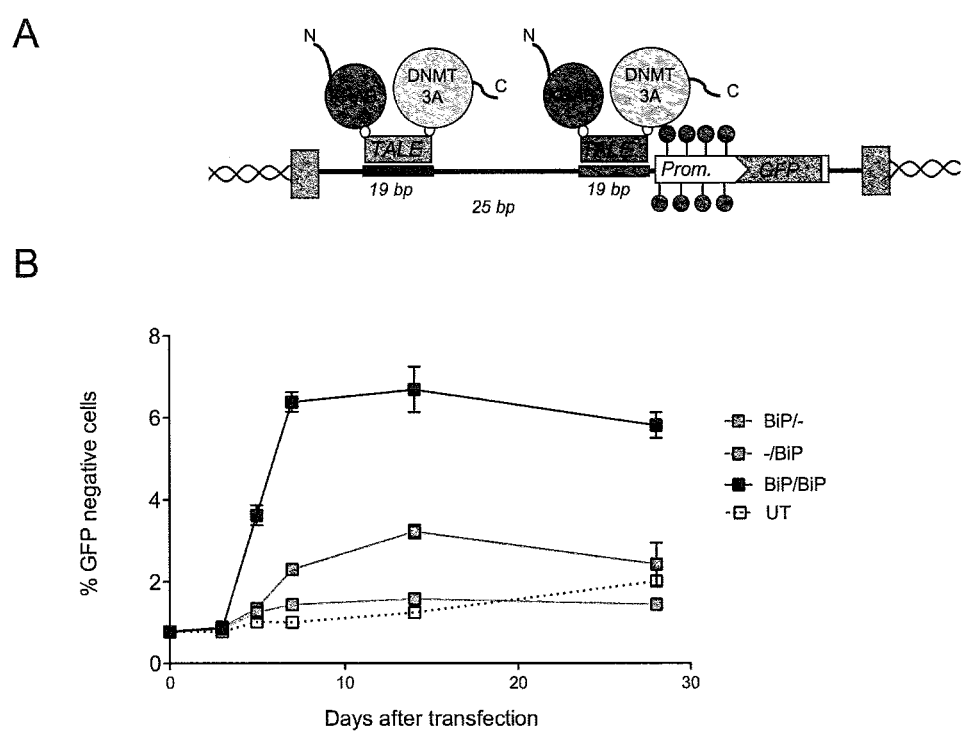

In parallel to these studies we developed bipartite ATRs by coupling two effector domains on the same TALE, i.e. the KRAB domain at the N terminus and the DNMT3A domain at the C terminus of the TALEs (FIG. 10A). Even if transient transfection of the individual proteins was not sufficient to induce appreciable levels of gene silencing, their combination was sufficient to silence eGFP in up to 7% of the treated cells (FIG. 10B; data are represented as mean±SEM, n=3). The advantages provided by such an approach are that multiple effector domains can be delivered to the same target site while reducing the number of different mRNAs required to be produced and transfected.

Permanent Epigenetic Silencing in Human HSPCs by Using Different Combinations of ATRs Primary haematopoietic stem cells (HSPCs) are a clinically relevant human cell type for most of the ex vivo gene therapy applications (Biffi, A. et al. (2013) Science 341:1233158; Aiuti, A. et al. (2013) Science 341:1233151; Aiuti, A. et al. (2009) N. Engl. J. Med. 360, 447-458; Cartier, N. et al. (2009) Science 326:818-23; Hacein-Bey-Abina, S. et al. (2010) N. Engl. J. Med. 363:355-64; Cavazzana-Calvo, M. et al. (2010) Nature 467:318-22) due to their life-long self-renewal capacity and multilineage differentiation potential. HSPC differentiation is accompanied by global chromatin remodelling, which results in a progressive transition from an open chromatin configuration to a more compacted and repressive one. As such, this cell type represents the most appropriate and stringent model to test efficacy and prove stability of our epigenetic platform. To assess if the delivery of various ATR combinations was sufficient to induce significant levels of silencing in human HSPCs, we transduced human cord blood-derived CD34+ cells from healthy individuals with the TetO7/eGFP-reporter LV described in FIG. 5A. We then transfected the cells with in vitro transcribed mRNAs encoding for tetR:D3A, tetR:K or tetR:D3L, either alone or in combinations. Transfected and un-transfected cells were then grown in liquid culture for 2 weeks in myeloid-differentiation conditions or plated in semi-solid media for a Colony Forming Unit-Cells (CFU-C) assay (for the layout of these experiments refer to FIG. 11A).

Figure 11:
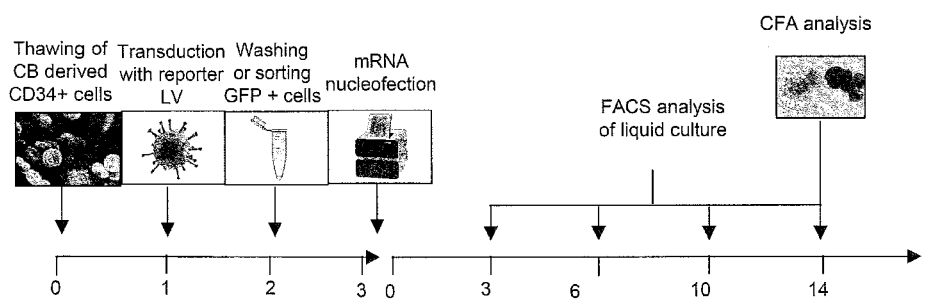
Figure 11:
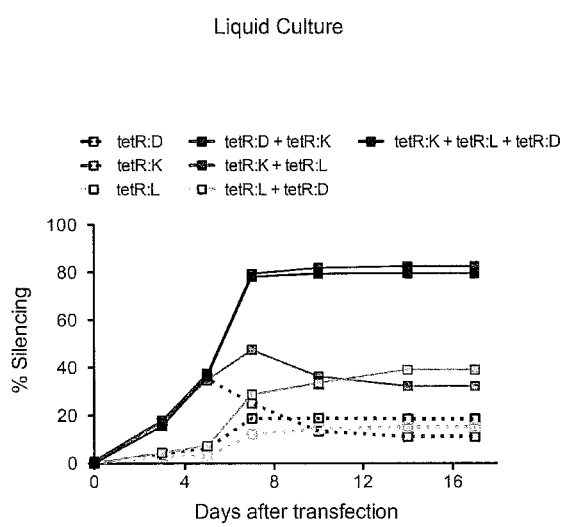
Figure 11:
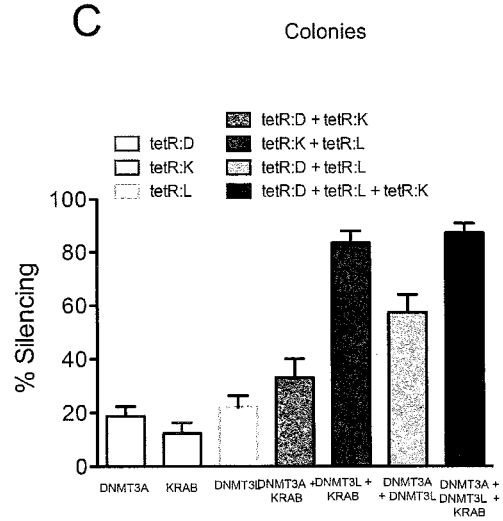

Flow cytometry analyses of the cells grown in liquid culture showed that treatment with the tetR:K resulted in a transient wave of eGFP repression that was then maintained in up to 20% of the treated cells until the end of the experiment (FIG. 11B; data are represented as mean±SEM, n=3). A similar phenotype was observed in CD34+ cells transfected with mRNA encoding for tetR:D3A and tetR:D3L. Treatment with tetR:K/tetR:D3A combination or with tetR:D3A/tetR:D3L combination resulted in a cooperative effect, showing that up to 40% of the treated cells fully silenced eGFP expression. Strikingly, by combining tetR:D3L/tetR:K or tetR:D3L/tetR:K/tetR:D3A we reached up to 90% of silencing of the reporter gene. Importantly, similar levels of silencing were observed in erythroid and myeloid cells originating in the CFU-C assay (FIG. 11C; data are represented as mean±SEM, n=3), thus indicating that silencing was maintained even upon HSPC differentiation.

Figure 12:
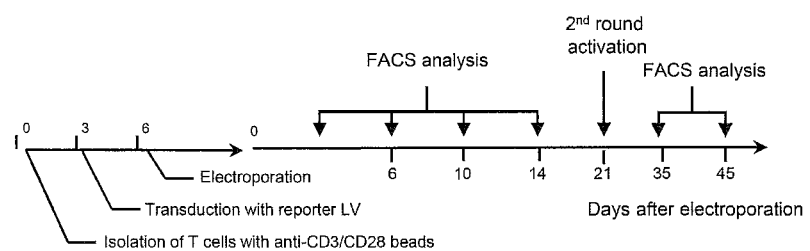
Figure 12:
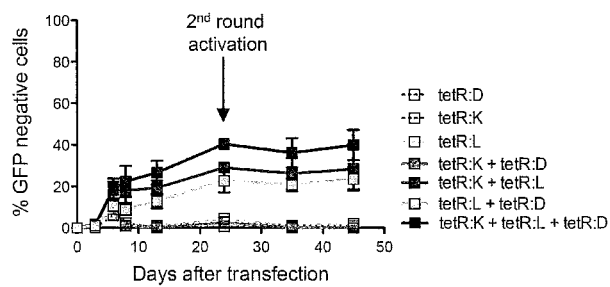

Permanent Epigenetic Silencing in Human T Lymphocytes Using Different Combinations of ATRs To assess if the delivery of various ATR combinations was sufficient to induce significant levels of silencing in human T lymphocytes, a clinically relevant cell type for many cell-based gene therapy applications including cancer immunotherapy, we transduced human T cells from healthy individuals with the TetO7/eGFP-reporter LV described in FIG. 5A. We then transfected the cells with in vitro transcribed mRNAs encoding for tetR:D3A, tetR:K or tetR:

D3L, either alone or in various combinations. Transfected and un-transfected cells were then kept in liquid culture for 3 weeks in media enriched with IL-15 and IL-7 before reactivation (for the layout of these experiments, refer to FIG. 12A).

Flow cytometry analyses of the cells showed that treatment with individual ATRs and tetR:D3A/tetR:K resulted in no or transient eGFP repression. On the other hand treatment with all the other possible ATR combinations resulted in permanent silencing of the reporter gene. Importantly, the levels of silencing measured during the initial phase of cell proliferation and in the resting phase were super-imposable, indicating that silencing is maintained even after the transcriptional and metabolic states of the cells have changed (FIG. 12B; data are represented as mean±SEM, n=3).

Permanent Epigenetic Silencing of a Human Endogenous Gene Using Custom-Made ATRs In order to assess if the results obtained with the eGFP reporter system could also be translated to an endogenous gene embedded in its natural epigenetic context, we generated custom-made TALEs targeting the promoter region of the B2-Microglobulin (B2M) gene (the amino acid sequences of these TALEs and the nucleotide sequences of their corresponding binding sites are listed in Table 3), and fused these TALEs to the KRAB, DNMT3A and DNMT3L effector domains (for a schematic of the system refer to FIG. 13A). The spacer length between the first and the second, or between the second and the third TALE is 1 or 20 bp, respectively. We then co-transfected HEK-293T cells with the plasmids encoding for these novel ATRs and analysed the cells by flow cytometry for B2M expression.

At 50 days post-transfection, when the percentage of B2M-negative cells was stable, we measured a significant fraction of B2M-negative cells only in the conditions treated with the TALE:D3A+TALE:D3L and the TALE:D3A+TALE:D3L+TALE:K combinations (FIG. 13B; data are represented as mean±SEM, n=3; ***p<0.0001, one-way anova and Bonferroni post-test). Remarkably, up to 80% of the cells treated with all the ATRs permanently lost B2M surface expression. In parallel experiments, we sorted the B2M-negative and the B2M-positive cells, and analysed them for surface expression of MHC-I molecules, which require B2M to be presented on the plasma membrane. We found that, contrary to the B2M-positive cells, nearly all the B2M-negative cells were also negative for MHC-I expression (FIG. 13C). We also performed on the B2M-negative and B2M-positive sorted cells gene expression analysis and found that the negative cells expressed ~100-fold less B2M that the positive cells (FIG. 13D; data are represented as mean±SEM, n=3). Then we assessed if the three effector domains were capable of inducing permanent epigenetic silencing also when targeted to the B2M gene via the RNA-guided CRISPR/Cas9 system. To this aim, we fused in frame to a catalytically dead Cas9 (D10A+H840A; dCas9; amino acid sequence listed in Table 4) the KRAB, the DNMT3A or the DNMT3L effector domains (FIG. 13E; top drawings), and designed 11 guide RNAs (gRNAs; nucleotide sequences listed in Table 4) targeting the promoter region of the B2M gene (FIG. 13E; bottom schematic, arrows indicate the location of the CRISPR/dCas9 target sites). We then co-transfected HEK-293T cells with plasmids expressing the 11 B2M gRNAs together with all the possible combinations of the plasmids encoding for the dCas9 fusion proteins. Flow cytometry analysis of the treated HEK-293T cells 33 days after transfection showed that only the dCas9:K+dCas9:D3L, dCas9:D3A+dCas9:D3L and dCas9:K+dCas9:D3a+dCas9:D3L combinations were able to induce silencing of the B2M gene (FIG. 13F; data are represented as mean±SEM, n=3). We then assessed if B2M silencing was resistant to IFN-γ treatment, a potent inducer of B2M expression (Vraetz, T. et al. (1999) Nephrol. Dial. Transplant. 14:2137-43; Gobin, S. J. et al. (2003) Blood 101:3058-64). For this experiment, we used wild-type and B2M-negative cells, the latter being sorted from the triple ATR treated conditions described in FIGS. 13B and 13F. As expected, IFN-γ treatment caused a significant upregulation in the expression of the 2'-5'-oligoadenylate synthetase 1 (OAS1) gene (>100-fold) in all cell types tested (FIG. 13G). On the other hand, while wild-type cells significantly upregulated B2M expression upon IFN-γ treatment both at the transcriptional and at the protein level, no increase in the expression of this gene was measured in the B2M-negative cells (FIG. 13G and FIG. 13H, respectively).

Figure 14:
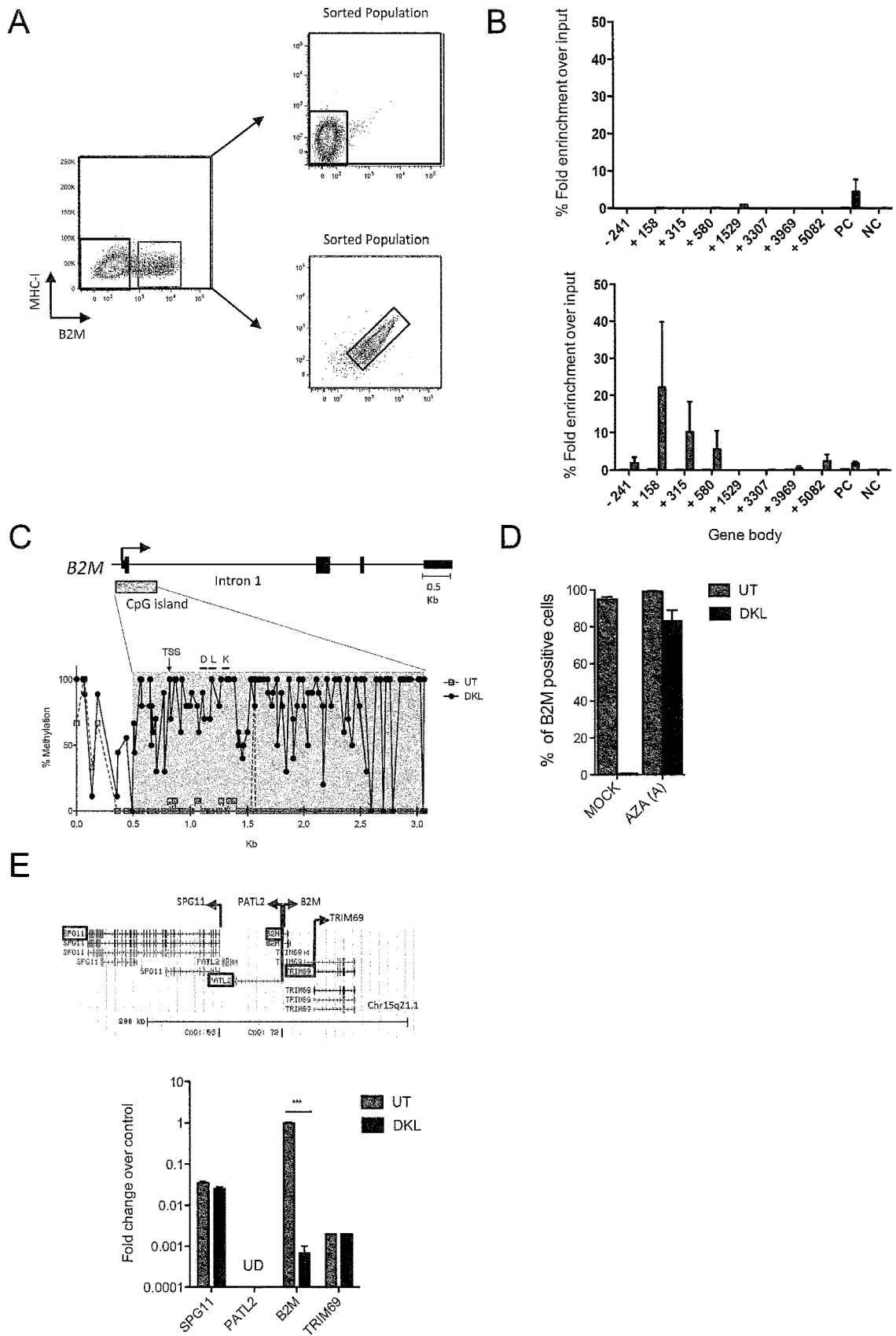

In order to assess if silencing induced by our ATRs was associated with the deposition of repressive epigenetic marks on the targeted gene, we analysed the epigenetic state of the B2M gene in wild-type and silenced cells. To this aim, we sorted to purity the cells treated with plasmid encoding for the triple TALE:ATR combination in order to obtain a pure population of silenced cells (FIG. 14A, showing representative FACS dot plot). Chromatin Immunoprecipitation (ChIP) followed by quantitative PCR analysis for the RNA polymerase II (RNA PolII) on the promoter region and the gene body of B2M showed complete absence of this protein in silenced cells, while it was highly enriched at the promoter region of untreated cells (the PPP1R12C and the CCR5 gene were used as positive or negative controls for these experiments, respectively; FIG. 14B). We also performed bisulfite analysis of B2M CpG island and found that in untreated cells the promoter region was almost deprived of 5 mC at the level of the CpGs (less than 1%), while the same region in silenced cells was highly decorated with de novo DNA methylation (more than 80% on average) (FIG. 14C). DNA methylation was also responsible for silencing maintenance as AZA treatment was associated to re-expression of the B2M gene in previously silenced cells (FIG. 14D). Finally, in order to address if silencing was confined to the B2M gene, we performed transcriptional analysis of the B2M locus by RT-qPCR (FIG. 14E top schematic), and found that the only gene that was down-regulated upon transient delivery of the triple ATR combination was B2M, while expression of its neighbouring gene was unaffected (FIG. 14E).

Figure 15:
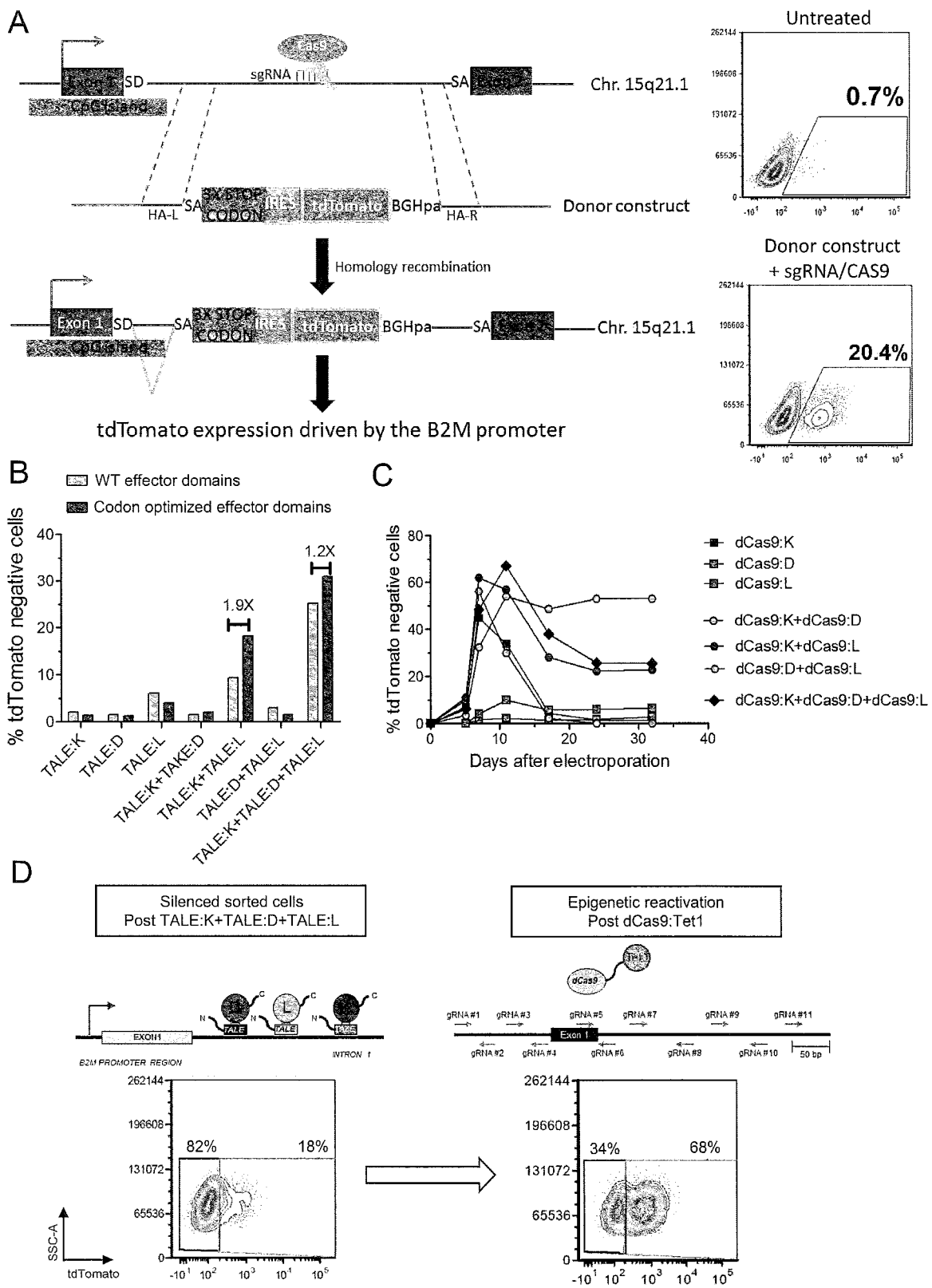

In parallel to these experiments, we also tested silencing of the B2M gene in K-562 cells. Because this cell line does not express the MHC-I, which is strictly required for B2M surface expression, we targeted the coding sequence of the fluorescent marker tdTomato into the first intron of the B2M gene in order to faithfully report for the B2M transcriptional state (FIG. 15A). After gene targeting by CRISPR/Cas9, the tdTomato positive cells were sorted and then electroporated with plasmids encoding for either TALE- or CRISPR/dCas9-based ATRs against the B2M promoter/enhancer (the target sequences of these ATRs are the same as those of FIG. 13). Concerning the TALE-based ATRs, we found that both the TALE:D3L+TALE:K and the TALE:D3A+TALE:D3L+TALE:K combinations were able to stably silence B2M expression, with the triple ATR combination being the best performing (FIG. 15B). Condon-optimisation of the effector domains of the TALE-based ATRs improved silencing efficiency of the above-mentioned combinations (FIG. 15B; compare the red versus the green bars). Concerning the silencing activity of the CRISPR/dCas9-based ATRs, we found that all but the dCas9:D3A+dCas9:K combination was able to induce high silencing efficiency of the B2M gene (up to 55% of stably silenced cells; FIG. 15C). Finally, targeting of dCas9 fused to the catalytic domain of the TET1 enzyme (which is known to demethylate DNA; Maeder, M. L. et al. (2013) Nat. Biotechnol. 31:1137-42) to the B2M promoter/enhancer of sorted silenced cells resulted in reactivation of the expression of this gene (FIG. 15D), further corroborating the notion that silencing induced by the triple ATR combination is dependent on DNA methylation.

Figure 16:
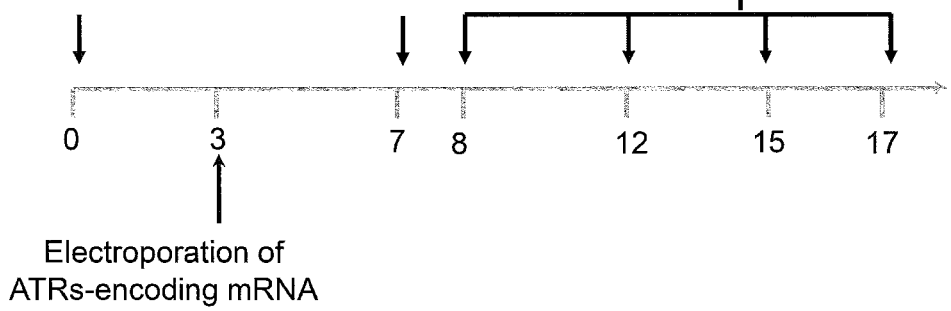
Figure 16:
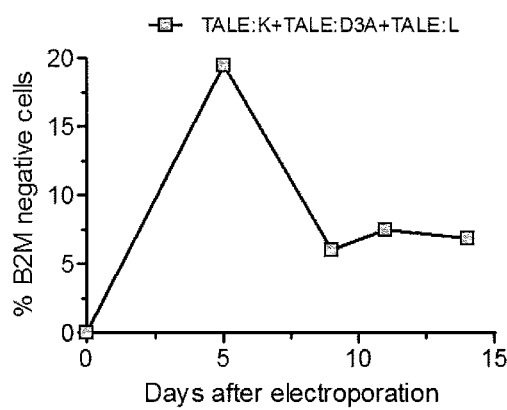
Figure 16:
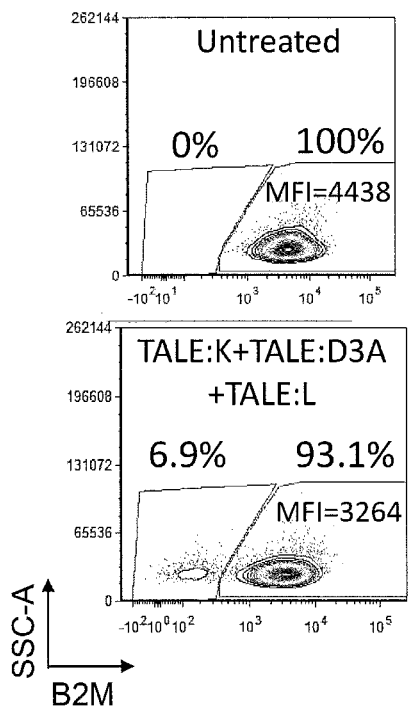

To assess if B2M silencing could also be effective in primary human T lymphocytes, we electroporated human T cells from a healthy donor with in vitro transcribed mRNAs encoding for the TALE:K+TALE:D3A+TALE:D3L ATRs described above. Transfected and un-transfected cells were then kept in liquid culture for 2 weeks in media enriched with IL-15 and IL-7 (experimental scheme in FIG. 16A). Flow cytometry analyses of the cells showed that treatment with the TALE:K+TALE:D3A+TALE:D3L ATRs resulted in silencing of the B2M gene (kinetic of silencing in FIG. 16B, FACS plots in FIG. 16C).

Figure 17:
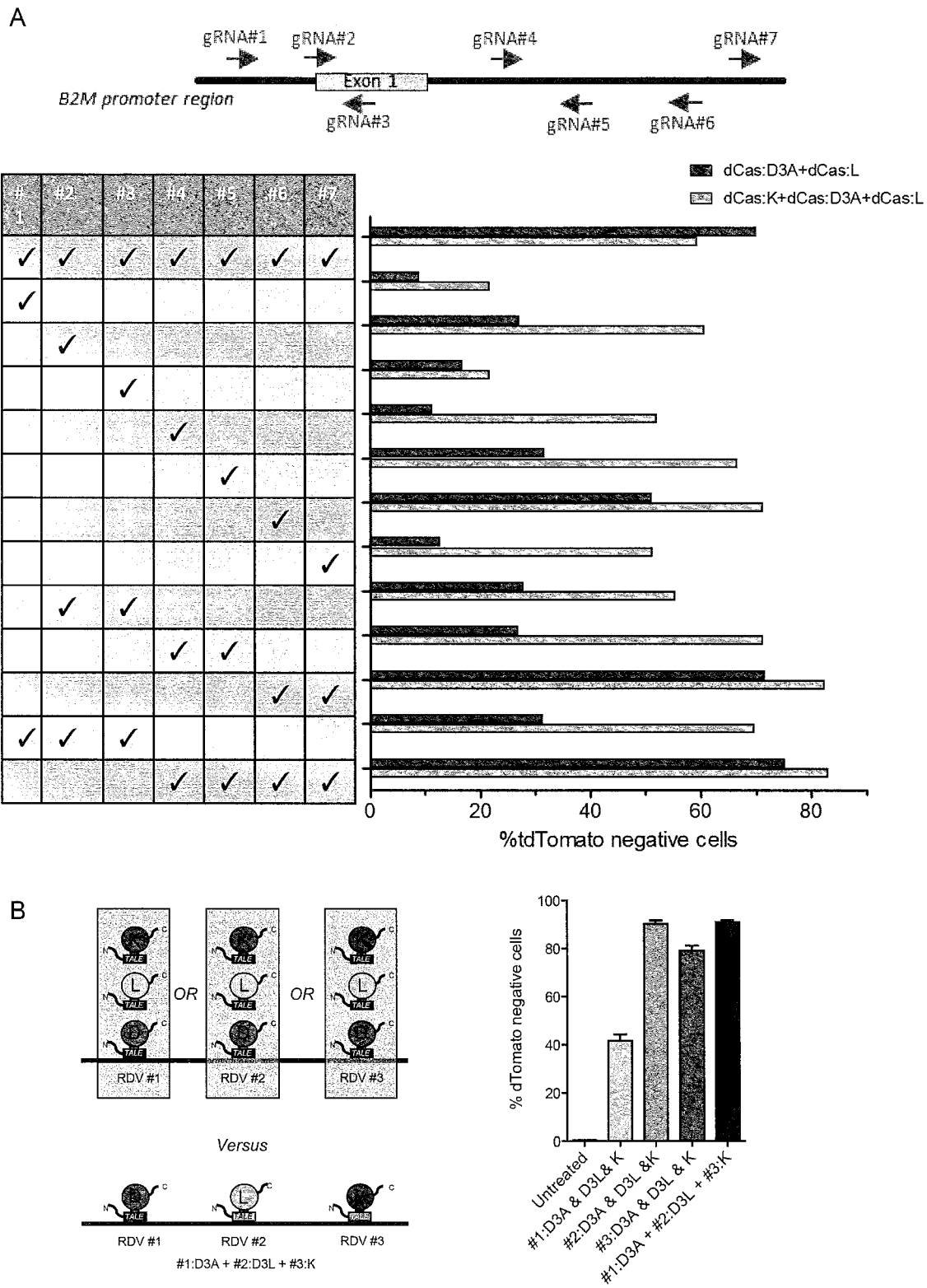

Intriguingly, functional deconvolution of 7 gRNAs into quartets until individual singlets showed that even one gRNA was sufficient to drive efficient silencing of B2M with both the triple and the dCas9:D3A+dCas9:D3L combination (FIG. 17). Unexpectedly, some of the single gRNA were able to induce silencing efficiencies that were comparable to those measured in the 7 gRNA pool. Furthermore, in several instances, we observed that the triple ATR combination was performing better than the dCas9:D3A+dCas9:D3L combination. Altogether, these data indicates that even one well properly positioned gRNA tethering the three ATRs on the target gene can induce its efficient silencing.

Similarly, we also investigated if a single TALE protein was sufficient to induce efficient and permanent epigenetic silencing. To this aim we generated four TALE proteins, to each of which we fused the three different effector domains, namely KRAB, DNMT3A and DNMT3L (FIG. 17B; schematic on the left). As a model we used the TALE proteins targeting B2M gene and the K562 B2M tdTomato reporter cell line previously described (FIGS. 13A and 15A, respectively). Unexpectedly, also in the conditions in which the repressive domains were competing for the same binding site on the B2M gene, we obtained efficient and permanent gene silencing of the B2M gene (FIG. 17B, grey bars in the histogram). The different degree of efficiency was most likely reflecting the different binding affinity of the TALEs, with some of these working as efficiently as the control condition in which each effector domain was fused to a different DNA-binding domain (FIG. 17B; dark blue bar in the histogram).

Overall, these data show for the first time to our knowledge permanent silencing of an endogenous gene in human cells using custom made ATRs. Importantly, silencing was fully resistant to external stimuli impinging on the B2M promoter/enhancer, thus providing another line of evidence of the stability of the epigenetic modifications deposed by the triple ATRs combination. Moreover, we provide evidence of the broad applicability of our strategy by tethering the repressor domains to the endogenous gene by means of two different DNA binding technologies, namely TALE and CRISPR/Cas9.

Figure 18:
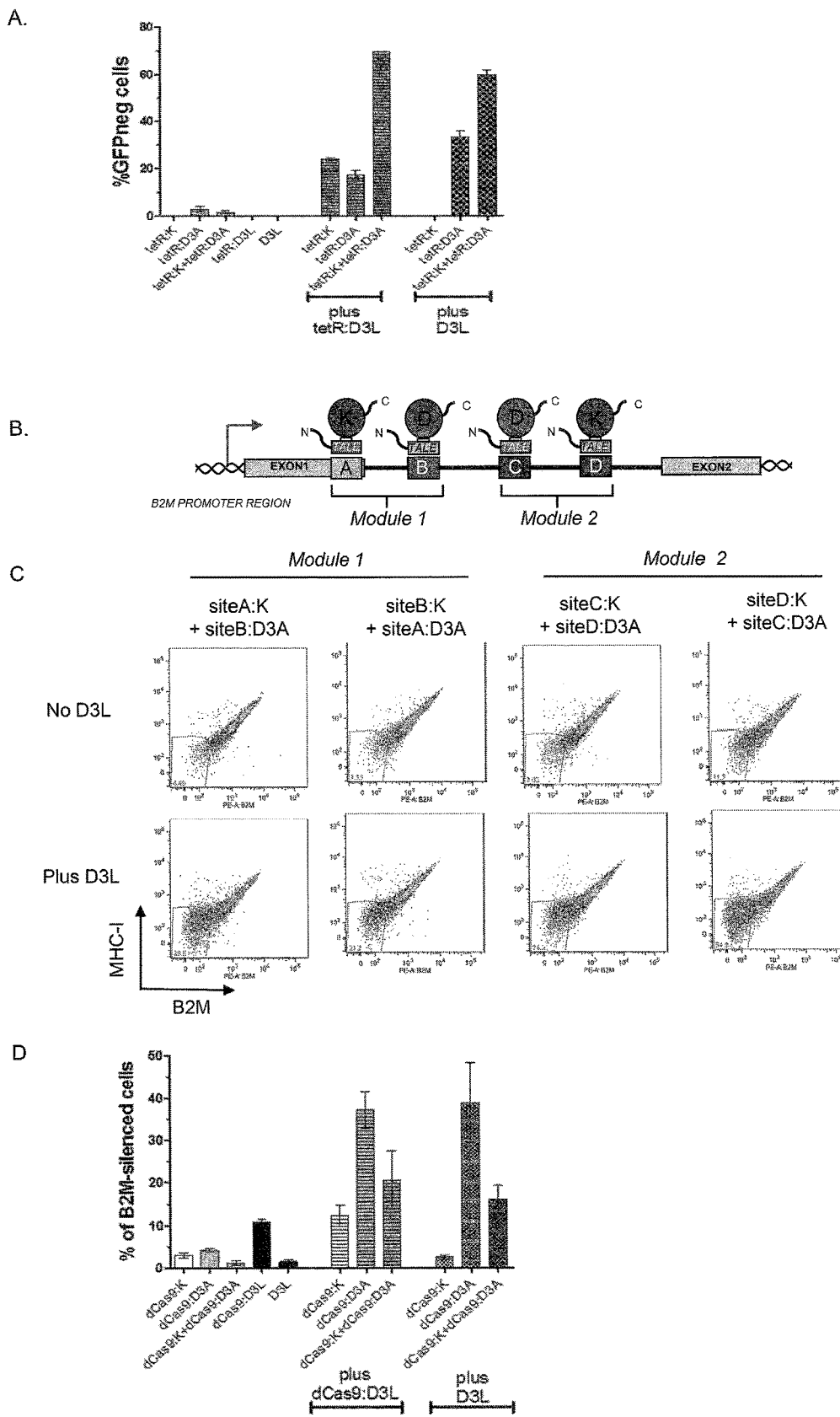

Transient Expression of an Un-Targeted DNMT3L Improves and Rescues Silencing Efficiency of the DNMT3A+KRAB Based ATRs in Refractory Cell Types In order to reduce the number of different ATRs to design and construct, we investigated if at least one of the effector domains can be delivered to the cells without a DNA binding domain, and still be able to effectively cooperate with the other two ATRs targeted on the desired gene of interest. To assess if delivery of an un-targeted DNMT3L (hereafter referred to as D3L) might be as effective as its targeted counterpart in cooperating with the other two effector domains (specifically DNMT3A and KRAB), we initially took advantage of the TetO7/tetR system. We thus transfected the TetO7.LV-reporter B-lymphoblastoid cells with in vitro transcribed mRNAs encoding for the tetR-based ATRs and for the un-targeted D3L, and measured by time-course flow cytometry analysis the percentage of eGFP-negative cells in the different transfection conditions (FIG. 18A; data are represented as mean±range, n=2). At 27 days post-transfection we found little if any silencing in cells treated with either the individual ATRs or the tetR:K+tetR:D3A combination. Instead, up to 70% of the cells treated with the combination of the 3 ATRs become eGFP-negative. The targeted tetR:D3L synergised also with tetR:K or tetR:D3A, although the levels of silencing measured in these two experimental conditions were 3.5-fold lower (~20% eGFP-negative cells) than those measured with the triple ATR combination (FIG. 18A; compare the plus tetR:D3L conditions). These data are in line with those previously found with the TetO7.LV-reporter B-lymphoblastoid cell line, in which the unexpected drop in the silencing efficiency of the tetR:D3A+tetR:K combination was completely rescued by inclusion of the tetR:D3L to the cocktail (see FIG. 7G for comparison). When the un-targeted D3L was delivered either alone or in combination with the tetR:K, no eGFP-negative cells were found. On the other hand, D3L was able to effectively synergise with both the tetR:D3A and the tetR:D3A+tetR:K combination (FIG. 18A; see the plus D3L conditions). Importantly, the levels of silencing measured in these two experimental conditions were comparable to those found by co-tethering DNMT3L and DNMT3A; or DNMT3L, DNMT3A and KRAB to the TetO7 sequence. These data indicate that the un-targeted D3L can effectively synergise with the KRAB+DNMT3A combination.

We then assessed if these findings also held true with ATRs based on custom-made DNA binding domains. To this end, we selected 4 different TALE binding sites in the B2M promoter region and constructed the corresponding TALE DNA binding domains (a schematic of the B2M locus showing the different TALEs binding sites is depicted in FIG. 18B; the amino acid sequences of the TALE A and the nucleotide sequences of its corresponding binding sites is listed in Table 5; TALEs B, C and D were described previously and correspond to TALE #1, #2 and #3 of Table 3). Each of these TALEs were equipped with KRAB or DNMT3A. The 4 different TALE binding sites constitute two independent silencing modules (Module 1: site A plus site B; Module 2: site C plus site D), at which the TALE: D3A and TALE:K can bind in two different orders (siteA: K-siteB:D3A or siteA:D3A-siteB:K). We then transfected HEK-293T cells with plasmids encoding for the TALE-based ATRs and for the untargeted D3L, and measured by time-course flow cytometry analysis the percentage of double B2M/MHCl-negative cells in the different transfection conditions (FIG. 18C). At 12 days post-transfection we measured a low fraction of B2M/MHCl-negative cells in all the conditions treated with the TALE:D3A+TALE:K combination (upper plots in FIG. 18C). On the other hand, co-treatment of the cells with the combination of the two ATRs plus the untargeted D3L resulted on average in a 5-fold increase in the efficiency of silencing (lower plots FIG. 18C) over the levels measured in the absence of D3L. This increase was independent of the relative order of binding of the TALE proteins on the B2M promoter and was confirmed for both of the silencing modules.

Finally, we performed similar experiments using ATRs based on the CRISPR/Cas9 system (FIG. 18D; data are represented as mean±SEM, n=3). Here, we found that transient expression of D3L in HEK-293T cells transfected with the dCas9:K+dCas9:D3A ATRs plus the B2M gRNAs (those used in FIG. 13E) resulted in levels of gene silencing comparable to those obtained with the triple combination of the dCas9-based ATRs plus the B2M gRNAs (FIG. 18D). Similar results were obtained by delivering D3L with the DNMT3A ATR.

Overall, these data clearly show that the un-targeted DNMT3L can effectively replace its targeted counterpart in our cocktail of ATRs.

Figure 19:
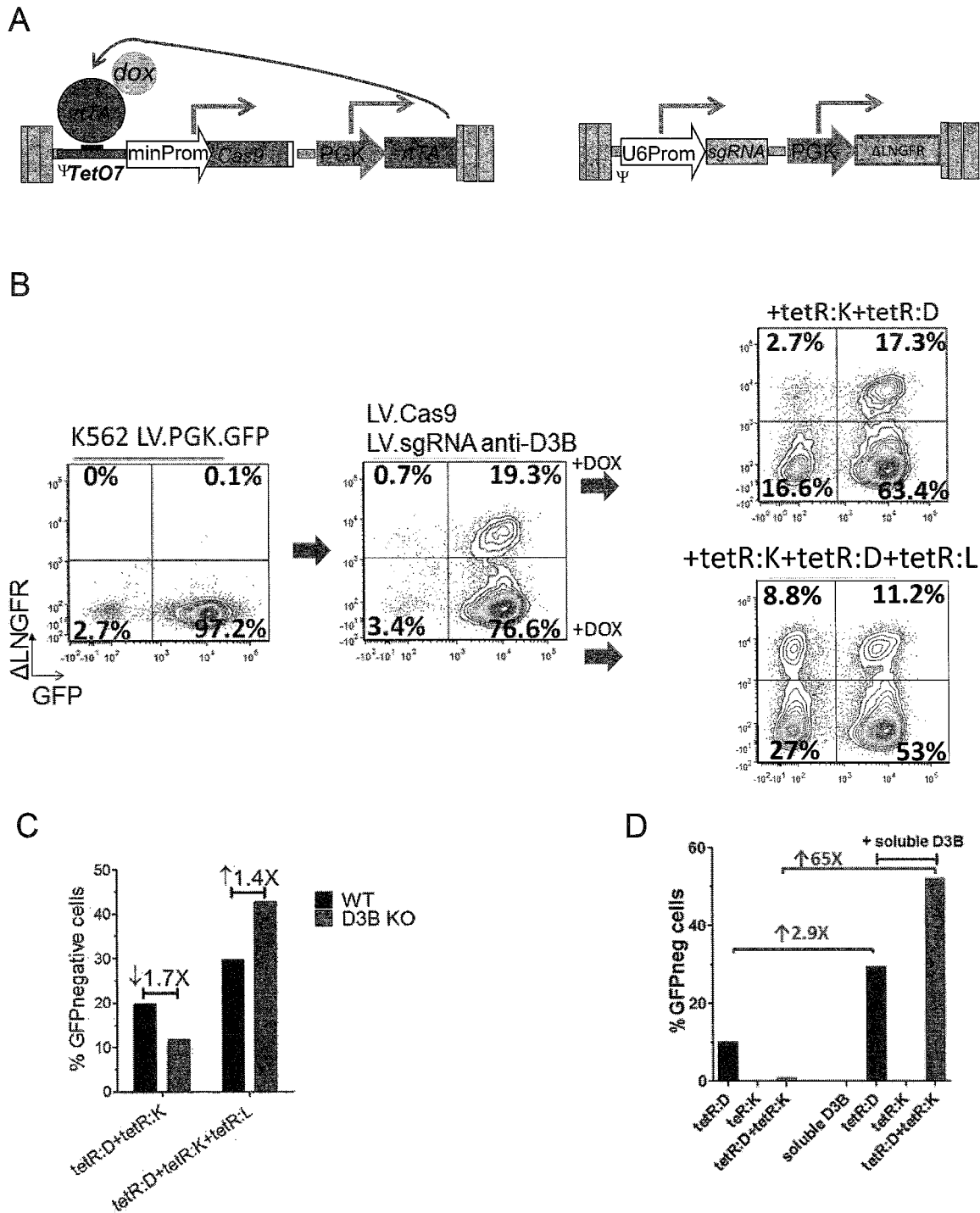

Transient Expression of an Untargeted DNMT3B Rescues Silencing Efficiency of the DNMT3A+KRAB Based ATRs in Refractory Cell Types Considering the role of the DNMT3B in the establishment of de novo DNA methylation, we asked if the endogenous DNMT3B could cooperate with our ATRs. To answer this question, we performed a genetic knock-out of DNMT3B by CRISPR/Cas9 in the TetO7.LV K562 reporter cell line. To do this, we transduced the cells with two lentiviral vectors, one encoding for a doxycycline-inducible Cas9 nuclease (Wang, T. et al. (2014) Science 343:80-4) and another encoding for both a gRNA against the exon 2 of the DNMT3B gene and the ΔLNGFR marker (schematic of the vectors in FIG. 19A; middle FACS plot for the double transduced cells). Upon Cas9 activation by doxycycline administration, we electroporated the cells with plasmids encoding for the different combinations of the ATRs, and then measured by flow cytometry the efficiency of silencing in the ΔLNGFR-positive and -negative cells. By comparing these numbers, we can appreciate if inactivation of the DNMT3B gene improves or not the efficiency of silencing of the different ATR combination. Here, we observed that the subpopulation expressing the gRNAs anti-DNMT3B (i.e. ΔLNGFR-positive cells) was less permissive than wild-type cells (i.e. those negative for ΔLNGFR) to silencing by tetRK+tetR:D3A combination (FIG. 19B and FIG. 19C; upper right FACS plot), thus indicating that the endogenous DNMT3B is a relevant partner of these two ATRs. Remarkably, genetic knock-out of DNMT3B increased silencing efficiency of the tetR:K+tetR:D3A+tetR:D3L combination, thus suggesting that in this case DNMT3B is acting as a decoy for these ATRs (FIG. 19B and FIG. 19C; bottom right FACS plot). For all the other ATR combinations and the individual ATR, inactivation of DNMT3B did not cause any significant difference in the silencing efficiency as compared to wild-type cells. Furthermore, considering that, in contrast to K562 cells, the B-lymphoblastoid cell line described above lacks DNMT3B expression (as measured by RT-qPCR analysis), we asked if DNMT3B overexpression could increase ATRs silencing efficiency in this cell line refractory to the DNMT3A+KRAB combination. In particular, we transiently transfected the TetO7.LV B-lymphoblastoid reporter cell line with an mRNA encoding for the full-length DNMT3B (without fusing it to the tetR DNA binding domain; the amino acid sequence of the DNMT3B is in Table 1) with or without the two ATRs. Remarkably, DNMT3B overexpression significantly rescued activity of the tetR:K+tetR:D3A combination, enabling stable eGFP silencing in 52% of the treated cells, with a 65-fold increase compared to tetR:K+tetR:D3A alone (FIG. 19C). Of note, DNMT3B overexpression generated also a 2.9-fold increase in the silencing efficiency of the tetR:D3A condition (FIG. 19D).

Overall, these data clearly show that the un-targeted DNMT3B can effectively rescue activity of the DNMT3A+KRAB combination in refractory cell types.

Silencing of the BCL11A Gene Using Both CRISPR/dCas9- and TALE-Based ATRs.

Figure 20:
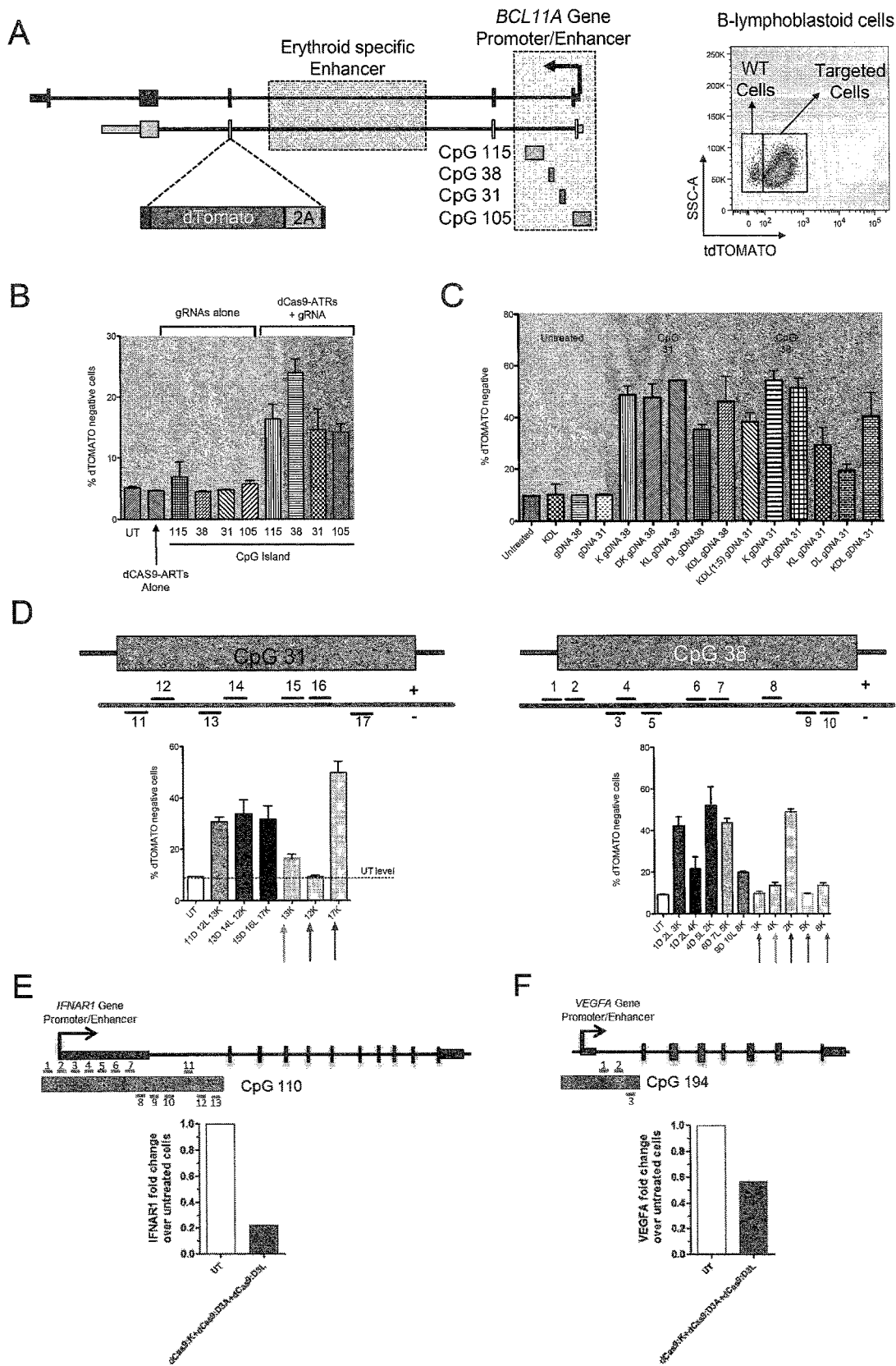

We then exploited the ATR combination to silence BCL11A, a gene whose repression has been proposed as a potential therapeutic intervention for β-Thalassemia and Sickle Cell Anaemia. To easily assess activity of the ATRs on the BCL11A gene, we targeted the tdTomato transgene within the third exon of the gene in human B-lymphoblastoid cells by means of gene targeting with CRISPR/Cas-based technology (FIG. 20A). Such targeting strategy allows expressing the tdTomato transgene from the regulatory sequences of the BCL11A gene, thus faithfully reporting the expression level of this gene. We then enriched to near purity the tdTomato-positive cells by cell sorting, and targeted 4 CpG islands in the promoter/enhancer region of this gene with CRISPR/dCas9-based ATRs containing DNMT3A or DNMT3L. Each of the 4 CpG island was individually interrogated using a separate pool of gRNAs (also known as CRISPR; the nucleotide sequences of the gRNAs are reported in Table 6). By comparing tdTomato expression between treated and untreated controls, we were able to measure the relative contribution of each island to the expression of BCL11A (FIG. 20B). When compared to control-treated cells, silencing of each CpG island was associated with long-term stable repression of BCL11A expression (shown here as % of tdTomato-negative cells), although the extent of silencing of this gene varied according to the CpG island targeted by the ATRs. We then selected the CpG island 31 and 38 for further studies aiming at assessing the activity of the triple ATR combination. In these studies we also included all possible double-ATR combinations and the single KRAB-based ATRs. Remarkably, all conditions tested were able to induce significant levels of gene silencing, with epigenetic editing of CpG 38 (the best responsive island in the previous experiments) with the triple ATR combination resulting in up to 55% gene silencing (FIG. 20C). Finally, we designed 17 different TALE-based ATRs targeting the CpG island 31 and 38 (7 and 10 TALE protein, respectively; the amino acid sequences of these TALEs and their cognate target sequences are listed in Table 7; FIG. 20D top schematics), and tested their silencing activity either as a triple-ATR combination or as KRAB-based ATR. Silencing of both CpG island with all triple ATR combination resulted in effective and long-term silencing of BCL11A (reaching up to 55% of tdTomato-negative cells), while silencing with TALE:KRAB was associated with different degrees of gene silencing, some being as efficient as the triple ATR combination, while others being completely inactive. Overall, these data show the feasibility of permanently silencing the human BCL11A gene.

Silencing of Additional Human Endogenous Genes Using CRISPR/dCas9-Based ATRs.

We finally challenged our epigenetic silencing technology against two additional human endogenous genes, that are the Interferon (alpha, beta and omega) Receptor 1 (IFNAR1) gene and the Vascular Endothelial Growth Factor A (VEGFA) gene. Both genes show a CpG island at the gene promoter/enhancer region. Therefore, we designed 13 gRNAs against the IFNAR1 CpG island (FIG. 20E, Top) 3 gRNAs against the VEGFA CpG island (FIG. 20F, Top) (the nucleotide sequences of the gRNAs are reported in Table 6).

Interestingly, by electroporating K562 cells with plasmids encoding for the pool of 13 gRNAs against the IFNAR1 gene plus the triple dCas9-based ATRs combination, we achieved long-term downregulation of the IFNAR1 transcript level (0.22 fold change) in treated cells compared to the untreated sample (FIG. 20E, Bottom). Furthermore, by electroporating K562 cells with plasmids encoding for the pool of 3 gRNAs against the VEGFA gene plus the triple dCas9-based ATRs combination, we achieved long-term downregulation of the VEGFA transcript level (0.57 fold change) in treated cells compared to the untreated sample (FIG. 20F, Bottom). Overall, these data show the feasibility of silencing various human endogenous genes by CRISPR/dCas9-based ATRs.

Material and Methods

Lentiviral Vectors and ATR Constructions

The ATR-reporter Lentiviral Vectors (LV) containing the TetO7 sequence or the TALE binding sites, and the DNMT3B gRNA-expressing LV were generated from the self-inactivating transfer construct pCCLsin-.cPPT.hPGK.eGFP.Wpre (Follenzi, A. et al. (2000) Nat. Genet. 25:217-22), while ATR-expressing Bid.LVs were generated from the transfer construct pCCLsin.cPPT.dLNG-FR.mhCMV.hPGK.GFP.Wpre (Gentner, B. et al. (2010) Sci. Transl. Med. 2: 58ra84). The doxycycline-inducible Cas9 expressing vector was obtained from Addgene (pCW-Cas9; #50661; Wang, T. et al. (2014) Science 343:80-4). LV stocks were prepared as previously described (Follenzi, A. et al. (2002) Methods Mol. Med. 69:259-74). Briefly, HEK293T cells were cotransfected by calcium phosphate precipitation with the transfer construct plasmid, the pMD.Lg/pRRE packaging plasmid, the pMD2.VSV-G envelope-encoding plasmid and pRSV-Rev in the following amounts: 35/12.5/9/6.25 µg DNA per 15 cm dish, respectively. Vector particles were concentrated 300-fold by ultracentrifugation and titred by serial dilution on HEK293T cells as previously described (Cantore, A. et al. (2015) Sci. Transl. Med. 7: 277ra28). All other tetR-based ATRs were generated by replacing the KRAB domain in tetR:KRAB (which is itself discussed in Szulc, J. et al. (2006) Nat. Methods 3:109-16) with the relevant other effector domains. TALE-based ATRs were generated using a modified version of the Golden Gate TALEN Kit 2.0a (Addgene, Kit #1000000024; Cermak, T. et al. (2011) Nucleic Acids Res. 39: e82) containing the following architectural changes: the Golden Gate TALE C- and N-terminal subregions were replaced with the +163 and a +63 terminal deletions, respectively. These constructs were adapted to accommodate in frame the effector domains. The Cas9-based ATRs were generated by replacing the VP160 transactivator from the plasmid pAC154-dual-dCas9VP160-sgExpression (Addgene #48240; Cheng, A. W. et al. (2013) Cell Res. 23:1163-71) with the effector domains or with the catalytic domain of TET1.

Cell Culture Conditions and Engineering

Human Epstein-Barr Virus-immortalised B lymphocytes (B-lymphoblastoid cells) and U-937 cells were maintained in RPMI-1640 (Sigma); HEK293T and K-562 in IMDM (Sigma); NIH/3T3 in DMEM (Sigma). All media were supplemented with 10% FBS (Foetal Bovine Serum; Euro-Clone), L-glutamine (EuroClone) and 1% Penicillin/Streptomycin (100 U/mL final concentration; EuroClone). Cells were cultured at 37° C. in a 5% $CO_2$ humidified incubator. The reporter cell lines were generated by transducing the cells with the indicated ATR-reporter LVs at a Multiplicity of Infection (MOI) of 0.1, and then enriched for eGFP expression using a MoFlo XDP Cell Sorter (Beckman Coulter). The reporter cell lines with targeted integration were generated as follows: i) for the insertion of the eGFP-cassette into the AAVS1 locus, we co-transfected a donor construct (containing the TetO7 sequence downstream or upstream of the cassette; 1.5 g of donor plasmid) and the previously described AAVS1-ZFNs in forms or mRNAs (0.5 µg each ZFN; Lombardo, A. et al. (2011) Nat. Methods 8:861-9). Single-cell derived clones were then obtained by limiting dilution plating, and analysed by Southern blot to confirm targeted integration of the cassette as previously described (Lombardo, A. et al. (2011) Nat. Methods 8:861-9); ii) for the insertion of the tdTomato cassette within the third exon of BCL11A, we co-transfected a donor construct containing the tdTomato transgene fused to 2A self-catalytic peptide (2 µg), together with a plasmid encoding for Cas9 (1 µg) and another expressing a gRNA targeting exon 3 (125 ng; sequence of the gRNA: 5'-GGAGCTCTAATCCC-CACGCCTGG-3', SEQ ID NO: 110); iii) a similar targeting strategy to that used for BCL11A was used to insert a splice acceptor-IRES-tdTomato cassette into intron 1 of B2M (sequence of the gRNA: 5'-AGGCTACTAGCCCCAT-CAAGAGG-3'. SEQ ID NO: 111). Both the tdTomato cell lines were generated by FACS-sorting of the positive cells.

To test activity of the ATRs, the reporter cell lines were transduced with the ATR-expressing Bid.LV at a MOI of 10, or transfected with plasmids or in vitro transcribed mRNAs expressing the ATRs (4D-Nucleofector™ System; Lonza) according to the manufacturer's instruction for K-562, U937 and NIH/3T3, or using the pulse program EW-113 and the SF solution for B-lymphoblastoid cells. We routinely transfected 2 µg of nucleic acid (both plasmid and in vitro transcribed mRNA) for each tetR- or TALE-based ATR, except for experiments conducted in non-saturating conditions in which we used 500 ng of plasmid encoding for each of the ATRs. On the other hand, we electroporated 1-2 µg of plasmid encoding for the dCas9-based ATRs and 125-250 ng of plasmids expressing for the gRNAs. In vitro transcribed mRNAs were produced as previously described (Genovese, P. et al. (2014) Nature 510:235-40). When indicated, cells were treated with 1 µM of 5-Aza-2-deoxycytidine (AZA, Sigma) or with 12 µg/mL of doxycycline (Sigma). The AZA-containing media was replaced every day, and the cells were analysed by flow cytometry at day 4 and 7 after treatment. When indicated, cells were treated with 500 U/mL of Recombinant Human IFN-γ (R&D Systems). The IFN-γ-containing media was replaced every day, and the cells were analysed by flow cytometry at day 2 and 4 after treatment. Cord-blood derived CD34+ cells from healthy donors were purchased from Lonza. $10^6$ CD34+ cells/mL were stimulated overnight in serum-free StemSpan medium (StemCell Technologies) supplemented with penicillin, streptomycin and the following human early-acting cytokines: Stem Cell Factor (SCF) 50 ng/ml, Flt3 ligand (Flt3-L) 50 ng/mL, thrombopoietin (TPO) 50 ng/ml, and interleukin 6 (IL-6) 50 ng/ml (all purchased from Peprotech). The cells were then transduced with the TetO7-reporter LV at MOI of 30-50. After 48 hours, the cells were electroporated with 2 µg of the ATR-encoding mRNAs (P3 Primary Cell 4D-Nucleofector X Kit, program EO-100; Lonza). 1 µM of SR1 (BioVision Inc.) was added at every medium change. After one week in stimulating media, cells were grown in liquid culture in IMDM 10% FBS. For CFC assays, 800 cells/plate were seeded one day after electroporation in methylcellulose-based medium (MethoCult H4434, Stem-Cell Technologies). Two weeks after plating, colonies were counted and identified according to morphological criteria and analysed by flow cytometry.

Resting T-lymphocytes were isolated from Peripheral Blood Mononuclear Cells (PBMCs) of healthy donors by leukapheresis and Ficoll-Hypaque gradient separation. The cells were activated and sorted using magnetic beads conjugated to antibodies to CD3 and CD28 (ClinExVivo CD3/CD28; Invitrogen), following the manufacturer instructions, and grown at a concentration of $1 \times 10^6$ cells per mL in RPMI (Sigma) supplemented with penicillin, streptomycin, 10% FBS and 5 ng/ml of IL-7 and IL-15 (PeproTech) as previously described (Kaneko, S. et al. (2009) Blood 113:1006-15). After three days in culture, the cells were transduced with the TetO7-reporter the LV at the MOI of 10. Three days after transduction, the cells were washed and electroplated with 2 µg of mRNA encoding for the ATRs. To test silencing resistance to polyclonal TCR stimulation, we co-cultured the bulk-treated T-lymphocytes with a pool of 6000 rad irradiated PMBCs from unrelated donors and 10000 rad irradiated JY cells in presence of anti-CD3 antibody (OKT3) 30 ng/ml (Orthoclone, Milan, Italy) and human recombinant IL-2 50 U/mL (PrepoTech). Regarding silencing of B2M in primary T-lymphocytes, these cells were isolated from PBMCs of a healthy donor by leukapheresis, Ficoll-Hypaque gradient separation and final selection with the Pan T Cell Isolation Kit (Miltenyi Biotec). The T-cells were then activated with magnetic beads conjugated to antibodies to CD3 and CD28 (ClinExVivo CD3/CD28; Invitrogen), following the manufacturer's instructions, and grown at a concentration of $1 \times 10^6$ cells per mL in RPMI (Sigma) supplemented with penicillin, streptomycin, 10% FBS and 5 ng/ML of IL-7 and IL-15 (PeproTech) as previously described (Kaneko, S. et al. (2009) Blood 113:1006-15). After three days in culture, the cells were electroporated with in vitro transcribed mRNA encoding for TALE-based ATRs and kept in culture for further 2 weeks, with beads removal 4 days post electroporation. The use of human CB-derived CD34+ cells and of primary T-lymphocytes was approved by the San Raffaele Hospital Bioethical Committee.

Flow Cytometry and Gene Expression Analyses

For immunophenotypic analysis of Bid.LV transduced cells, CD34+ cells and their progeny, and T lymphocytes (performed by FACSCanto II; BD Pharmingen) we used the following antibodies.

| Antibody | Conjugated | Company |
|---|---|---|
| anti-human CD133/2 | PE | Miltenyi Biotec |
| anti-human CD34 | PECy7 | BD Pharmingen |
| anti-human CD90 | APC | BD Pharmingen |
| anti-human CD45 | PB | BioLegend |
| anti-human CD3 | PE | BD Pharmingen |
| anti-human CD13 | APC | BD Pharmingen |
| anti-human CD33 | PeCy7 | BD Pharmingen |
| anti-human CD235a | PE, APC | BD Pharmingen |
| anti-human B2M | PE | Biolegend |
| anti-human MHC-I | APC | Santa Cruz Biotechnology, Inc |
| anti-human CD271 | Alexa Fluor 647 | BD Pharmingen |

Aminoactinomicin D (7-AAD) positive, nonviable cells were excluded from the analysis, and $1-5 \times 10^5$ viable cells were scored per analysis. Single stained and FMO stained cells were used as controls.

For the gene expression analyses, total RNA extracted from $2-6 \times 10^6$ cells (RNeasy Mini kit; 5 Qiagen) was reverse-transcribed using random examers according to the SuperScript III First-Strand Synthesis System (Invitrogen) manufacturer's protocol. We analysed 15-100 ng of cDNA from K-562 and HEK293T cells in triplicate with TaqMan Gene Expression assays (Applied Biosystems).

| Catalog number | Gene Name [ID] |
|---|---|
| Hs00215284_m1 | NLR family, pyrin domain containing 2 [NLRP2] |
| Hs00212574_m1 | Glycoprotein VI (platelet) [GP6] |
| Hs00293416_m1 | Retinol dehydrogenase 13 (all-trans/9-cis) [RDH13] |
| Hs00373719_m1 | EPS8-like 1 [EPS8L1] |
| Hs01085949_m1 | Protein phosphatase 1, regulatory (inhibitor) subunit 12C [PPP1R12C] |
| Hs00165957_m1 | Troponin T type 1 (skeletal, slow) [TNNT1] |
| Hs00162848_m1 | Troponin I type 3 (cardiac) [TNNI3] |
| Hs00332766_m1 | Chromosome 19 open reading frame 51 [C19orf51] |
| Hs00162516_m1 | Synaptotagmin V [SYT5] |
| Hs00936202_m1 | Protein tyrosine phosphatase, receptor type, H [PTPRH] |
| Hs00382401_m1 | Transmembrane protein 86B [TMEM86B] |
| Hs00208777_m1 | SAPS domain family, member 1 [SAPS1] |
| Hs99999907_m1 | Beta-2-microglobulin [B2M] |
| Hs02758991_g1 | Glyceraldehyde-3-phosphate dehydrogenase [GAPDH] |
| Hs01060665_g1 | Actin beta [ACTB] |
| Hs99999909_m1 | Hypoxanthine phosphoribosyltransferase 1 [HPRT1] |
| Hs00973637_m1 | 2'-5'-oligoadenylate synthetase 1 [OAS1] |
| Hs00276752_m1 | Spastic paraplegia 11 [SPG11] |
| Hs01388797_m1 | Protein associated with topoisomerase II homolog 2 [PATL2] |
| Hs04399718_m1 | Tripartite motif containing 69 [TRIM69] |
| Hs00900055_m1 | Vascular Endothelial Growth Factor A [VEGFA] |
| Hs01066116_m1 | Interferon (alpha, beta and omega) Receptor 1 [IFNAR1] |

The gene expression assay used to detect the eGFP transcript was previously described (Lombardo, A. et al. (2011) Nat. Methods 8:861-9). Real-time PCRs were performed with a ViiA 7 Real-Time PCR System (Applied Biosystems) and dedicated software was used to extract raw data (Ct and raw fluorescence). Genes with a Ct value ≥37 were excluded from the analyses. The relative expression level of each gene was calculated by the $\Delta\Delta Ct$ method, normalised to HPRT or B2M expression (housekeeping gene controls), and represented as fold change relative to the mock-treated samples (calibrator).

Molecular Analyses

For bisulfite sequencing, genomic DNA was extracted with DNeasy Blood & Tissue Kit or QIAamp DNA Mini Kit (QIAGEN) and then treated with EpiTect Bisulfite kit (Qiagen) according to manufacturer's instructions. The converted products were then used to PCR amplify the B2M-promoter region using the primers listed below. PCR fragments were purified and cloned into pCRII-TOPO TA (Invitrogen), and five to ten clones for each sample were verified by sequencing using the M13 universal primer.

|  |  | (SEQ ID NO: 112) |
|---|---|---|
| BIS B2M #1 F | GTTGTGTTTTTTGGGGAAGTTAG | |

|  |  | (SEQ ID NO: 113) |
|---|---|---|
| BIS B2M #1 R | AAAATTCCTCCCTATATCCTTA | |

|  |  | (SEQ ID NO: 114) |
|---|---|---|
| BIS B2M #2 F | AAGAATGGAGAAATTTTGTAGGGAATT | |

|  |  | (SEQ ID NO: 115) |
|---|---|---|
| BIS B2M #2 R | ACCACCAAAAAAAACTTAAAAAAAA | |

|  |  | (SEQ ID NO: 116) |
|---|---|---|
| BIS B2M #3 F | TTTTTTTGGTTTGGAGGTTATTTAG | |

|  |  | (SEQ ID NO: 117) |
|---|---|---|
| BIS B2M #3 R | CAAAACACATAAAATCCTTAACACA | |

```
                                        (SEQ ID NO: 118)
BIS B2M #4 F     TTTTAGATTGGAGAGTTGTGGATTT (SEQ ID NO: 119)
BIS B2M #4 R     AATTTTACAACTCCCCTAACTAACA
```

Chromatin immunoprecipitation (ChIP) analysis was performed as previously described (Lombardo, A. et al. (2011) Nat. Methods 8:861-9) using 5-10 μg of ChIP-grade antibodies (Abcam) raised against the human H3 or the RNA Polymerase II CTD repeat YSPTSPS. IgG isotypes were also used as controls. The primers used for these studies are listed below. The percentage of enrichment of RNA PolII for each investigated site was calculated by the ΔCt method using the Input as normaliser.

```
                                        (SEQ ID NO: 120)
B2M -241 F       GCAAGTCACTTAGCATCTCTGGG (SEQ ID NO: 121)
B2M -241 R       TTGCTGTCTGTACATCGGCG (SEQ ID NO: 122)
B2M +158 F       TCTCTCGCTCCGTGACTTCC (SEQ ID NO: 123)
B2M +158 R       CGCTTCCCCGAGATCCAGCC (SEQ ID NO: 124)
B2M +315 F       AGGGGAGACCTTTGGCCTAC (SEQ ID NO: 125)
B2M +315 R       CTCTGACGCTTATCGACGCC (SEQ ID NO: 126)
B2M +580 F       AGACTGGAGAGCTGTGGACTTCG (SEQ ID NO: 127)
B2M +580 R       GCCAAGCATTCTACAAACGTCG (SEQ ID NO: 128)
B2M +1529 F      CAGTCAGGGGAGCTGTAAAACC (SEQ ID NO: 129)
B2M +1529 R      TTGCCAGGTACTTAGAAAGTGC (SEQ ID NO: 130)
B2M +3307 F      CCTTGGGTTGATCCACTTAGG (SEQ ID NO: 131)
B2M +3307 R      TAGTAGAGTGCCTGGGACATAGC (SEQ ID NO: 132)
B2M +3969 F      GTGTCTGGGTTTCATCCATCCG (SEQ ID NO: 133)
B2M +3969 R      GCTGAAAGACAAGTCTGAATGC (SEQ ID NO: 134)
B2M +5082 F      AGGATAAAGGCAGGTGGTTACC (SEQ ID NO: 135)
B2M +5082 R      AGATGTCCAATGTGGAAATGGC (SEQ ID NO: 136)
CCR5 -305 F      AGTCTGACTACAGAGGCCACTGG (SEQ ID NO: 137)
CCR5 R -255      AGGCAAATGAGACCCCAAACAGC (SEQ ID NO: 138)
PPP1R12C -861 F  TAAGAACCGAGGACAAGTAGTGC (SEQ ID NO: 139)
PPP1R12C -768R   TGCTGGGATGACGAGCGTAAGC
```

Statistical Analysis

One-way ANOVA test with Bonferroni's multiple comparison post-test was used to assess statistical significance of differences in gene expression among all samples (P<0.05).

TABLE 1

```
ZNF10
                                                            (SEQ ID NO: 1)
ALSPQHSAVTQGSIIKNKEGMDAKSLTAWSRTLVTFKDVFVDFTREEWKLLDTAQQIVYRNVMLENYK
NLVSLGYQLTKPDVILRLEKGEEPWLVEREIHQETHPDSETAFEIKSSV

DNMT3A
                                                            (SEQ ID NO: 8)
TYGLLRRREDWPSRLQMFFANNHDQEFDPPKVYPPVPAEKRKPIRVLSLFDGIATGLLVLKDLGIQVD
RYIASEVCEDSITVGMVRHQGKIMYVGDVRSVTQKHIQEWGPFDLVIGGSPCNDLSIVNPARKGLYEG
TGRLFFEFYRLLHDARPKEGDDRPFFWLFENVVAMGVSDKRDISRFLESNPVMIDAKEVSAAHRARYF
WGNLPGMNRPLASTVNDKLELQECLEHGRIAKFSKVRTITTRSNSIKQGKDQHFPVFMNEKEDILWCT
EMERVFGFPVHYTDVSNMSRLARQRLLGRSWSVPVIRHLFAPLKEYFACV

EZH2 (short variant)
                                                            (SEQ ID NO: 140)
NVSCKNCSIQRGSKKHLLLAPSDVAGWGIFIKDPVQKNEFISEYCGEIISQDEADRRGKVYDKYMCSF
LFNLNNDFVVDATRKGNKIRFANHSVNPNCYAKVMMVNGDHRIGIFAKRAIQTGEELFFDYRYSQADA
LKYVGIEREMEIP EZH2 (long variant)
                                                            (SEQ ID NO: 141)
RLWAAHCRKIQLKKDGSSNHVYNYQPCDHPRQPCDSSCPCVIAQNFCEKFCQCSSECQNRFPGCRCKA
QCNTKQCPCYLAVRECDPDLCLTCGAADHWDSKNVSCKNCSIQRGSKKHLLLAPSDVAGWGIFIKDPV
QKNEFISEYCGEIISQDEADRRGKVYDKYMCSFLFNLNNDFVVDATRKGNKIRFANHSVNPNCYAKVM
MVNGDHRIGIFAKRAIQTGEELFFDYRYSQADALKYVGIEREMEIP TLE1
                                                            (SEQ ID NO: 142)
MFPQSRHPTPHQAAGQPFKFTIPESLDRIKEEFQFLQAQYHSLKLECEKLASEKTEMQRHYVMYYEMS
YGLNIEMHKQTEIAKRLNTICAQVIPFLSQEHQQQVAQAVERAKQVTMAELNAIIGQQQLQAQHLSHG G9A (short variant)
                                                            (SEQ ID NO: 143)
LNRKLRLGVGNRAIRTEKIICRDVARGYENVPIPCVNGVDGEPCPEDYKYISENCETSTMNIDRNITH
```

TABLE 1-continued

LQHCTCVDDCSSSNCLCGQLSIRCWYDKDGRLLQEFNKIEPPLIFECNQACSCWRNCKNRVVQSGIKV
RLQLYRTAKMGWGVRALQTIPQGTFICEYVGELISDAEADVREDDSYLFDLDNKDGEVYCIDARYYGN
ISRFINHLCDPNIIPVRVFMLHQDLRFPRIAFFSSRDIRTGEELGFDYGDRFWDIKSKYFTCQCGSEK
CKHSAEAIALEQSRLARLDPHPELLPELGSLPPVNT

G9A (long variant)                                              (SEQ ID NO: 144)
LEKALVIQESERRKKLRFHPRQLYLSVKQGELQKVILMLLDNLDPNFQSDQQSKRTPLHAAAQKSVE
ICHVLLQAGANINAVDKQQRTPLMEAVVNNHLEVARYMVQRGGCVYSKEEDGSTCLHHAAKIGNLEMV
SLLLSTGQVDVNAQDSGGWTPIIWAAEHKHIEVIRMLLTRGADVTLTDNEENICLHWASFTGSAAIAE
VLLNARCDLHAVNYHGDTPLHIAARESYHDCVLLFLSRGANPELRNKEGDTAWDLTPERSDVWFALQL
NRKLRLGVNRAIRTEKIICRDVARGYENVPIPCVNGVDGEPCPEDYKYISENCETSTMNIDRNITHL
QHCTCVDDCSSSNCLCGQLSIRCWYDKDGRLLQEFNKIEPPLIFECNQACSCWRNCKNRVVQSGIKVR
LQLYRTAKMGWGVRALQTIPQGTFICEYVGELISDAEADVREDDSYLFDLDNKDGEVYCIDARYYGNI
SRFINHLCDPNIIPVRVFMLHQDLRFPRIAFFSSRDIRTGEELGFDYGDRFWDIKSKYFTCQCGSEKC
KHSAEAIALEQSRLARLDPHPELLPELGSLPPVNT SETDB1                                                          (SEQ ID NO: 12)
MSSLPGCIGLDAATATVESEEIAELQQAVVEELGISMEELRHFIDEELEKMDCVQQRKKQLAELETWV
IQKESEVAHVDQLFDDASRAVTNCESLVKDFYSKLGLQYRDSSSEDESSRPTEIIEIPDEDDDVLSID
SGDAGSRTPKDQKLREAMAALRKSAQDVQKFMDAVNKKSSSQDLHKGTLSQMSGELSKDGDLIVSMRI
LGKKRTKTWHKGTLIAIQTVGPGKKYKVKFDNKGKSLLSGNHIAYDYHPPADKLYVGSRVVAKYKDGN
QVWLYAGIVAETPNVKNKLRFLIFFDDGYASYVTQSELYPICRPLKKTWEDIEDISCRDFIEEYVTAY
PNRPMVLLKSGQLIKTEWEGTWWKSRVEEVDGSLVRILFLDDKRCEWIYRGSTRLEPMFSMKTSSASA
LEKKQGQLRTRPNMGAVRSKGPVVQYTQDLTGTGTQFKPVEPPQPTAPPAPPFPPAPPLSPQAGDSDL
ESQLAQSRKQVAKKSTSFRPGSVGSGHSSPTSPALSENVSGGKPGINQTYRSPLGSTASAPAPSALPA
PPAPPVFHGMLERAPAEPSYRAPMEKLFYLPHVCSYTCLSRVRPMRNEQYRGKNPLLVPLLYDFRRMT
ARRRVNRKMGPHVIYKTPCGLCLRTMQEIERYLFETGCDFLFLEMFCLDPYVLVDRKFQPYKPFYYIL
DITYGKEDVPLSCVNEIDTTPPPQVAYSKERIPGKGVFINTGPEFLVGCDCKDGCRDKSKCACHQLTI
QATACTPGGQINPNSGYQKRLEECLPTGVYECNKRCKCDPNMCTNRLVQHGLQVRLQLFKTQNKGWG
IRCLDDIAKGSFVCIYAGKILTDDFADKEGLEMGDEYFANLDHIESVENFKEGYESDAPCSSDSSGVD
LKDQEDGNSGTEDPEESNDDSSDDNFCKDEDFSTSSVWRSYATRRQTRGQKENGLSETTSKDSHPPDL
GPPHIPVPPSIPVGGCNPPSSEETPKNKVASWLSCNSVSEGGFADSDHSSSFKTNEGGEGRAGGSRME
AEKASTSGLGIKDEGDIKQAKKEDTDDRNKMSVVTESSRNYGYNPSPVKPEGLRRPPSKTSMHQSRRL
MASAQSNPDDVLTLSSSTESEGESGTSRKPTAGQTSATAVDSDDIQTISSGSEGDDFEDKKNMTGPMK
RQVAVKSTRGFALKSTHGIAIKSTNMASVDKGESAPVRKNTRQFYDGEESCYIIDAKLEGNLGRYLNH
SCSPNLFVQNVFVDTHDLRFPWVAFFASKRIRAGTELTWDYNYEVGSVEGKELLCCCGAIECRGRLL SUV420H2                                                        (SEQ ID NO: 145)
MGPDRVTARELCENDDLATSLVLDPYLGFRTHKMNVSPVPPLRRQQHLRSALETFLRQRDLEAAYRAL
TLGGWTARYFQSRGPRQEAALKTHVYRYLRAFLPESGFTILPCTRYSMETNGAKIVSTRAWKKNEKLE
LLVGCIAELREADEGLLRAGENDFSIMYSTRKRSAQLWLGPAAFINHDCKPNCKFVPADGNAACVKVL
RDIEPGDEVTCFYGEGFFGEKNEHCECHTCERKGEGAFRTRPREPALPPRPLDKYQLRETKRRLQQGL
DSGSRQG HP1-α                                                           (SEQ ID NO: 146)
MGKKTKRTADSSSSEDEEEYVVEKVLDRRVVKGQVEYLLKWKGFSEEHNTWEPEKNLDCPELISEFMK
KYKKMKEGENNKPREKSESNKRKSNFSNSADDIKSKKKREQSNDIARGFERGLEPEKIIGATDSCGDL
MFLMKWKDTDEADLVLAKEANVKCPQIVIAFYEERLTWHAYPEDAENKEKETAKS DNMT3L                                                          (SEQ ID NO: 11)
MAAIPALDPEAEPSMDVILVGSSELSSSVSPGTGRDLIAYEVKANQRNIEDICICCGSLQVHTQHPLF
EGGICAPCKDKFLDALFLYDDDGYQSYCSICCSGETLLICDPCDTRCYCFECVDSLVGPGTSGKVHA
MSNWVCYLCLPSSRSGLLQRRRKWRSQLKAFYDRESENPLEMFETVPVWRRQPVRVLSLFEDIKKELT
SLGFLESGSDPGQLKHVVDVTDTVRKDVEEWGPFDLVYGATPPLGHTCDRPPSWYLFQFHRLLQYARP
KPGSPRPFFWMFVDNLVLNKEDLDVASRFLEMEPVTIPDVHGGSLQNAVRVWSNIPAIRSRHWALVSE
EELSLLAQNKQSSKLAAKWPTKLVKNCFLPLREYFKYFSTELTSSL DNMT3B                                                          (SEQ ID NO: 36)
MVAELISEEDLEFMKGDTRHLNGEEDAGGREDSILVNGACSDQSSDSPPILEAIRTPEIRGRRSSSRL
SKREVSSLLSYTQDLTGDGDGEDGDGSDTPVMPKLFRETRTRSESPAVRTRNNNSVSSRERHRPSPRS
TRGRQGRNHVDESPVEFPATRSLRRRATASAGTPWPSPPSSYLTIDLTDDTEDTHGTPQSSSTPYARL
AQDSQQGGMESPQVEADSGDGDSSEYQDGKEFGIGDLVWGKIKGFSWWPAMVVSWKATSKRQAMSGMR
WVQWFGDGKFSEVSADKLVALGLFSQHFNLATFNKLVSYRKAMYHALEKARVRAGKTFPSSPGDSLED
QLKPMLEWAHGGFKPTGIEGLKPNNTQPENKTRRRTADDSATSDYCPAPKRLKTNCYNNGKDRGDEDQ
SREQMASDVANNKSSLEDGCLSCGRKNPVSFHPLFEGGLCQTCRDRFLELFYMYDDDGYQSYCTVCCE
GRELLLCSNTSCCRCFCVECLEVLVGTGTAAEAKLQEPWSCYMCLPQRCHGVLRRRKDWNVRLQAFFT
SDTGLEYEAPKLYPAIPAARRRPIRVLSLFDGIATGYLVLKELGIKVGKYVASEVCEESIAVGTVKHE
GNIKYVNDVRNITKKNIEEWGPFDLVIGGSPCNDLSNVNPARKGLYEGTGRLFFEFYHLLNYSRPKEG
DDRPFFWMFENVVAMKVGDKRDISRFLECNPVMIDAIKVSAAHRARYFWGNLPGMNRPVIASKNDKLE
LQDCLEYNRIAKLKKVQTITTTKSNSIKOGKNQLFPVVMNGKEDVLWCTELERIFGFPVHYTDVSNMGR
GARQKLLGRSWSVPVIRHLFAPLKDYFACE

TABLE 2

TALE forward (SEQ ID NO: 14)
MGKPIPNPLLGLDSTGGMAPKKKRKVDGGVDLRTLGYSQQQQEKIKPKVR
STVAQHHEALVGHGFTHAHIVALSQHPAALGTVAVKYQDMIAALPEATHE
AIVGVGKQWSGARALEALLTVAGELRGPPLQLDTGQLLKIAKRGGVTAVE
AVHAWRNALTGAPLNLTPEQVVAIASNIGGKQALETVQRLLPVLCQAHGL
TPEQVVAIASHDGGKQALETVQRLLPVLCQAHGLTPEQVVAIASHDGGKQ
ALETVQRLLPVLCQAHGLTPEQVVAIASHDGGKQALETVQRLLPVLCQAH
GLTPEQVVAIASNIGGKQALETVQRLLPVLCQAHGLTPEQVVAIASNNGG
KQALETVQRLLPVLCQAHGLTPEQVVAIASNIGGKQALETVQRLLPVLCQ
AHGLTPEQVVAIASNGGGKQALETVQRLLPVLCQAHGLTPEQVVAIASNG
GGKQALETVQRLLPVLCQAHGLTPEQVVAIASNNGGKQALETVQRLLPVL
CQAHGLTPEQVVAIASNNGGKQALETVQRLLPVLCQAHGLTPEQVVAIAS
HDGGKQALETVQRLLPVLCQAHGLTPEQVVAIASHDGGKQALETVQRLLP
VLCQAHGLTPEQVVAIASHDGGKQALETVQRLLPVLCQAHGLTPEQVVAI
ASHDGGKQALETVQRLLPVLCQAHGLTPEQVVAIASNIGGKQALETVQRL
LPVLCQAHGLTPEQVVAIASHDGGKQALETVQRLLPVLCQAHGLTPQQVV
AIASNGGGRPALESIVAQLSRPDPALAALTNDHLVALACLGGRPALDAVK
KGLPHAPALIKRTNRRIPERTSHRVA TALE reverse (SEQ ID NO: 15)
MGKPIPNPLLGLDSTGGMAPKKKRKVDGGVDLRTLGYSQQQQEKIKPKVR
STVAQHHEALVGHGFTHAHIVALSQHPAALGTVAVKYQDMIAALPEATHE
AIVGVGKQWSGARALEALLTVAGELRGPPLQLDTGQLLKIAKRGGVTAVE
AVHAWRNALTGAPLNLTPEQVVAIASNIGGKQALETVQRLLPVLCQAHGL
TPEQVVAIASHDGGKQALETVQRLLPVLCQAHGLTPEQVVAIASHDGGKQ
ALETVQRLLPVLCQAHGLTPEQVVAIASNGGGKQALETVQRLLPVLCQAH
GLTPEQVVAIASNIGGKQALETVQRLLPVLCQAHGLTPEQVVAIASNNGG
KQALETVQRLLPVLCQAHGLTPEQVVAIASNIGGKQALETVQRLLPVLCQ
AHGLTPEQVVAIASNNGGKQALETVQRLLPVLCQAHGLTPEQVVAIASNN
GGKQALETVQRLLPVLCQAHGLTPEQVVAIASNIGGKQALETVQRLLPVL
CQAHGLTPEQVVAIASNNGGKQALETVQRLLPVLCQAHGLTPEQVVAIAS
NIGGKQALETVQRLLPVLCQAHGLTPEQVVAIASNIGGKQALETVQRLLP
VLCQAHGLTPEQVVAIASNIGGKQALETVQRLLPVLCQAHGLTPEQVVAI
ASNNGGKQALETVQRLLPVLCQAHGLTPEQVVAIASNNGGKQALETVQRL
LPVLCQAHGLTPEQVVAIASNGGGKQALETVQRLLPVLCQAHGLTPQQVV
AIASNGGGRPALESIVAQLSRPDPALAALTNDHLVALACLGGRPALDAVK
KGLPHAPALIKRTNRRIPERTSHRVA Nucleotide sequences of the corresponding
TALE binding sites TALE forward (SEQ ID NO: 34)
5'-TACCCAGATTGGCCCCACT-3'

TALE reverse (SEQ ID NO: 35)
5'-TACCTAGAGGAGAAAGGTT-3'

TABLE 3

Amino acid sequences of the TALEs
targeting the B2M promoter region

TALE #1

(SEQ ID NO: 16)
MGKPIPNPLLGLDSTGGMAPKKKRKVDGGVDLRTLGYSQQQQEKIKPKVR
STVAQHHEALVGHGFTHAHIVALSQHPAALGTVAVKYQDMIAALPEATHE
AIVGVGKQWSGARALEALLTVAGELRGPPLQLDTGQLLKIAKRGGVTAVE
AVHAWRNALTGAPLNLTPDQVVAIASNGGGKQALETVQRLLPVLCQDHGLTPDQVVAIASHDGGKQ
ALETVQRLLPVLCQDHGLTPDQVVAIASNGGGKQALETVQRLLPVLCQDH
GLTPDQVVAIASHDGGKQALETVQRLLPVLCQDHGLTPDQVVAIASHDGG
KQALETVQRLLPVLCQDHGLTPDQVVAIASNGGGKQALETVQRLLPVLCQ
DHGLTPDQVVAIASNIGGKQALETVQRLLPVLCQDHGLTPDQVVAIASHD
GGKQALETVQRLLPVLCQDHGLTPDQVVAIASHDGGKQALETVQRLLPVL
CQDHGLTPDQVVAIASHDGGKQALETVQRLLPVLCQDHGLTPDQVVAIAS
NGGGKQALETVQRLLPVLCQDHGLTPDQVVAIASHDGGKQALETVQRLLP
VLCQDHGLTPDQVVAIASHDGGKQALETVQRLLPVLCQDHGLTPDQVVAI
ASHDGGKQALETVQRLLPVLCQDHGLTPDQVVAIASNHGGKQALETVQRL
LPVLCQDHGLTPDQVVAIASHDGGKQALETVQRLLPVLCQDHGLTPDQVV
AIASNGGGKQALESIVAQLSRPDPALAALTNDHLVALACLGGRPALDAVK
KGLPHAPALIKRTNRRIPERTSHRVAGSGGG

TABLE 3-continued

TALE #2

(SEQ ID NO: 18)
MGKPIPNPLLGLDSTGGMAPKKKRKVDGGVDLRTLGYSQQQQEKIKPKVR
STVAQHHEALVGHGFTHAHIVALSQHPAALGTVAVKYQDMIAALPEATHE
AIVGVGKQWSGARALEALLTVAGELRGPPLQLDTGQLLKIAKRGGVTAVE
AVHAWRNALTGAPLNLTPDQVVAIASNNGGKQALETVQRLLPVLCQDHGL
TPDQVVAIASNGGGKQALETVQRLLPVLCQDHGLTPDQVVAIASNGGGKQ
ALETVQRLLPVLCQDHGLTPDQVVAIASHDGGKQALETVQRLLPVLCQDH
GLTPDQVVAIASHDGGKQALETVQRLLPVLCQDHGLTPDQVVAIASNGGG
KQALETVQRLLPVLCQDHGLTPDQVVAIASNGGGKQALETVQRLLPVLCQ
DHGLTPDQVVAIASHDGGKQALETVQRLLPVLCQDHGLTPDQVVAIASHD
GGKQALETVQRLLPVLCQDHGLTPDQVVAIASHDGGKQALETVQRLLPVL
CQDHGLTPDQVVAIASHDGGKQALETVQRLLPVLCQDHGLTPDQVVAIAS
NGGGKQALETVQRLLPVLCQDHGLTPDQVVAIASHDGGKQALETVQRLLP
VLCQDHGLTPDQVVAIASHDGGKQALETVQRLLPVLCQDHGLTPDQVVAI
ASHDGGKQALETVQRLLPVLCQDHGLTPDQVVAIASNGGGKQALETVQRL
LPVLCQDHGLTPDQVVAIASHDGGKQALETVQRLLPVLCQDHGLTPDQVV
AIASNGGGKQALESIVAQLSRPDPALAALTNDHLVALACLGGRPALDAVK
KGLPHAPALIKRTNRRIPERTSHRVAGSGGG

TALE #3

(SEQ ID NO: 20)
MGKPIPNPLLGLDSTGGMAPKKKRKVDGGVDLRTLGYSQQQQEKIKPKVR
STVAQHHEALVGHGFTHAHIVALSQHPAALGTVAVKYQDMIAALPEATHE
AIVGVGKQWSGARALEALLTVAGELRGPPLQLDTGQLLKIAKRGGVTAVE
AVHAWRNALTGAPLNLTPDQVVAIASHDGGKQALETVQRLLPVLCQDHGL
TPDQVVAIASNNGGKQALETVQRLLPVLCQDHGLTPDQVVAIASHDGGKQ
ALETVQRLLPVLCQDHGLTPDQVVAIASNGGGKQALETVQRLLPVLCQDH
GLTPDQVVAIASHDGGKQALETVQRLLPVLCQDHGLTPDQVVAIASHDGG
KQALETVQRLLPVLCQDHGLTPDQVVAIASNNGGKQALETVQRLLPVLCQ
DHGLTPDQVVAIASNGGGKQALETVQRLLPVLCQDHGLTPDQVVAIASNN
GGKQALETVQRLLPVLCQDHGLTPDQVVAIASNIGGKQALETVQRLLPVL
CQDHGLTPDQVVAIASHDGGKQALETVQRLLPVLCQDHGLTPDQVVAIAS
NGGGKQALETVQRLLPVLCQDHGLTPDQVVAIASNGGGKQALETVQRLLP
VLCQDHGLTPDQVVAIASHDGGKQALETVQRLLPVLCQDHGLTPDQVVAI
ASHDGGKQALETVQRLLPVLCQDHGLTPDQVVAIASHDGGKQALETVQRL
LPVLCQDHGLTPDQVVAIASNGGGKQALETVQRLLPVLCQDHGLTPDQVV
AIASNGGGKQALESIVAQLSRPDPALAALTNDHLVALACLGGRPALDAVK
KGLPHAPALIKRTNRRIPERTSHRVAGSGGG

Nucleotide sequences of the corresponding
TALE binding sites

TALE #1

(SEQ ID NO: 17)
5'-TCTCTCCTACCCTCCCGCT-3'

TALE #2

(SEQ ID NO: 19)
5'-TGGTCCTTCCTCTCCCGCT-3'

TALE #3

(SEQ ID NO: 21)
5'-TCGCTCCGTGACTTCCCTT-3'

TABLE 4

Catalytically inactive Cas9 (dCas9)

(SEQ ID NO: 22)
MGGRRVRWEVYISRALWLTREPTAYWLIEINTTHYRETQATGATMYPYDV
PDYASPKKKRKVEASDKKYSIGLAIGTNSVGWAVITDEYKVPSKKFKVLG
NTDRHSIKKNLIGALLFDSGETAEATRLKRTARRRYTRRKNRICYLQEIF
SNEMAKVDDSFFHRLEESFLVEEDKKHERHPIFGNIVDEVAYHEKYPTIY
HLRKKLVDSTDKADLRLIYLALAHMIKFRGHFLIEGDLNPDNSDVDKLFI
QLVQTYNQLFEENPINASGVDAKAILSARLSKSRRLENLIAQLPGEKKNG
LFGNLIALSLGLTPNFKSNFDLAEDAKLQLSKDTYDDDLDNLLAQIGDQY
ADLFLAAKNLSDAILLSDILRVNTEITKAPLSASMIKRYDEHHQDLTLLK
ALVRQQLPEKYKEIFFDQSKNGYAGYIDGGASQEEFYKFIKPILEKMDGT
EELLVKLNREDLLRKQRTFDNGSIPHQIHLGELHAILRRQEDFYPFLKDN
REKIEKILTFRIPYYVGPLARGNSRFAWMTRKSEETITPWNFEEVVDKGA
SAQSFIERMTNFDKNLPNEKVLPKHSLLYEYFTVYNELTKVKYVTEGMRK
PAFLSGEQKKAIVDLLFKTNRKVTVKQLKEDYFKKIECFDSVEISGVEDR
FNASLGTYHDLLKIIKDKDFLDNEENEDILEDIVLTLTLFEDREMIEERL
KTYAHLFDDKVMKQLKRRRYTGWGRLSRKLINGIRDKQSGKTILDFLKSD
GFANRNFMQLIHDDSLTFKEDIQKAQVSGQGDSLHEHIANLAGSPAIKKG

TABLE 4-continued

ILQTVKVVDELVKVMGRHKPENIVIEMARENQTTQKGQKNSRERMKRIEE
GIKELGSQILKEHPVENTQLQNEKLYLYYLQNGRDMYVDQELDINRLSDY
DVDAIVPQSFLKDDSIDNKVLTRSDKNRGKSDNVPSEEVVKKMKNYWRQL
LNAKLITQRKFDNLTKAERGGLSELDKAGFIKRQLVETRQITKHVAQILD
SRMNTKYDENDKLIREVKVITLKSKLVSDFRKDFQFYKVREINNYHHAHD
AYLNAVVGTALIKKYPKLESEFVYGDYKVYDVRKMIAKSEQEIGKATAKY
FFYSNIMNFFKTEITLANGEIRKRPLIETNGETGEIVWDKGRDFATVRKV
LSMPQVNIVKKTEVQTGGFSKESILPKRNSDKLIARKKDWDPKKYGGFDS
PTVAYSVLVVAKVEKGKSKKLKSVKELLGITIMERSSFEKNPIDFLEAKG
YKEVVKKDLIIKLPKYSLFELENGRKRMLASAGELQKGNELALPSKYVNFL
YLASHYEKLKGSPEDNEQKQLFVEQHKHYLDEIIEQISEFSKRVILADAN
LDKVLSAYNKHRDKPIREQAENIIHLFTLTNLGAPAAFKYFDTTIDRKRY
TSTKEVLDATLIHQSITGLYETRIDLSQLGGDSPKKKRKVG

Nucleotide sequences of the target sites of
the B2M gRNAs gRNA #1

(SEQ ID NO: 23)
TATAAGTGGAGGCGTCGCGC gRNA #2
(SEQ ID NO: 24)
GCCCGAATGCTGTCAGCTTC gRNA #3
(SEQ ID NO: 25)
TGCGTCGCTGGCTTGGAGAC gRNA #4
(SEQ ID NO: 26)
CCAATCAGGACAAGGCCCGC gRNA #5
(SEQ ID NO: 27)
AGGGTAGGAGAGACTCACGC gRNA #6
(SEQ ID NO: 28)
GCGGGCCACCAAGGAGAACT gRNA #7
(SEQ ID NO: 29)
GCTACTCTCTCTTTCTGGCC gRNA #8
(SEQ ID NO: 30)
CTCCCGCTCTGCACCCTCTG gRNA #9
(SEQ ID NO: 31)
TTTGGCCTACGGCGACGGGA gRNA #10
(SEQ ID NO: 32)
GGGGCAAGTAGCGCGCGTCC gRNA #11
(SEQ ID NO: 33)
TAGTCCAGGGCTGGATCTCG

Nucleotide sequences of the B2M gRNAs (SEQ ID NO: 149)
gRNA #1: UAUAAGUGGAGGCGUCGCGC (SEQ ID NO: 150)
gRNA #2: GCCCGAAUGCUGUCAGCUUC (SEQ ID NO: 151)
gRNA #3: UGCGUCGCUGGCUUGGAGAC (SEQ ID NO: 152)
gRNA #4: CCAAUCAGGACAAGGCCCGC (SEQ ID NO: 153)
gRNA #5: AGGGUAGGAGAGACUCACGC (SEQ ID NO: 154)
gRNA #6: GCGGGCCACCAAGGAGAACU TABLE 4-continued (SEQ ID NO: 155)
gRNA #7: GCUACUCUCUCUUUCUGGCC (SEQ ID NO: 156)
gRNA #8: CUCCCGCUCUGCACCCUCUG (SEQ ID NO: 157)
gRNA #9: UUUGGCCUACGGCGACGGGA (SEQ ID NO: 158)
gRNA #10: GGGGCAAGUAGCGCGCGUCC (SEQ ID NO: 159)
gRNA #11: UAGUCCAGGGCUGGAUCUCG Amino acid sequence of the TALE A targeting
the B2M promoter region TALE A
(SEQ ID NO: 147)
MGKPIPNPLLGLDSTGGMAPKKKRKVDGGVDLRTLGYSQQQQEKIKPKVR
STVAQHHEALVGHGFTHAHIVALSQHPAALGTVAVKYQDMIAALPEATHE
AIVGVGKQWSGARALEALLTVAGELRGPPLQLDTGQLLKIAKRGGVTAVE
AVHAWRNALTGAPLNLTPDQVVAIASNNGGKQALETVQRLLPVLCQDHGL
TPDQVVAIASHDGGKQALETVQRLLPVLCQDHGLTPDQVVAIASNGGGKQ
ALETVQRLLPVLCQDHGLTPDQVVAIASHDGGKQALETVQRLLPVLCQDH
GLTPDQVVAIASNNGGKQALETVQRLLPVLCQDHGLTPDQVVAIASHDGG
KQALETVQRLLPVLCQDHGLTPDQVVAIASNNGGKQALETVQRLLPVLCQ
DHGLTPDQVVAIASHDGGKQALETVQRLLPVLCQDHGLTPDQVVAIASNG
GGKQALETVQRLLPVLCQDHGLTPDQVVAIASNIGGKQALETVQRLLPVL
CQDHGLTPDQVVAIASHDGGKQALETVQRLLPVLCQDHGLTPDQVVAIAS
NGGGKQALETVQRLLPVLCQDHGLTPDQVVAIASHDGGKQALETVQRLLP
VLCQDHGLTPDQVVAIASNGGGKQALETVQRLLPVLCQDHGLTPDQVVAI
ASHDGGKQALETVQRLLPVLCQDHGLTPDQVVAIASNGGGKQALETVQRL
LPVLCQDHGLTPDQVVAIASHDGGKQALETVQRLLPVLCQDHGLTPDQVV
AIASNGGGKQALESIVAQLSRPDPALAALTNDHLVALACLGGRPALDAVK
KGLPHAPALIKRTNRRIPERTSHRVAGSGGG Nucleotide sequence of the corresponding
TALE binding site

TALE A
(SEQ ID NO: 148)
5'-TGCTCGCGCTACTCTCTCT-3'

TABLE 6

Nucleotide sequences of the gRNAs
targeting BCL11A (SEQ ID NO: 71)
gRNA #1 against CpG 105: GCCUUUCUGCAGACGUUCCC (SEQ ID NO: 72)
gRNA #2 against CpG 105: UGGGUGUGCGCCUUGGCCGG (SEQ ID NO: 73)
gRNA #3 against CpG 105: CGGUGGUGAGAUGACCGCCU (SEQ ID NO: 74)
gRNA #4 against CpG 105: GGAAUGUGCUCACGGCGCCG (SEQ ID NO: 75)
gRNA #5 against CpG 105: GACUGCCCGCGCUUUGUCCU (SEQ ID NO: 76)
gRNA #6 against CpG 105: CCAGAGUCUGGCCCCCGGAG (SEQ ID NO: 77)
gRNA #7 against CpG 105: UCUGCGACCCUUAGGAGCCG TABLE 6-continued

| | |
|---|---|
| gRNA #8 against CpG 105: | (SEQ ID NO: 78)<br>GAGCGCCCCGCCAAGCGACU |
| gRNA #9 against CpG 105: | (SEQ ID NO: 79)<br>CAAGUCUCCAGGAGCCCGCG |
| gRNA #10 against CpG 105: | (SEQ ID NO: 80)<br>CGCGGAAUCCAGCCUAAGUU |
| gRNA #11 against CpG 105: | (SEQ ID NO: 81)<br>CCCGCUGCGGAGCUGUAACU |
| gRNA #1 against CpG 31: | (SEQ ID NO: 82)<br>CGCUCCUGAGUCCGCGGAGU |
| gRNA #2 against CpG 31: | (SEQ ID NO: 83)<br>CACGGCUCUCCCCGUCGCCG |
| gRNA #3 against CpG 31: | (SEQ ID NO: 84)<br>CCGCCUUUUGUUCCGGCCAG |
| gRNA #4 against CpG 31: | (SEQ ID NO: 85)<br>GCGCGAGGAGCCGGCACAAA |
| gRNA #5 against CpG 31: | (SEQ ID NO: 86)<br>GCCACUUUCUCACUAUUGUG |
| gRNA #6 against CpG 31: | (SEQ ID NO: 87)<br>GCUGCCUCUGAGGUUCGGUC |
| gRNA #7 against CpG 31: | (SEQ ID NO: 88)<br>AAGGGCAGGAGCUAGGGCCG |
| gRNA #8 against CpG 31: | (SEQ ID NO: 89)<br>GAGCCCGGACUGCUGCCUCC |
| gRNA #1 against CpG 38: | (SEQ ID NO: 90)<br>GUUUACAAGCACCGCGUGUG |
| gRNA #2 against CpG 38: | (SEQ ID NO: 91)<br>AACAGACAGAGGACCGAGCG |
| gRNA #3 against CpG 38: | (SEQ ID NO: 92)<br>GGCGCCGGGUGGGCGAUCCG |
| gRNA #4 against CpG 38: | (SEQ ID NO: 93)<br>GGUCGGGCAAGGCCCGGGCG |
| gRNA #5 against CpG 38: | (SEQ ID NO: 94)<br>AAGAGGUCUCGGCAUUGUGC |
| gRNA #6 against CpG 38: | (SEQ ID NO: 95)<br>GUUCCACAGCUUCGGGACCG |
| gRNA #7 against CpG 38: | (SEQ ID NO: 96)<br>GAAAUCGGCUGGGUGAAACU |
| gRNA #8 against CpG 38: | (SEQ ID NO: 97)<br>GCAGUGUCUCCGCGCCAGCC |
| gRNA #9 against CpG 38: | (SEQ ID NO: 98)<br>CCUCCCCUCCCCUCCGCCCU |
| gRNA #1 against CpG 115: | (SEQ ID NO: 99)<br>UCCUCCUGUCCCGGGGUUAA |
| gRNA #2 against CpG 115: | (SEQ ID NO: 100)<br>CAUCUUUUGGGACACUCUAGG |
| gRNA #3 against CpG 115: | (SEQ ID NO: 101)<br>AAGUCAGGCCCUUCUUCGAA |
| gRNA #4 against CpG 115: | (SEQ ID NO: 102)<br>GCAGCCUGGACUGCGCGCCC |
| gRNA #5 against CpG 115: | (SEQ ID NO: 103)<br>UGCCCGGCGAUUCUCGUCCG |
| gRNA #6 against CpG 115: | (SEQ ID NO: 104)<br>UGAGCCAUUCGGUCGCUAGG |
| gRNA #7 against CpG 115: | (SEQ ID NO: 105)<br>GGUGGUACUGAGGACCGGGA |
| gRNA #8 against CpG 115: | (SEQ ID NO: 107)<br>AUUUUCUGGGUGCUCAGAGG |
| gRNA #9 against CpG 115: | (SEQ ID NO: 108)<br>UGGUCUCAGCUCGCGCACGG |
| gRNA #10 against CpG 115: | (SEQ ID NO: 109)<br>ACAAAGACAUACGGGUGAU |
| Nucleotide sequences of the gRNAs targeting IFNAR1 | |
| gRNA #1: | (SEQ ID NO: 106)<br>AGGAACGGCGCGUGCGCGGA |
| gRNA #2: | (SEQ ID NO: 161)<br>AAGAGGCGGCGCGUGCGUAG |
| gRNA #3: | (SEQ ID NO: 162)<br>GGGCGGUGUGACUUAGGACG |
| gRNA #4: | (SEQ ID NO: 163)<br>CCAGAUGAUGGUCGUCCUCC |
| gRNA #5: | (SEQ ID NO: 164)<br>GACCCUAGUGCUCGUCGCCG |
| gRNA #6: | (SEQ ID NO: 165)<br>UGGGUGUUGUCCGCAGCCGC |
| gRNA #7: | (SEQ ID NO: 166)<br>ACGGGGGCGGCGAUGCUGUU |
| gRNA #8: | (SEQ ID NO: 167)<br>GACCGAAGGUUUCCCAGACU |
| gRNA #9: | (SEQ ID NO: 168)<br>GUCGGGUUUAAUCUUUGGCG |
| gRNA #10: | (SEQ ID NO: 169)<br>CGCUCCCGAGGACCCGUACA |
| gRNA #11: | (SEQ ID NO: 170)<br>CGGGUCCCACCCCCGUGAAA |
| gRNA #12: | (SEQ ID NO: 171)<br>UCAAACUCGACACAAAGCUC |
| gRNA #13: | (SEQ ID NO: 172)<br>GCGGAGCCGCGGUACUUUCC |
| Nucleotide sequences of the gRNAs targeting VEGFA | |
| gRNA #1: | (SEQ ID NO: 173)<br>GGCGCGCGCGCUAGGUGGGA |
| gRNA #2: | (SEQ ID NO: 174)<br>AGAGAGGCUCACCGCCCACG |
| gRNA #3: | (SEQ ID NO: 175)<br>GUACGUGCGGUGACUCCGGU |

TABLE 7

Amino acid sequence of the TALEs targeting the BCL11A gene

TALE BCL11A #1

(SEQ ID NO: 37)

MGKPIPNPLLGLDSTGGMAPKKKRKVDGGVDLRTLGYSQQQQEKIKPKVRSTVAQHHEALVGHGFTHA
HIVALSQHPAALGTVAVKYQDMIAALPEATHEAIVGVGKQWSGARALEALLTVAGELRGPPLQLDTGQ
LLKIAKRGGVTAVEAVHAWRNALTGAPLNLTPDQVVAIASHDGGKQALETVQRLLPVLCQDHGLTPDQ
VVAIASHDGGKQALETVQRLLPVLCQDHGLTPDQVVAIASNDGGKQALETVQRLLPVLCQDHGLTPDQ
VVAIASNNGGKQALETVQRLLPVLCQDHGLTPDQVVAIASNGGGKQALETVQRLLPVLCQDHGLTPDQ
VVAIASNGGGKQALETVQRLLPVLCQDHGLTPDQVVAIASHDGGKQALETVQRLLPVLCQDHGLTPDQ
VVAIASHDGGKQALETVQRLLPVLCQDHGLTPDQVVAIASNNGGKQALETVQRLLPVLCQDHGLTPDQ
VVAIASHDGGKQALETVQRLLPVLCQDHGLTPDQVVAIASHDGGKQALETVQRLLPVLCQDHGLTPDQ
VVAIASHDGGKQALETVQRLLPVLCQDHGLTPDQVVAIASHDGGKQALETVQRLLPVLCQDHGLTPDQ
VVAIASHDGGKQALETVQRLLPVLCQDHGLTPDQVVAIASNIGGKQALETVQRLLPVLCQDHGLTPDQ
VVAIASNNGGKQALETVQRLLPVLCQDHGLTPDQVVAIASHDGGKQALETVQRLLPVLCQDHGLTPDQ
VVAIASNIGGKQALESIVAQLSRPDPALAALTNDHLVALACLGGRPALDAVKKGLPHAPALIKRTNRR
IPERTSHRVAGSGGG

Nucleotide sequence of the corresponding TALE binding site (SEQ ID NO: 38)

5'-TCCAAAAGCCAGTCTCACC-3'

TALE BCL11A #2

(SEQ ID NO: 39)

MGKPIPNPLLGLDSTGGMAPKKKRKVDGGVDLRTLGYSQQQQEKIKPKVRSTVAQHHEALVGHGFTHA
HIVALSQHPAALGTVAVKYQDMIAALPEATHEAIVGVGKQWSGARALEALLTVAGELRGPPLQLDTGQ
LLKIAKRGGVTAVEAVHAWRNALTGAPLNLTPDQVVAIASNNGGKQALETVQRLLPVLCQDHGLTPDQ
VVAIASHDGGKQALETVQRLLPVLCQDHGLTPDQVVAIASHDGGKQALETVQRLLPVLCQDHGLTPDQ
VVAIASNNGGKQALETVQRLLPVLCQDHGLTPDQVVAIASNIGGKQALETVQRLLPVLCQDHGLTPDQ
VVAIASNNGGKQALETVQRLLPVLCQDHGLTPDQVVAIASNIGGKQALETVQRLLPVLCQDHGLTPDQ
VVAIASHDGGKQALETVQRLLPVLCQDHGLTPDQVVAIASHDGGKQALETVQRLLPVLCQDHGLTPDQ
VVAIASNGGGKQALETVQRLLPVLCQDHGLTPDQVVAIASHDGGKQALETVQRLLPVLCQDHGLTPDQ
VVAIASHDGGKQALETVQRLLPVLCQDHGLTPDQVVAIASNGGGKQALETVQRLLPVLCQDHGLTPDQ
VVAIASHDGGKQALETVQRLLPVLCQDHGLTPDQVVAIASNGGGKQALETVQRLLPVLCQDHGLTPDQ
VVAIASHDGGKQALETVQRLLPVLCQDHGLTPDQVVAIASNNGGKQALETVQRLLPVLCQDHGLTPDQ
VVAIASNIGGKQALESIVAQLSRPDPALAALTNDHLVALACLGGRPALDAVKKGLPHAPALIKRTNRR
IPERTSHRVAGSGGG (SEQ ID NO: 40)

5'-TCTCCCGGGAATCGTTTT-3'

TALE BCL11A #3

(SEQ ID NO: 41)

MGKPIPNPLLGLDSTGGMAPKKKRKVDGGVDLRTLGYSQQQQEKIKPKVRSTVAQHHEALVGHGFTHA
HIVALSQHPAALGTVAVKYQDMIAALPEATHEAIVGVGKQWSGARALEALLTVAGELRGPPLQLDTGQ
LLKIAKRGGVTAVEAVHAWRNALTGAPLNLTPDQVVAIASHDGGKQALETVQRLLPVLCQDHGLTPDQ
VVAIASNNGGKQALETVQRLLPVLCQDHGLTPDQVVAIASNNGGKQALETVQRLLPVLCQDHGLTPDQ
VVAIASHDGGKQALETVQRLLPVLCQDHGLTPDQVVAIASNGGGKQALETVQRLLPVLCQDHGLTPDQ
VVAIASNGGGKQALETVQRLLPVLCQDHGLTPDQVVAIASHDGGKQALETVQRLLPVLCQDHGLTPDQ
VVAIASNNGGKQALETVQRLLPVLCQDHGLTPDQVVAIASHDGGKQALETVQRLLPVLCQDHGLTPDQ
VVAIASNIGGKQALETVQRLLPVLCQDHGLTPDQVVAIASNIGGKQALETVQRLLPVLCQDHGLTPDQ
VVAIASNIGGKQALETVQRLLPVLCQDHGLTPDQVVAIASNHGGKQALETVQRLLPVLCQDHGLTPDQ
VVAIASHDGGKQALETVQRLLPVLCQDHGLTPDQVVAIASNIGGKQALETVQRLLPVLCQDHGLTPDQ
VVAIASNGGGKQALETVQRLLPVLCQDHGLTPDQVVAIASNGGGKQALETVQRLLPVLCQDHGLTPDQ
VVAIASNGGGKQALESIVAQLSRPDPALAALTNDHLVALACLGGRPALDAVKKGLPHAPALIKRTNRR
IPERTSHRVAGSGGG (SEQ ID NO: 42)

5'-TCCTCCCGCTGCACACTTG-3'

TALE BCL11A #4

(SEQ ID NO: 43)

MGKPIPNPLLGLDSTGGMAPKKKRKVDGGVDLRTLGYSQQQQEKIKPKVRSTVAQHHEALVGHGFTHA
HIVALSQHPAALGTVAVKYQDMIAALPEATHEAIVGVGKQWSGARALEALLTVAGELRGPPLQLDTGQ
LLKIAKRGGVTAVEAVHAWRNALTGAPLNLTPDQVVAIASHDGGKQALETVQRLLPVLCQDHGLTPDQ
VVAIASHDGGKQALETVQRLLPVLCQDHGLTPDQVVAIASNIGGKQALETVQRLLPVLCQDHGLTPDQ
VVAIASNIGGKQALETVQRLLPVLCQDHGLTPDQVVAIASNIGGKQALETVQRLLPVLCQDHGLTPDQ
VVAIASNNGGKQALETVQRLLPVLCQDHGLTPDQVVAIASHDGGKQALETVQRLLPVLCQDHGLTPDQ
VVAIASHDGGKQALETVQRLLPVLCQDHGLTPDQVVAIASNNGGKQALETVQRLLPVLCQDHGLTPDQ
VVAIASNIGGKQALETVQRLLPVLCQDHGLTPDQVVAIASNNGGKQALETVQRLLPVLCQDHGLTPDQ
VVAIASNGGGKQALETVQRLLPVLCQDHGLTPDQVVAIASNGGGKQALETVQRLLPVLCQDHGLTPDQ
VVAIASNGGGKQALETVQRLLPVLCQDHGLTPDQVVAIASHDGGKQALETVQRLLPVLCQDHGLTPDQ
VVAIASNIGGKQALETVQRLLPVLCQDHGLTPDQVVAIASHDGGKQALETVQRLLPVLCQDHGLTPDQ
VVAIASHDGGKQALESIVAQLSRPDPALAALTNDHLVALACLGGRPALDAVKKGLPHAPALIKRTNRR
IPERTSHRVAGSGGG

TABLE 7-continued (SEQ ID NO: 44)
5'-TAGTCATCCCCACAATAGT-3'

TALE BCL11A #5

(SEQ ID NO: 45)
MGKPIPNPLLGLDSTGGMAPKKKRKVDGGVDLRTLGYSQQQQEKIKPKVRSTVAQHHEALVGHGFTHA
HIVALSQHPAALGTVAVKYQDMIAALPEATHEAIVGVGKQWSGARALEALLTVAGELRGPPLQLDTGQ
LLKIAKRGGVTAVEAVHAWRNALTGAPLNLTPDQVVAIASNIGGKQALETVQRLLPVLCQDHGLTPDQ
VVAIASHDGGKQALETVQRLLPVLCQDHGLTPDQVVAIASNIGGKQALETVQRLLPVLCQDHGLTPDQ
VVAIASNNGGKQALETVQRLLPVLCQDHGLTPDQVVAIASNGGGKQALETVQRLLPVLCQDHGLTPDQ
VVAIASNGGGKQALETVQRLLPVLCQDHGLTPDQVVAIASNNGGKQALETVQRLLPVLCQDHGLTPDQ
VVAIASHDGGKQALETVQRLLPVLCQDHGLTPDQVVAIASHDGGKQALETVQRLLPVLCQDHGLTPDQ
VVAIASHDGGKQALETVQRLLPVLCQDHGLTPDQVVAIASNGGGKQALETVQRLLPVLCQDHGLTPDQ
VVAIASNNGGKQALETVQRLLPVLCQDHGLTPDQVVAIASHDGGKQALETVQRLLPVLCQDHGLTPDQ
VVAIASNIGGKQALETVQRLLPVLCQDHGLTPDQVVAIASNIGGKQALETVQRLLPVLCQDHGLTPDQ
VVAIASNIGGKQALETVQRLLPVLCQDHGLTPDQVVAIASNIGGKQALETVQRLLPVLCQDHGLTPDQ
VVAIASNGGGKQALESIVAQLSRPDPALAALTNDHLVALACLGGRPALDAVKKGLPHAPALIKRTNRR
IPERTSHRVAGSGGG (SEQ ID NO: 46)
5'-TCCCGCTGCCTTTTGTGCC-3'

TALE BCL11A #6

(SEQ ID NO: 47)
MGKPIPNPLLGLDSTGGMAPKKKRKVDGGVDLRTLGYSQQQQEKIKPKVRSTVAQHHEALVGHGFTHA
HIVALSQHPAALGTVAVKYQDMIAALPEATHEAIVGVGKQWSGARALEALLTVAGELRGPPLQLDTGQ
LLKIAKRGGVTAVEAVHAWRNALTGAPLNLTPDQVVAIASHDGGKQALETVQRLLPVLCQDHGLTPDQ
VVAIASHDGGKQALETVQRLLPVLCQDHGLTPDQVVAIASNNGGKQALETVQRLLPVLCQDHGLTPDQ
VVAIASHDGGKQALETVQRLLPVLCQDHGLTPDQVVAIASNHGGKQALETVQRLLPVLCQDHGLTPDQ
VVAIASHDGGKQALETVQRLLPVLCQDHGLTPDQVVAIASNGGGKQALETVQRLLPVLCQDHGLTPDQ
VVAIASNNGGKQALETVQRLLPVLCQDHGLTPDQVVAIASNNGGKQALETVQRLLPVLCQDHGLTPDQ
VVAIASNNGGKQALETVQRLLPVLCQDHGLTPDQVVAIASNGGGKQALETVQRLLPVLCQDHGLTPDQ
VVAIASNIGGKQALETVQRLLPVLCQDHGLTPDQVVAIASNGGGKQALETVQRLLPVLCQDHGLTPDQ
VVAIASNGGGKQALETVQRLLPVLCQDHGLTPDQVVAIASNGGGKQALETVQRLLPVLCQDHGLTPDQ
VVAIASNGGGKQALETVQRLLPVLCQDHGLTPDQVVAIASHDGGKQALETVQRLLPVLCQDHGLTPDQ
VVAIASNGGGKQALESIVAQLSRPDPALAALTNDHLVALACLGGRPALDAVKKGLPHAPALIKRTNRR
IPERTSHRVAGSGGG (SEQ ID NO: 48)
5'-TCCTCGCGCTTGCCCTCCC-3'

TALE BCL11A #7

(SEQ ID NO: 49)
MGKPIPNPLLGLDSTGGMAPKKKRKVDGGVDLRTLGYSQQQQEKIKPKVRSTVAQHHEALVGHGFTHA
HIVALSQHPAALGTVAVKYQDMIAALPEATHEAIVGVGKQWSGARALEALLTVAGELRGPPLQLDTGQ
LLKIAKRGGVTAVEAVHAWRNALTGAPLNLTPDQVVAIASHDGGKQALETVQRLLPVLCQDHGLTPDQ
VVAIASNGGGKQALETVQRLLPVLCQDHGLTPDQVVAIASHDGGKQALETVQRLLPVLCQDHGLTPDQ
VVAIASNGGGKQALETVQRLLPVLCQDHGLTPDQVVAIASNGGGKQALETVQRLLPVLCQDHGLTPDQ
VVAIASNNGGKQALETVQRLLPVLCQDHGLTPDQVVAIASNGGGKQALETVQRLLPVLCQDHGLTPDQ
VVAIASHDGGKQALETVQRLLPVLCQDHGLTPDQVVAIASHDGGKQALETVQRLLPVLCQDHGLTPDQ
VVAIASNIGGKQALETVQRLLPVLCQDHGLTPDQVVAIASHDGGKQALETVQRLLPVLCQDHGLTPDQ
VVAIASNIGGKQALETVQRLLPVLCQDHGLTPDQVVAIASNHGGKQALETVQRLLPVLCQDHGLTPDQ
VVAIASHDGGKQALETVQRLLPVLCQDHGLTPDQVVAIASNGGGKQALETVQRLLPVLCQDHGLTPDQ
VVAIASHDGGKQALETVQRLLPVLCQDHGLTPDQVVAIASNNGGKQALETVQRLLPVLCQDHGLTPDQ
VVAIASNNGGKQALESIVAQLSRPDPALAALTNDHLVALACLGGRPALDAVKKGLPHAPALIKRTNRR
IPERTSHRVAGSGGG (SEQ ID NO: 50)
5'-TCCCCCGGCCCTAGCTCCT-3'

TALE BCL11A #8

(SEQ ID NO: 51)
MGKPIPNPLLGLDSTGGMAPKKKRKVDGGVDLRTLGYSQQQQEKIKPKVRSTVAQHHEALVGHGFTHA
HIVALSQHPAALGTVAVKYQDMIAALPEATHEAIVGVGKQWSGARALEALLTVAGELRGPPLQLDTGQ
LLKIAKRGGVTAVEAVHAWRNALTGAPLNLTPDQVVAIASHDGGKQALETVQRLLPVLCQDHGLTPDQ
VVAIASNGGGKQALETVQRLLPVLCQDHGLTPDQVVAIASHDGGKQALETVQRLLPVLCQDHGLTPDQ
VVAIASHDGGKQALETVQRLLPVLCQDHGLTPDQVVAIASHDGGKQALETVQRLLPVLCQDHGLTPDQ
VVAIASNNGGKQALETVQRLLPVLCQDHGLTPDQVVAIASHDGGKQALETVQRLLPVLCQDHGLTPDQ
VVAIASHDGGKQALETVQRLLPVLCQDHGLTPDQVVAIASNNGGKQALETVQRLLPVLCQDHGLTPDQ
VVAIASNIGGKQALETVQRLLPVLCQDHGLTPDQVVAIASHDGGKQALETVQRLLPVLCQDHGLTPDQ
VVAIASNGGGKQALETVQRLLPVLCQDHGLTPDQVVAIASNHGGKQALETVQRLLPVLCQDHGLTPDQ
VVAIASHDGGKQALETVQRLLPVLCQDHGLTPDQVVAIASNHGGKQALETVQRLLPVLCQDHGLTPDQ
VVAIASHDGGKQALETVQRLLPVLCQDHGLTPDQVVAIASHDGGKQALETVQRLLPVLCQDHGLTPDQ
VVAIASNGGGKQALESIVAQLSRPDPALAALTNDHLVALACLGGRPALDAVKKGLPHAPALIKRTNRR
IPERTSHRVAGSGGG

TABLE 7-continued (SEQ ID NO: 52)
5'-TCCTGGTCCGCCCCCAGCA-3'

TALE BCL11A #9

(SEQ ID NO: 53)
MGKPIPNPLLGLDSTGGMAPKKKRKVDGGVDLRTLGYSQQQQEKIKPKVRSTVAQHHEALVGHGFTHA
HIVALSQHPAALGTVAVKYQDMIAALPEATHEAIVGVGKQWSGARALEALLTVAGELRGPPLQLDTGQ
LLKIAKRGGVTAVEAVHAWRNALTGAPLNLTPDQVVAIASHDGGKQALETVQRLLPVLCQDHGLTPDQ
VVAIASHDGGKQALETVQRLLPVLCQDHGLTPDQVVAIASHDGGKQALETVQRLLPVLCQDHGLTPDQ
VVAIASNGGGKQALETVQRLLPVLCQDHGLTPDQVVAIASNGGGKQALETVQRLLPVLCQDHGLTPDQ
VVAIASNNGGKQALETVQRLLPVLCQDHGLTPDQVVAIASHDGGKQALETVQRLLPVLCQDHGLTPDQ
VVAIASNGGGKQALETVQRLLPVLCQDHGLTPDQVVAIASNNGGKQALETVQRLLPVLCQDHGLTPDQ
VVAIASHDGGKQALETVQRLLPVLCQDHGLTPDQVVAIASHDGGKQALETVQRLLPVLCQDHGLTPDQ
VVAIASNIGGKQALETVQRLLPVLCQDHGLTPDQVVAIASNIGGKQALETVQRLLPVLCQDHGLTPDQ
VVAIASNIGGKQALETVQRLLPVLCQDHGLTPDQVVAIASHDGGKQALETVQRLLPVLCQDHGLTPDQ
VVAIASNGGGKQALETVQRLLPVLCQDHGLTPDQVVAIASNGGGKQALETVQRLLPVLCQDHGLTPDQ
VVAIASNGGGKQALESIVAQLSRPDPALAALTNDHLVALACLGGRPALDAVKKGLPHAPALIKRTNRR
IPERTSHRVAGSGGG (SEQ ID NO: 54)
5'-TGCCGAGACCTCTTCTCGA-3'

TALE BCL11A #10

(SEQ ID NO: 55)
MGKPIPNPLLGLDSTGGMAPKKKRKVDGGVDLRTLGYSQQQQEKIKPKVRSTVAQHHEALVGHGFTHA
HIVALSQHPAALGTVAVKYQDMIAALPEATHEAIVGVGKQWSGARALEALLTVAGELRGPPLQLDTGQ
LLKIAKRGGVTAVEAVHAWRNALTGAPLNLTPDQVVAIASNNGGKQALETVKRLLPVLCQDHGLTPDQ
VVAIASNNGGKQALETVQRLLPVLCQDHGLTPDQVVAIASHDGGKQALETVQRLLPVLCQDHGLTPDQ
VVAIASHDGGKQALETVQRLLPVLCQDHGLTPDQVVAIASHDGGKQALETVQRLLPVLCQDHGLTPDQ
VVAIASHDGGKQALETVQRLLPVLCQDHGLTPDQVVAIASNGGGKQALETVQRLLPVLCQDHGLTPDQ
VVAIASHDGGKQALETVQRLLPVLCQDHGLTPDQVVAIASNIGGKQALETVQRLLPVLCQDHGLTPDQ
VVAIASHDGGKQALETVQRLLPVLCQDHGLTPDQVVAIASNNGGKQALETVQRLLPVLCQDHGLTPDQ
VVAIASHDGGKQALETVQRLLPVLCQDHGLTPDQVVAIASHDGGKQALETVQRLLPVLCQDHGLTPDQ
VVAIASNGGGKQALETVQRLLPVLCQDHGLTPDQVVAIASNGGGKQALETVQRLLPVLCQDHGLTPDQ
VVAIASNGGGKQALETVQRLLPVLCQDHGLTPDQVVAIASHDGGKQALETVQRLLPVLCQDHGLTPDQ
VVAIASNGGGKQALESIVAQLSRPDPALAALTNDHLVALACLGGRPALDAVKKGLPHAPALIKRTNRR
IPERTSHRVAGSGGG (SEQ ID NO: 56)
5'-TCGGCTTTGCAAAGCATTT-3'

TALE BCL11A #11

(SEQ ID NO: 57)
MGKPIPNPLLGLDSTGGMAPKKKRKVDGGVDLRTLGYSQQQQEKIKPKVRSTVAQHHEALVGHGFTHA
HIVALSQHPAALGTVAVKYQDMIAALPEATHEAIVGVGKQWSGARALEALLTVAGELRGPPLQLDTGQ
LLKIAKRGGVTAVEAVHAWRNALTGAPLNLTPDQVVAIASHDGGKQALETVQRLLPVLCQDHGLTPDQ
VVAIASNGGGKQALETVQRLLPVLCQDHGLTPDQVVAIASHDGGKQALETVQRLLPVLCQDHGLTPDQ
VVAIASHDGGKQALETVQRLLPVLCQDHGLTPDQVVAIASHDGGKQALETVQRLLPVLCQDHGLTPDQ
VVAIASHDGGKQALETVQRLLPVLCQDHGLTPDQVVAIASNNGGKQALETVQRLLPVLCQDHGLTPDQ
VVAIASNNGGKQALETVQRLLPVLCQDHGLTPDQVVAIASNNGGKQALETVQRLLPVLCQDHGLTPDQ
VVAIASNIGGKQALETVQRLLPVLCQDHGLTPDQVVAIASNIGGKQALETVQRLLPVLCQDHGLTPDQ
VVAIASNGGGKQALETVQRLLPVLCQDHGLTPDQVVAIASHDGGKQALETVQRLLPVLCQDHGLTPDQ
VVAIASNNGGKQALETVQRLLPVLCQDHGLTPDQVVAIASNGGGKQALETVQRLLPVLCQDHGLTPDQ
VVAIASNGGGKQALETVQRLLPVLCQDHGLTPDQVVAIASNGGGKQALETVQRLLPVLCQDHGLTPDQ
VVAIASNGGGKQALESIVAQLSRPDPALAALTNDHLVALACLGGRPALDAVKKGLPHAPALIKRTNRR
IPERTSHRVAGSGGG (SEQ ID NO: 58)
5'-TGCAAAGCCGAGTTTCACC-3'

TALE BCL11A #12

(SEQ ID NO: 59)
MGKPIPNPLLGLDSTGGMAPKKKRKVDGGVDLRTLGYSQQQQEKIKPKVRSTVAQHHEALVGHGFTHA
HIVALSQHPAALGTVAVKYQDMIAALPEATHEAIVGVGKQWSGARALEALLTVAGELRGPPLQLDTGQ
LLKIAKRGGVTAVEAVHAWRNALTGAPLNLTPDQVVAIASHDGGKQALETVQRLLPVLCQDHGLTPDQ
VVAIASHDGGKQALETVQRLLPVLCQDHGLTPDQVVAIASNIGGKQALETVQRLLPVLCQDHGLTPDQ
VVAIASNIGGKQALETVQRLLPVLCQDHGLTPDQVVAIASNIGGKQALETVQRLLPVLCQDHGLTPDQ
VVAIASNIGGKQALETVQRLLPVLCQDHGLTPDQVVAIASNHGGKQALETVQRLLPVLCQDHGLTPDQ
VVAIASHDGGKQALETVQRLLPVLCQDHGLTPDQVVAIASHDGGKQALETVQRLLPVLCQDHGLTPDQ
VVAIASNIGGKQALETVQRLLPVLCQDHGLTPDQVVAIASNNGGKQALETVQRLLPVLCQDHGLTPDQ
VVAIASNGGGKQALETVQRLLPVLCQDHGLTPDQVVAIASHDGGKQALETVQRLLPVLCQDHGLTPDQ
VVAIASNGGGKQALETVQRLLPVLCQDHGLTPDQVVAIASHDGGKQALETVQRLLPVLCQDHGLTPDQ
VVAIASNIGGKQALETVQRLLPVLCQDHGLTPDQVVAIASHDGGKQALETVQRLLPVLCQDHGLTPDQ
VVAIASHDGGKQALESIVAQLSRPDPALAALTNDHLVALACLGGRPALDAVKKGLPHAPALIKRTNRR
IPERTSHRVAGSGGG

TABLE 7-continued (SEQ ID NO: 60)
5'-TACAGTTGCCCTGCAAAAT-3'

TALE BCL11A #13

(SEQ ID NO: 61)
MGKPIPNPLLGLDSTGGMAPKKKRKVDGGVDLRTLGYSQQQQEKIKPKVRSTVAQHHEALVGHGFTHA
HIVALSQHPAALGTVAVKYQDMIAALPEATHEAIVGVGKQWSGARALEALLTVAGELRGPPLQLDTGQ
LLKIAKRGGVTAVEAVHAWRNALTGAPLNLTPDQVVAIASHDGGKQALETVQRLLPVLCQDHGLTPDQ
VVAIASHDGGKQALETVQRLLPVLCQDHGLTPDQVVAIASNGGGKQALETVQRLLPVLCQDHGLTPDQ
VVAIASHDGGKQALETVQRLLPVLCQDHGLTPDQVVAIASHDGGKQALETVQRLLPVLCQDHGLTPDQ
VVAIASHDGGKQALETVQRLLPVLCQDHGLTPDQVVAIASNNGGKQALETVQRLLPVLCQDHGLTPDQ
VVAIASHDGGKQALETVQRLLPVLCQDHGLTPDQVVAIASHDGGKQALETVQRLLPVLCQDHGLTPDQ
VVAIASNNGGKQALETVQRLLPVLCQDHGLTPDQVVAIASHDGGKQALETVQRLLPVLCQDHGLTPDQ
VVAIASNIGGKQALETVQRLLPVLCQDHGLTPDQVVAIASHDGGKQALETVQRLLPVLCQDHGLTPDQ
VVAIASNIGGKQALETVQRLLPVLCQDHGLTPDQVVAIASHDGGKQALETVQRLLPVLCQDHGLTPDQ
VVAIASNGGGKQALETVQRLLPVLCQDHGLTPDQVVAIASNGGGKQALETVQRLLPVLCQDHGLTPDQ
VVAIASNNGGKQALESIVAQLSRPDPALAALTNDHLVALACLGGRPALDAVKKGLPHAPALIKRTNRR
IPERTSHRVAGSGGG (SEQ ID NO: 62)
5'-TCCGCCCTGGGTACTTTCT-3'

TALE BCL11A #14

(SEQ ID NO: 63)
MGKPIPNPLLGLDSTGGMAPKKKRKVDGGVDLRTLGYSQQQQEKIKPKVRSTVAQHHEALVGHGFTHA
HIVALSQHPAALGTVAVKYQDMIAALPEATHEAIVGVGKQWSGARALEALLTVAGELRGPPLQLDTGQ
LLKIAKRGGVTAVEAVHAWRNALTGAPLNLTPDQVVAIASNIGGKQALETVQRLLPVLCQDHGLTPDQ
VVAIASNNGGKQALETVQRLLPVLCQDHGLTPDQVVAIASHDGGKQALETVQRLLPVLCQDHGLTPDQ
VVAIASHDGGKQALETVQRLLPVLCQDHGLTPDQVVAIASNIGGKQALETVQRLLPVLCQDHGLTPDQ
VVAIASNGGGKQALETVQRLLPVLCQDHGLTPDQVVAIASHDGGKQALETVQRLLPVLCQDHGLTPDQ
VVAIASHDGGKQALETVQRLLPVLCQDHGLTPDQVVAIASHDGGKQALETVQRLLPVLCQDHGLTPDQ
VVAIASHDGGKQALETVQRLLPVLCQDHGLTPDQVVAIASNIGGKQALETVQRLLPVLCQDHGLTPDQ
VVAIASHDGGKQALETVQRLLPVLCQDHGLTPDQVVAIASNIGGKQALETVQRLLPVLCQDHGLTPDQ
VVAIASNIGGKQALETVQRLLPVLCQDHGLTPDQVVAIASNGGGKQALETVQRLLPVLCQDHGLTPDQ
VVAIASNIGGKQALETVQRLLPVLCQDHGLTPDQVVAIASNNGGKQALETVQRLLPVLCQDHGLTPDQ
VVAIASNGGGKQALESIVAQLSRPDPALAALTNDHLVALACLGGRPALDAVKKGLPHAPALIKRTNRR
IPERTSHRVAGSGGG (SEQ ID NO: 64)
5'-TCTCTTGTCCACAGCTCGG-3'

TALE BCL11A #15

(SEQ ID NO: 65)
MGKPIPNPLLGLDSTGGMAPKKKRKVDGGVDLRTLGYSQQQQEKIKPKVRSTVAQHHEALVGHGFTHA
HIVALSQHPAALGTVAVKYQDMIAALPEATHEAIVGVGKQWSGARALEALLTVAGELRGPPLQLDTGQ
LLKIAKRGGVTAVEAVHAWRNALTGAPLNLTPDQVVAIASHDGGKQALETVQRLLPVLCQDHGLTPDQ
VVAIASHDGGKQALETVQRLLPVLCQDHGLTPDQVVAIASHDGGKQALETVQRLLPVLCQDHGLTPDQ
VVAIASNNGGKQALETVQRLLPVLCQDHGLTPDQVVAIASHDGGKQALETVQRLLPVLCQDHGLTPDQ
VVAIASNGGGKQALETVQRLLPVLCQDHGLTPDQVVAIASNNGGKQALETVQRLLPVLCQDHGLTPDQ
VVAIASHDGGKQALETVQRLLPVLCQDHGLTPDQVVAIASHDGGKQALETVQRLLPVLCQDHGLTPDQ
VVAIASNGGGKQALETVQRLLPVLCQDHGLTPDQVVAIASNGGGKQALETVQRLLPVLCQDHGLTPDQ
VVAIASNGGGKQALETVQRLLPVLCQDHGLTPDQVVAIASNGGGKQALETVQRLLPVLCQDHGLTPDQ
VVAIASNNGGKQALETVQRLLPVLCQDHGLTPDQVVAIASNGGGKQALETVQRLLPVLCQDHGLTPDQ
VVAIASNGGGKQALETVQRLLPVLCQDHGLTPDQVVAIASHDGGKQALETVQRLLPVLCQDHGLTPDQ
VVAIASHDGGKQALESIVAQLSRPDPALAALTNDHLVALACLGGRPALDAVKKGLPHAPALIKRTNRR
IPERTSHRVAGSGGG (SEQ ID NO: 66)
5'-TCTCCCGCTGACTGCGCCT-3'

TALE BCL11A #16

(SEQ ID NO: 67)
MGKPIPNPLLGLDSTGGMAPKKKRKVDGGVDLRTLGYSQQQQEKIKPKVRSTVAQHHEALVGHGFTHA
HIVALSQHPAALGTVAVKYQDMIAALPEATHEAIVGVGKQWSGARALEALLTVAGELRGPPLQLDTGQ
LLKIAKRGGVTAVEAVHAWRNALTGAPLNLTPDQVVAIASNGGGKQALETVQRLLPVLCQDHGLTPDQ
VVAIASHDGGKQALETVQRLLPVLCQDHGLTPDQVVAIASNNGGKQALETVQRLLPVLCQDHGLTPDQ
VVAIASHDGGKQALETVQRLLPVLCQDHGLTPDQVVAIASNNGGKQALETVQRLLPVLCQDHGLTPDQ
VVAIASHDGGKQALETVQRLLPVLCQDHGLTPDQVVAIASHDGGKQALETVQRLLPVLCQDHGLTPDQ
VVAIASNGGGKQALETVQRLLPVLCQDHGLTPDQVVAIASNNGGKQALETVQRLLPVLCQDHGLTPDQ
VVAIASHDGGKQALETVQRLLPVLCQDHGLTPDQVVAIASHDGGKQALETVQRLLPVLCQDHGLTPDQ
VVAIASHDGGKQALETVQRLLPVLCQDHGLTPDQVVAIASNGGGKQALETVQRLLPVLCQDHGLTPDQ
VVAIASHDGGKQALETVQRLLPVLCQDHGLTPDQVVAIASHDGGKQALETVQRLLPVLCQDHGLTPDQ
VVAIASHDGGKQALESIVAQLSRPDPALAALTNDHLVALACLGGRPALDAVKKGLPHAPALIKRTNRR
IPERTSHRVAGSGGG

TABLE 7-continued (SEQ ID NO: 68)
5'-TCCCTTGCTGCCAAACTTT-3'

TALE BCL11A #17

(SEQ ID NO: 69)
MGKPIPNPLLGLDSTGGMAPKKKRKVDGGVDLRTLGYSQQQQEKIKPKVRSTVAQHHEALVGHGFTHA
HIVALSQHPAALGTVAVKYQDMIAALPEATHEAIVGVGKQWSGARALEALLTVAGELRGPPLQLDTGQ
LLKIAKRGGVTAVEAVHAWRNALTGAPLNLTPDQVVAIASHDGGKQALETVQRLLPVLCQDHGLTPDQ
VVAIASHDGGKQALETVQRLLPVLCQDHGLTPDQVVAIASHDGGKQALETVQRLLPVLCQDHGLTPDQ
VVAIASHDGGKQALETVQRLLPVLCQDHGLTPDQVVAIASHDGGKQALETVQRLLPVLCQDHGLTPDQ
VVAIASNNGGKQALETVQRLLPVLCQDHGLTPDQVVAIASNNGGKQALETVQRLLPVLCQDHGLTPDQ
VVAIASHDGGKQALETVQRLLPVLCQDHGLTPDQVVAIASHDGGKQALETVQRLLPVLCQDHGLTPDQ
VVAIASHDGGKQALETVQRLLPVLCQDHGLTPDQVVAIASNGGGKQALETVQRLLPVLCQDHGLTPDQ
VVAIASNIGGKQALETVQRLLPVLCQDHGLTPDQVVAIASNNGGKQALETVQRLLPVLCQDHGLTPDQ
VVAIASHDGGKQALETVQRLLPVLCQDHGLTPDQVVAIASNGGGKQALETVQRLLPVLCQDHGLTPDQ
VVAIASHDGGKQALETVQRLLPVLCQDHGLTPDQVVAIASHDGGKQALETVQRLLPVLCQDHGLTPDQ
VVAIASNGGGKQALESIVAQLSRPDPALAALTNDHLVALACLGGRPALDAVKKGLPHAPALIKRTNRR
IPERTSHRVAGSGGG (SEQ ID NO: 70)
5'-TGGGCCCTCACGCCTTTCT-3'

All publications mentioned in the above specification are herein incorporated by reference. Various modifications and variations of the described products, uses, methods and kits of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention, which are obvious to those skilled in biochemistry and biotechnology or related fields, are intended to be within the scope of the following claims.

The invention claimed is:

1. A product comprising a combination of artificial transcription repressors (ATRs) selected from the group consisting of: (a) and (b), and (a) and (c), or polynucleotides encoding therefor, wherein:
   (a) is an ATR comprising a DNA-binding domain operably linked to a Krüppel-associated box (KRAB) domain or homologue thereof;
   (b) is an ATR comprising a DNA-binding domain operably linked to a DNA methyltransferase 3A (DNMT3A) domain or homologue thereof; and
   (c) is an ATR comprising a DNA-binding domain operably linked to a DNA (cytosine-5)-methyltransferase 3-like (DNMT3L) domain or homologue thereof.

2. The product of claim 1, wherein:
   (i) the KRAB domain or homologue thereof comprises an amino acid sequence that has at least 60% identity to any one of SEQ ID NOs: 1-7;
   (ii) the DNMT3A domain or homologue thereof comprises an amino acid sequence that has at least 60% identity to SEQ ID NO: 8;
   (iii) the DNMT3L domain or homologue thereof comprises an amino acid sequence that has at least 60% identity to SEQ ID NO: 11; and/or
   (iv) the DNA-binding domain of (a), (b), or (c) comprises a domain independently selected from a transcription-activator like effector (TALE) DNA-binding domain, a zinc finger domain, a tetracycline-controlled repressor (tetR) DNA-binding domain, a meganuclease or a Clustered Regularly Interspaced Short Palindromic Repeats (CRISPR)/Cas system.

3. The product of claim 1, wherein the polynucleotides encoding the ATRs are in the form of a single vector or are comprised within separate vectors.

4. A method of gene therapy comprising transfecting a cell with the polynucleotides encoding the two or more ATRs as defined in claim 3, optionally wherein the transfection is carried out ex vivo.

5. The product of claim 1, further comprising a separate effector protein that is not operably linked to a DNA-binding domain, or polynucleotide encoding therefor, wherein the separate effector protein that is not operably linked to a DNA-binding domain comprises a domain selected from groups (a), (b), (c) or (d):
   (a) a KRAB domain or homologue thereof;
   (b) a DNMT3A, DNMT3B or DNMT1 domain or homologue thereof;
   (c) a DNMT3L domain or homologue thereof; and
   (d) a SETDB1 domain or homologue thereof.

6. The product of claim 1 in the form of a pharmaceutical composition further comprising a pharmaceutically acceptable carrier, diluent or excipient.

7. A cell comprising the ATRs as defined in claim 1.

8. A cell wherein said cell is a descendant of the cell of claim 7.

9. The product of claim 1 comprising an artificial transcription repressor (ATR) comprising a DNA-binding domain operably linked to a KRAB domain or homologue thereof, an ATR comprising a DNA-binding domain operably linked to a DNMT3L domain or homologue thereof, and an ATR comprising a DNA-binding domain operably linked to a DNMT3A domain or homologue thereof, or polynucleotides encoding therefor.

10. The product of claim 1 comprising an artificial transcription repressor (ATR) comprising a DNA-binding domain operably linked to a KRAB domain or homologue thereof, and an ATR comprising a DNA-binding domain operably linked to a DNMT3L domain or homologue thereof, or polynucleotides encoding therefor.

11. The product of claim 1 comprising an artificial transcription repressor (ATR) comprising a DNA-binding domain operably linked to a KRAB domain or homologue thereof, and an ATR comprising a DNA-binding domain operably linked to a DNMT3A domain or homologue thereof, or polynucleotides encoding therefor.

12. A method of gene therapy comprising administering the product of claim 1 to a subject, wherein the ATRs are administered simultaneously, sequentially or separately.

13. The method of claim 12, wherein:
   (i) transient expression of the two or more ATRs in a cell silences a target gene;
   (ii) delivery of the two or more ATRs to a cell permanently silences a target gene;
   (iii) delivery of the two or more ATRs to a cell permanently silences a target gene in the cell's progeny; and/or
   (iv) the DNA-binding domains of the different ATRs are selected to bind to binding sites that are separated by 0-30 bp, optionally wherein the DNA-binding domains are TALE DNA-binding domains or CRISPR/Cas systems.

14. A method of silencing a target gene comprising the step of administering the product of claim 1 to a cell.

15. An artificial transcription repressor (ATR) comprising a DNA-binding domain operably linked to two or more domains selected from groups (a), (b), or (c); wherein the two or more domains comprise: (a) and (b), or (a) and (c); wherein:
   (a) is a Krüppel-associated box (KRAB) domain or homologue thereof;
   (b) is a DNA methyltransferase 3A (DNMT3A) domain or homologue thereof; and
   (c) is a DNA (cytosine-5)-methyltransferase 3-like (DNMT3L) domain or homologue thereof;
   optionally wherein the DNA-binding domain comprises a transcription-activator like effector (TALE) DNA-binding domain, a zinc finger domain, a tetracycline-controlled repressor (tetR) DNA-binding domain, a meganuclease, or a Clustered Regularly Interspaced Short Palindromic Repeats (CRISPR)/Cas system.

16. A polynucleotide encoding the ATR of claim 15.

17. A cell comprising the ATR as defined in claim 15.

18. A cell wherein said cell is a descendant of the cell of claim 17.

19. The ATR of claim 15, wherein the ATR comprises a DNA-binding domain operably linked to a KRAB domain or homologue thereof, a DNTM3A domain or homologue thereof, and a DNMT3L domain or homologue thereof.

20. The ATR of claim 15, wherein the ATR comprises a DNA-binding domain operably linked to a KRAB domain or homologue thereof, and a DNMT3L domain or homologue thereof.

21. The ATR of claim 15, wherein the ATR comprises a DNA-binding domain operably linked to a KRAB domain or homologue thereof, and a DNTM3A domain or homologue thereof.

22. A product comprising two or more different artificial transcription repressors (ATRs), or polynucleotides encoding therefor, wherein the two or more different ATRs individually comprise a DNA-binding domain operably linked to two or more domains selected from groups (a), (b), or (c); wherein the two or more domains comprise: (a) and (b), or (a) and (c); wherein:
   (a) is a Krüppel-associated box (KRAB) domain or homologue thereof;
   (b) is a DNA methyltransferase 3A (DNMT3A) domain or homologue thereof; and
   (c) is a DNA (cytosine-5)-methyltransferase 3-like (DNMT3L) domain or homologue thereof;
   optionally wherein the DNA-binding domains of the two or more different ATRs are individually selected from the group consisting of a transcription-activator like effector (TALE) DNA-binding domain, a zinc finger domain, a tetracycline-controlled repressor (tetR) DNA-binding domain, a meganuclease, and a Clustered Regularly Interspaced Short Palindromic Repeats (CRISPR)/Cas system.

23. A cell comprising the ATRs as defined in claim 22.

24. A cell wherein said cell is a descendant of the cell of claim 23.

* * * * *

SEQUENCE LISTING

<160> NUMBER OF SEQ ID NOS: 175

<210> SEQ ID NO 1
<211> LENGTH: 117
<212> TYPE: PRT
<213> ORGANISM: Homo sapiens

<400> SEQUENCE: 1

Ala Leu Ser Pro Gln His Ser Ala Val Thr Gln Gly Ser Ile Ile Lys
1               5                   10                  15

Asn Lys Glu Gly Met Asp Ala Lys Ser Leu Thr Ala Trp Ser Arg Thr
            20                  25                  30

Leu Val Thr Phe Lys Asp Val Phe Val Asp Phe Thr Arg Glu Glu Trp
        35                  40                  45

Lys Leu Leu Asp Thr Ala Gln Gln Ile Val Tyr Arg Asn Val Met Leu
    50                  55                  60

Glu Asn Tyr Lys Asn Leu Val Ser Leu Gly Tyr Gln Leu Thr Lys Pro
65                  70                  75                  80

Asp Val Ile Leu Arg Leu Glu Lys Gly Glu Glu Pro Trp Leu Val Glu
                85                  90                  95

Arg Glu Ile His Gln Glu Thr His Pro Asp Ser Glu Thr Ala Phe Glu
            100                 105                 110

Ile Lys Ser Ser Val
        115

<210> SEQ ID NO 2
<211> LENGTH: 72
<212> TYPE: PRT
<213> ORGANISM: Homo sapiens

<400> SEQUENCE: 2

```
Ile Thr Leu Glu Asp Val Ala Val Asp Phe Thr Trp Glu Glu Trp Gln
1               5                   10                  15

Leu Leu Gly Ala Ala Gln Lys Asp Leu Tyr Arg Asp Val Met Leu Glu
            20                  25                  30

Asn Tyr Ser Asn Leu Val Ala Val Gly Tyr Gln Ala Ser Lys Pro Asp
        35                  40                  45

Ala Leu Phe Lys Leu Glu Gln Gly Glu Gln Leu Trp Thr Ile Glu Asp
    50                  55                  60

Gly Ile His Ser Gly Ala Cys Ser
65              70
```

<210> SEQ ID NO 3
<211> LENGTH: 73
<212> TYPE: PRT
<213> ORGANISM: Homo sapiens

<400> SEQUENCE: 3

```
Val Met Phe Glu Glu Val Ser Val Cys Phe Thr Ser Glu Glu Trp Ala
1               5                   10                  15

Cys Leu Gly Pro Ile Gln Arg Ala Leu Tyr Trp Asp Val Met Leu Glu
            20                  25                  30

Asn Tyr Gly Asn Val Thr Ser Leu Glu Trp Glu Thr Met Thr Glu Asn
        35                  40                  45

Glu Glu Val Thr Ser Lys Pro Ser Ser Gln Arg Ala Asp Ser His
    50                  55                  60

Lys Gly Thr Ser Lys Arg Leu Gln Gly
65              70
```

<210> SEQ ID NO 4
<211> LENGTH: 72
<212> TYPE: PRT
<213> ORGANISM: Homo sapiens

<400> SEQUENCE: 4

```
Val Ser Phe Lys Asp Val Ala Val Asp Phe Thr Gln Glu Glu Trp Gln
1               5                   10                  15

Gln Leu Asp Pro Asp Glu Lys Ile Thr Tyr Arg Asp Val Met Leu Glu
            20                  25                  30

Asn Tyr Ser His Leu Val Ser Val Gly Tyr Asp Thr Thr Lys Pro Asn
        35                  40                  45

Val Ile Ile Lys Leu Glu Gln Gly Glu Glu Pro Trp Ile Met Gly Gly
    50                  55                  60

Glu Phe Pro Cys Gln His Ser Pro
65              70
```

<210> SEQ ID NO 5
<211> LENGTH: 74
<212> TYPE: PRT
<213> ORGANISM: Homo sapiens

<400> SEQUENCE: 5

```
Val Lys Ile Glu Asp Met Ala Val Ser Leu Ile Leu Glu Glu Trp Gly
1               5                   10                  15

Cys Gln Asn Leu Ala Arg Arg Asn Leu Ser Arg Asp Asn Arg Gln Glu
            20                  25                  30

Asn Tyr Gly Ser Ala Phe Pro Gln Gly Gly Glu Asn Arg Asn Glu Asn
        35                  40                  45

Glu Glu Ser Thr Ser Lys Ala Glu Thr Ser Glu Asp Ser Ala Ser Arg
```

```
                 50                  55                  60

Gly Glu Thr Thr Gly Arg Ser Gln Lys Glu
 65                  70

<210> SEQ ID NO 6
<211> LENGTH: 72
<212> TYPE: PRT
<213> ORGANISM: Homo sapiens

<400> SEQUENCE: 6

Leu Thr Phe Lys Asp Val Phe Val Asp Phe Thr Leu Glu Glu Trp Gln
  1               5                  10                  15

Gln Leu Asp Ser Ala Gln Lys Asn Leu Tyr Arg Asp Val Met Leu Glu
                 20                  25                  30

Asn Tyr Ser His Leu Val Ser Val Gly Tyr Leu Val Ala Lys Pro Asp
             35                  40                  45

Val Ile Phe Arg Leu Gly Pro Gly Glu Glu Ser Trp Met Ala Asp Gly
         50                  55                  60

Gly Thr Pro Val Arg Thr Cys Ala
 65                  70

<210> SEQ ID NO 7
<211> LENGTH: 72
<212> TYPE: PRT
<213> ORGANISM: Homo sapiens

<400> SEQUENCE: 7

Val Thr Phe Glu Asp Val Thr Leu Gly Phe Thr Pro Glu Glu Trp Gly
  1               5                  10                  15

Leu Leu Asp Leu Lys Gln Lys Ser Leu Tyr Arg Glu Val Met Leu Glu
                 20                  25                  30

Asn Tyr Arg Asn Leu Val Ser Val Glu His Gln Leu Ser Lys Pro Asp
             35                  40                  45

Val Val Ser Gln Leu Glu Glu Ala Glu Asp Phe Trp Pro Val Glu Arg
         50                  55                  60

Gly Ile Pro Gln Asp Thr Ile Pro
 65                  70

<210> SEQ ID NO 8
<211> LENGTH: 322
<212> TYPE: PRT
<213> ORGANISM: Homo sapiens

<400> SEQUENCE: 8

Thr Tyr Gly Leu Leu Arg Arg Arg Glu Asp Trp Pro Ser Arg Leu Gln
  1               5                  10                  15

Met Phe Phe Ala Asn Asn His Asp Gln Glu Phe Asp Pro Pro Lys Val
                 20                  25                  30

Tyr Pro Pro Val Pro Ala Glu Lys Arg Lys Pro Ile Arg Val Leu Ser
             35                  40                  45

Leu Phe Asp Gly Ile Ala Thr Gly Leu Leu Val Leu Lys Asp Leu Gly
         50                  55                  60

Ile Gln Val Asp Arg Tyr Ile Ala Ser Glu Val Cys Glu Asp Ser Ile
 65                  70                  75                  80

Thr Val Gly Met Val Arg His Gln Gly Lys Ile Met Tyr Val Gly Asp
                 85                  90                  95

Val Arg Ser Val Thr Gln Lys His Ile Gln Glu Trp Gly Pro Phe Asp
                100                 105                 110
```

-continued

```
Leu Val Ile Gly Gly Ser Pro Cys Asn Asp Leu Ser Ile Val Asn Pro
            115                 120                 125

Ala Arg Lys Gly Leu Tyr Glu Gly Thr Gly Arg Leu Phe Phe Glu Phe
130                 135                 140

Tyr Arg Leu Leu His Asp Ala Arg Pro Lys Glu Gly Asp Asp Arg Pro
145                 150                 155                 160

Phe Phe Trp Leu Phe Glu Asn Val Val Ala Met Gly Val Ser Asp Lys
                165                 170                 175

Arg Asp Ile Ser Arg Phe Leu Glu Ser Asn Pro Val Met Ile Asp Ala
                180                 185                 190

Lys Glu Val Ser Ala Ala His Arg Ala Arg Tyr Phe Trp Gly Asn Leu
                195                 200                 205

Pro Gly Met Asn Arg Pro Leu Ala Ser Thr Val Asn Asp Lys Leu Glu
            210                 215                 220

Leu Gln Glu Cys Leu Glu His Gly Arg Ile Ala Lys Phe Ser Lys Val
225                 230                 235                 240

Arg Thr Ile Thr Thr Arg Ser Asn Ser Ile Lys Gln Gly Lys Asp Gln
                245                 250                 255

His Phe Pro Val Phe Met Asn Glu Lys Glu Asp Ile Leu Trp Cys Thr
                260                 265                 270

Glu Met Glu Arg Val Phe Gly Phe Pro Val His Tyr Thr Asp Val Ser
            275                 280                 285

Asn Met Ser Arg Leu Ala Arg Gln Arg Leu Leu Gly Arg Ser Trp Ser
            290                 295                 300

Val Pro Val Ile Arg His Leu Phe Ala Pro Leu Lys Glu Tyr Phe Ala
305                 310                 315                 320

Cys Val

<210> SEQ ID NO 9
<211> LENGTH: 322
<212> TYPE: PRT
<213> ORGANISM: Homo sapiens

<400> SEQUENCE: 9

Cys His Gly Val Leu Arg Arg Lys Asp Trp Asn Val Arg Leu Gln
1               5                   10                  15

Ala Phe Phe Thr Ser Asp Thr Gly Leu Glu Tyr Glu Ala Pro Lys Leu
                20                  25                  30

Tyr Pro Ala Ile Pro Ala Ala Arg Arg Pro Ile Arg Val Leu Ser
            35                  40                  45

Leu Phe Asp Gly Ile Ala Thr Gly Tyr Leu Val Leu Lys Glu Leu Gly
50                  55                  60

Ile Lys Val Gly Lys Tyr Val Ala Ser Glu Val Cys Glu Glu Ser Ile
65                  70                  75                  80

Ala Val Gly Thr Val Lys His Glu Gly Asn Ile Lys Tyr Val Asn Asp
                85                  90                  95

Val Arg Asn Ile Thr Lys Lys Asn Ile Glu Glu Trp Gly Pro Phe Asp
                100                 105                 110

Leu Val Ile Gly Gly Ser Pro Cys Asn Asp Leu Ser Asn Val Asn Pro
            115                 120                 125

Ala Arg Lys Gly Leu Tyr Glu Gly Thr Gly Arg Leu Phe Phe Glu Phe
130                 135                 140

Tyr His Leu Leu Asn Tyr Ser Arg Pro Lys Glu Gly Asp Asp Arg Pro
145                 150                 155                 160
```

```
Phe Phe Trp Met Phe Glu Asn Val Val Ala Met Lys Val Gly Asp Lys
                165                 170                 175

Arg Asp Ile Ser Arg Phe Leu Glu Cys Asn Pro Val Met Ile Asp Ala
            180                 185                 190

Ile Lys Val Ser Ala Ala His Arg Ala Arg Tyr Phe Trp Gly Asn Leu
        195                 200                 205

Pro Gly Met Asn Arg Pro Val Ile Ala Ser Lys Asn Asp Lys Leu Glu
    210                 215                 220

Leu Gln Asp Cys Leu Glu Tyr Asn Arg Ile Ala Lys Leu Lys Lys Val
225                 230                 235                 240

Gln Thr Ile Thr Thr Lys Ser Asn Ser Ile Lys Gln Gly Lys Asn Gln
                245                 250                 255

Leu Phe Pro Val Val Met Asn Gly Lys Glu Asp Val Leu Trp Cys Thr
            260                 265                 270

Glu Leu Glu Arg Ile Phe Gly Phe Pro Val His Tyr Thr Asp Val Ser
        275                 280                 285

Asn Met Gly Arg Gly Ala Arg Gln Lys Leu Leu Gly Arg Ser Trp Ser
    290                 295                 300

Val Pro Val Ile Arg His Leu Phe Ala Pro Leu Lys Asp Tyr Phe Ala
305                 310                 315                 320

Cys Glu

<210> SEQ ID NO 10
<211> LENGTH: 478
<212> TYPE: PRT
<213> ORGANISM: Homo sapiens

<400> SEQUENCE: 10

Leu Arg Thr Leu Asp Val Phe Ser Gly Cys Gly Gly Leu Ser Glu Gly
1               5                   10                  15

Phe His Gln Ala Gly Ile Ser Asp Thr Leu Trp Ala Ile Glu Met Trp
                20                  25                  30

Asp Pro Ala Ala Gln Ala Phe Arg Leu Asn Asn Pro Gly Ser Thr Val
            35                  40                  45

Phe Thr Glu Asp Cys Asn Ile Leu Leu Lys Leu Val Met Ala Gly Glu
    50                  55                  60

Thr Thr Asn Ser Arg Gly Gln Arg Leu Pro Gln Lys Gly Asp Val Glu
65                  70                  75                  80

Met Leu Cys Gly Gly Pro Pro Cys Gln Gly Phe Ser Gly Met Asn Arg
                85                  90                  95

Phe Asn Ser Arg Thr Tyr Ser Lys Phe Lys Asn Ser Leu Val Val Ser
            100                 105                 110

Phe Leu Ser Tyr Cys Asp Tyr Tyr Arg Pro Arg Phe Phe Leu Leu Glu
        115                 120                 125

Asn Val Arg Asn Phe Val Ser Phe Lys Arg Ser Met Val Leu Lys Leu
    130                 135                 140

Thr Leu Arg Cys Leu Val Arg Met Gly Tyr Gln Cys Thr Phe Gly Val
145                 150                 155                 160

Leu Gln Ala Gly Gln Tyr Gly Val Ala Gln Thr Arg Arg Arg Ala Ile
                165                 170                 175

Ile Leu Ala Ala Ala Pro Gly Glu Lys Leu Pro Leu Phe Pro Glu Pro
            180                 185                 190

Leu His Val Phe Ala Pro Arg Ala Cys Gln Leu Ser Val Val Val Asp
        195                 200                 205
```

```
Asp Lys Lys Phe Val Ser Asn Ile Thr Arg Leu Ser Gly Pro Phe
    210                 215                 220

Arg Thr Ile Thr Val Arg Asp Thr Met Ser Asp Leu Pro Glu Val Arg
225                 230                 235                 240

Asn Gly Ala Ser Ala Leu Glu Ile Ser Tyr Asn Gly Glu Pro Gln Ser
                245                 250                 255

Trp Phe Gln Arg Gln Leu Arg Gly Ala Gln Tyr Gln Pro Ile Leu Arg
            260                 265                 270

Asp His Ile Cys Lys Asp Met Ser Ala Leu Val Ala Ala Arg Met Arg
        275                 280                 285

His Ile Pro Leu Ala Pro Gly Ser Asp Trp Arg Asp Leu Pro Asn Ile
    290                 295                 300

Glu Val Arg Leu Ser Asp Gly Thr Met Ala Arg Lys Leu Arg Tyr Thr
305                 310                 315                 320

His His Asp Arg Lys Asn Gly Arg Ser Ser Gly Ala Leu Arg Gly
                325                 330                 335

Val Cys Ser Cys Val Glu Ala Gly Lys Ala Cys Asp Pro Ala Ala Arg
                340                 345                 350

Gln Phe Asn Thr Leu Ile Pro Trp Cys Leu Pro His Thr Gly Asn Arg
            355                 360                 365

His Asn His Trp Ala Gly Leu Tyr Gly Arg Leu Glu Trp Asp Gly Phe
        370                 375                 380

Phe Ser Thr Thr Val Thr Asn Pro Glu Pro Met Gly Lys Gln Gly Arg
385                 390                 395                 400

Val Leu His Pro Glu Gln His Arg Val Val Ser Val Arg Glu Cys Ala
                405                 410                 415

Arg Ser Gln Gly Phe Pro Asp Thr Tyr Arg Leu Phe Gly Asn Ile Leu
            420                 425                 430

Asp Lys His Arg Gln Val Gly Asn Ala Val Pro Pro Leu Ala Lys
        435                 440                 445

Ala Ile Gly Leu Glu Ile Lys Leu Cys Met Leu Ala Lys Ala Arg Glu
    450                 455                 460

Ser Ala Ser Ala Lys Ile Lys Glu Glu Ala Ala Lys Asp
465                 470                 475

<210> SEQ ID NO 11
<211> LENGTH: 386
<212> TYPE: PRT
<213> ORGANISM: Homo sapiens

<400> SEQUENCE: 11

Met Ala Ala Ile Pro Ala Leu Asp Pro Glu Ala Glu Pro Ser Met Asp
1               5                   10                  15

Val Ile Leu Val Gly Ser Ser Glu Leu Ser Ser Ser Val Ser Pro Gly
                20                  25                  30

Thr Gly Arg Asp Leu Ile Ala Tyr Glu Val Lys Ala Asn Gln Arg Asn
            35                  40                  45

Ile Glu Asp Ile Cys Ile Cys Cys Gly Ser Leu Gln Val His Thr Gln
    50                  55                  60

His Pro Leu Phe Glu Gly Gly Ile Cys Ala Pro Cys Lys Asp Lys Phe
65                  70                  75                  80

Leu Asp Ala Leu Phe Leu Tyr Asp Asp Asp Gly Tyr Gln Ser Tyr Cys
                85                  90                  95

Ser Ile Cys Cys Ser Gly Glu Thr Leu Leu Ile Cys Gly Asn Pro Asp
```

```
            100                 105                 110
Cys Thr Arg Cys Tyr Cys Phe Glu Cys Val Asp Ser Leu Val Gly Pro
        115                 120                 125

Gly Thr Ser Gly Lys Val His Ala Met Ser Asn Trp Val Cys Tyr Leu
130                 135                 140

Cys Leu Pro Ser Ser Arg Ser Gly Leu Leu Gln Arg Arg Lys Trp
145                 150                 155                 160

Arg Ser Gln Leu Lys Ala Phe Tyr Asp Arg Glu Ser Glu Asn Pro Leu
                165                 170                 175

Glu Met Phe Glu Thr Val Pro Val Trp Arg Arg Gln Pro Val Arg Val
            180                 185                 190

Leu Ser Leu Phe Glu Asp Ile Lys Lys Glu Leu Thr Ser Leu Gly Phe
        195                 200                 205

Leu Glu Ser Gly Ser Asp Pro Gly Gln Leu Lys His Val Val Asp Val
    210                 215                 220

Thr Asp Thr Val Arg Lys Asp Val Glu Trp Gly Pro Phe Asp Leu
225                 230                 235                 240

Val Tyr Gly Ala Thr Pro Pro Leu Gly His Thr Cys Asp Arg Pro Pro
                245                 250                 255

Ser Trp Tyr Leu Phe Gln Phe His Arg Leu Leu Gln Tyr Ala Arg Pro
            260                 265                 270

Lys Pro Gly Ser Pro Arg Pro Phe Phe Trp Met Phe Val Asp Asn Leu
        275                 280                 285

Val Leu Asn Lys Glu Asp Leu Asp Val Ala Ser Arg Phe Leu Glu Met
    290                 295                 300

Glu Pro Val Thr Ile Pro Asp Val His Gly Gly Ser Leu Gln Asn Ala
305                 310                 315                 320

Val Arg Val Trp Ser Asn Ile Pro Ala Ile Arg Ser Arg His Trp Ala
                325                 330                 335

Leu Val Ser Glu Glu Leu Ser Leu Leu Ala Gln Asn Lys Gln Ser
            340                 345                 350

Ser Lys Leu Ala Ala Lys Trp Pro Thr Lys Leu Val Lys Asn Cys Phe
        355                 360                 365

Leu Pro Leu Arg Glu Tyr Phe Lys Tyr Phe Ser Thr Glu Leu Thr Ser
    370                 375                 380

Ser Leu
385

<210> SEQ ID NO 12
<211> LENGTH: 1291
<212> TYPE: PRT
<213> ORGANISM: Homo sapiens

<400> SEQUENCE: 12

Met Ser Ser Leu Pro Gly Cys Ile Gly Leu Asp Ala Ala Thr Ala Thr
1               5                   10                  15

Val Glu Ser Glu Glu Ile Ala Glu Leu Gln Gln Ala Val Val Glu Glu
                20                  25                  30

Leu Gly Ile Ser Met Glu Glu Leu Arg His Phe Ile Asp Glu Glu Leu
            35                  40                  45

Glu Lys Met Asp Cys Val Gln Gln Arg Lys Lys Gln Leu Ala Glu Leu
        50                  55                  60

Glu Thr Trp Val Ile Gln Lys Glu Ser Glu Val Ala His Val Asp Gln
65                  70                  75                  80
```

-continued

```
Leu Phe Asp Asp Ala Ser Arg Ala Val Thr Asn Cys Glu Ser Leu Val
             85                  90                  95

Lys Asp Phe Tyr Ser Lys Leu Gly Leu Gln Tyr Arg Asp Ser Ser Ser
            100                 105                 110

Glu Asp Glu Ser Ser Arg Pro Thr Glu Ile Ile Glu Ile Pro Asp Glu
            115                 120                 125

Asp Asp Asp Val Leu Ser Ile Asp Ser Gly Asp Ala Gly Ser Arg Thr
            130                 135                 140

Pro Lys Asp Gln Lys Leu Arg Glu Ala Met Ala Ala Leu Arg Lys Ser
145                 150                 155                 160

Ala Gln Asp Val Gln Lys Phe Met Asp Ala Val Asn Lys Lys Ser Ser
                165                 170                 175

Ser Gln Asp Leu His Lys Gly Thr Leu Ser Gln Met Ser Gly Glu Leu
            180                 185                 190

Ser Lys Asp Gly Asp Leu Ile Val Ser Met Arg Ile Leu Gly Lys Lys
            195                 200                 205

Arg Thr Lys Thr Trp His Lys Gly Thr Leu Ile Ala Ile Gln Thr Val
            210                 215                 220

Gly Pro Gly Lys Lys Tyr Lys Val Lys Phe Asp Asn Lys Gly Lys Ser
225                 230                 235                 240

Leu Leu Ser Gly Asn His Ile Ala Tyr Asp Tyr His Pro Pro Ala Asp
                245                 250                 255

Lys Leu Tyr Val Gly Ser Arg Val Val Ala Lys Tyr Lys Asp Gly Asn
                260                 265                 270

Gln Val Trp Leu Tyr Ala Gly Ile Val Ala Glu Thr Pro Asn Val Lys
            275                 280                 285

Asn Lys Leu Arg Phe Leu Ile Phe Phe Asp Asp Gly Tyr Ala Ser Tyr
            290                 295                 300

Val Thr Gln Ser Glu Leu Tyr Pro Ile Cys Arg Pro Leu Lys Lys Thr
305                 310                 315                 320

Trp Glu Asp Ile Glu Asp Ile Ser Cys Arg Asp Phe Ile Glu Glu Tyr
                325                 330                 335

Val Thr Ala Tyr Pro Asn Arg Pro Met Val Leu Leu Lys Ser Gly Gln
            340                 345                 350

Leu Ile Lys Thr Glu Trp Glu Gly Thr Trp Lys Ser Arg Val Glu
            355                 360                 365

Glu Val Asp Gly Ser Leu Val Arg Ile Leu Phe Leu Asp Asp Lys Arg
            370                 375                 380

Cys Glu Trp Ile Tyr Arg Gly Ser Thr Arg Leu Glu Pro Met Phe Ser
385                 390                 395                 400

Met Lys Thr Ser Ser Ala Ser Ala Leu Glu Lys Lys Gln Gly Gln Leu
                405                 410                 415

Arg Thr Arg Pro Asn Met Gly Ala Val Arg Ser Lys Gly Pro Val Val
            420                 425                 430

Gln Tyr Thr Gln Asp Leu Thr Gly Thr Gly Thr Gln Phe Lys Pro Val
            435                 440                 445

Glu Pro Pro Gln Pro Thr Ala Pro Ala Pro Pro Phe Pro Pro Ala
450                 455                 460

Pro Pro Leu Ser Pro Gln Ala Gly Asp Ser Asp Leu Glu Ser Gln Leu
465                 470                 475                 480

Ala Gln Ser Arg Lys Gln Val Ala Lys Lys Ser Thr Ser Phe Arg Pro
                485                 490                 495

Gly Ser Val Gly Ser Gly His Ser Ser Pro Thr Ser Pro Ala Leu Ser
```

```
                500             505             510
    Glu Asn Val Ser Gly Lys Pro Gly Ile Asn Gln Thr Tyr Arg Ser
            515                 520                 525
    Pro Leu Gly Ser Thr Ala Ser Ala Pro Ala Pro Ser Ala Leu Pro Ala
            530                 535                 540
    Pro Pro Ala Pro Pro Val Phe His Gly Met Leu Glu Arg Ala Pro Ala
    545                 550                 555                 560
    Glu Pro Ser Tyr Arg Ala Pro Met Glu Lys Leu Phe Tyr Leu Pro His
                565                 570                 575
    Val Cys Ser Tyr Thr Cys Leu Ser Arg Val Arg Pro Met Arg Asn Glu
                580                 585                 590
    Gln Tyr Arg Gly Lys Asn Pro Leu Leu Val Pro Leu Leu Tyr Asp Phe
                595                 600                 605
    Arg Arg Met Thr Ala Arg Arg Val Asn Arg Lys Met Gly Phe His
                610                 615                 620
    Val Ile Tyr Lys Thr Pro Cys Gly Leu Cys Leu Arg Thr Met Gln Glu
    625                 630                 635                 640
    Ile Glu Arg Tyr Leu Phe Glu Thr Gly Cys Asp Phe Leu Phe Leu Glu
                645                 650                 655
    Met Phe Cys Leu Asp Pro Tyr Val Leu Val Asp Arg Lys Phe Gln Pro
                660                 665                 670
    Tyr Lys Pro Phe Tyr Tyr Ile Leu Asp Ile Thr Tyr Gly Lys Glu Asp
                675                 680                 685
    Val Pro Leu Ser Cys Val Asn Glu Ile Asp Thr Thr Pro Pro Gln
                690                 695                 700
    Val Ala Tyr Ser Lys Glu Arg Ile Pro Gly Lys Gly Val Phe Ile Asn
    705                 710                 715                 720
    Thr Gly Pro Glu Phe Leu Val Gly Cys Asp Cys Lys Asp Gly Cys Arg
                        725                 730                 735
    Asp Lys Ser Lys Cys Ala Cys His Gln Leu Thr Ile Gln Ala Thr Ala
                    740                 745                 750
    Cys Thr Pro Gly Gly Gln Ile Asn Pro Asn Ser Gly Tyr Gln Tyr Lys
                    755                 760                 765
    Arg Leu Glu Glu Cys Leu Pro Thr Gly Val Tyr Glu Cys Asn Lys Arg
                    770                 775                 780
    Cys Lys Cys Asp Pro Asn Met Cys Thr Asn Arg Leu Val Gln His Gly
                    785                 790                 795                 800
    Leu Gln Val Arg Leu Gln Leu Phe Lys Thr Gln Asn Lys Gly Trp Gly
                        805                 810                 815
    Ile Arg Cys Leu Asp Asp Ile Ala Lys Gly Ser Phe Val Cys Ile Tyr
                    820                 825                 830
    Ala Gly Lys Ile Leu Thr Asp Asp Phe Ala Asp Lys Glu Gly Leu Glu
                    835                 840                 845
    Met Gly Asp Glu Tyr Phe Ala Asn Leu Asp His Ile Glu Ser Val Glu
                    850                 855                 860
    Asn Phe Lys Glu Gly Tyr Glu Ser Asp Ala Pro Cys Ser Ser Asp Ser
    865                 870                 875                 880
    Ser Gly Val Asp Leu Lys Asp Gln Glu Asp Gly Asn Ser Gly Thr Glu
                        885                 890                 895
    Asp Pro Glu Glu Ser Asn Asp Asp Ser Ser Asp Asp Asn Phe Cys Lys
                        900                 905                 910
    Asp Glu Asp Phe Ser Thr Ser Ser Val Trp Arg Ser Tyr Ala Thr Arg
                        915                 920                 925
```

```
Arg Gln Thr Arg Gly Gln Lys Glu Asn Gly Leu Ser Glu Thr Thr Ser
    930                 935                 940

Lys Asp Ser His Pro Pro Asp Leu Gly Pro Pro His Ile Pro Val Pro
945                 950                 955                 960

Pro Ser Ile Pro Val Gly Gly Cys Asn Pro Pro Ser Ser Glu Glu Thr
            965                 970                 975

Pro Lys Asn Lys Val Ala Ser Trp Leu Ser Cys Asn Ser Val Ser Glu
            980                 985                 990

Gly Gly Phe Ala Asp Ser Asp Ser His Ser Ser Phe Lys Thr Asn Glu
            995                1000               1005

Gly Gly Glu Gly Arg Ala Gly Gly Ser Arg Met Glu Ala Glu Lys
    1010                1015                1020

Ala Ser Thr Ser Gly Leu Gly Ile Lys Asp Glu Gly Asp Ile Lys
    1025                1030                1035

Gln Ala Lys Lys Glu Asp Thr Asp Asp Arg Asn Lys Met Ser Val
    1040                1045                1050

Val Thr Glu Ser Ser Arg Asn Tyr Gly Tyr Asn Pro Ser Pro Val
    1055                1060                1065

Lys Pro Glu Gly Leu Arg Arg Pro Pro Ser Lys Thr Ser Met His
    1070                1075                1080

Gln Ser Arg Arg Leu Met Ala Ser Ala Gln Ser Asn Pro Asp Asp
    1085                1090                1095

Val Leu Thr Leu Ser Ser Ser Thr Glu Ser Glu Gly Glu Ser Gly
    1100                1105                1110

Thr Ser Arg Lys Pro Thr Ala Gly Gln Thr Ser Ala Thr Ala Val
    1115                1120                1125

Asp Ser Asp Asp Ile Gln Thr Ile Ser Ser Gly Ser Glu Gly Asp
    1130                1135                1140

Asp Phe Glu Asp Lys Lys Asn Met Thr Gly Pro Met Lys Arg Gln
    1145                1150                1155

Val Ala Val Lys Ser Thr Arg Gly Phe Ala Leu Lys Ser Thr His
    1160                1165                1170

Gly Ile Ala Ile Lys Ser Thr Asn Met Ala Ser Val Asp Lys Gly
    1175                1180                1185

Glu Ser Ala Pro Val Arg Lys Asn Thr Arg Gln Phe Tyr Asp Gly
    1190                1195                1200

Glu Glu Ser Cys Tyr Ile Ile Asp Ala Lys Leu Glu Gly Asn Leu
    1205                1210                1215

Gly Arg Tyr Leu Asn His Ser Cys Ser Pro Asn Leu Phe Val Gln
    1220                1225                1230

Asn Val Phe Val Asp Thr His Asp Leu Arg Phe Pro Trp Val Ala
    1235                1240                1245

Phe Phe Ala Ser Lys Arg Ile Arg Ala Gly Thr Glu Leu Thr Trp
    1250                1255                1260

Asp Tyr Asn Tyr Glu Val Gly Ser Val Glu Gly Lys Glu Leu Leu
    1265                1270                1275

Cys Cys Cys Gly Ala Ile Glu Cys Arg Gly Arg Leu Leu
    1280                1285                1290

<210> SEQ ID NO 13
<211> LENGTH: 565
<212> TYPE: PRT
<213> ORGANISM: Homo sapiens
```

```
<400> SEQUENCE: 13

Val Gly Cys Asp Cys Lys Asp Gly Cys Arg Asp Lys Ser Lys Cys Ala
1               5                   10                  15

Cys His Gln Leu Thr Ile Gln Ala Thr Ala Cys Thr Pro Gly Gly Gln
            20                  25                  30

Ile Asn Pro Asn Ser Gly Tyr Gln Tyr Lys Arg Leu Glu Glu Cys Leu
            35                  40                  45

Pro Thr Gly Val Tyr Glu Cys Asn Lys Arg Cys Lys Cys Asp Pro Asn
        50                  55                  60

Met Cys Thr Asn Arg Leu Val Gln His Gly Leu Gln Val Arg Leu Gln
65                  70                  75                  80

Leu Phe Lys Thr Gln Asn Lys Gly Trp Gly Ile Arg Cys Leu Asp Asp
                85                  90                  95

Ile Ala Lys Gly Ser Phe Val Cys Ile Tyr Ala Gly Lys Ile Leu Thr
            100                 105                 110

Asp Asp Phe Ala Asp Lys Glu Gly Leu Glu Met Gly Asp Glu Tyr Phe
        115                 120                 125

Ala Asn Leu Asp His Ile Glu Ser Val Glu Asn Phe Lys Glu Gly Tyr
    130                 135                 140

Glu Ser Asp Ala Pro Cys Ser Ser Asp Ser Gly Val Asp Leu Lys
145                 150                 155                 160

Asp Gln Glu Asp Gly Asn Ser Gly Thr Glu Asp Pro Glu Glu Ser Asn
                165                 170                 175

Asp Asp Ser Ser Asp Asp Asn Phe Cys Lys Asp Glu Asp Phe Ser Thr
            180                 185                 190

Ser Ser Val Trp Arg Ser Tyr Ala Thr Arg Arg Gln Thr Arg Gly Gln
        195                 200                 205

Lys Glu Asn Gly Leu Ser Glu Thr Thr Ser Lys Asp Ser His Pro Pro
210                 215                 220

Asp Leu Gly Pro Pro His Ile Pro Val Pro Pro Ser Ile Pro Val Gly
225                 230                 235                 240

Gly Cys Asn Pro Pro Ser Ser Glu Glu Thr Pro Lys Asn Lys Val Ala
                245                 250                 255

Ser Trp Leu Ser Cys Asn Ser Val Ser Glu Gly Gly Phe Ala Asp Ser
            260                 265                 270

Asp Ser His Ser Ser Phe Lys Thr Asn Glu Gly Gly Glu Gly Arg Ala
        275                 280                 285

Gly Gly Ser Arg Met Glu Ala Glu Lys Ala Ser Thr Ser Gly Leu Gly
    290                 295                 300

Ile Lys Asp Glu Gly Asp Ile Lys Gln Ala Lys Lys Glu Asp Thr Asp
305                 310                 315                 320

Asp Arg Asn Lys Met Ser Val Val Thr Glu Ser Ser Arg Asn Tyr Gly
                325                 330                 335

Tyr Asn Pro Ser Pro Val Lys Pro Glu Gly Leu Arg Arg Pro Pro Ser
            340                 345                 350

Lys Thr Ser Met His Gln Ser Arg Arg Leu Met Ala Ser Ala Gln Ser
        355                 360                 365

Asn Pro Asp Asp Val Leu Thr Leu Ser Ser Thr Glu Ser Glu Gly
    370                 375                 380

Glu Ser Gly Thr Ser Arg Lys Pro Thr Ala Gly Gln Thr Ser Ala Thr
385                 390                 395                 400

Ala Val Asp Ser Asp Asp Ile Gln Thr Ile Ser Ser Gly Ser Glu Gly
                405                 410                 415
```

```
Asp Asp Phe Glu Asp Lys Lys Asn Met Thr Gly Pro Met Lys Arg Gln
                420                 425                 430

Val Ala Val Lys Ser Thr Arg Gly Phe Ala Leu Lys Ser Thr His Gly
            435                 440                 445

Ile Ala Ile Lys Ser Thr Asn Met Ala Ser Val Asp Lys Gly Glu Ser
        450                 455                 460

Ala Pro Val Arg Lys Asn Thr Arg Gln Phe Tyr Asp Gly Glu Glu Ser
465                 470                 475                 480

Cys Tyr Ile Ile Asp Ala Lys Leu Glu Gly Asn Leu Gly Arg Tyr Leu
                485                 490                 495

Asn His Ser Cys Ser Pro Asn Leu Phe Val Gln Asn Val Phe Val Asp
            500                 505                 510

Thr His Asp Leu Arg Phe Pro Trp Val Ala Phe Phe Ala Ser Lys Arg
        515                 520                 525

Ile Arg Ala Gly Thr Glu Leu Thr Trp Asp Tyr Asn Tyr Glu Val Gly
530                 535                 540

Ser Val Glu Gly Lys Glu Leu Leu Cys Cys Cys Gly Ala Ile Glu Cys
545                 550                 555                 560

Arg Gly Arg Leu Leu
                565

<210> SEQ ID NO 14
<211> LENGTH: 826
<212> TYPE: PRT
<213> ORGANISM: Artificial Sequence
<220> FEATURE:
<223> OTHER INFORMATION: Transcription-activator like effector (TALE)
      domain

<400> SEQUENCE: 14

Met Gly Lys Pro Ile Pro Asn Pro Leu Leu Gly Leu Asp Ser Thr Gly
1               5                   10                  15

Gly Met Ala Pro Lys Lys Lys Arg Lys Val Asp Gly Gly Val Asp Leu
            20                  25                  30

Arg Thr Leu Gly Tyr Ser Gln Gln Gln Gln Glu Lys Ile Lys Pro Lys
        35                  40                  45

Val Arg Ser Thr Val Ala Gln His His Glu Ala Leu Val Gly His Gly
    50                  55                  60

Phe Thr His Ala His Ile Val Ala Leu Ser Gln His Pro Ala Ala Leu
65                  70                  75                  80

Gly Thr Val Ala Val Lys Tyr Gln Asp Met Ile Ala Ala Leu Pro Glu
                85                  90                  95

Ala Thr His Glu Ala Ile Val Gly Val Gly Lys Gln Trp Ser Gly Ala
            100                 105                 110

Arg Ala Leu Glu Ala Leu Leu Thr Val Ala Gly Glu Leu Arg Gly Pro
        115                 120                 125

Pro Leu Gln Leu Asp Thr Gly Gln Leu Leu Lys Ile Ala Lys Arg Gly
    130                 135                 140

Gly Val Thr Ala Val Glu Ala Val His Ala Trp Arg Asn Ala Leu Thr
145                 150                 155                 160

Gly Ala Pro Leu Asn Leu Thr Pro Glu Gln Val Val Ala Ile Ala Ser
                165                 170                 175

Asn Ile Gly Gly Lys Gln Ala Leu Glu Thr Val Gln Arg Leu Leu Pro
            180                 185                 190

Val Leu Cys Gln Ala His Gly Leu Thr Pro Glu Gln Val Val Ala Ile
```

-continued

```
                195                 200                 205
Ala Ser His Asp Gly Gly Lys Gln Ala Leu Glu Thr Val Gln Arg Leu
210                 215                 220

Leu Pro Val Leu Cys Gln Ala His Gly Leu Thr Pro Glu Gln Val Val
225                 230                 235                 240

Ala Ile Ala Ser His Asp Gly Gly Lys Gln Ala Leu Glu Thr Val Gln
                245                 250                 255

Arg Leu Leu Pro Val Leu Cys Gln Ala His Gly Leu Thr Pro Glu Gln
                260                 265                 270

Val Val Ala Ile Ala Ser His Asp Gly Gly Lys Gln Ala Leu Glu Thr
            275                 280                 285

Val Gln Arg Leu Leu Pro Val Leu Cys Gln Ala His Gly Leu Thr Pro
            290                 295                 300

Glu Gln Val Val Ala Ile Ala Ser Asn Ile Gly Gly Lys Gln Ala Leu
305                 310                 315                 320

Glu Thr Val Gln Arg Leu Leu Pro Val Leu Cys Gln Ala His Gly Leu
                325                 330                 335

Thr Pro Glu Gln Val Val Ala Ile Ala Ser Asn Asn Gly Gly Lys Gln
                340                 345                 350

Ala Leu Glu Thr Val Gln Arg Leu Leu Pro Val Leu Cys Gln Ala His
            355                 360                 365

Gly Leu Thr Pro Glu Gln Val Val Ala Ile Ala Ser Asn Ile Gly Gly
            370                 375                 380

Lys Gln Ala Leu Glu Thr Val Gln Arg Leu Leu Pro Val Leu Cys Gln
385                 390                 395                 400

Ala His Gly Leu Thr Pro Glu Gln Val Val Ala Ile Ala Ser Asn Gly
                405                 410                 415

Gly Gly Lys Gln Ala Leu Glu Thr Val Gln Arg Leu Leu Pro Val Leu
                420                 425                 430

Cys Gln Ala His Gly Leu Thr Pro Glu Gln Val Val Ala Ile Ala Ser
            435                 440                 445

Asn Gly Gly Gly Lys Gln Ala Leu Glu Thr Val Gln Arg Leu Leu Pro
450                 455                 460

Val Leu Cys Gln Ala His Gly Leu Thr Pro Glu Gln Val Val Ala Ile
465                 470                 475                 480

Ala Ser Asn Asn Gly Gly Lys Gln Ala Leu Glu Thr Val Gln Arg Leu
                485                 490                 495

Leu Pro Val Leu Cys Gln Ala His Gly Leu Thr Pro Glu Gln Val Val
                500                 505                 510

Ala Ile Ala Ser Asn Asn Gly Gly Lys Gln Ala Leu Glu Thr Val Gln
            515                 520                 525

Arg Leu Leu Pro Val Leu Cys Gln Ala His Gly Leu Thr Pro Glu Gln
            530                 535                 540

Val Val Ala Ile Ala Ser His Asp Gly Gly Lys Gln Ala Leu Glu Thr
545                 550                 555                 560

Val Gln Arg Leu Leu Pro Val Leu Cys Gln Ala His Gly Leu Thr Pro
                565                 570                 575

Glu Gln Val Val Ala Ile Ala Ser His Asp Gly Gly Lys Gln Ala Leu
                580                 585                 590

Glu Thr Val Gln Arg Leu Leu Pro Val Leu Cys Gln Ala His Gly Leu
            595                 600                 605

Thr Pro Glu Gln Val Val Ala Ile Ala Ser His Asp Gly Gly Lys Gln
            610                 615                 620
```

```
Ala Leu Glu Thr Val Gln Arg Leu Leu Pro Val Leu Cys Gln Ala His
625                 630                 635                 640

Gly Leu Thr Pro Glu Gln Val Val Ala Ile Ala Ser His Asp Gly Gly
            645                 650                 655

Lys Gln Ala Leu Glu Thr Val Gln Arg Leu Leu Pro Val Leu Cys Gln
        660                 665                 670

Ala His Gly Leu Thr Pro Glu Gln Val Val Ala Ile Ala Ser Asn Ile
    675                 680                 685

Gly Gly Lys Gln Ala Leu Glu Thr Val Gln Arg Leu Leu Pro Val Leu
690                 695                 700

Cys Gln Ala His Gly Leu Thr Pro Glu Gln Val Val Ala Ile Ala Ser
705                 710                 715                 720

His Asp Gly Gly Lys Gln Ala Leu Glu Thr Val Gln Arg Leu Leu Pro
                725                 730                 735

Val Leu Cys Gln Ala His Gly Leu Thr Pro Gln Gln Val Val Ala Ile
            740                 745                 750

Ala Ser Asn Gly Gly Gly Arg Pro Ala Leu Glu Ser Ile Val Ala Gln
        755                 760                 765

Leu Ser Arg Pro Asp Pro Ala Leu Ala Ala Leu Thr Asn Asp His Leu
    770                 775                 780

Val Ala Leu Ala Cys Leu Gly Gly Arg Pro Ala Leu Asp Ala Val Lys
785                 790                 795                 800

Lys Gly Leu Pro His Ala Pro Ala Leu Ile Lys Arg Thr Asn Arg Arg
                805                 810                 815

Ile Pro Glu Arg Thr Ser His Arg Val Ala
            820                 825

<210> SEQ ID NO 15
<211> LENGTH: 826
<212> TYPE: PRT
<213> ORGANISM: Artificial Sequence
<220> FEATURE:
<223> OTHER INFORMATION: TALE domain

<400> SEQUENCE: 15

Met Gly Lys Pro Ile Pro Asn Pro Leu Leu Gly Leu Asp Ser Thr Gly
1               5                   10                  15

Gly Met Ala Pro Lys Lys Lys Arg Lys Val Asp Gly Gly Val Asp Leu
            20                  25                  30

Arg Thr Leu Gly Tyr Ser Gln Gln Gln Gln Glu Lys Ile Lys Pro Lys
        35                  40                  45

Val Arg Ser Thr Val Ala Gln His His Glu Ala Leu Val Gly His Gly
    50                  55                  60

Phe Thr His Ala His Ile Val Ala Leu Ser Gln His Pro Ala Ala Leu
65                  70                  75                  80

Gly Thr Val Ala Val Lys Tyr Gln Asp Met Ile Ala Ala Leu Pro Glu
                85                  90                  95

Ala Thr His Glu Ala Ile Val Gly Val Gly Lys Gln Trp Ser Gly Ala
            100                 105                 110

Arg Ala Leu Glu Ala Leu Leu Thr Val Ala Gly Glu Leu Arg Gly Pro
        115                 120                 125

Pro Leu Gln Leu Asp Thr Gly Gln Leu Leu Lys Ile Ala Lys Arg Gly
    130                 135                 140

Gly Val Thr Ala Val Glu Ala Val His Ala Trp Arg Asn Ala Leu Thr
145                 150                 155                 160
```

-continued

```
Gly Ala Pro Leu Asn Leu Thr Pro Glu Gln Val Val Ala Ile Ala Ser
            165                 170                 175

Asn Ile Gly Gly Lys Gln Ala Leu Glu Thr Val Gln Arg Leu Leu Pro
            180                 185                 190

Val Leu Cys Gln Ala His Gly Leu Thr Pro Glu Gln Val Val Ala Ile
            195                 200                 205

Ala Ser His Asp Gly Gly Lys Gln Ala Leu Glu Thr Val Gln Arg Leu
            210                 215                 220

Leu Pro Val Leu Cys Gln Ala His Gly Leu Thr Pro Glu Gln Val Val
225                 230                 235                 240

Ala Ile Ala Ser His Asp Gly Gly Lys Gln Ala Leu Glu Thr Val Gln
            245                 250                 255

Arg Leu Leu Pro Val Leu Cys Gln Ala His Gly Leu Thr Pro Glu Gln
            260                 265                 270

Val Val Ala Ile Ala Ser Asn Gly Gly Lys Gln Ala Leu Glu Thr
            275                 280                 285

Val Gln Arg Leu Leu Pro Val Leu Cys Gln Ala His Gly Leu Thr Pro
            290                 295                 300

Glu Gln Val Val Ala Ile Ala Ser Asn Ile Gly Gly Lys Gln Ala Leu
305                 310                 315                 320

Glu Thr Val Gln Arg Leu Leu Pro Val Leu Cys Gln Ala His Gly Leu
            325                 330                 335

Thr Pro Glu Gln Val Val Ala Ile Ala Ser Asn Asn Gly Gly Lys Gln
            340                 345                 350

Ala Leu Glu Thr Val Gln Arg Leu Leu Pro Val Leu Cys Gln Ala His
            355                 360                 365

Gly Leu Thr Pro Glu Gln Val Val Ala Ile Ala Ser Asn Ile Gly Gly
            370                 375                 380

Lys Gln Ala Leu Glu Thr Val Gln Arg Leu Leu Pro Val Leu Cys Gln
385                 390                 395                 400

Ala His Gly Leu Thr Pro Glu Gln Val Val Ala Ile Ala Ser Asn Asn
            405                 410                 415

Gly Gly Lys Gln Ala Leu Glu Thr Val Gln Arg Leu Leu Pro Val Leu
            420                 425                 430

Cys Gln Ala His Gly Leu Thr Pro Glu Gln Val Val Ala Ile Ala Ser
            435                 440                 445

Asn Asn Gly Gly Lys Gln Ala Leu Glu Thr Val Gln Arg Leu Leu Pro
450                 455                 460

Val Leu Cys Gln Ala His Gly Leu Thr Pro Glu Gln Val Val Ala Ile
465                 470                 475                 480

Ala Ser Asn Ile Gly Gly Lys Gln Ala Leu Glu Thr Val Gln Arg Leu
            485                 490                 495

Leu Pro Val Leu Cys Gln Ala His Gly Leu Thr Pro Glu Gln Val Val
            500                 505                 510

Ala Ile Ala Ser Asn Asn Gly Gly Lys Gln Ala Leu Glu Thr Val Gln
            515                 520                 525

Arg Leu Leu Pro Val Leu Cys Gln Ala His Gly Leu Thr Pro Glu Gln
            530                 535                 540

Val Val Ala Ile Ala Ser Asn Ile Gly Gly Lys Gln Ala Leu Glu Thr
545                 550                 555                 560

Val Gln Arg Leu Leu Pro Val Leu Cys Gln Ala His Gly Leu Thr Pro
            565                 570                 575
```

Glu Gln Val Val Ala Ile Ala Ser Asn Ile Gly Gly Lys Gln Ala Leu
            580                 585                 590

Glu Thr Val Gln Arg Leu Leu Pro Val Leu Cys Gln Ala His Gly Leu
        595                 600                 605

Thr Pro Glu Gln Val Val Ala Ile Ala Ser Asn Ile Gly Gly Lys Gln
610                 615                 620

Ala Leu Glu Thr Val Gln Arg Leu Leu Pro Val Leu Cys Gln Ala His
625                 630                 635                 640

Gly Leu Thr Pro Glu Gln Val Val Ala Ile Ala Ser Asn Asn Gly Gly
                645                 650                 655

Lys Gln Ala Leu Glu Thr Val Gln Arg Leu Leu Pro Val Leu Cys Gln
            660                 665                 670

Ala His Gly Leu Thr Pro Glu Gln Val Val Ala Ile Ala Ser Asn Asn
        675                 680                 685

Gly Gly Lys Gln Ala Leu Glu Thr Val Gln Arg Leu Leu Pro Val Leu
690                 695                 700

Cys Gln Ala His Gly Leu Thr Pro Glu Gln Val Val Ala Ile Ala Ser
705                 710                 715                 720

Asn Gly Gly Gly Lys Gln Ala Leu Glu Thr Val Gln Arg Leu Leu Pro
                725                 730                 735

Val Leu Cys Gln Ala His Gly Leu Thr Pro Gln Gln Val Val Ala Ile
            740                 745                 750

Ala Ser Asn Gly Gly Gly Arg Pro Ala Leu Glu Ser Ile Val Ala Gln
        755                 760                 765

Leu Ser Arg Pro Asp Pro Ala Leu Ala Ala Leu Thr Asn Asp His Leu
770                 775                 780

Val Ala Leu Ala Cys Leu Gly Gly Arg Pro Ala Leu Asp Ala Val Lys
785                 790                 795                 800

Lys Gly Leu Pro His Ala Pro Ala Leu Ile Lys Arg Thr Asn Arg Arg
                805                 810                 815

Ile Pro Glu Arg Thr Ser His Arg Val Ala
            820                 825

<210> SEQ ID NO 16
<211> LENGTH: 831
<212> TYPE: PRT
<213> ORGANISM: Artificial Sequence
<220> FEATURE:
<223> OTHER INFORMATION: TALE domain

<400> SEQUENCE: 16

Met Gly Lys Pro Ile Pro Asn Pro Leu Leu Gly Leu Asp Ser Thr Gly
1               5                   10                  15

Gly Met Ala Pro Lys Lys Lys Arg Lys Val Asp Gly Gly Val Asp Leu
            20                  25                  30

Arg Thr Leu Gly Tyr Ser Gln Gln Gln Gln Glu Lys Ile Lys Pro Lys
        35                  40                  45

Val Arg Ser Thr Val Ala Gln His His Glu Ala Leu Val Gly His Gly
50                  55                  60

Phe Thr His Ala His Ile Val Ala Leu Ser Gln His Pro Ala Ala Leu
65                  70                  75                  80

Gly Thr Val Ala Val Lys Tyr Gln Asp Met Ile Ala Ala Leu Pro Glu
                85                  90                  95

Ala Thr His Glu Ala Ile Val Gly Val Gly Lys Gln Trp Ser Gly Ala
            100                 105                 110

```
Arg Ala Leu Glu Ala Leu Leu Thr Val Ala Gly Glu Leu Arg Gly Pro
            115                 120                 125
Pro Leu Gln Leu Asp Thr Gly Gln Leu Lys Ile Ala Lys Arg Gly
130                 135                 140
Gly Val Thr Ala Val Glu Ala Val His Ala Trp Arg Asn Ala Leu Thr
145                 150                 155                 160
Gly Ala Pro Leu Asn Leu Thr Pro Asp Gln Val Ala Ile Ala Ser
                165                 170                 175
His Asp Gly Gly Lys Gln Ala Leu Glu Thr Val Gln Arg Leu Leu Pro
                180                 185                 190
Val Leu Cys Gln Asp His Gly Leu Thr Pro Asp Gln Val Val Ala Ile
                195                 200                 205
Ala Ser Asn Gly Gly Gly Lys Gln Ala Leu Glu Thr Val Gln Arg Leu
210                 215                 220
Leu Pro Val Leu Cys Gln Asp His Gly Leu Thr Pro Asp Gln Val Val
225                 230                 235                 240
Ala Ile Ala Ser His Asp Gly Gly Lys Gln Ala Leu Glu Thr Val Gln
                245                 250                 255
Arg Leu Leu Pro Val Leu Cys Gln Asp His Gly Leu Thr Pro Asp Gln
                260                 265                 270
Val Val Ala Ile Ala Ser Asn Gly Gly Gly Lys Gln Ala Leu Glu Thr
                275                 280                 285
Val Gln Arg Leu Leu Pro Val Leu Cys Gln Asp His Gly Leu Thr Pro
290                 295                 300
Asp Gln Val Val Ala Ile Ala Ser His Asp Gly Gly Lys Gln Ala Leu
305                 310                 315                 320
Glu Thr Val Gln Arg Leu Leu Pro Val Leu Cys Gln Asp His Gly Leu
                325                 330                 335
Thr Pro Asp Gln Val Val Ala Ile Ala Ser His Asp Gly Gly Lys Gln
                340                 345                 350
Ala Leu Glu Thr Val Gln Arg Leu Leu Pro Val Leu Cys Gln Asp His
                355                 360                 365
Gly Leu Thr Pro Asp Gln Val Val Ala Ile Ala Ser Asn Gly Gly Gly
370                 375                 380
Lys Gln Ala Leu Glu Thr Val Gln Arg Leu Leu Pro Val Leu Cys Gln
385                 390                 395                 400
Asp His Gly Leu Thr Pro Asp Gln Val Val Ala Ile Ala Ser Asn Ile
                405                 410                 415
Gly Gly Lys Gln Ala Leu Glu Thr Val Gln Arg Leu Leu Pro Val Leu
                420                 425                 430
Cys Gln Asp His Gly Leu Thr Pro Asp Gln Val Val Ala Ile Ala Ser
                435                 440                 445
His Asp Gly Gly Lys Gln Ala Leu Glu Thr Val Gln Arg Leu Leu Pro
450                 455                 460
Val Leu Cys Gln Asp His Gly Leu Thr Pro Asp Gln Val Val Ala Ile
465                 470                 475                 480
Ala Ser His Asp Gly Gly Lys Gln Ala Leu Glu Thr Val Gln Arg Leu
                485                 490                 495
Leu Pro Val Leu Cys Gln Asp His Gly Leu Thr Pro Asp Gln Val Val
                500                 505                 510
Ala Ile Ala Ser His Asp Gly Gly Lys Gln Ala Leu Glu Thr Val Gln
                515                 520                 525
Arg Leu Leu Pro Val Leu Cys Gln Asp His Gly Leu Thr Pro Asp Gln
```

```
Val Val Ala Ile Ala Ser Asn Gly Gly Lys Gln Ala Leu Glu Thr
545                 550                 555                 560

Val Gln Arg Leu Leu Pro Val Leu Cys Gln Asp His Gly Leu Thr Pro
            565                 570                 575

Asp Gln Val Val Ala Ile Ala Ser His Asp Gly Gly Lys Gln Ala Leu
        580                 585                 590

Glu Thr Val Gln Arg Leu Leu Pro Val Leu Cys Gln Asp His Gly Leu
    595                 600                 605

Thr Pro Asp Gln Val Val Ala Ile Ala Ser His Asp Gly Gly Lys Gln
610                 615                 620

Ala Leu Glu Thr Val Gln Arg Leu Leu Pro Val Leu Cys Gln Asp His
625                 630                 635                 640

Gly Leu Thr Pro Asp Gln Val Val Ala Ile Ala Ser His Asp Gly Gly
            645                 650                 655

Lys Gln Ala Leu Glu Thr Val Gln Arg Leu Leu Pro Val Leu Cys Gln
        660                 665                 670

Asp His Gly Leu Thr Pro Asp Gln Val Val Ala Ile Ala Ser Asn His
    675                 680                 685

Gly Gly Lys Gln Ala Leu Glu Thr Val Gln Arg Leu Leu Pro Val Leu
690                 695                 700

Cys Gln Asp His Gly Leu Thr Pro Asp Gln Val Val Ala Ile Ala Ser
705                 710                 715                 720

His Asp Gly Gly Lys Gln Ala Leu Glu Thr Val Gln Arg Leu Leu Pro
            725                 730                 735

Val Leu Cys Gln Asp His Gly Leu Thr Pro Asp Gln Val Val Ala Ile
        740                 745                 750

Ala Ser Asn Gly Gly Lys Gln Ala Leu Glu Ser Ile Val Ala Gln
    755                 760                 765

Leu Ser Arg Pro Asp Pro Ala Leu Ala Ala Leu Thr Asn Asp His Leu
770                 775                 780

Val Ala Leu Ala Cys Leu Gly Gly Arg Pro Ala Leu Asp Ala Val Lys
785                 790                 795                 800

Lys Gly Leu Pro His Ala Pro Ala Leu Ile Lys Arg Thr Asn Arg Arg
            805                 810                 815

Ile Pro Glu Arg Thr Ser His Arg Val Ala Gly Ser Gly Gly Gly
        820                 825                 830
```

<210> SEQ ID NO 17
<211> LENGTH: 19
<212> TYPE: DNA
<213> ORGANISM: Artificial Sequence
<220> FEATURE:
<223> OTHER INFORMATION: Binding site

<400> SEQUENCE: 17
tctctcctac cctcccgct                                           19

<210> SEQ ID NO 18
<211> LENGTH: 831
<212> TYPE: PRT
<213> ORGANISM: Artificial Sequence
<220> FEATURE:
<223> OTHER INFORMATION: TALE domain

<400> SEQUENCE: 18

Met Gly Lys Pro Ile Pro Asn Pro Leu Leu Gly Leu Asp Ser Thr Gly

-continued

```
1               5                   10                  15
Gly Met Ala Pro Lys Lys Arg Lys Val Asp Gly Val Asp Leu
                20                  25                  30
Arg Thr Leu Gly Tyr Ser Gln Gln Gln Glu Lys Ile Lys Pro Lys
                35                  40                  45
Val Arg Ser Thr Val Ala Gln His His Glu Ala Leu Val Gly His Gly
         50                  55                  60
Phe Thr His Ala His Ile Val Ala Leu Ser Gln His Pro Ala Ala Leu
 65                  70                  75                  80
Gly Thr Val Ala Val Lys Tyr Gln Asp Met Ile Ala Ala Leu Pro Glu
                85                  90                  95
Ala Thr His Glu Ala Ile Val Gly Val Gly Lys Gln Trp Ser Gly Ala
                100                 105                 110
Arg Ala Leu Glu Ala Leu Leu Thr Val Ala Gly Glu Leu Arg Gly Pro
                115                 120                 125
Pro Leu Gln Leu Asp Thr Gly Gln Leu Leu Lys Ile Ala Lys Arg Gly
                130                 135                 140
Gly Val Thr Ala Val Glu Ala Val His Ala Trp Arg Asn Ala Leu Thr
145                 150                 155                 160
Gly Ala Pro Leu Asn Leu Thr Pro Asp Gln Val Val Ala Ile Ala Ser
                165                 170                 175
Asn Asn Gly Gly Lys Gln Ala Leu Glu Thr Val Gln Arg Leu Leu Pro
                180                 185                 190
Val Leu Cys Gln Asp His Gly Leu Thr Pro Asp Gln Val Val Ala Ile
                195                 200                 205
Ala Ser Asn Asn Gly Gly Lys Gln Ala Leu Glu Thr Val Gln Arg Leu
210                 215                 220
Leu Pro Val Leu Cys Gln Asp His Gly Leu Thr Pro Asp Gln Val Val
225                 230                 235                 240
Ala Ile Ala Ser Asn Gly Gly Lys Gln Ala Leu Glu Thr Val Gln
                245                 250                 255
Arg Leu Leu Pro Val Leu Cys Gln Asp His Gly Leu Thr Pro Asp Gln
                260                 265                 270
Val Val Ala Ile Ala Ser His Asp Gly Gly Lys Gln Ala Leu Glu Thr
                275                 280                 285
Val Gln Arg Leu Leu Pro Val Leu Cys Gln Asp His Gly Leu Thr Pro
                290                 295                 300
Asp Gln Val Val Ala Ile Ala Ser His Asp Gly Gly Lys Gln Ala Leu
305                 310                 315                 320
Glu Thr Val Gln Arg Leu Leu Pro Val Leu Cys Gln Asp His Gly Leu
                325                 330                 335
Thr Pro Asp Gln Val Val Ala Ile Ala Ser Asn Gly Gly Lys Gln
                340                 345                 350
Ala Leu Glu Thr Val Gln Arg Leu Leu Pro Val Leu Cys Gln Asp His
                355                 360                 365
Gly Leu Thr Pro Asp Gln Val Val Ala Ile Ala Ser Asn Gly Gly Gly
                370                 375                 380
Lys Gln Ala Leu Glu Thr Val Gln Arg Leu Leu Pro Val Leu Cys Gln
385                 390                 395                 400
Asp His Gly Leu Thr Pro Asp Gln Val Val Ala Ile Ala Ser His Asp
                405                 410                 415
Gly Gly Lys Gln Ala Leu Glu Thr Val Gln Arg Leu Leu Pro Val Leu
                420                 425                 430
```

```
Cys Gln Asp His Gly Leu Thr Pro Asp Gln Val Val Ala Ile Ala Ser
        435                 440                 445
His Asp Gly Gly Lys Gln Ala Leu Glu Thr Val Gln Arg Leu Leu Pro
    450                 455                 460
Val Leu Cys Gln Asp His Gly Leu Thr Pro Asp Gln Val Val Ala Ile
465                 470                 475                 480
Ala Ser Asn Gly Gly Lys Gln Ala Leu Glu Thr Val Gln Arg Leu
                485                 490                 495
Leu Pro Val Leu Cys Gln Asp His Gly Leu Thr Pro Asp Gln Val Val
            500                 505                 510
Ala Ile Ala Ser His Asp Gly Gly Lys Gln Ala Leu Glu Thr Val Gln
        515                 520                 525
Arg Leu Leu Pro Val Leu Cys Gln Asp His Gly Leu Thr Pro Asp Gln
    530                 535                 540
Val Val Ala Ile Ala Ser Asn Gly Gly Lys Gln Ala Leu Glu Thr
545                 550                 555                 560
Val Gln Arg Leu Leu Pro Val Leu Cys Gln Asp His Gly Leu Thr Pro
                565                 570                 575
Asp Gln Val Val Ala Ile Ala Ser His Asp Gly Gly Lys Gln Ala Leu
            580                 585                 590
Glu Thr Val Gln Arg Leu Leu Pro Val Leu Cys Gln Asp His Gly Leu
        595                 600                 605
Thr Pro Asp Gln Val Val Ala Ile Ala Ser His Asp Gly Gly Lys Gln
    610                 615                 620
Ala Leu Glu Thr Val Gln Arg Leu Leu Pro Val Leu Cys Gln Asp His
625                 630                 635                 640
Gly Leu Thr Pro Asp Gln Val Val Ala Ile Ala Ser His Asp Gly Gly
                645                 650                 655
Lys Gln Ala Leu Glu Thr Val Gln Arg Leu Leu Pro Val Leu Cys Gln
            660                 665                 670
Asp His Gly Leu Thr Pro Asp Gln Val Val Ala Ile Ala Ser Asn Gly
        675                 680                 685
Gly Gly Lys Gln Ala Leu Glu Thr Val Gln Arg Leu Leu Pro Val Leu
    690                 695                 700
Cys Gln Asp His Gly Leu Thr Pro Asp Gln Val Val Ala Ile Ala Ser
705                 710                 715                 720
His Asp Gly Gly Lys Gln Ala Leu Glu Thr Val Gln Arg Leu Leu Pro
                725                 730                 735
Val Leu Cys Gln Asp His Gly Leu Thr Pro Asp Gln Val Val Ala Ile
            740                 745                 750
Ala Ser Asn Gly Gly Lys Gln Ala Leu Glu Ser Ile Val Ala Gln
        755                 760                 765
Leu Ser Arg Pro Asp Pro Ala Leu Ala Ala Leu Thr Asn Asp His Leu
    770                 775                 780
Val Ala Leu Ala Cys Leu Gly Gly Arg Pro Ala Leu Asp Ala Val Lys
785                 790                 795                 800
Lys Gly Leu Pro His Ala Pro Ala Leu Ile Lys Arg Thr Asn Arg Arg
                805                 810                 815
Ile Pro Glu Arg Thr Ser His Arg Val Ala Gly Ser Gly Gly Gly
            820                 825                 830

<210> SEQ ID NO 19
<211> LENGTH: 19
```

```
<212> TYPE: DNA
<213> ORGANISM: Artificial Sequence
<220> FEATURE:
<223> OTHER INFORMATION: Binding site

<400> SEQUENCE: 19
tggtccttcc tctcccgct                                                    19

<210> SEQ ID NO 20
<211> LENGTH: 831
<212> TYPE: PRT
<213> ORGANISM: Artificial Sequence
<220> FEATURE:
<223> OTHER INFORMATION: TALE domain

<400> SEQUENCE: 20
```

| | | | | | | | | | | | | | | |
|---|---|---|---|---|---|---|---|---|---|---|---|---|---|---|
| Met | Gly | Lys | Pro | Ile | Pro | Asn | Pro | Leu | Leu | Gly | Leu | Asp | Ser | Thr | Gly |
| 1 | | | | 5 | | | | | 10 | | | | | 15 | |
| Gly | Met | Ala | Pro | Lys | Lys | Lys | Arg | Lys | Val | Asp | Gly | Gly | Val | Asp | Leu |
| | | | 20 | | | | | 25 | | | | | 30 | | |
| Arg | Thr | Leu | Gly | Tyr | Ser | Gln | Gln | Gln | Gln | Glu | Lys | Ile | Lys | Pro | Lys |
| | | 35 | | | | | 40 | | | | | 45 | | | |
| Val | Arg | Ser | Thr | Val | Ala | Gln | His | His | Glu | Ala | Leu | Val | Gly | His | Gly |
| 50 | | | | | 55 | | | | | 60 | | | | | |
| Phe | Thr | His | Ala | His | Ile | Val | Ala | Leu | Ser | Gln | His | Pro | Ala | Ala | Leu |
| 65 | | | | | 70 | | | | | 75 | | | | | 80 |
| Gly | Thr | Val | Ala | Val | Lys | Tyr | Gln | Asp | Met | Ile | Ala | Ala | Leu | Pro | Glu |
| | | | | 85 | | | | | 90 | | | | | 95 | |
| Ala | Thr | His | Glu | Ala | Ile | Val | Gly | Val | Gly | Lys | Gln | Trp | Ser | Gly | Ala |
| | | | 100 | | | | | 105 | | | | | 110 | | |
| Arg | Ala | Leu | Glu | Ala | Leu | Leu | Thr | Val | Ala | Gly | Glu | Leu | Arg | Gly | Pro |
| | | 115 | | | | | 120 | | | | | 125 | | | |
| Pro | Leu | Gln | Leu | Asp | Thr | Gly | Gln | Leu | Leu | Lys | Ile | Ala | Lys | Arg | Gly |
| 130 | | | | | 135 | | | | | 140 | | | | | |
| Gly | Val | Thr | Ala | Val | Glu | Ala | Val | His | Ala | Trp | Arg | Asn | Ala | Leu | Thr |
| 145 | | | | | 150 | | | | | 155 | | | | | 160 |
| Gly | Ala | Pro | Leu | Asn | Leu | Thr | Pro | Asp | Gln | Val | Val | Ala | Ile | Ala | Ser |
| | | | | 165 | | | | | 170 | | | | | 175 | |
| His | Asp | Gly | Gly | Lys | Gln | Ala | Leu | Glu | Thr | Val | Gln | Arg | Leu | Leu | Pro |
| | | | 180 | | | | | 185 | | | | | 190 | | |
| Val | Leu | Cys | Gln | Asp | His | Gly | Leu | Thr | Pro | Asp | Gln | Val | Val | Ala | Ile |
| | | 195 | | | | | 200 | | | | | 205 | | | |
| Ala | Ser | Asn | Asn | Gly | Gly | Lys | Gln | Ala | Leu | Glu | Thr | Val | Gln | Arg | Leu |
| 210 | | | | | 215 | | | | | 220 | | | | | |
| Leu | Pro | Val | Leu | Cys | Gln | Asp | His | Gly | Leu | Thr | Pro | Asp | Gln | Val | Val |
| 225 | | | | | 230 | | | | | 235 | | | | | 240 |
| Ala | Ile | Ala | Ser | His | Asp | Gly | Gly | Lys | Gln | Ala | Leu | Glu | Thr | Val | Gln |
| | | | | 245 | | | | | 250 | | | | | 255 | |
| Arg | Leu | Leu | Pro | Val | Leu | Cys | Gln | Asp | His | Gly | Leu | Thr | Pro | Asp | Gln |
| | | | 260 | | | | | 265 | | | | | 270 | | |
| Val | Val | Ala | Ile | Ala | Ser | Asn | Gly | Gly | Lys | Gln | Ala | Leu | Glu | Thr |
| | | 275 | | | | | 280 | | | | | 285 | | | |
| Val | Gln | Arg | Leu | Leu | Pro | Val | Leu | Cys | Gln | Asp | His | Gly | Leu | Thr | Pro |
| | | 290 | | | | | 295 | | | | | 300 | | | |
| Asp | Gln | Val | Val | Ala | Ile | Ala | Ser | His | Asp | Gly | Gly | Lys | Gln | Ala | Leu |
| 305 | | | | | 310 | | | | | 315 | | | | | 320 |

-continued

```
Glu Thr Val Gln Arg Leu Leu Pro Val Leu Cys Gln Asp His Gly Leu
            325                 330                 335

Thr Pro Asp Gln Val Val Ala Ile Ala Ser His Asp Gly Gly Lys Gln
            340                 345                 350

Ala Leu Glu Thr Val Gln Arg Leu Leu Pro Val Leu Cys Gln Asp His
            355                 360                 365

Gly Leu Thr Pro Asp Gln Val Val Ala Ile Ala Ser Asn Asn Gly Gly
            370                 375                 380

Lys Gln Ala Leu Glu Thr Val Gln Arg Leu Leu Pro Val Leu Cys Gln
385                 390                 395                 400

Asp His Gly Leu Thr Pro Asp Gln Val Val Ala Ile Ala Ser Asn Gly
            405                 410                 415

Gly Gly Lys Gln Ala Leu Glu Thr Val Gln Arg Leu Leu Pro Val Leu
            420                 425                 430

Cys Gln Asp His Gly Leu Thr Pro Asp Gln Val Val Ala Ile Ala Ser
            435                 440                 445

Asn Asn Gly Gly Lys Gln Ala Leu Glu Thr Val Gln Arg Leu Leu Pro
            450                 455                 460

Val Leu Cys Gln Asp His Gly Leu Thr Pro Asp Gln Val Val Ala Ile
465                 470                 475                 480

Ala Ser Asn Ile Gly Gly Lys Gln Ala Leu Glu Thr Val Gln Arg Leu
            485                 490                 495

Leu Pro Val Leu Cys Gln Asp His Gly Leu Thr Pro Asp Gln Val Val
            500                 505                 510

Ala Ile Ala Ser His Asp Gly Gly Lys Gln Ala Leu Glu Thr Val Gln
            515                 520                 525

Arg Leu Leu Pro Val Leu Cys Gln Asp His Gly Leu Thr Pro Asp Gln
            530                 535                 540

Val Val Ala Ile Ala Ser Asn Gly Gly Gly Lys Gln Ala Leu Glu Thr
545                 550                 555                 560

Val Gln Arg Leu Leu Pro Val Leu Cys Gln Asp His Gly Leu Thr Pro
            565                 570                 575

Asp Gln Val Val Ala Ile Ala Ser Asn Gly Gly Gly Lys Gln Ala Leu
            580                 585                 590

Glu Thr Val Gln Arg Leu Leu Pro Val Leu Cys Gln Asp His Gly Leu
            595                 600                 605

Thr Pro Asp Gln Val Val Ala Ile Ala Ser His Asp Gly Gly Lys Gln
            610                 615                 620

Ala Leu Glu Thr Val Gln Arg Leu Leu Pro Val Leu Cys Gln Asp His
625                 630                 635                 640

Gly Leu Thr Pro Asp Gln Val Val Ala Ile Ala Ser His Asp Gly Gly
            645                 650                 655

Lys Gln Ala Leu Glu Thr Val Gln Arg Leu Leu Pro Val Leu Cys Gln
            660                 665                 670

Asp His Gly Leu Thr Pro Asp Gln Val Val Ala Ile Ala Ser His Asp
            675                 680                 685

Gly Gly Lys Gln Ala Leu Glu Thr Val Gln Arg Leu Leu Pro Val Leu
            690                 695                 700

Cys Gln Asp His Gly Leu Thr Pro Asp Gln Val Val Ala Ile Ala Ser
705                 710                 715                 720

Asn Gly Gly Gly Lys Gln Ala Leu Glu Thr Val Gln Arg Leu Leu Pro
            725                 730                 735

Val Leu Cys Gln Asp His Gly Leu Thr Pro Asp Gln Val Val Ala Ile
```

```
                    740                 745                 750
Ala Ser Asn Gly Gly Lys Gln Ala Leu Glu Ser Ile Val Ala Gln
        755                 760                 765

Leu Ser Arg Pro Asp Pro Ala Leu Ala Leu Thr Asn Asp His Leu
    770                 775                 780

Val Ala Leu Ala Cys Leu Gly Gly Arg Pro Ala Leu Asp Ala Val Lys
785                 790                 795                 800

Lys Gly Leu Pro His Ala Pro Ala Leu Ile Lys Arg Thr Asn Arg Arg
                805                 810                 815

Ile Pro Glu Arg Thr Ser His Arg Val Ala Gly Ser Gly Gly Gly
        820                 825                 830

<210> SEQ ID NO 21
<211> LENGTH: 19
<212> TYPE: DNA
<213> ORGANISM: Artificial Sequence
<220> FEATURE:
<223> OTHER INFORMATION: Binding site

<400> SEQUENCE: 21
tcgctccgtg acttcccttt                                            19

<210> SEQ ID NO 22
<211> LENGTH: 1441
<212> TYPE: PRT
<213> ORGANISM: Artificial Sequence
<220> FEATURE:
<223> OTHER INFORMATION: Artificial transcription repressor (ATR)
      sequence, catalytically inactive Cas9

<400> SEQUENCE: 22

Met Gly Gly Arg Val Arg Trp Glu Val Tyr Ile Ser Arg Ala Leu
1               5                   10                  15

Trp Leu Thr Arg Glu Pro Thr Ala Tyr Trp Leu Ile Glu Ile Asn Thr
            20                  25                  30

Thr His Tyr Arg Glu Thr Gln Ala Thr Gly Ala Thr Met Tyr Pro Tyr
        35                  40                  45

Asp Val Pro Asp Tyr Ala Ser Pro Lys Lys Lys Arg Lys Val Glu Ala
    50                  55                  60

Ser Asp Lys Lys Tyr Ser Ile Gly Leu Ala Ile Gly Thr Asn Ser Val
65              70                  75                  80

Gly Trp Ala Val Ile Thr Asp Glu Tyr Lys Val Pro Ser Lys Lys Phe
                85                  90                  95

Lys Val Leu Gly Asn Thr Asp Arg His Ser Ile Lys Lys Asn Leu Ile
            100                 105                 110

Gly Ala Leu Leu Phe Asp Ser Gly Glu Thr Ala Glu Ala Thr Arg Leu
        115                 120                 125

Lys Arg Thr Ala Arg Arg Tyr Thr Arg Arg Lys Asn Arg Ile Cys
    130                 135                 140

Tyr Leu Gln Glu Ile Phe Ser Asn Glu Met Ala Lys Val Asp Asp Ser
145                 150                 155                 160

Phe Phe His Arg Leu Glu Glu Ser Phe Leu Val Glu Glu Asp Lys Lys
                165                 170                 175

His Glu Arg His Pro Ile Phe Gly Asn Ile Val Asp Glu Val Ala Tyr
            180                 185                 190

His Glu Lys Tyr Pro Thr Ile Tyr His Leu Arg Lys Lys Leu Val Asp
        195                 200                 205
```

Ser Thr Asp Lys Ala Asp Leu Arg Leu Ile Tyr Leu Ala Leu Ala His
210                 215                 220

Met Ile Lys Phe Arg Gly His Phe Leu Ile Glu Gly Asp Leu Asn Pro
225                 230                 235                 240

Asp Asn Ser Asp Val Asp Lys Leu Phe Ile Gln Leu Val Gln Thr Tyr
            245                 250                 255

Asn Gln Leu Phe Glu Glu Asn Pro Ile Asn Ala Ser Gly Val Asp Ala
            260                 265                 270

Lys Ala Ile Leu Ser Ala Arg Leu Ser Lys Ser Arg Arg Leu Glu Asn
            275                 280                 285

Leu Ile Ala Gln Leu Pro Gly Glu Lys Lys Asn Gly Leu Phe Gly Asn
290                 295                 300

Leu Ile Ala Leu Ser Leu Gly Leu Thr Pro Asn Phe Lys Ser Asn Phe
305                 310                 315                 320

Asp Leu Ala Glu Asp Ala Lys Leu Gln Leu Ser Lys Asp Thr Tyr Asp
            325                 330                 335

Asp Asp Leu Asp Asn Leu Leu Ala Gln Ile Gly Asp Gln Tyr Ala Asp
            340                 345                 350

Leu Phe Leu Ala Ala Lys Asn Leu Ser Asp Ala Ile Leu Leu Ser Asp
            355                 360                 365

Ile Leu Arg Val Asn Thr Glu Ile Thr Lys Ala Pro Leu Ser Ala Ser
370                 375                 380

Met Ile Lys Arg Tyr Asp Glu His His Gln Asp Leu Thr Leu Leu Lys
385                 390                 395                 400

Ala Leu Val Arg Gln Gln Leu Pro Glu Lys Tyr Lys Glu Ile Phe Phe
            405                 410                 415

Asp Gln Ser Lys Asn Gly Tyr Ala Gly Tyr Ile Asp Gly Gly Ala Ser
            420                 425                 430

Gln Glu Glu Phe Tyr Lys Phe Ile Lys Pro Ile Leu Glu Lys Met Asp
            435                 440                 445

Gly Thr Glu Glu Leu Leu Val Lys Leu Asn Arg Glu Asp Leu Leu Arg
450                 455                 460

Lys Gln Arg Thr Phe Asp Asn Gly Ser Ile Pro His Gln Ile His Leu
465                 470                 475                 480

Gly Glu Leu His Ala Ile Leu Arg Arg Gln Glu Asp Phe Tyr Pro Phe
            485                 490                 495

Leu Lys Asp Asn Arg Glu Lys Ile Glu Lys Ile Leu Thr Phe Arg Ile
            500                 505                 510

Pro Tyr Tyr Val Gly Pro Leu Ala Arg Gly Asn Ser Arg Phe Ala Trp
            515                 520                 525

Met Thr Arg Lys Ser Glu Glu Thr Ile Thr Pro Trp Asn Phe Glu Glu
530                 535                 540

Val Val Asp Lys Gly Ala Ser Ala Gln Ser Phe Ile Glu Arg Met Thr
545                 550                 555                 560

Asn Phe Asp Lys Asn Leu Pro Asn Glu Lys Val Leu Pro Lys His Ser
            565                 570                 575

Leu Leu Tyr Glu Tyr Phe Thr Val Tyr Asn Glu Leu Thr Lys Val Lys
            580                 585                 590

Tyr Val Thr Glu Gly Met Arg Lys Pro Ala Phe Leu Ser Gly Glu Gln
            595                 600                 605

Lys Lys Ala Ile Val Asp Leu Leu Phe Lys Thr Asn Arg Lys Val Thr
610                 615                 620

Val Lys Gln Leu Lys Glu Asp Tyr Phe Lys Lys Ile Glu Cys Phe Asp

```
                625                 630                 635                 640
Ser Val Glu Ile Ser Gly Val Glu Asp Arg Phe Asn Ala Ser Leu Gly
                        645                 650                 655

Thr Tyr His Asp Leu Leu Lys Ile Ile Lys Asp Lys Asp Phe Leu Asp
                        660                 665                 670

Asn Glu Glu Asn Glu Asp Ile Leu Glu Asp Ile Val Leu Thr Leu Thr
                        675                 680                 685

Leu Phe Glu Asp Arg Glu Met Ile Glu Glu Arg Leu Lys Thr Tyr Ala
            690                 695                 700

His Leu Phe Asp Asp Lys Val Met Lys Gln Leu Lys Arg Arg Arg Tyr
        705                 710                 715                 720

Thr Gly Trp Gly Arg Leu Ser Arg Lys Leu Ile Asn Gly Ile Arg Asp
                        725                 730                 735

Lys Gln Ser Gly Lys Thr Ile Leu Asp Phe Leu Lys Ser Asp Gly Phe
                    740                 745                 750

Ala Asn Arg Asn Phe Met Gln Leu Ile His Asp Asp Ser Leu Thr Phe
                    755                 760                 765

Lys Glu Asp Ile Gln Lys Ala Gln Val Ser Gly Gln Gly Asp Ser Leu
            770                 775                 780

His Glu His Ile Ala Asn Leu Ala Gly Ser Pro Ala Ile Lys Lys Gly
        785                 790                 795                 800

Ile Leu Gln Thr Val Lys Val Val Asp Glu Leu Val Lys Val Met Gly
                        805                 810                 815

Arg His Lys Pro Glu Asn Ile Val Ile Glu Met Ala Arg Glu Asn Gln
                    820                 825                 830

Thr Thr Gln Lys Gly Gln Lys Asn Ser Arg Glu Arg Met Lys Arg Ile
            835                 840                 845

Glu Glu Gly Ile Lys Glu Leu Gly Ser Gln Ile Leu Lys Glu His Pro
        850                 855                 860

Val Glu Asn Thr Gln Leu Gln Asn Glu Lys Leu Tyr Leu Tyr Tyr Leu
865                 870                 875                 880

Gln Asn Gly Arg Asp Met Tyr Val Asp Gln Glu Leu Asp Ile Asn Arg
                    885                 890                 895

Leu Ser Asp Tyr Asp Val Asp Ala Ile Val Pro Gln Ser Phe Leu Lys
                900                 905                 910

Asp Asp Ser Ile Asp Asn Lys Val Leu Thr Arg Ser Asp Lys Asn Arg
                915                 920                 925

Gly Lys Ser Asp Asn Val Pro Ser Glu Glu Val Val Lys Lys Met Lys
        930                 935                 940

Asn Tyr Trp Arg Gln Leu Leu Asn Ala Lys Leu Ile Thr Gln Arg Lys
945                 950                 955                 960

Phe Asp Asn Leu Thr Lys Ala Glu Arg Gly Gly Leu Ser Glu Leu Asp
                    965                 970                 975

Lys Ala Gly Phe Ile Lys Arg Gln Leu Val Glu Thr Arg Gln Ile Thr
                980                 985                 990

Lys His Val Ala Gln Ile Leu Asp Ser Arg Met Asn Thr Lys Tyr Asp
        995                 1000                1005

Glu Asn Asp Lys Leu Ile Arg Glu Val Lys Val Ile Thr Leu Lys
        1010                1015                1020

Ser Lys Leu Val Ser Asp Phe Arg Lys Asp Phe Gln Phe Tyr Lys
        1025                1030                1035

Val Arg Glu Ile Asn Asn Tyr His His Ala His Asp Ala Tyr Leu
        1040                1045                1050
```

```
Asn Ala Val Val Gly Thr Ala Leu Ile Lys Lys Tyr Pro Lys Leu
    1055            1060            1065

Glu Ser Glu Phe Val Tyr Gly Asp Tyr Lys Val Tyr Asp Val Arg
    1070            1075            1080

Lys Met Ile Ala Lys Ser Glu Gln Glu Ile Gly Lys Ala Thr Ala
    1085            1090            1095

Lys Tyr Phe Phe Tyr Ser Asn Ile Met Asn Phe Phe Lys Thr Glu
    1100            1105            1110

Ile Thr Leu Ala Asn Gly Glu Ile Arg Lys Arg Pro Leu Ile Glu
    1115            1120            1125

Thr Asn Gly Glu Thr Gly Glu Ile Val Trp Asp Lys Gly Arg Asp
    1130            1135            1140

Phe Ala Thr Val Arg Lys Val Leu Ser Met Pro Gln Val Asn Ile
    1145            1150            1155

Val Lys Lys Thr Glu Val Gln Thr Gly Gly Phe Ser Lys Glu Ser
    1160            1165            1170

Ile Leu Pro Lys Arg Asn Ser Asp Lys Leu Ile Ala Arg Lys Lys
    1175            1180            1185

Asp Trp Asp Pro Lys Lys Tyr Gly Gly Phe Asp Ser Pro Thr Val
    1190            1195            1200

Ala Tyr Ser Val Leu Val Val Ala Lys Val Glu Lys Gly Lys Ser
    1205            1210            1215

Lys Lys Leu Lys Ser Val Lys Glu Leu Leu Gly Ile Thr Ile Met
    1220            1225            1230

Glu Arg Ser Ser Phe Glu Lys Asn Pro Ile Asp Phe Leu Glu Ala
    1235            1240            1245

Lys Gly Tyr Lys Glu Val Lys Lys Asp Leu Ile Ile Lys Leu Pro
    1250            1255            1260

Lys Tyr Ser Leu Phe Glu Leu Glu Asn Gly Arg Lys Arg Met Leu
    1265            1270            1275

Ala Ser Ala Gly Glu Leu Gln Lys Gly Asn Glu Leu Ala Leu Pro
    1280            1285            1290

Ser Lys Tyr Val Asn Phe Leu Tyr Leu Ala Ser His Tyr Glu Lys
    1295            1300            1305

Leu Lys Gly Ser Pro Glu Asp Asn Glu Gln Lys Gln Leu Phe Val
    1310            1315            1320

Glu Gln His Lys His Tyr Leu Asp Glu Ile Ile Glu Gln Ile Ser
    1325            1330            1335

Glu Phe Ser Lys Arg Val Ile Leu Ala Asp Ala Asn Leu Asp Lys
    1340            1345            1350

Val Leu Ser Ala Tyr Asn Lys His Arg Asp Lys Pro Ile Arg Glu
    1355            1360            1365

Gln Ala Glu Asn Ile Ile His Leu Phe Thr Leu Thr Asn Leu Gly
    1370            1375            1380

Ala Pro Ala Ala Phe Lys Tyr Phe Asp Thr Thr Ile Asp Arg Lys
    1385            1390            1395

Arg Tyr Thr Ser Thr Lys Glu Val Leu Asp Ala Thr Leu Ile His
    1400            1405            1410

Gln Ser Ile Thr Gly Leu Tyr Glu Thr Arg Ile Asp Leu Ser Gln
    1415            1420            1425

Leu Gly Gly Asp Ser Pro Lys Lys Lys Arg Lys Val Gly
    1430            1435            1440
```

```
<210> SEQ ID NO 23
<211> LENGTH: 20
<212> TYPE: DNA
<213> ORGANISM: Artificial Sequence
<220> FEATURE:
<223> OTHER INFORMATION: Genomic target site for guide RNA (gRNA) #1 for
      beta2-microglobulin gene

<400> SEQUENCE: 23
tataagtgga ggcgtcgcgc                                                    20

<210> SEQ ID NO 24
<211> LENGTH: 20
<212> TYPE: DNA
<213> ORGANISM: Artificial Sequence
<220> FEATURE:
<223> OTHER INFORMATION: Genomic target site for gRNA #2 for beta2-
      microglobulin gene

<400> SEQUENCE: 24
gcccgaatgc tgtcagcttc                                                    20

<210> SEQ ID NO 25
<211> LENGTH: 20
<212> TYPE: DNA
<213> ORGANISM: Artificial Sequence
<220> FEATURE:
<223> OTHER INFORMATION: Genomic target site for gRNA #3 for beta2-
      microglobulin gene

<400> SEQUENCE: 25
tgcgtcgctg gcttggagac                                                    20

<210> SEQ ID NO 26
<211> LENGTH: 20
<212> TYPE: DNA
<213> ORGANISM: Artificial Sequence
<220> FEATURE:
<223> OTHER INFORMATION: Genomic target site for gRNA #4 for beta2-
      microglobulin gene

<400> SEQUENCE: 26
ccaatcagga caaggcccgc                                                    20

<210> SEQ ID NO 27
<211> LENGTH: 20
<212> TYPE: DNA
<213> ORGANISM: Artificial Sequence
<220> FEATURE:
<223> OTHER INFORMATION: Genomic target site for gRNA #5 for beta2-
      microglobulin gene

<400> SEQUENCE: 27
agggtaggag agactcacgc                                                    20

<210> SEQ ID NO 28
<211> LENGTH: 20
<212> TYPE: DNA
<213> ORGANISM: Artificial Sequence
<220> FEATURE:
<223> OTHER INFORMATION: Genomic target site for gRNA #6 for beta2-
      microglobulin gene

<400> SEQUENCE: 28
gcgggccacc aaggagaact                                                    20
```

-continued

```
<210> SEQ ID NO 29
<211> LENGTH: 20
<212> TYPE: DNA
<213> ORGANISM: Artificial Sequence
<220> FEATURE:
<223> OTHER INFORMATION: Genomic target site for gRNA #7 for beta2-
      microglobulin gene

<400> SEQUENCE: 29
gctactctct ctttctggcc                                                   20

<210> SEQ ID NO 30
<211> LENGTH: 20
<212> TYPE: DNA
<213> ORGANISM: Artificial Sequence
<220> FEATURE:
<223> OTHER INFORMATION: Genomic target site for gRNA #8 for beta2-
      microglobulin gene

<400> SEQUENCE: 30
ctcccgctct gcaccctctg                                                   20

<210> SEQ ID NO 31
<211> LENGTH: 20
<212> TYPE: DNA
<213> ORGANISM: Artificial Sequence
<220> FEATURE:
<223> OTHER INFORMATION: Genomic target site for gRNA #9 for beta2-
      microglobulin gene

<400> SEQUENCE: 31
tttggcctac ggcgacggga                                                   20

<210> SEQ ID NO 32
<211> LENGTH: 20
<212> TYPE: DNA
<213> ORGANISM: Artificial Sequence
<220> FEATURE:
<223> OTHER INFORMATION: Genomic target site for gRNA #10 for beta2-
      microglobulin gene

<400> SEQUENCE: 32
ggggcaagta gcgcgcgtcc                                                   20

<210> SEQ ID NO 33
<211> LENGTH: 20
<212> TYPE: DNA
<213> ORGANISM: Artificial Sequence
<220> FEATURE:
<223> OTHER INFORMATION: Genomic target site for gRNA #11 for beta2-
      microglobulin gene

<400> SEQUENCE: 33
tagtccaggg ctggatctcg                                                   20

<210> SEQ ID NO 34
<211> LENGTH: 19
<212> TYPE: DNA
<213> ORGANISM: Artificial Sequence
<220> FEATURE:
<223> OTHER INFORMATION: Binding site

<400> SEQUENCE: 34
tacccagatt ggccccact                                                    19

<210> SEQ ID NO 35
<211> LENGTH: 19
```

```
<212> TYPE: DNA
<213> ORGANISM: Artificial Sequence
<220> FEATURE:
<223> OTHER INFORMATION: Binding site

<400> SEQUENCE: 35
tacctagagg agaaaggtt                                              19

<210> SEQ ID NO 36
<211> LENGTH: 846
<212> TYPE: PRT
<213> ORGANISM: Homo sapiens

<400> SEQUENCE: 36
```

Met Val Ala Glu Leu Ile Ser Glu Glu Asp Leu Glu Phe Met Lys Gly
1               5                   10                  15

Asp Thr Arg His Leu Asn Gly Glu Glu Asp Ala Gly Gly Arg Glu Asp
            20                  25                  30

Ser Ile Leu Val Asn Gly Ala Cys Ser Asp Gln Ser Ser Asp Ser Pro
        35                  40                  45

Pro Ile Leu Glu Ala Ile Arg Thr Pro Glu Ile Arg Gly Arg Arg Ser
    50                  55                  60

Ser Ser Arg Leu Ser Lys Arg Glu Val Ser Ser Leu Leu Ser Tyr Thr
65                  70                  75                  80

Gln Asp Leu Thr Gly Asp Gly Asp Gly Glu Asp Gly Asp Gly Ser Asp
                85                  90                  95

Thr Pro Val Met Pro Lys Leu Phe Arg Glu Thr Arg Thr Arg Ser Glu
            100                 105                 110

Ser Pro Ala Val Arg Thr Arg Asn Asn Asn Ser Val Ser Ser Arg Glu
        115                 120                 125

Arg His Arg Pro Ser Pro Arg Ser Thr Arg Gly Arg Gln Gly Arg Asn
    130                 135                 140

His Val Asp Glu Ser Pro Val Glu Phe Pro Ala Thr Arg Ser Leu Arg
145                 150                 155                 160

Arg Arg Ala Thr Ala Ser Ala Gly Thr Pro Trp Pro Ser Pro Pro Ser
                165                 170                 175

Ser Tyr Leu Thr Ile Asp Leu Thr Asp Asp Thr Glu Asp Thr His Gly
            180                 185                 190

Thr Pro Gln Ser Ser Ser Thr Pro Tyr Ala Arg Leu Ala Gln Asp Ser
        195                 200                 205

Gln Gln Gly Gly Met Glu Ser Pro Gln Val Glu Ala Asp Ser Gly Asp
    210                 215                 220

Gly Asp Ser Ser Glu Tyr Gln Asp Gly Lys Glu Phe Gly Ile Gly Asp
225                 230                 235                 240

Leu Val Trp Gly Lys Ile Lys Gly Phe Ser Trp Trp Pro Ala Met Val
                245                 250                 255

Val Ser Trp Lys Ala Thr Ser Lys Arg Gln Ala Met Ser Gly Met Arg
            260                 265                 270

Trp Val Gln Trp Phe Gly Asp Gly Lys Phe Ser Glu Val Ser Ala Asp
        275                 280                 285

Lys Leu Val Ala Leu Gly Leu Phe Ser Gln His Phe Asn Leu Ala Thr
    290                 295                 300

Phe Asn Lys Leu Val Ser Tyr Arg Lys Ala Met Tyr His Ala Leu Glu
305                 310                 315                 320

Lys Ala Arg Val Arg Ala Gly Lys Thr Phe Pro Ser Ser Pro Gly Asp
                325                 330                 335

```
Ser Leu Glu Asp Gln Leu Lys Pro Met Leu Glu Trp Ala His Gly Gly
            340                 345                 350

Phe Lys Pro Thr Gly Ile Glu Gly Leu Lys Pro Asn Asn Thr Gln Pro
            355                 360                 365

Glu Asn Lys Thr Arg Arg Thr Ala Asp Asp Ser Ala Thr Ser Asp
370                 375                 380

Tyr Cys Pro Ala Pro Lys Arg Leu Lys Thr Asn Cys Tyr Asn Asn Gly
385                 390                 395                 400

Lys Asp Arg Gly Asp Glu Asp Gln Ser Arg Glu Gln Met Ala Ser Asp
                405                 410                 415

Val Ala Asn Asn Lys Ser Ser Leu Glu Asp Gly Cys Leu Ser Cys Gly
            420                 425                 430

Arg Lys Asn Pro Val Ser Phe His Pro Leu Phe Glu Gly Gly Leu Cys
            435                 440                 445

Gln Thr Cys Arg Asp Arg Phe Leu Glu Leu Phe Tyr Met Tyr Asp Asp
        450                 455                 460

Asp Gly Tyr Gln Ser Tyr Cys Thr Val Cys Cys Glu Gly Arg Glu Leu
465                 470                 475                 480

Leu Leu Cys Ser Asn Thr Ser Cys Cys Arg Cys Phe Cys Val Glu Cys
                485                 490                 495

Leu Glu Val Leu Val Gly Thr Gly Thr Ala Ala Glu Ala Lys Leu Gln
            500                 505                 510

Glu Pro Trp Ser Cys Tyr Met Cys Leu Pro Gln Arg Cys His Gly Val
            515                 520                 525

Leu Arg Arg Arg Lys Asp Trp Asn Val Arg Leu Gln Ala Phe Phe Thr
        530                 535                 540

Ser Asp Thr Gly Leu Glu Tyr Glu Ala Pro Lys Leu Tyr Pro Ala Ile
545                 550                 555                 560

Pro Ala Ala Arg Arg Arg Pro Ile Arg Val Leu Ser Leu Phe Asp Gly
                565                 570                 575

Ile Ala Thr Gly Tyr Leu Val Leu Lys Glu Leu Gly Ile Lys Val Gly
            580                 585                 590

Lys Tyr Val Ala Ser Glu Val Cys Glu Glu Ser Ile Ala Val Gly Thr
        595                 600                 605

Val Lys His Glu Gly Asn Ile Lys Tyr Val Asn Asp Val Arg Asn Ile
    610                 615                 620

Thr Lys Lys Asn Ile Glu Glu Trp Gly Pro Phe Asp Leu Val Ile Gly
625                 630                 635                 640

Gly Ser Pro Cys Asn Asp Leu Ser Asn Val Asn Pro Ala Arg Lys Gly
                645                 650                 655

Leu Tyr Glu Gly Thr Gly Arg Leu Phe Phe Glu Phe Tyr His Leu Leu
            660                 665                 670

Asn Tyr Ser Arg Pro Lys Glu Gly Asp Asp Arg Pro Phe Phe Trp Met
        675                 680                 685

Phe Glu Asn Val Val Ala Met Lys Val Gly Asp Lys Arg Asp Ile Ser
        690                 695                 700

Arg Phe Leu Glu Cys Asn Pro Val Met Ile Asp Ala Ile Lys Val Ser
705                 710                 715                 720

Ala Ala His Arg Ala Arg Tyr Phe Trp Gly Asn Leu Pro Gly Met Asn
                725                 730                 735

Arg Pro Val Ile Ala Ser Lys Asn Asp Lys Leu Glu Leu Gln Asp Cys
            740                 745                 750
```

```
Leu Glu Tyr Asn Arg Ile Ala Lys Leu Lys Val Gln Thr Ile Thr
            755                 760                 765

Thr Lys Ser Asn Ser Ile Lys Gln Gly Lys Asn Gln Leu Phe Pro Val
    770                 775                 780

Val Met Asn Gly Lys Glu Asp Val Leu Trp Cys Thr Glu Leu Glu Arg
785                 790                 795                 800

Ile Phe Gly Phe Pro Val His Tyr Thr Asp Val Ser Asn Met Gly Arg
                805                 810                 815

Gly Ala Arg Gln Lys Leu Leu Gly Arg Ser Trp Ser Val Pro Val Ile
                820                 825                 830

Arg His Leu Phe Ala Pro Leu Lys Asp Tyr Phe Ala Cys Glu
            835                 840                 845

<210> SEQ ID NO 37
<211> LENGTH: 831
<212> TYPE: PRT
<213> ORGANISM: Artificial Sequence
<220> FEATURE:
<223> OTHER INFORMATION: TALE domain BCL11A #1

<400> SEQUENCE: 37

Met Gly Lys Pro Ile Pro Asn Pro Leu Leu Gly Leu Asp Ser Thr Gly
1               5                   10                  15

Gly Met Ala Pro Lys Lys Lys Arg Lys Val Asp Gly Gly Val Asp Leu
            20                  25                  30

Arg Thr Leu Gly Tyr Ser Gln Gln Gln Gln Glu Lys Ile Lys Pro Lys
        35                  40                  45

Val Arg Ser Thr Val Ala Gln His His Glu Ala Leu Val Gly His Gly
    50                  55                  60

Phe Thr His Ala His Ile Val Ala Leu Ser Gln His Pro Ala Ala Leu
65                  70                  75                  80

Gly Thr Val Ala Val Lys Tyr Gln Asp Met Ile Ala Ala Leu Pro Glu
                85                  90                  95

Ala Thr His Glu Ala Ile Val Gly Val Gly Lys Gln Trp Ser Gly Ala
            100                 105                 110

Arg Ala Leu Glu Ala Leu Leu Thr Val Ala Gly Glu Leu Arg Gly Pro
        115                 120                 125

Pro Leu Gln Leu Asp Thr Gly Gln Leu Leu Lys Ile Ala Lys Arg Gly
    130                 135                 140

Gly Val Thr Ala Val Glu Ala Val His Ala Trp Arg Asn Ala Leu Thr
145                 150                 155                 160

Gly Ala Pro Leu Asn Leu Thr Pro Asp Gln Val Val Ala Ile Ala Ser
                165                 170                 175

His Asp Gly Gly Lys Gln Ala Leu Glu Thr Val Gln Arg Leu Leu Pro
            180                 185                 190

Val Leu Cys Gln Asp His Gly Leu Thr Pro Asp Gln Val Val Ala Ile
        195                 200                 205

Ala Ser His Asp Gly Gly Lys Gln Ala Leu Glu Thr Val Gln Arg Leu
    210                 215                 220

Leu Pro Val Leu Cys Gln Asp His Gly Leu Thr Pro Asp Gln Val Val
225                 230                 235                 240

Ala Ile Ala Ser Asn Gly Gly Lys Gln Ala Leu Glu Thr Val Gln
                245                 250                 255

Arg Leu Leu Pro Val Leu Cys Gln Asp His Gly Leu Thr Pro Asp Gln
            260                 265                 270
```

```
Val Val Ala Ile Ala Ser Asn Asn Gly Gly Lys Gln Ala Leu Glu Thr
                275                 280                 285

Val Gln Arg Leu Leu Pro Val Leu Cys Gln Asp His Gly Leu Thr Pro
    290                 295                 300

Asp Gln Val Val Ala Ile Ala Ser Asn Asn Gly Gly Lys Gln Ala Leu
305                 310                 315                 320

Glu Thr Val Gln Arg Leu Leu Pro Val Leu Cys Gln Asp His Gly Leu
                325                 330                 335

Thr Pro Asp Gln Val Val Ala Ile Ala Ser Asn Gly Gly Gly Lys Gln
                340                 345                 350

Ala Leu Glu Thr Val Gln Arg Leu Leu Pro Val Leu Cys Gln Asp His
        355                 360                 365

Gly Leu Thr Pro Asp Gln Val Val Ala Ile Ala Ser His Asp Gly Gly
        370                 375                 380

Lys Gln Ala Leu Glu Thr Val Gln Arg Leu Leu Pro Val Leu Cys Gln
385                 390                 395                 400

Asp His Gly Leu Thr Pro Asp Gln Val Val Ala Ile Ala Ser His Asp
                405                 410                 415

Gly Gly Lys Gln Ala Leu Glu Thr Val Gln Arg Leu Leu Pro Val Leu
                420                 425                 430

Cys Gln Asp His Gly Leu Thr Pro Asp Gln Val Val Ala Ile Ala Ser
        435                 440                 445

Asn Asn Gly Gly Lys Gln Ala Leu Glu Thr Val Gln Arg Leu Leu Pro
450                 455                 460

Val Leu Cys Gln Asp His Gly Leu Thr Pro Asp Gln Val Val Ala Ile
465                 470                 475                 480

Ala Ser His Asp Gly Gly Lys Gln Ala Leu Glu Thr Val Gln Arg Leu
                485                 490                 495

Leu Pro Val Leu Cys Gln Asp His Gly Leu Thr Pro Asp Gln Val Val
                500                 505                 510

Ala Ile Ala Ser His Asp Gly Gly Lys Gln Ala Leu Glu Thr Val Gln
        515                 520                 525

Arg Leu Leu Pro Val Leu Cys Gln Asp His Gly Leu Thr Pro Asp Gln
        530                 535                 540

Val Val Ala Ile Ala Ser His Asp Gly Gly Lys Gln Ala Leu Glu Thr
545                 550                 555                 560

Val Gln Arg Leu Leu Pro Val Leu Cys Gln Asp His Gly Leu Thr Pro
                565                 570                 575

Asp Gln Val Val Ala Ile Ala Ser His Asp Gly Gly Lys Gln Ala Leu
                580                 585                 590

Glu Thr Val Gln Arg Leu Leu Pro Val Leu Cys Gln Asp His Gly Leu
        595                 600                 605

Thr Pro Asp Gln Val Val Ala Ile Ala Ser His Asp Gly Gly Lys Gln
        610                 615                 620

Ala Leu Glu Thr Val Gln Arg Leu Leu Pro Val Leu Cys Gln Asp His
625                 630                 635                 640

Gly Leu Thr Pro Asp Gln Val Val Ala Ile Ala Ser Asn Ile Gly Gly
                645                 650                 655

Lys Gln Ala Leu Glu Thr Val Gln Arg Leu Leu Pro Val Leu Cys Gln
                660                 665                 670

Asp His Gly Leu Thr Pro Asp Gln Val Val Ala Ile Ala Ser Asn Asn
        675                 680                 685

Gly Gly Lys Gln Ala Leu Glu Thr Val Gln Arg Leu Leu Pro Val Leu
```

```
              690              695              700
Cys Gln Asp His Gly Leu Thr Pro Asp Gln Val Val Ala Ile Ala Ser
705             710              715              720

His Asp Gly Gly Lys Gln Ala Leu Glu Thr Val Gln Arg Leu Leu Pro
                725              730              735

Val Leu Cys Gln Asp His Gly Leu Thr Pro Asp Gln Val Val Ala Ile
            740              745              750

Ala Ser Asn Ile Gly Gly Lys Gln Ala Leu Glu Ser Ile Val Ala Gln
        755              760              765

Leu Ser Arg Pro Asp Pro Ala Leu Ala Ala Leu Thr Asn Asp His Leu
    770              775              780

Val Ala Leu Ala Cys Leu Gly Gly Arg Pro Ala Leu Asp Ala Val Lys
785              790              795              800

Lys Gly Leu Pro His Ala Pro Ala Leu Ile Lys Arg Thr Asn Arg Arg
                805              810              815

Ile Pro Glu Arg Thr Ser His Arg Val Ala Gly Ser Gly Gly Gly
                820              825              830
```

<210> SEQ ID NO 38
<211> LENGTH: 19
<212> TYPE: DNA
<213> ORGANISM: Artificial Sequence
<220> FEATURE:
<223> OTHER INFORMATION: BCL11A gene binding site

<400> SEQUENCE: 38
tccaaaagcc agtctcacc                                          19

<210> SEQ ID NO 39
<211> LENGTH: 831
<212> TYPE: PRT
<213> ORGANISM: Artificial Sequence
<220> FEATURE:
<223> OTHER INFORMATION: TALE domain BCL11A #2

<400> SEQUENCE: 39

```
Met Gly Lys Pro Ile Pro Asn Pro Leu Leu Gly Leu Asp Ser Thr Gly
1               5                10               15

Gly Met Ala Pro Lys Lys Lys Arg Lys Val Asp Gly Gly Val Asp Leu
            20              25               30

Arg Thr Leu Gly Tyr Ser Gln Gln Gln Gln Glu Lys Ile Lys Pro Lys
        35              40               45

Val Arg Ser Thr Val Ala Gln His His Glu Ala Leu Val Gly His Gly
50              55               60

Phe Thr His Ala His Ile Val Ala Leu Ser Gln His Pro Ala Ala Leu
65              70               75               80

Gly Thr Val Ala Val Lys Tyr Gln Asp Met Ile Ala Ala Leu Pro Glu
                85              90               95

Ala Thr His Glu Ala Ile Val Gly Val Gly Lys Gln Trp Ser Gly Ala
            100             105              110

Arg Ala Leu Glu Ala Leu Leu Thr Val Ala Gly Glu Leu Arg Gly Pro
        115             120              125

Pro Leu Gln Leu Asp Thr Gly Gln Leu Leu Lys Ile Ala Lys Arg Gly
    130             135              140

Gly Val Thr Ala Val Glu Ala Val His Ala Trp Arg Asn Ala Leu Thr
145             150              155              160

Gly Ala Pro Leu Asn Leu Thr Pro Asp Gln Val Val Ala Ile Ala Ser
```

```
                165                 170                 175
Asn Asn Gly Gly Lys Gln Ala Leu Glu Thr Val Gln Arg Leu Leu Pro
            180                 185                 190

Val Leu Cys Gln Asp His Gly Leu Thr Pro Asp Gln Val Val Ala Ile
            195                 200                 205

Ala Ser His Asp Gly Gly Lys Gln Ala Leu Glu Thr Val Gln Arg Leu
            210                 215                 220

Leu Pro Val Leu Cys Gln Asp His Gly Leu Thr Pro Asp Gln Val Val
225                 230                 235                 240

Ala Ile Ala Ser His Asp Gly Gly Lys Gln Ala Leu Glu Thr Val Gln
                245                 250                 255

Arg Leu Leu Pro Val Leu Cys Gln Asp His Gly Leu Thr Pro Asp Gln
            260                 265                 270

Val Val Ala Ile Ala Ser Asn Asn Gly Gly Lys Gln Ala Leu Glu Thr
            275                 280                 285

Val Gln Arg Leu Leu Pro Val Leu Cys Gln Asp His Gly Leu Thr Pro
            290                 295                 300

Asp Gln Val Val Ala Ile Ala Ser Asn Ile Gly Gly Lys Gln Ala Leu
305                 310                 315                 320

Glu Thr Val Gln Arg Leu Leu Pro Val Leu Cys Gln Asp His Gly Leu
                325                 330                 335

Thr Pro Asp Gln Val Val Ala Ile Ala Ser Asn Asn Gly Gly Lys Gln
            340                 345                 350

Ala Leu Glu Thr Val Gln Arg Leu Leu Pro Val Leu Cys Gln Asp His
            355                 360                 365

Gly Leu Thr Pro Asp Gln Val Val Ala Ile Ala Ser Asn Ile Gly Gly
            370                 375                 380

Lys Gln Ala Leu Glu Thr Val Gln Arg Leu Leu Pro Val Leu Cys Gln
385                 390                 395                 400

Asp His Gly Leu Thr Pro Asp Gln Val Val Ala Ile Ala Ser His Asp
                405                 410                 415

Gly Gly Lys Gln Ala Leu Glu Thr Val Gln Arg Leu Leu Pro Val Leu
            420                 425                 430

Cys Gln Asp His Gly Leu Thr Pro Asp Gln Val Val Ala Ile Ala Ser
            435                 440                 445

His Asp Gly Gly Lys Gln Ala Leu Glu Thr Val Gln Arg Leu Leu Pro
            450                 455                 460

Val Leu Cys Gln Asp His Gly Leu Thr Pro Asp Gln Val Val Ala Ile
465                 470                 475                 480

Ala Ser Asn Gly Gly Gly Lys Gln Ala Leu Glu Thr Val Gln Arg Leu
                485                 490                 495

Leu Pro Val Leu Cys Gln Asp His Gly Leu Thr Pro Asp Gln Val Val
            500                 505                 510

Ala Ile Ala Ser His Asp Gly Gly Lys Gln Ala Leu Glu Thr Val Gln
            515                 520                 525

Arg Leu Leu Pro Val Leu Cys Gln Asp His Gly Leu Thr Pro Asp Gln
            530                 535                 540

Val Val Ala Ile Ala Ser Asn Gly Gly Gly Lys Gln Ala Leu Glu Thr
545                 550                 555                 560

Val Gln Arg Leu Leu Pro Val Leu Cys Gln Asp His Gly Leu Thr Pro
                565                 570                 575

Asp Gln Val Val Ala Ile Ala Ser Asn Gly Gly Gly Lys Gln Ala Leu
            580                 585                 590
```

```
Glu Thr Val Gln Arg Leu Leu Pro Val Leu Cys Gln Asp His Gly Leu
        595                 600                 605

Thr Pro Asp Gln Val Val Ala Ile Ala Ser His Asp Gly Gly Lys Gln
    610                 615                 620

Ala Leu Glu Thr Val Gln Arg Leu Leu Pro Val Leu Cys Gln Asp His
625                 630                 635                 640

Gly Leu Thr Pro Asp Gln Val Val Ala Ile Ala Ser Asn Gly Gly Gly
                645                 650                 655

Lys Gln Ala Leu Glu Thr Val Gln Arg Leu Leu Pro Val Leu Cys Gln
            660                 665                 670

Asp His Gly Leu Thr Pro Asp Gln Val Val Ala Ile Ala Ser His Asp
                675                 680                 685

Gly Gly Lys Gln Ala Leu Glu Thr Val Gln Arg Leu Leu Pro Val Leu
        690                 695                 700

Cys Gln Asp His Gly Leu Thr Pro Asp Gln Val Val Ala Ile Ala Ser
705                 710                 715                 720

Asn Asn Gly Gly Lys Gln Ala Leu Glu Thr Val Gln Arg Leu Leu Pro
                725                 730                 735

Val Leu Cys Gln Asp His Gly Leu Thr Pro Asp Gln Val Val Ala Ile
            740                 745                 750

Ala Ser Asn Ile Gly Gly Lys Gln Ala Leu Glu Ser Ile Val Ala Gln
                755                 760                 765

Leu Ser Arg Pro Asp Pro Ala Leu Ala Ala Leu Thr Asn Asp His Leu
        770                 775                 780

Val Ala Leu Ala Cys Leu Gly Gly Arg Pro Ala Leu Asp Ala Val Lys
785                 790                 795                 800

Lys Gly Leu Pro His Ala Pro Ala Leu Ile Lys Arg Thr Asn Arg Arg
                805                 810                 815

Ile Pro Glu Arg Thr Ser His Arg Val Ala Gly Ser Gly Gly
            820                 825                 830

<210> SEQ ID NO 40
<211> LENGTH: 19
<212> TYPE: DNA
<213> ORGANISM: Artificial Sequence
<220> FEATURE:
<223> OTHER INFORMATION: BCL11A gene binding site

<400> SEQUENCE: 40
tctccccggg aatcgtttt                                              19

<210> SEQ ID NO 41
<211> LENGTH: 831
<212> TYPE: PRT
<213> ORGANISM: Artificial Sequence
<220> FEATURE:
<223> OTHER INFORMATION: TALE domain BCL11A #3

<400> SEQUENCE: 41

Met Gly Lys Pro Ile Pro Asn Pro Leu Leu Gly Leu Asp Ser Thr Gly
1               5                   10                  15

Gly Met Ala Pro Lys Lys Lys Arg Lys Val Asp Gly Gly Val Asp Leu
            20                  25                  30

Arg Thr Leu Gly Tyr Ser Gln Gln Gln Gln Glu Lys Ile Lys Pro Lys
        35                  40                  45

Val Arg Ser Thr Val Ala Gln His His Glu Ala Leu Val Gly His Gly
    50                  55                  60
```

```
Phe Thr His Ala His Ile Val Ala Leu Ser Gln His Pro Ala Ala Leu
 65                  70                  75                  80

Gly Thr Val Ala Val Lys Tyr Gln Asp Met Ile Ala Ala Leu Pro Glu
                 85                  90                  95

Ala Thr His Glu Ala Ile Val Gly Val Gly Lys Gln Trp Ser Gly Ala
            100                 105                 110

Arg Ala Leu Glu Ala Leu Leu Thr Val Ala Gly Glu Leu Arg Gly Pro
        115                 120                 125

Pro Leu Gln Leu Asp Thr Gly Gln Leu Leu Lys Ile Ala Lys Arg Gly
    130                 135                 140

Gly Val Thr Ala Val Glu Ala Val His Ala Trp Arg Asn Ala Leu Thr
145                 150                 155                 160

Gly Ala Pro Leu Asn Leu Thr Pro Asp Gln Val Val Ala Ile Ala Ser
                165                 170                 175

His Asp Gly Gly Lys Gln Ala Leu Glu Thr Val Gln Arg Leu Leu Pro
            180                 185                 190

Val Leu Cys Gln Asp His Gly Leu Thr Pro Asp Gln Val Val Ala Ile
        195                 200                 205

Ala Ser Asn Asn Gly Gly Lys Gln Ala Leu Glu Thr Val Gln Arg Leu
    210                 215                 220

Leu Pro Val Leu Cys Gln Asp His Gly Leu Thr Pro Asp Gln Val Val
225                 230                 235                 240

Ala Ile Ala Ser Asn Asn Gly Gly Lys Gln Ala Leu Glu Thr Val Gln
                245                 250                 255

Arg Leu Leu Pro Val Leu Cys Gln Asp His Gly Leu Thr Pro Asp Gln
            260                 265                 270

Val Val Ala Ile Ala Ser His Asp Gly Gly Lys Gln Ala Leu Glu Thr
        275                 280                 285

Val Gln Arg Leu Leu Pro Val Leu Cys Gln Asp His Gly Leu Thr Pro
    290                 295                 300

Asp Gln Val Val Ala Ile Ala Ser Asn Gly Gly Gly Lys Gln Ala Leu
305                 310                 315                 320

Glu Thr Val Gln Arg Leu Leu Pro Val Leu Cys Gln Asp His Gly Leu
                325                 330                 335

Thr Pro Asp Gln Val Val Ala Ile Ala Ser Asn Gly Gly Gly Lys Gln
            340                 345                 350

Ala Leu Glu Thr Val Gln Arg Leu Leu Pro Val Leu Cys Gln Asp His
        355                 360                 365

Gly Leu Thr Pro Asp Gln Val Val Ala Ile Ala Ser Asn Gly Gly Gly
    370                 375                 380

Lys Gln Ala Leu Glu Thr Val Gln Arg Leu Leu Pro Val Leu Cys Gln
385                 390                 395                 400

Asp His Gly Leu Thr Pro Asp Gln Val Val Ala Ile Ala Ser Asn Asn
                405                 410                 415

Gly Gly Lys Gln Ala Leu Glu Thr Val Gln Arg Leu Leu Pro Val Leu
            420                 425                 430

Cys Gln Asp His Gly Leu Thr Pro Asp Gln Val Val Ala Ile Ala Ser
        435                 440                 445

His Asp Gly Gly Lys Gln Ala Leu Glu Thr Val Gln Arg Leu Leu Pro
    450                 455                 460

Val Leu Cys Gln Asp His Gly Leu Thr Pro Asp Gln Val Val Ala Ile
465                 470                 475                 480
```

```
Ala Ser Asn Ile Gly Gly Lys Gln Ala Leu Glu Thr Val Gln Arg Leu
                485                 490                 495
Leu Pro Val Leu Cys Gln Asp His Gly Leu Thr Pro Asp Gln Val Val
            500                 505                 510
Ala Ile Ala Ser Asn Ile Gly Gly Lys Gln Ala Leu Glu Thr Val Gln
        515                 520                 525
Arg Leu Leu Pro Val Leu Cys Gln Asp His Gly Leu Thr Pro Asp Gln
    530                 535                 540
Val Val Ala Ile Ala Ser Asn Ile Gly Gly Lys Gln Ala Leu Glu Thr
545                 550                 555                 560
Val Gln Arg Leu Leu Pro Val Leu Cys Gln Asp His Gly Leu Thr Pro
                565                 570                 575
Asp Gln Val Val Ala Ile Ala Ser Asn His Gly Gly Lys Gln Ala Leu
            580                 585                 590
Glu Thr Val Gln Arg Leu Leu Pro Val Leu Cys Gln Asp His Gly Leu
        595                 600                 605
Thr Pro Asp Gln Val Val Ala Ile Ala Ser His Asp Gly Gly Lys Gln
    610                 615                 620
Ala Leu Glu Thr Val Gln Arg Leu Leu Pro Val Leu Cys Gln Asp His
625                 630                 635                 640
Gly Leu Thr Pro Asp Gln Val Val Ala Ile Ala Ser Asn Ile Gly Gly
                645                 650                 655
Lys Gln Ala Leu Glu Thr Val Gln Arg Leu Leu Pro Val Leu Cys Gln
            660                 665                 670
Asp His Gly Leu Thr Pro Asp Gln Val Val Ala Ile Ala Ser Asn Gly
        675                 680                 685
Gly Gly Lys Gln Ala Leu Glu Thr Val Gln Arg Leu Leu Pro Val Leu
    690                 695                 700
Cys Gln Asp His Gly Leu Thr Pro Asp Gln Val Val Ala Ile Ala Ser
705                 710                 715                 720
Asn Gly Gly Gly Lys Gln Ala Leu Glu Thr Val Gln Arg Leu Leu Pro
                725                 730                 735
Val Leu Cys Gln Asp His Gly Leu Thr Pro Asp Gln Val Val Ala Ile
            740                 745                 750
Ala Ser Asn Gly Gly Gly Lys Gln Ala Leu Glu Ser Ile Val Ala Gln
        755                 760                 765
Leu Ser Arg Pro Asp Pro Ala Leu Ala Ala Leu Thr Asn Asp His Leu
    770                 775                 780
Val Ala Leu Ala Cys Leu Gly Gly Arg Pro Ala Leu Asp Ala Val Lys
785                 790                 795                 800
Lys Gly Leu Pro His Ala Pro Ala Leu Ile Lys Arg Thr Asn Arg Arg
                805                 810                 815
Ile Pro Glu Arg Thr Ser His Arg Val Ala Gly Ser Gly Gly Gly
            820                 825                 830
```

<210> SEQ ID NO 42
<211> LENGTH: 19
<212> TYPE: DNA
<213> ORGANISM: Artificial Sequence
<220> FEATURE:
<223> OTHER INFORMATION: BCL11A gene binding site

<400> SEQUENCE: 42
tcctcccgct gcacacttg         19

```
<210> SEQ ID NO 43
<211> LENGTH: 831
<212> TYPE: PRT
<213> ORGANISM: Artificial Sequence
<220> FEATURE:
<223> OTHER INFORMATION: TALE domain BCL11A #4

<400> SEQUENCE: 43

Met Gly Lys Pro Ile Pro Asn Pro Leu Leu Gly Leu Asp Ser Thr Gly
1               5                   10                  15

Gly Met Ala Pro Lys Lys Lys Arg Lys Val Asp Gly Val Asp Leu
            20                  25                  30

Arg Thr Leu Gly Tyr Ser Gln Gln Gln Gln Glu Lys Ile Lys Pro Lys
            35                  40                  45

Val Arg Ser Thr Val Ala Gln His His Glu Ala Leu Val Gly His Gly
        50                  55                  60

Phe Thr His Ala His Ile Val Ala Leu Ser Gln His Pro Ala Ala Leu
65                  70                  75                  80

Gly Thr Val Ala Val Lys Tyr Gln Asp Met Ile Ala Ala Leu Pro Glu
                85                  90                  95

Ala Thr His Glu Ala Ile Val Gly Val Gly Lys Gln Trp Ser Gly Ala
            100                 105                 110

Arg Ala Leu Glu Ala Leu Leu Thr Val Ala Gly Glu Leu Arg Gly Pro
        115                 120                 125

Pro Leu Gln Leu Asp Thr Gly Gln Leu Leu Lys Ile Ala Lys Arg Gly
    130                 135                 140

Gly Val Thr Ala Val Glu Ala Val His Ala Trp Arg Asn Ala Leu Thr
145                 150                 155                 160

Gly Ala Pro Leu Asn Leu Thr Pro Asp Gln Val Val Ala Ile Ala Ser
                165                 170                 175

Asn Asn Gly Gly Lys Gln Ala Leu Glu Thr Val Gln Arg Leu Leu Pro
            180                 185                 190

Val Leu Cys Gln Asp His Gly Leu Thr Pro Asp Gln Val Val Ala Ile
        195                 200                 205

Ala Ser His Asp Gly Gly Lys Gln Ala Leu Glu Thr Val Gln Arg Leu
    210                 215                 220

Leu Pro Val Leu Cys Gln Asp His Gly Leu Thr Pro Asp Gln Val Val
225                 230                 235                 240

Ala Ile Ala Ser Asn Ile Gly Gly Lys Gln Ala Leu Glu Thr Val Gln
                245                 250                 255

Arg Leu Leu Pro Val Leu Cys Gln Asp His Gly Leu Thr Pro Asp Gln
            260                 265                 270

Val Val Ala Ile Ala Ser Asn Ile Gly Gly Lys Gln Ala Leu Glu Thr
        275                 280                 285

Val Gln Arg Leu Leu Pro Val Leu Cys Gln Asp His Gly Leu Thr Pro
    290                 295                 300

Asp Gln Val Val Ala Ile Ala Ser Asn Ile Gly Gly Lys Gln Ala Leu
305                 310                 315                 320

Glu Thr Val Gln Arg Leu Leu Pro Val Leu Cys Gln Asp His Gly Leu
                325                 330                 335

Thr Pro Asp Gln Val Val Ala Ile Ala Ser Asn Asn Gly Gly Lys Gln
            340                 345                 350

Ala Leu Glu Thr Val Gln Arg Leu Leu Pro Val Leu Cys Gln Asp His
        355                 360                 365

Gly Leu Thr Pro Asp Gln Val Val Ala Ile Ala Ser His Asp Gly Gly
```

```
            370             375             380
Lys Gln Ala Leu Glu Thr Val Gln Arg Leu Leu Pro Val Leu Cys Gln
385                 390                 395                 400

Asp His Gly Leu Thr Pro Asp Gln Val Val Ala Ile Ala Ser His Asp
                405                 410                 415

Gly Gly Lys Gln Ala Leu Glu Thr Val Gln Arg Leu Leu Pro Val Leu
                420                 425                 430

Cys Gln Asp His Gly Leu Thr Pro Asp Gln Val Val Ala Ile Ala Ser
            435                 440                 445

Asn Asn Gly Gly Lys Gln Ala Leu Glu Thr Val Gln Arg Leu Leu Pro
450                 455                 460

Val Leu Cys Gln Asp His Gly Leu Thr Pro Asp Gln Val Val Ala Ile
465                 470                 475                 480

Ala Ser Asn Ile Gly Gly Lys Gln Ala Leu Glu Thr Val Gln Arg Leu
                    485                 490                 495

Leu Pro Val Leu Cys Gln Asp His Gly Leu Thr Pro Asp Gln Val Val
                500                 505                 510

Ala Ile Ala Ser Asn Asn Gly Gly Lys Gln Ala Leu Glu Thr Val Gln
            515                 520                 525

Arg Leu Leu Pro Val Leu Cys Gln Asp His Gly Leu Thr Pro Asp Gln
530                 535                 540

Val Val Ala Ile Ala Ser Asn Gly Gly Gly Lys Gln Ala Leu Glu Thr
545                 550                 555                 560

Val Gln Arg Leu Leu Pro Val Leu Cys Gln Asp His Gly Leu Thr Pro
                565                 570                 575

Asp Gln Val Val Ala Ile Ala Ser Asn Gly Gly Gly Lys Gln Ala Leu
            580                 585                 590

Glu Thr Val Gln Arg Leu Leu Pro Val Leu Cys Gln Asp His Gly Leu
            595                 600                 605

Thr Pro Asp Gln Val Val Ala Ile Ala Ser Asn Gly Gly Gly Lys Gln
            610                 615                 620

Ala Leu Glu Thr Val Gln Arg Leu Leu Pro Val Leu Cys Gln Asp His
625                 630                 635                 640

Gly Leu Thr Pro Asp Gln Val Val Ala Ile Ala Ser His Asp Gly Gly
                645                 650                 655

Lys Gln Ala Leu Glu Thr Val Gln Arg Leu Leu Pro Val Leu Cys Gln
                660                 665                 670

Asp His Gly Leu Thr Pro Asp Gln Val Val Ala Ile Ala Ser Asn Ile
            675                 680                 685

Gly Gly Lys Gln Ala Leu Glu Thr Val Gln Arg Leu Leu Pro Val Leu
            690                 695                 700

Cys Gln Asp His Gly Leu Thr Pro Asp Gln Val Val Ala Ile Ala Ser
705                 710                 715                 720

His Asp Gly Gly Lys Gln Ala Leu Glu Thr Val Gln Arg Leu Leu Pro
                725                 730                 735

Val Leu Cys Gln Asp His Gly Leu Thr Pro Asp Gln Val Val Ala Ile
                740                 745                 750

Ala Ser His Asp Gly Gly Lys Gln Ala Leu Glu Ser Ile Val Ala Gln
            755                 760                 765

Leu Ser Arg Pro Asp Pro Ala Leu Ala Ala Leu Thr Asn Asp His Leu
            770                 775                 780

Val Ala Leu Ala Cys Leu Gly Gly Arg Pro Ala Leu Asp Ala Val Lys
785                 790                 795                 800
```

```
Lys Gly Leu Pro His Ala Pro Ala Leu Ile Lys Arg Thr Asn Arg Arg
                805                 810                 815

Ile Pro Glu Arg Thr Ser His Arg Val Ala Gly Ser Gly Gly Gly
                820                 825                 830

<210> SEQ ID NO 44
<211> LENGTH: 19
<212> TYPE: DNA
<213> ORGANISM: Artificial Sequence
<220> FEATURE:
<223> OTHER INFORMATION: BCL11A gene binding site

<400> SEQUENCE: 44
tagtcatccc cacaatagt                                                    19

<210> SEQ ID NO 45
<211> LENGTH: 831
<212> TYPE: PRT
<213> ORGANISM: Artificial Sequence
<220> FEATURE:
<223> OTHER INFORMATION: TALE domain BCL11A #5

<400> SEQUENCE: 45

Met Gly Lys Pro Ile Pro Asn Pro Leu Leu Gly Leu Asp Ser Thr Gly
1               5                   10                  15

Gly Met Ala Pro Lys Lys Lys Arg Lys Val Asp Gly Gly Val Asp Leu
                20                  25                  30

Arg Thr Leu Gly Tyr Ser Gln Gln Gln Gln Glu Lys Ile Lys Pro Lys
            35                  40                  45

Val Arg Ser Thr Val Ala Gln His His Glu Ala Leu Val Gly His Gly
        50                  55                  60

Phe Thr His Ala His Ile Val Ala Leu Ser Gln His Pro Ala Ala Leu
65                  70                  75                  80

Gly Thr Val Ala Val Lys Tyr Gln Asp Met Ile Ala Ala Leu Pro Glu
                85                  90                  95

Ala Thr His Glu Ala Ile Val Gly Val Gly Lys Gln Trp Ser Gly Ala
            100                 105                 110

Arg Ala Leu Glu Ala Leu Leu Thr Val Ala Gly Glu Leu Arg Gly Pro
        115                 120                 125

Pro Leu Gln Leu Asp Thr Gly Gln Leu Leu Lys Ile Ala Lys Arg Gly
    130                 135                 140

Gly Val Thr Ala Val Glu Ala Val His Ala Trp Arg Asn Ala Leu Thr
145                 150                 155                 160

Gly Ala Pro Leu Asn Leu Thr Pro Asp Gln Val Val Ala Ile Ala Ser
                165                 170                 175

Asn Ile Gly Gly Lys Gln Ala Leu Glu Thr Val Gln Arg Leu Leu Pro
            180                 185                 190

Val Leu Cys Gln Asp His Gly Leu Thr Pro Asp Gln Val Val Ala Ile
        195                 200                 205

Ala Ser His Asp Gly Gly Lys Gln Ala Leu Glu Thr Val Gln Arg Leu
    210                 215                 220

Leu Pro Val Leu Cys Gln Asp His Gly Leu Thr Pro Asp Gln Val Val
225                 230                 235                 240

Ala Ile Ala Ser Asn Ile Gly Gly Lys Gln Ala Leu Glu Thr Val Gln
                245                 250                 255

Arg Leu Leu Pro Val Leu Cys Gln Asp His Gly Leu Thr Pro Asp Gln
            260                 265                 270
```

```
Val Val Ala Ile Ala Ser Asn Asn Gly Gly Lys Gln Ala Leu Glu Thr
            275                 280                 285

Val Gln Arg Leu Leu Pro Val Leu Cys Gln Asp His Gly Leu Thr Pro
        290                 295                 300

Asp Gln Val Val Ala Ile Ala Ser Asn Gly Gly Gly Lys Gln Ala Leu
305                 310                 315                 320

Glu Thr Val Gln Arg Leu Leu Pro Val Leu Cys Gln Asp His Gly Leu
                325                 330                 335

Thr Pro Asp Gln Val Val Ala Ile Ala Ser Asn Gly Gly Gly Lys Gln
            340                 345                 350

Ala Leu Glu Thr Val Gln Arg Leu Leu Pro Val Leu Cys Gln Asp His
        355                 360                 365

Gly Leu Thr Pro Asp Gln Val Val Ala Ile Ala Ser Asn Asn Gly Gly
        370                 375                 380

Lys Gln Ala Leu Glu Thr Val Gln Arg Leu Leu Pro Val Leu Cys Gln
385                 390                 395                 400

Asp His Gly Leu Thr Pro Asp Gln Val Val Ala Ile Ala Ser His Asp
                405                 410                 415

Gly Gly Lys Gln Ala Leu Glu Thr Val Gln Arg Leu Leu Pro Val Leu
            420                 425                 430

Cys Gln Asp His Gly Leu Thr Pro Asp Gln Val Val Ala Ile Ala Ser
        435                 440                 445

His Asp Gly Gly Lys Gln Ala Leu Glu Thr Val Gln Arg Leu Leu Pro
        450                 455                 460

Val Leu Cys Gln Asp His Gly Leu Thr Pro Asp Gln Val Val Ala Ile
465                 470                 475                 480

Ala Ser His Asp Gly Gly Lys Gln Ala Leu Glu Thr Val Gln Arg Leu
                485                 490                 495

Leu Pro Val Leu Cys Gln Asp His Gly Leu Thr Pro Asp Gln Val Val
            500                 505                 510

Ala Ile Ala Ser Asn Gly Gly Gly Lys Gln Ala Leu Glu Thr Val Gln
        515                 520                 525

Arg Leu Leu Pro Val Leu Cys Gln Asp His Gly Leu Thr Pro Asp Gln
        530                 535                 540

Val Val Ala Ile Ala Ser Asn Asn Gly Gly Lys Gln Ala Leu Glu Thr
545                 550                 555                 560

Val Gln Arg Leu Leu Pro Val Leu Cys Gln Asp His Gly Leu Thr Pro
                565                 570                 575

Asp Gln Val Val Ala Ile Ala Ser His Asp Gly Gly Lys Gln Ala Leu
            580                 585                 590

Glu Thr Val Gln Arg Leu Leu Pro Val Leu Cys Gln Asp His Gly Leu
        595                 600                 605

Thr Pro Asp Gln Val Val Ala Ile Ala Ser Asn Ile Gly Gly Lys Gln
        610                 615                 620

Ala Leu Glu Thr Val Gln Arg Leu Leu Pro Val Leu Cys Gln Asp His
625                 630                 635                 640

Gly Leu Thr Pro Asp Gln Val Val Ala Ile Ala Ser Asn Ile Gly Gly
                645                 650                 655

Lys Gln Ala Leu Glu Thr Val Gln Arg Leu Leu Pro Val Leu Cys Gln
            660                 665                 670

Asp His Gly Leu Thr Pro Asp Gln Val Val Ala Ile Ala Ser Asn Ile
        675                 680                 685
```

```
Gly Gly Lys Gln Ala Leu Glu Thr Val Gln Arg Leu Leu Pro Val Leu
            690                 695                 700
Cys Gln Asp His Gly Leu Thr Pro Asp Gln Val Val Ala Ile Ala Ser
705                 710                 715                 720
Asn Ile Gly Gly Lys Gln Ala Leu Glu Thr Val Gln Arg Leu Leu Pro
            725                 730                 735
Val Leu Cys Gln Asp His Gly Leu Thr Pro Asp Gln Val Val Ala Ile
            740                 745                 750
Ala Ser Asn Gly Gly Lys Gln Ala Leu Glu Ser Ile Val Ala Gln
            755                 760                 765
Leu Ser Arg Pro Asp Pro Ala Leu Ala Ala Leu Thr Asn Asp His Leu
            770                 775                 780
Val Ala Leu Ala Cys Leu Gly Gly Arg Pro Ala Leu Asp Ala Val Lys
785                 790                 795                 800
Lys Gly Leu Pro His Ala Pro Ala Leu Ile Lys Arg Thr Asn Arg Arg
            805                 810                 815
Ile Pro Glu Arg Thr Ser His Arg Val Ala Gly Ser Gly Gly Gly
            820                 825                 830
```

<210> SEQ ID NO 46
<211> LENGTH: 19
<212> TYPE: DNA
<213> ORGANISM: Artificial Sequence
<220> FEATURE:
<223> OTHER INFORMATION: BCL11A gene binding site

<400> SEQUENCE: 46
tcccgctgcc ttttgtgcc                                              19

<210> SEQ ID NO 47
<211> LENGTH: 831
<212> TYPE: PRT
<213> ORGANISM: Artificial Sequence
<220> FEATURE:
<223> OTHER INFORMATION: TALE domain BCL11A #6

<400> SEQUENCE: 47

```
Met Gly Lys Pro Ile Pro Asn Pro Leu Leu Gly Leu Asp Ser Thr Gly
1               5                   10                  15
Gly Met Ala Pro Lys Lys Lys Arg Lys Val Asp Gly Gly Val Asp Leu
            20                  25                  30
Arg Thr Leu Gly Tyr Ser Gln Gln Gln Gln Glu Lys Ile Lys Pro Lys
            35                  40                  45
Val Arg Ser Thr Val Ala Gln His His Glu Ala Leu Val Gly His Gly
50                  55                  60
Phe Thr His Ala His Ile Val Ala Leu Ser Gln His Pro Ala Ala Leu
65                  70                  75                  80
Gly Thr Val Ala Val Lys Tyr Gln Asp Met Ile Ala Ala Leu Pro Glu
            85                  90                  95
Ala Thr His Glu Ala Ile Val Gly Val Gly Lys Gln Trp Ser Gly Ala
            100                 105                 110
Arg Ala Leu Glu Ala Leu Leu Thr Val Ala Gly Glu Leu Arg Gly Pro
            115                 120                 125
Pro Leu Gln Leu Asp Thr Gly Gln Leu Leu Lys Ile Ala Lys Arg Gly
            130                 135                 140
Gly Val Thr Ala Val Glu Ala Val His Ala Trp Arg Asn Ala Leu Thr
145                 150                 155                 160
```

-continued

Gly Ala Pro Leu Asn Leu Thr Pro Asp Gln Val Ala Ile Ala Ser
                165                 170                 175

His Asp Gly Gly Lys Gln Ala Leu Glu Thr Val Gln Arg Leu Leu Pro
            180                 185                 190

Val Leu Cys Gln Asp His Gly Leu Thr Pro Asp Gln Val Val Ala Ile
        195                 200                 205

Ala Ser His Asp Gly Gly Lys Gln Ala Leu Glu Thr Val Gln Arg Leu
    210                 215                 220

Leu Pro Val Leu Cys Gln Asp His Gly Leu Thr Pro Asp Gln Val Val
225                 230                 235                 240

Ala Ile Ala Ser Asn Asn Gly Gly Lys Gln Ala Leu Glu Thr Val Gln
                245                 250                 255

Arg Leu Leu Pro Val Leu Cys Gln Asp His Gly Leu Thr Pro Asp Gln
            260                 265                 270

Val Val Ala Ile Ala Ser His Asp Gly Gly Lys Gln Ala Leu Glu Thr
        275                 280                 285

Val Gln Arg Leu Leu Pro Val Leu Cys Gln Asp His Gly Leu Thr Pro
    290                 295                 300

Asp Gln Val Val Ala Ile Ala Ser His Asp Gly Gly Lys Gln Ala Leu
305                 310                 315                 320

Glu Thr Val Gln Arg Leu Leu Pro Val Leu Cys Gln Asp His Gly Leu
                325                 330                 335

Thr Pro Asp Gln Val Val Ala Ile Ala Ser His Asp Gly Gly Lys Gln
            340                 345                 350

Ala Leu Glu Thr Val Gln Arg Leu Leu Pro Val Leu Cys Gln Asp His
        355                 360                 365

Gly Leu Thr Pro Asp Gln Val Val Ala Ile Ala Ser Asn Gly Gly Gly
    370                 375                 380

Lys Gln Ala Leu Glu Thr Val Gln Arg Leu Leu Pro Val Leu Cys Gln
385                 390                 395                 400

Asp His Gly Leu Thr Pro Asp Gln Val Val Ala Ile Ala Ser Asn Asn
                405                 410                 415

Gly Gly Lys Gln Ala Leu Glu Thr Val Gln Arg Leu Leu Pro Val Leu
            420                 425                 430

Cys Gln Asp His Gly Leu Thr Pro Asp Gln Val Val Ala Ile Ala Ser
        435                 440                 445

Asn Asn Gly Gly Lys Gln Ala Leu Glu Thr Val Gln Arg Leu Leu Pro
    450                 455                 460

Val Leu Cys Gln Asp His Gly Leu Thr Pro Asp Gln Val Val Ala Ile
465                 470                 475                 480

Ala Ser Asn Asn Gly Gly Lys Gln Ala Leu Glu Thr Val Gln Arg Leu
                485                 490                 495

Leu Pro Val Leu Cys Gln Asp His Gly Leu Thr Pro Asp Gln Val Val
            500                 505                 510

Ala Ile Ala Ser Asn Gly Gly Lys Gln Ala Leu Glu Thr Val Gln
        515                 520                 525

Arg Leu Leu Pro Val Leu Cys Gln Asp His Gly Leu Thr Pro Asp Gln
    530                 535                 540

Val Val Ala Ile Ala Ser Asn Ile Gly Gly Lys Gln Ala Leu Glu Thr
545                 550                 555                 560

Val Gln Arg Leu Leu Pro Val Leu Cys Gln Asp His Gly Leu Thr Pro
                565                 570                 575

Asp Gln Val Val Ala Ile Ala Ser His Asp Gly Gly Lys Gln Ala Leu

```
                580                 585                 590
Glu Thr Val Gln Arg Leu Leu Pro Val Leu Cys Gln Asp His Gly Leu
            595                 600                 605

Thr Pro Asp Gln Val Val Ala Ile Ala Ser Asn Gly Gly Lys Gln
        610                 615                 620

Ala Leu Glu Thr Val Gln Arg Leu Leu Pro Val Leu Cys Gln Asp His
625                 630                 635                 640

Gly Leu Thr Pro Asp Gln Val Val Ala Ile Ala Ser Asn Gly Gly Gly
                645                 650                 655

Lys Gln Ala Leu Glu Thr Val Gln Arg Leu Leu Pro Val Leu Cys Gln
            660                 665                 670

Asp His Gly Leu Thr Pro Asp Gln Val Val Ala Ile Ala Ser Asn Gly
        675                 680                 685

Gly Gly Lys Gln Ala Leu Glu Thr Val Gln Arg Leu Leu Pro Val Leu
    690                 695                 700

Cys Gln Asp His Gly Leu Thr Pro Asp Gln Val Val Ala Ile Ala Ser
705                 710                 715                 720

His Asp Gly Gly Lys Gln Ala Leu Glu Thr Val Gln Arg Leu Leu Pro
                725                 730                 735

Val Leu Cys Gln Asp His Gly Leu Thr Pro Asp Gln Val Val Ala Ile
            740                 745                 750

Ala Ser Asn Gly Gly Lys Gln Ala Leu Glu Ser Ile Val Ala Gln
        755                 760                 765

Leu Ser Arg Pro Asp Pro Ala Leu Ala Ala Leu Thr Asn Asp His Leu
    770                 775                 780

Val Ala Leu Ala Cys Leu Gly Gly Arg Pro Ala Leu Asp Ala Val Lys
785                 790                 795                 800

Lys Gly Leu Pro His Ala Pro Ala Leu Ile Lys Arg Thr Asn Arg Arg
                805                 810                 815

Ile Pro Glu Arg Thr Ser His Arg Val Ala Gly Ser Gly Gly
            820                 825                 830

<210> SEQ ID NO 48
<211> LENGTH: 19
<212> TYPE: DNA
<213> ORGANISM: Artificial Sequence
<220> FEATURE:
<223> OTHER INFORMATION: BCL11A gene binding site

<400> SEQUENCE: 48
tcctcgcgct tgccctccc                                                    19

<210> SEQ ID NO 49
<211> LENGTH: 831
<212> TYPE: PRT
<213> ORGANISM: Artificial Sequence
<220> FEATURE:
<223> OTHER INFORMATION: TALE domain BCL11A #7

<400> SEQUENCE: 49

Met Gly Lys Pro Ile Pro Asn Pro Leu Leu Gly Leu Asp Ser Thr Gly
1               5                   10                  15

Gly Met Ala Pro Lys Lys Lys Arg Lys Val Asp Gly Gly Val Asp Leu
            20                  25                  30

Arg Thr Leu Gly Tyr Ser Gln Gln Gln Gln Glu Lys Ile Lys Pro Lys
        35                  40                  45

Val Arg Ser Thr Val Ala Gln His His Glu Ala Leu Val Gly His Gly
```

-continued

```
                50                  55                  60
        Phe Thr His Ala His Ile Val Ala Leu Ser Gln His Pro Ala Ala Leu
         65                  70                  75                  80
        Gly Thr Val Ala Val Lys Tyr Gln Asp Met Ile Ala Ala Leu Pro Glu
                            85                  90                  95
        Ala Thr His Glu Ala Ile Val Gly Val Gly Lys Gln Trp Ser Gly Ala
                        100                 105                 110
        Arg Ala Leu Glu Ala Leu Leu Thr Val Ala Gly Glu Leu Arg Gly Pro
                    115                 120                 125
        Pro Leu Gln Leu Asp Thr Gly Gln Leu Leu Lys Ile Ala Lys Arg Gly
                130                 135                 140
        Gly Val Thr Ala Val Glu Ala Val His Ala Trp Arg Asn Ala Leu Thr
        145                 150                 155                 160
        Gly Ala Pro Leu Asn Leu Thr Pro Asp Gln Val Val Ala Ile Ala Ser
                        165                 170                 175
        His Asp Gly Gly Lys Gln Ala Leu Glu Thr Val Gln Arg Leu Leu Pro
                    180                 185                 190
        Val Leu Cys Gln Asp His Gly Leu Thr Pro Asp Gln Val Val Ala Ile
                195                 200                 205
        Ala Ser Asn Gly Gly Lys Gln Ala Leu Glu Thr Val Gln Arg Leu
        210                 215                 220
        Leu Pro Val Leu Cys Gln Asp His Gly Leu Thr Pro Asp Gln Val Val
        225                 230                 235                 240
        Ala Ile Ala Ser His Asp Gly Gly Lys Gln Ala Leu Glu Thr Val Gln
                        245                 250                 255
        Arg Leu Leu Pro Val Leu Cys Gln Asp His Gly Leu Thr Pro Asp Gln
                    260                 265                 270
        Val Val Ala Ile Ala Ser Asn Gly Gly Lys Gln Ala Leu Glu Thr
                275                 280                 285
        Val Gln Arg Leu Leu Pro Val Leu Cys Gln Asp His Gly Leu Thr Pro
                290                 295                 300
        Asp Gln Val Val Ala Ile Ala Ser Asn Gly Gly Gly Lys Gln Ala Leu
        305                 310                 315                 320
        Glu Thr Val Gln Arg Leu Leu Pro Val Leu Cys Gln Asp His Gly Leu
                        325                 330                 335
        Thr Pro Asp Gln Val Val Ala Ile Ala Ser Asn Asn Gly Gly Lys Gln
                    340                 345                 350
        Ala Leu Glu Thr Val Gln Arg Leu Leu Pro Val Leu Cys Gln Asp His
                355                 360                 365
        Gly Leu Thr Pro Asp Gln Val Val Ala Ile Ala Ser Asn Gly Gly Gly
                370                 375                 380
        Lys Gln Ala Leu Glu Thr Val Gln Arg Leu Leu Pro Val Leu Cys Gln
        385                 390                 395                 400
        Asp His Gly Leu Thr Pro Asp Gln Val Val Ala Ile Ala Ser His Asp
                        405                 410                 415
        Gly Gly Lys Gln Ala Leu Glu Thr Val Gln Arg Leu Leu Pro Val Leu
                    420                 425                 430
        Cys Gln Asp His Gly Leu Thr Pro Asp Gln Val Val Ala Ile Ala Ser
                435                 440                 445
        His Asp Gly Gly Lys Gln Ala Leu Glu Thr Val Gln Arg Leu Leu Pro
                450                 455                 460
        Val Leu Cys Gln Asp His Gly Leu Thr Pro Asp Gln Val Val Ala Ile
        465                 470                 475                 480
```

```
Ala Ser Asn Ile Gly Gly Lys Gln Ala Leu Glu Thr Val Gln Arg Leu
            485                 490                 495

Leu Pro Val Leu Cys Gln Asp His Gly Leu Thr Pro Asp Gln Val Val
            500                 505                 510

Ala Ile Ala Ser His Asp Gly Lys Gln Ala Leu Glu Thr Val Gln
            515                 520                 525

Arg Leu Leu Pro Val Leu Cys Gln Asp His Gly Leu Thr Pro Asp Gln
        530                 535                 540

Val Val Ala Ile Ala Ser Asn Ile Gly Gly Lys Gln Ala Leu Glu Thr
545                 550                 555                 560

Val Gln Arg Leu Leu Pro Val Leu Cys Gln Asp His Gly Leu Thr Pro
                565                 570                 575

Asp Gln Val Val Ala Ile Ala Ser Asn His Gly Gly Lys Gln Ala Leu
            580                 585                 590

Glu Thr Val Gln Arg Leu Leu Pro Val Leu Cys Gln Asp His Gly Leu
            595                 600                 605

Thr Pro Asp Gln Val Val Ala Ile Ala Ser His Asp Gly Gly Lys Gln
            610                 615                 620

Ala Leu Glu Thr Val Gln Arg Leu Leu Pro Val Leu Cys Gln Asp His
625                 630                 635                 640

Gly Leu Thr Pro Asp Gln Val Val Ala Ile Ala Ser Asn Gly Gly
                645                 650                 655

Lys Gln Ala Leu Glu Thr Val Gln Arg Leu Leu Pro Val Leu Cys Gln
                660                 665                 670

Asp His Gly Leu Thr Pro Asp Gln Val Val Ala Ile Ala Ser His Asp
            675                 680                 685

Gly Gly Lys Gln Ala Leu Glu Thr Val Gln Arg Leu Leu Pro Val Leu
            690                 695                 700

Cys Gln Asp His Gly Leu Thr Pro Asp Gln Val Val Ala Ile Ala Ser
705                 710                 715                 720

Asn Asn Gly Gly Lys Gln Ala Leu Glu Thr Val Gln Arg Leu Leu Pro
                725                 730                 735

Val Leu Cys Gln Asp His Gly Leu Thr Pro Asp Gln Val Val Ala Ile
                740                 745                 750

Ala Ser Asn Asn Gly Gly Lys Gln Ala Leu Glu Ser Ile Val Ala Gln
            755                 760                 765

Leu Ser Arg Pro Asp Pro Ala Leu Ala Ala Leu Thr Asn Asp His Leu
            770                 775                 780

Val Ala Leu Ala Cys Leu Gly Gly Arg Pro Ala Leu Asp Ala Val Lys
785                 790                 795                 800

Lys Gly Leu Pro His Ala Pro Ala Leu Ile Lys Arg Thr Asn Arg Arg
                805                 810                 815

Ile Pro Glu Arg Thr Ser His Arg Val Ala Gly Ser Gly Gly
                820                 825                 830

<210> SEQ ID NO 50
<211> LENGTH: 19
<212> TYPE: DNA
<213> ORGANISM: Artificial Sequence
<220> FEATURE:
<223> OTHER INFORMATION: BCL11A gene binding site

<400> SEQUENCE: 50
tcccccggcc ctagctcct                                                    19
```

```
<210> SEQ ID NO 51
<211> LENGTH: 831
<212> TYPE: PRT
<213> ORGANISM: Artificial Sequence
<220> FEATURE:
<223> OTHER INFORMATION: TALE domain BCL11A #8

<400> SEQUENCE: 51

Met Gly Lys Pro Ile Pro Asn Pro Leu Leu Gly Leu Asp Ser Thr Gly
1               5                   10                  15

Gly Met Ala Pro Lys Lys Lys Arg Lys Val Asp Gly Val Asp Leu
            20                  25                  30

Arg Thr Leu Gly Tyr Ser Gln Gln Gln Gln Glu Lys Ile Lys Pro Lys
        35                  40                  45

Val Arg Ser Thr Val Ala Gln His His Glu Ala Leu Val Gly His Gly
    50                  55                  60

Phe Thr His Ala His Ile Val Ala Leu Ser Gln His Pro Ala Ala Leu
65                  70                  75                  80

Gly Thr Val Ala Val Lys Tyr Gln Asp Met Ile Ala Ala Leu Pro Glu
                85                  90                  95

Ala Thr His Glu Ala Ile Val Gly Val Gly Lys Gln Trp Ser Gly Ala
            100                 105                 110

Arg Ala Leu Glu Ala Leu Leu Thr Val Ala Gly Glu Leu Arg Gly Pro
        115                 120                 125

Pro Leu Gln Leu Asp Thr Gly Gln Leu Leu Lys Ile Ala Lys Arg Gly
    130                 135                 140

Gly Val Thr Ala Val Glu Ala Val His Ala Trp Arg Asn Ala Leu Thr
145                 150                 155                 160

Gly Ala Pro Leu Asn Leu Thr Pro Asp Gln Val Val Ala Ile Ala Ser
                165                 170                 175

His Asp Gly Gly Lys Gln Ala Leu Glu Thr Val Gln Arg Leu Leu Pro
            180                 185                 190

Val Leu Cys Gln Asp His Gly Leu Thr Pro Asp Gln Val Val Ala Ile
        195                 200                 205

Ala Ser Asn Gly Gly Lys Gln Ala Leu Glu Thr Val Gln Arg Leu
    210                 215                 220

Leu Pro Val Leu Cys Gln Asp His Gly Leu Thr Pro Asp Gln Val Val
225                 230                 235                 240

Ala Ile Ala Ser His Asp Gly Gly Lys Gln Ala Leu Glu Thr Val Gln
                245                 250                 255

Arg Leu Leu Pro Val Leu Cys Gln Asp His Gly Leu Thr Pro Asp Gln
            260                 265                 270

Val Val Ala Ile Ala Ser His Asp Gly Gly Lys Gln Ala Leu Glu Thr
        275                 280                 285

Val Gln Arg Leu Leu Pro Val Leu Cys Gln Asp His Gly Leu Thr Pro
    290                 295                 300

Asp Gln Val Val Ala Ile Ala Ser His Asp Gly Gly Lys Gln Ala Leu
305                 310                 315                 320

Glu Thr Val Gln Arg Leu Leu Pro Val Leu Cys Gln Asp His Gly Leu
                325                 330                 335

Thr Pro Asp Gln Val Val Ala Ile Ala Ser Asn Asn Gly Gly Lys Gln
            340                 345                 350

Ala Leu Glu Thr Val Gln Arg Leu Leu Pro Val Leu Cys Gln Asp His
        355                 360                 365
```

```
Gly Leu Thr Pro Asp Gln Val Val Ala Ile Ala Ser His Asp Gly Gly
    370                 375                 380

Lys Gln Ala Leu Glu Thr Val Gln Arg Leu Leu Pro Val Leu Cys Gln
385                 390                 395                 400

Asp His Gly Leu Thr Pro Asp Gln Val Val Ala Ile Ala Ser Asn Gly
                405                 410                 415

Gly Gly Lys Gln Ala Leu Glu Thr Val Gln Arg Leu Leu Pro Val Leu
            420                 425                 430

Cys Gln Asp His Gly Leu Thr Pro Asp Gln Val Val Ala Ile Ala Ser
                435                 440                 445

Asn Asn Gly Gly Lys Gln Ala Leu Glu Thr Val Gln Arg Leu Leu Pro
450                 455                 460

Val Leu Cys Gln Asp His Gly Leu Thr Pro Asp Gln Val Val Ala Ile
465                 470                 475                 480

Ala Ser Asn Ile Gly Gly Lys Gln Ala Leu Glu Thr Val Gln Arg Leu
                485                 490                 495

Leu Pro Val Leu Cys Gln Asp His Gly Leu Thr Pro Asp Gln Val Val
                500                 505                 510

Ala Ile Ala Ser His Asp Gly Gly Lys Gln Ala Leu Glu Thr Val Gln
            515                 520                 525

Arg Leu Leu Pro Val Leu Cys Gln Asp His Gly Leu Thr Pro Asp Gln
            530                 535                 540

Val Val Ala Ile Ala Ser Asn Gly Gly Gly Lys Gln Ala Leu Glu Thr
545                 550                 555                 560

Val Gln Arg Leu Leu Pro Val Leu Cys Gln Asp His Gly Leu Thr Pro
                565                 570                 575

Asp Gln Val Val Ala Ile Ala Ser Asn His Gly Gly Lys Gln Ala Leu
                580                 585                 590

Glu Thr Val Gln Arg Leu Leu Pro Val Leu Cys Gln Asp His Gly Leu
            595                 600                 605

Thr Pro Asp Gln Val Val Ala Ile Ala Ser His Asp Gly Gly Lys Gln
            610                 615                 620

Ala Leu Glu Thr Val Gln Arg Leu Leu Pro Val Leu Cys Gln Asp His
625                 630                 635                 640

Gly Leu Thr Pro Asp Gln Val Val Ala Ile Ala Ser Asn His Gly Gly
                645                 650                 655

Lys Gln Ala Leu Glu Thr Val Gln Arg Leu Leu Pro Val Leu Cys Gln
                660                 665                 670

Asp His Gly Leu Thr Pro Asp Gln Val Val Ala Ile Ala Ser His Asp
            675                 680                 685

Gly Gly Lys Gln Ala Leu Glu Thr Val Gln Arg Leu Leu Pro Val Leu
            690                 695                 700

Cys Gln Asp His Gly Leu Thr Pro Asp Gln Val Val Ala Ile Ala Ser
705                 710                 715                 720

His Asp Gly Gly Lys Gln Ala Leu Glu Thr Val Gln Arg Leu Leu Pro
                725                 730                 735

Val Leu Cys Gln Asp His Gly Leu Thr Pro Asp Gln Val Val Ala Ile
                740                 745                 750

Ala Ser Asn Gly Gly Gly Lys Gln Ala Leu Glu Ser Ile Val Ala Gln
            755                 760                 765

Leu Ser Arg Pro Asp Pro Ala Leu Ala Ala Leu Thr Asn Asp His Leu
            770                 775                 780

Val Ala Leu Ala Cys Leu Gly Gly Arg Pro Ala Leu Asp Ala Val Lys
```

```
                785                 790                 795                 800
Lys Gly Leu Pro His Ala Pro Ala Leu Ile Lys Arg Thr Asn Arg Arg
                805                 810                 815

Ile Pro Glu Arg Thr Ser His Arg Val Ala Gly Ser Gly Gly Gly
            820                 825                 830

<210> SEQ ID NO 52
<211> LENGTH: 19
<212> TYPE: DNA
<213> ORGANISM: Artificial Sequence
<220> FEATURE:
<223> OTHER INFORMATION: BCL11A gene binding site

<400> SEQUENCE: 52
tcctggtccg cccccagca                                                    19

<210> SEQ ID NO 53
<211> LENGTH: 831
<212> TYPE: PRT
<213> ORGANISM: Artificial Sequence
<220> FEATURE:
<223> OTHER INFORMATION: TALE domain BCL11A #9

<400> SEQUENCE: 53

Met Gly Lys Pro Ile Pro Asn Pro Leu Leu Gly Leu Asp Ser Thr Gly
1               5                   10                  15

Gly Met Ala Pro Lys Lys Lys Arg Lys Val Asp Gly Val Asp Leu
            20                  25                  30

Arg Thr Leu Gly Tyr Ser Gln Gln Gln Gln Glu Lys Ile Lys Pro Lys
        35                  40                  45

Val Arg Ser Thr Val Ala Gln His His Glu Ala Leu Val Gly His Gly
    50                  55                  60

Phe Thr His Ala His Ile Val Ala Leu Ser Gln His Pro Ala Ala Leu
65                  70                  75                  80

Gly Thr Val Ala Val Lys Tyr Gln Asp Met Ile Ala Ala Leu Pro Glu
                85                  90                  95

Ala Thr His Glu Ala Ile Val Gly Val Gly Lys Gln Trp Ser Gly Ala
            100                 105                 110

Arg Ala Leu Glu Ala Leu Leu Thr Val Ala Gly Glu Leu Arg Gly Pro
        115                 120                 125

Pro Leu Gln Leu Asp Thr Gly Gln Leu Leu Lys Ile Ala Lys Arg Gly
    130                 135                 140

Gly Val Thr Ala Val Glu Ala Val His Ala Trp Arg Asn Ala Leu Thr
145                 150                 155                 160

Gly Ala Pro Leu Asn Leu Thr Pro Asp Gln Val Val Ala Ile Ala Ser
                165                 170                 175

His Asp Gly Gly Lys Gln Ala Leu Glu Thr Val Gln Arg Leu Leu Pro
            180                 185                 190

Val Leu Cys Gln Asp His Gly Leu Thr Pro Asp Gln Val Val Ala Ile
        195                 200                 205

Ala Ser His Asp Gly Gly Lys Gln Ala Leu Glu Thr Val Gln Arg Leu
    210                 215                 220

Leu Pro Val Leu Cys Gln Asp His Gly Leu Thr Pro Asp Gln Val Val
225                 230                 235                 240

Ala Ile Ala Ser His Asp Gly Gly Lys Gln Ala Leu Glu Thr Val Gln
                245                 250                 255

Arg Leu Leu Pro Val Leu Cys Gln Asp His Gly Leu Thr Pro Asp Gln
```

```
                260             265             270
Val Val Ala Ile Ala Ser Asn Gly Gly Gly Lys Gln Ala Leu Glu Thr
            275             280             285
Val Gln Arg Leu Leu Pro Val Leu Cys Gln Asp His Gly Leu Thr Pro
            290             295             300
Asp Gln Val Val Ala Ile Ala Ser Asn Gly Gly Gly Lys Gln Ala Leu
305             310             315             320
Glu Thr Val Gln Arg Leu Leu Pro Val Leu Cys Gln Asp His Gly Leu
                325             330             335
Thr Pro Asp Gln Val Val Ala Ile Ala Ser Asn Asn Gly Gly Lys Gln
                340             345             350
Ala Leu Glu Thr Val Gln Arg Leu Leu Pro Val Leu Cys Gln Asp His
            355             360             365
Gly Leu Thr Pro Asp Gln Val Val Ala Ile Ala Ser His Asp Gly Gly
            370             375             380
Lys Gln Ala Leu Glu Thr Val Gln Arg Leu Leu Pro Val Leu Cys Gln
385             390             395             400
Asp His Gly Leu Thr Pro Asp Gln Val Val Ala Ile Ala Ser Asn Gly
                405             410             415
Gly Gly Lys Gln Ala Leu Glu Thr Val Gln Arg Leu Leu Pro Val Leu
                420             425             430
Cys Gln Asp His Gly Leu Thr Pro Asp Gln Val Val Ala Ile Ala Ser
                435             440             445
Asn Asn Gly Gly Lys Gln Ala Leu Glu Thr Val Gln Arg Leu Leu Pro
        450             455             460
Val Leu Cys Gln Asp His Gly Leu Thr Pro Asp Gln Val Val Ala Ile
465             470             475             480
Ala Ser His Asp Gly Gly Lys Gln Ala Leu Glu Thr Val Gln Arg Leu
                485             490             495
Leu Pro Val Leu Cys Gln Asp His Gly Leu Thr Pro Asp Gln Val Val
                500             505             510
Ala Ile Ala Ser His Asp Gly Gly Lys Gln Ala Leu Glu Thr Val Gln
                515             520             525
Arg Leu Leu Pro Val Leu Cys Gln Asp His Gly Leu Thr Pro Asp Gln
            530             535             540
Val Val Ala Ile Ala Ser Asn Ile Gly Gly Lys Gln Ala Leu Glu Thr
545             550             555             560
Val Gln Arg Leu Leu Pro Val Leu Cys Gln Asp His Gly Leu Thr Pro
            565             570             575
Asp Gln Val Val Ala Ile Ala Ser Asn Ile Gly Gly Lys Gln Ala Leu
            580             585             590
Glu Thr Val Gln Arg Leu Leu Pro Val Leu Cys Gln Asp His Gly Leu
                595             600             605
Thr Pro Asp Gln Val Val Ala Ile Ala Ser Asn Ile Gly Gly Lys Gln
                610             615             620
Ala Leu Glu Thr Val Gln Arg Leu Leu Pro Val Leu Cys Gln Asp His
625             630             635             640
Gly Leu Thr Pro Asp Gln Val Val Ala Ile Ala Ser His Asp Gly Gly
                645             650             655
Lys Gln Ala Leu Glu Thr Val Gln Arg Leu Leu Pro Val Leu Cys Gln
                660             665             670
Asp His Gly Leu Thr Pro Asp Gln Val Val Ala Ile Ala Ser Asn Gly
                675             680             685
```

```
Gly Gly Lys Gln Ala Leu Glu Thr Val Gln Arg Leu Leu Pro Val Leu
        690                 695                 700
Cys Gln Asp His Gly Leu Thr Pro Asp Gln Val Val Ala Ile Ala Ser
705                 710                 715                 720
Asn Gly Gly Lys Gln Ala Leu Glu Thr Val Gln Arg Leu Leu Pro
                725                 730                 735
Val Leu Cys Gln Asp His Gly Leu Thr Pro Asp Gln Val Val Ala Ile
                740                 745                 750
Ala Ser Asn Gly Gly Lys Gln Ala Leu Glu Ser Ile Val Ala Gln
        755                 760                 765
Leu Ser Arg Pro Asp Pro Ala Leu Ala Ala Leu Thr Asn Asp His Leu
    770                 775                 780
Val Ala Leu Ala Cys Leu Gly Gly Arg Pro Ala Leu Asp Ala Val Lys
785                 790                 795                 800
Lys Gly Leu Pro His Ala Pro Ala Leu Ile Lys Arg Thr Asn Arg Arg
                805                 810                 815
Ile Pro Glu Arg Thr Ser His Arg Val Ala Gly Ser Gly Gly
            820                 825                 830
```

<210> SEQ ID NO 54
<211> LENGTH: 19
<212> TYPE: DNA
<213> ORGANISM: Artificial Sequence
<220> FEATURE:
<223> OTHER INFORMATION: BCL11A gene binding site

<400> SEQUENCE: 54
tgccgagacc tcttctcga                                                19

<210> SEQ ID NO 55
<211> LENGTH: 831
<212> TYPE: PRT
<213> ORGANISM: Artificial Sequence
<220> FEATURE:
<223> OTHER INFORMATION: TALE domain BCL11A #10

<400> SEQUENCE: 55

```
Met Gly Lys Pro Ile Pro Asn Pro Leu Leu Gly Leu Asp Ser Thr Gly
1               5                   10                  15
Gly Met Ala Pro Lys Lys Arg Lys Val Asp Gly Gly Val Asp Leu
            20                  25                  30
Arg Thr Leu Gly Tyr Ser Gln Gln Gln Gln Glu Lys Ile Lys Pro Lys
        35                  40                  45
Val Arg Ser Thr Val Ala Gln His His Glu Ala Leu Val Gly His Gly
    50                  55                  60
Phe Thr His Ala His Ile Val Ala Leu Ser Gln His Pro Ala Ala Leu
65                  70                  75                  80
Gly Thr Val Ala Val Lys Tyr Gln Asp Met Ile Ala Ala Leu Pro Glu
                85                  90                  95
Ala Thr His Glu Ala Ile Val Gly Val Gly Lys Gln Trp Ser Gly Ala
            100                 105                 110
Arg Ala Leu Glu Ala Leu Leu Thr Val Ala Gly Glu Leu Arg Gly Pro
        115                 120                 125
Pro Leu Gln Leu Asp Thr Gly Gln Leu Leu Lys Ile Ala Lys Arg Gly
    130                 135                 140
Gly Val Thr Ala Val Glu Ala Val His Ala Trp Arg Asn Ala Leu Thr
145                 150                 155                 160
```

```
Gly Ala Pro Leu Asn Leu Thr Pro Asp Gln Val Ala Ile Ala Ser
            165                 170                 175

Asn Asn Gly Gly Lys Gln Ala Leu Glu Thr Val Lys Arg Leu Leu Pro
        180                 185                 190

Val Leu Cys Gln Asp His Gly Leu Thr Pro Asp Gln Val Val Ala Ile
        195                 200                 205

Ala Ser Asn Asn Gly Gly Lys Gln Ala Leu Glu Thr Val Gln Arg Leu
210                 215                 220

Leu Pro Val Leu Cys Gln Asp His Gly Leu Thr Pro Asp Gln Val Val
225                 230                 235                 240

Ala Ile Ala Ser Asn Asn Gly Gly Lys Gln Ala Leu Glu Thr Val Gln
            245                 250                 255

Arg Leu Leu Pro Val Leu Cys Gln Asp His Gly Leu Thr Pro Asp Gln
            260                 265                 270

Val Val Ala Ile Ala Ser His Asp Gly Gly Lys Gln Ala Leu Glu Thr
        275                 280                 285

Val Gln Arg Leu Leu Pro Val Leu Cys Gln Asp His Gly Leu Thr Pro
        290                 295                 300

Asp Gln Val Val Ala Ile Ala Ser His Asp Gly Gly Lys Gln Ala Leu
305                 310                 315                 320

Glu Thr Val Gln Arg Leu Leu Pro Val Leu Cys Gln Asp His Gly Leu
            325                 330                 335

Thr Pro Asp Gln Val Val Ala Ile Ala Ser His Asp Gly Gly Lys Gln
            340                 345                 350

Ala Leu Glu Thr Val Gln Arg Leu Leu Pro Val Leu Cys Gln Asp His
        355                 360                 365

Gly Leu Thr Pro Asp Gln Val Val Ala Ile Ala Ser Asn Gly Gly Gly
        370                 375                 380

Lys Gln Ala Leu Glu Thr Val Gln Arg Leu Leu Pro Val Leu Cys Gln
385                 390                 395                 400

Asp His Gly Leu Thr Pro Asp Gln Val Val Ala Ile Ala Ser His Asp
            405                 410                 415

Gly Gly Lys Gln Ala Leu Glu Thr Val Gln Arg Leu Leu Pro Val Leu
            420                 425                 430

Cys Gln Asp His Gly Leu Thr Pro Asp Gln Val Val Ala Ile Ala Ser
        435                 440                 445

Asn Ile Gly Gly Lys Gln Ala Leu Glu Thr Val Gln Arg Leu Leu Pro
450                 455                 460

Val Leu Cys Gln Asp His Gly Leu Thr Pro Asp Gln Val Val Ala Ile
465                 470                 475                 480

Ala Ser His Asp Gly Gly Lys Gln Ala Leu Glu Thr Val Gln Arg Leu
            485                 490                 495

Leu Pro Val Leu Cys Gln Asp His Gly Leu Thr Pro Asp Gln Val Val
            500                 505                 510

Ala Ile Ala Ser Asn Asn Gly Gly Lys Gln Ala Leu Glu Thr Val Gln
        515                 520                 525

Arg Leu Leu Pro Val Leu Cys Gln Asp His Gly Leu Thr Pro Asp Gln
        530                 535                 540

Val Val Ala Ile Ala Ser His Asp Gly Gly Lys Gln Ala Leu Glu Thr
545                 550                 555                 560

Val Gln Arg Leu Leu Pro Val Leu Cys Gln Asp His Gly Leu Thr Pro
            565                 570                 575
```

```
Asp Gln Val Val Ala Ile Ala Ser His Asp Gly Gly Lys Gln Ala Leu
            580                 585                 590

Glu Thr Val Gln Arg Leu Leu Pro Val Leu Cys Gln Asp His Gly Leu
        595                 600                 605

Thr Pro Asp Gln Val Val Ala Ile Ala Ser Asn Gly Gly Lys Gln
    610                 615                 620

Ala Leu Glu Thr Val Gln Arg Leu Leu Pro Val Leu Cys Gln Asp His
625                 630                 635                 640

Gly Leu Thr Pro Asp Gln Val Val Ala Ile Ala Ser Asn Gly Gly
            645                 650                 655

Lys Gln Ala Leu Glu Thr Val Gln Arg Leu Leu Pro Val Leu Cys Gln
        660                 665                 670

Asp His Gly Leu Thr Pro Asp Gln Val Val Ala Ile Ala Ser Asn Gly
    675                 680                 685

Gly Gly Lys Gln Ala Leu Glu Thr Val Gln Arg Leu Leu Pro Val Leu
            690                 695                 700

Cys Gln Asp His Gly Leu Thr Pro Asp Gln Val Val Ala Ile Ala Ser
705                 710                 715                 720

His Asp Gly Gly Lys Gln Ala Leu Glu Thr Val Gln Arg Leu Leu Pro
            725                 730                 735

Val Leu Cys Gln Asp His Gly Leu Thr Pro Asp Gln Val Val Ala Ile
        740                 745                 750

Ala Ser Asn Gly Gly Gly Lys Gln Ala Leu Glu Ser Ile Val Ala Gln
            755                 760                 765

Leu Ser Arg Pro Asp Pro Ala Leu Ala Ala Leu Thr Asn Asp His Leu
        770                 775                 780

Val Ala Leu Ala Cys Leu Gly Gly Arg Pro Ala Leu Asp Ala Val Lys
785                 790                 795                 800

Lys Gly Leu Pro His Ala Pro Ala Leu Ile Lys Arg Thr Asn Arg Arg
            805                 810                 815

Ile Pro Glu Arg Thr Ser His Arg Val Ala Gly Ser Gly Gly
        820                 825                 830

<210> SEQ ID NO 56
<211> LENGTH: 19
<212> TYPE: DNA
<213> ORGANISM: Artificial Sequence
<220> FEATURE:
<223> OTHER INFORMATION: BCL11A gene binding site

<400> SEQUENCE: 56
tcggctttgc aaagcattt                                                19

<210> SEQ ID NO 57
<211> LENGTH: 831
<212> TYPE: PRT
<213> ORGANISM: Artificial Sequence
<220> FEATURE:
<223> OTHER INFORMATION: TALE domain BCL11A #11

<400> SEQUENCE: 57

Met Gly Lys Pro Ile Pro Asn Pro Leu Leu Gly Leu Asp Ser Thr Gly
1               5                   10                  15

Gly Met Ala Pro Lys Lys Lys Arg Lys Val Asp Gly Gly Val Asp Leu
            20                  25                  30

Arg Thr Leu Gly Tyr Ser Gln Gln Gln Gln Glu Lys Ile Lys Pro Lys
        35                  40                  45
```

```
Val Arg Ser Thr Val Ala Gln His His Glu Ala Leu Val Gly His Gly
 50                  55                  60

Phe Thr His Ala His Ile Val Ala Leu Ser Gln His Pro Ala Ala Leu
 65                  70                  75                  80

Gly Thr Val Ala Val Lys Tyr Gln Asp Met Ile Ala Ala Leu Pro Glu
                 85                  90                  95

Ala Thr His Glu Ala Ile Val Gly Val Gly Lys Gln Trp Ser Gly Ala
            100                 105                 110

Arg Ala Leu Glu Ala Leu Leu Thr Val Ala Gly Glu Leu Arg Gly Pro
            115                 120                 125

Pro Leu Gln Leu Asp Thr Gly Gln Leu Leu Lys Ile Ala Lys Arg Gly
130                 135                 140

Gly Val Thr Ala Val Glu Ala Val His Ala Trp Arg Asn Ala Leu Thr
145                 150                 155                 160

Gly Ala Pro Leu Asn Leu Thr Pro Asp Gln Val Val Ala Ile Ala Ser
                165                 170                 175

His Asp Gly Gly Lys Gln Ala Leu Glu Thr Val Gln Arg Leu Leu Pro
            180                 185                 190

Val Leu Cys Gln Asp His Gly Leu Thr Pro Asp Gln Val Val Ala Ile
            195                 200                 205

Ala Ser Asn Gly Gly Gly Lys Gln Ala Leu Glu Thr Val Gln Arg Leu
210                 215                 220

Leu Pro Val Leu Cys Gln Asp His Gly Leu Thr Pro Asp Gln Val Val
225                 230                 235                 240

Ala Ile Ala Ser His Asp Gly Gly Lys Gln Ala Leu Glu Thr Val Gln
                245                 250                 255

Arg Leu Leu Pro Val Leu Cys Gln Asp His Gly Leu Thr Pro Asp Gln
            260                 265                 270

Val Val Ala Ile Ala Ser His Asp Gly Gly Lys Gln Ala Leu Glu Thr
            275                 280                 285

Val Gln Arg Leu Leu Pro Val Leu Cys Gln Asp His Gly Leu Thr Pro
            290                 295                 300

Asp Gln Val Val Ala Ile Ala Ser His Asp Gly Gly Lys Gln Ala Leu
305                 310                 315                 320

Glu Thr Val Gln Arg Leu Leu Pro Val Leu Cys Gln Asp His Gly Leu
                325                 330                 335

Thr Pro Asp Gln Val Val Ala Ile Ala Ser His Asp Gly Gly Lys Gln
            340                 345                 350

Ala Leu Glu Thr Val Gln Arg Leu Leu Pro Val Leu Cys Gln Asp His
            355                 360                 365

Gly Leu Thr Pro Asp Gln Val Val Ala Ile Ala Ser Asn Asn Gly Gly
370                 375                 380

Lys Gln Ala Leu Glu Thr Val Gln Arg Leu Leu Pro Val Leu Cys Gln
385                 390                 395                 400

Asp His Gly Leu Thr Pro Asp Gln Val Val Ala Ile Ala Ser Asn Asn
                405                 410                 415

Gly Gly Lys Gln Ala Leu Glu Thr Val Gln Arg Leu Leu Pro Val Leu
            420                 425                 430

Cys Gln Asp His Gly Leu Thr Pro Asp Gln Val Val Ala Ile Ala Ser
            435                 440                 445

Asn Asn Gly Gly Lys Gln Ala Leu Glu Thr Val Gln Arg Leu Leu Pro
450                 455                 460

Val Leu Cys Gln Asp His Gly Leu Thr Pro Asp Gln Val Val Ala Ile
```

```
                465                 470                 475                 480
        Ala Ser Asn Ile Gly Gly Lys Gln Ala Leu Glu Thr Val Gln Arg Leu
                        485                 490                 495

Leu Pro Val Leu Cys Gln Asp His Gly Leu Thr Pro Asp Gln Val Val
                        500                 505                 510

Ala Ile Ala Ser Asn Ile Gly Gly Lys Gln Ala Leu Glu Thr Val Gln
                        515                 520                 525

Arg Leu Leu Pro Val Leu Cys Gln Asp His Gly Leu Thr Pro Asp Gln
                        530                 535                 540

Val Val Ala Ile Ala Ser Asn Gly Gly Lys Gln Ala Leu Glu Thr
        545                 550                 555                 560

Val Gln Arg Leu Leu Pro Val Leu Cys Gln Asp His Gly Leu Thr Pro
                        565                 570                 575

Asp Gln Val Val Ala Ile Ala Ser His Asp Gly Gly Lys Gln Ala Leu
                        580                 585                 590

Glu Thr Val Gln Arg Leu Leu Pro Val Leu Cys Gln Asp His Gly Leu
                        595                 600                 605

Thr Pro Asp Gln Val Val Ala Ile Ala Ser Asn Asn Gly Gly Lys Gln
                        610                 615                 620

Ala Leu Glu Thr Val Gln Arg Leu Leu Pro Val Leu Cys Gln Asp His
        625                 630                 635                 640

Gly Leu Thr Pro Asp Gln Val Val Ala Ile Ala Ser Asn Gly Gly Gly
                        645                 650                 655

Lys Gln Ala Leu Glu Thr Val Gln Arg Leu Leu Pro Val Leu Cys Gln
                        660                 665                 670

Asp His Gly Leu Thr Pro Asp Gln Val Val Ala Ile Ala Ser Asn Gly
                        675                 680                 685

Gly Gly Lys Gln Ala Leu Glu Thr Val Gln Arg Leu Leu Pro Val Leu
                        690                 695                 700

Cys Gln Asp His Gly Leu Thr Pro Asp Gln Val Val Ala Ile Ala Ser
        705                 710                 715                 720

Asn Gly Gly Gly Lys Gln Ala Leu Glu Thr Val Gln Arg Leu Leu Pro
                        725                 730                 735

Val Leu Cys Gln Asp His Gly Leu Thr Pro Asp Gln Val Val Ala Ile
                        740                 745                 750

Ala Ser Asn Gly Gly Gly Lys Gln Ala Leu Glu Ser Ile Val Ala Gln
                        755                 760                 765

Leu Ser Arg Pro Asp Pro Ala Leu Ala Ala Leu Thr Asn Asp His Leu
                        770                 775                 780

Val Ala Leu Ala Cys Leu Gly Gly Arg Pro Ala Leu Asp Ala Val Lys
        785                 790                 795                 800

Lys Gly Leu Pro His Ala Pro Ala Leu Ile Lys Arg Thr Asn Arg Arg
                        805                 810                 815

Ile Pro Glu Arg Thr Ser His Arg Val Ala Gly Ser Gly Gly
                        820                 825                 830

<210> SEQ ID NO 58
<211> LENGTH: 19
<212> TYPE: DNA
<213> ORGANISM: Artificial Sequence
<220> FEATURE:
<223> OTHER INFORMATION: BCL11A gene binding site

<400> SEQUENCE: 58
tgcaaagccg agtttcacc                                                     19
```

<210> SEQ ID NO 59
<211> LENGTH: 831
<212> TYPE: PRT
<213> ORGANISM: Artificial Sequence
<220> FEATURE:
<223> OTHER INFORMATION: TALE domain BCL11A #12

<400> SEQUENCE: 59

```
Met Gly Lys Pro Ile Pro Asn Pro Leu Leu Gly Leu Asp Ser Thr Gly
1               5                   10                  15

Gly Met Ala Pro Lys Lys Lys Arg Lys Val Asp Gly Gly Val Asp Leu
            20                  25                  30

Arg Thr Leu Gly Tyr Ser Gln Gln Gln Glu Lys Ile Lys Pro Lys
        35                  40                  45

Val Arg Ser Thr Val Ala Gln His His Glu Ala Leu Val Gly His Gly
    50                  55                  60

Phe Thr His Ala His Ile Val Ala Leu Ser Gln His Pro Ala Ala Leu
65                  70                  75                  80

Gly Thr Val Ala Val Lys Tyr Gln Asp Met Ile Ala Ala Leu Pro Glu
                85                  90                  95

Ala Thr His Glu Ala Ile Val Gly Val Gly Lys Gln Trp Ser Gly Ala
            100                 105                 110

Arg Ala Leu Glu Ala Leu Leu Thr Val Ala Gly Glu Leu Arg Gly Pro
        115                 120                 125

Pro Leu Gln Leu Asp Thr Gly Gln Leu Leu Lys Ile Ala Lys Arg Gly
    130                 135                 140

Gly Val Thr Ala Val Glu Ala Val His Ala Trp Arg Asn Ala Leu Thr
145                 150                 155                 160

Gly Ala Pro Leu Asn Leu Thr Pro Asp Gln Val Val Ala Ile Ala Ser
                165                 170                 175

His Asp Gly Gly Lys Gln Ala Leu Glu Thr Val Gln Arg Leu Leu Pro
            180                 185                 190

Val Leu Cys Gln Asp His Gly Leu Thr Pro Asp Gln Val Val Ala Ile
        195                 200                 205

Ala Ser His Asp Gly Gly Lys Gln Ala Leu Glu Thr Val Gln Arg Leu
    210                 215                 220

Leu Pro Val Leu Cys Gln Asp His Gly Leu Thr Pro Asp Gln Val Val
225                 230                 235                 240

Ala Ile Ala Ser Asn Ile Gly Gly Lys Gln Ala Leu Glu Thr Val Gln
                245                 250                 255

Arg Leu Leu Pro Val Leu Cys Gln Asp His Gly Leu Thr Pro Asp Gln
            260                 265                 270

Val Val Ala Ile Ala Ser Asn Ile Gly Gly Lys Gln Ala Leu Glu Thr
        275                 280                 285

Val Gln Arg Leu Leu Pro Val Leu Cys Gln Asp His Gly Leu Thr Pro
    290                 295                 300

Asp Gln Val Val Ala Ile Ala Ser Asn Ile Gly Gly Lys Gln Ala Leu
305                 310                 315                 320

Glu Thr Val Gln Arg Leu Leu Pro Val Leu Cys Gln Asp His Gly Leu
                325                 330                 335

Thr Pro Asp Gln Val Val Ala Ile Ala Ser Asn Ile Gly Gly Lys Gln
            340                 345                 350

Ala Leu Glu Thr Val Gln Arg Leu Leu Pro Val Leu Cys Gln Asp His
        355                 360                 365
```

```
Gly Leu Thr Pro Asp Gln Val Ala Ile Ala Ser Asn His Gly Gly
        370                 375                 380

Lys Gln Ala Leu Glu Thr Val Gln Arg Leu Leu Pro Val Leu Cys Gln
385                 390                 395                 400

Asp His Gly Leu Thr Pro Asp Gln Val Val Ala Ile Ala Ser His Asp
                    405                 410                 415

Gly Gly Lys Gln Ala Leu Glu Thr Val Gln Arg Leu Leu Pro Val Leu
                420                 425                 430

Cys Gln Asp His Gly Leu Thr Pro Asp Gln Val Val Ala Ile Ala Ser
                435                 440                 445

His Asp Gly Gly Lys Gln Ala Leu Glu Thr Val Gln Arg Leu Leu Pro
450                 455                 460

Val Leu Cys Gln Asp His Gly Leu Thr Pro Asp Gln Val Val Ala Ile
465                 470                 475                 480

Ala Ser Asn Ile Gly Gly Lys Gln Ala Leu Glu Thr Val Gln Arg Leu
                    485                 490                 495

Leu Pro Val Leu Cys Gln Asp His Gly Leu Thr Pro Asp Gln Val Val
                500                 505                 510

Ala Ile Ala Ser Asn Asn Gly Gly Lys Gln Ala Leu Glu Thr Val Gln
515                 520                 525

Arg Leu Leu Pro Val Leu Cys Gln Asp His Gly Leu Thr Pro Asp Gln
530                 535                 540

Val Val Ala Ile Ala Ser Asn Gly Gly Gly Lys Gln Ala Leu Glu Thr
545                 550                 555                 560

Val Gln Arg Leu Leu Pro Val Leu Cys Gln Asp His Gly Leu Thr Pro
                565                 570                 575

Asp Gln Val Val Ala Ile Ala Ser His Asp Gly Gly Lys Gln Ala Leu
                580                 585                 590

Glu Thr Val Gln Arg Leu Leu Pro Val Leu Cys Gln Asp His Gly Leu
                595                 600                 605

Thr Pro Asp Gln Val Val Ala Ile Ala Ser Asn Gly Gly Gly Lys Gln
                610                 615                 620

Ala Leu Glu Thr Val Gln Arg Leu Leu Pro Val Leu Cys Gln Asp His
625                 630                 635                 640

Gly Leu Thr Pro Asp Gln Val Val Ala Ile Ala Ser His Asp Gly Gly
                    645                 650                 655

Lys Gln Ala Leu Glu Thr Val Gln Arg Leu Leu Pro Val Leu Cys Gln
                660                 665                 670

Asp His Gly Leu Thr Pro Asp Gln Val Val Ala Ile Ala Ser Asn Ile
                675                 680                 685

Gly Gly Lys Gln Ala Leu Glu Thr Val Gln Arg Leu Leu Pro Val Leu
                690                 695                 700

Cys Gln Asp His Gly Leu Thr Pro Asp Gln Val Val Ala Ile Ala Ser
705                 710                 715                 720

His Asp Gly Gly Lys Gln Ala Leu Glu Thr Val Gln Arg Leu Leu Pro
                725                 730                 735

Val Leu Cys Gln Asp His Gly Leu Thr Pro Asp Gln Val Val Ala Ile
                740                 745                 750

Ala Ser His Asp Gly Gly Lys Gln Ala Leu Glu Ser Ile Val Ala Gln
                755                 760                 765

Leu Ser Arg Pro Asp Pro Ala Leu Ala Ala Leu Thr Asn Asp His Leu
770                 775                 780
```

```
Val Ala Leu Ala Cys Leu Gly Gly Arg Pro Ala Leu Asp Ala Val Lys
785                 790                 795                 800

Lys Gly Leu Pro His Ala Pro Ala Leu Ile Lys Arg Thr Asn Arg Arg
            805                 810                 815

Ile Pro Glu Arg Thr Ser His Arg Val Ala Gly Ser Gly Gly Gly
        820                 825                 830

<210> SEQ ID NO 60
<211> LENGTH: 19
<212> TYPE: DNA
<213> ORGANISM: Artificial Sequence
<220> FEATURE:
<223> OTHER INFORMATION: BCL11A gene binding site

<400> SEQUENCE: 60
tacagttgcc ctgcaaaat                                                 19

<210> SEQ ID NO 61
<211> LENGTH: 831
<212> TYPE: PRT
<213> ORGANISM: Artificial Sequence
<220> FEATURE:
<223> OTHER INFORMATION: TALE domain BCL11A #13

<400> SEQUENCE: 61

Met Gly Lys Pro Ile Pro Asn Pro Leu Leu Gly Leu Asp Ser Thr Gly
1               5                   10                  15

Gly Met Ala Pro Lys Lys Lys Arg Lys Val Asp Gly Val Asp Leu
            20                  25                  30

Arg Thr Leu Gly Tyr Ser Gln Gln Gln Glu Lys Ile Lys Pro Lys
        35                  40                  45

Val Arg Ser Thr Val Ala Gln His His Glu Ala Leu Val Gly His Gly
50                  55                  60

Phe Thr His Ala His Ile Val Ala Leu Ser Gln His Pro Ala Ala Leu
65                  70                  75                  80

Gly Thr Val Ala Val Lys Tyr Gln Asp Met Ile Ala Ala Leu Pro Glu
                85                  90                  95

Ala Thr His Glu Ala Ile Val Gly Val Gly Lys Gln Trp Ser Gly Ala
            100                 105                 110

Arg Ala Leu Glu Ala Leu Leu Thr Val Ala Gly Glu Leu Arg Gly Pro
        115                 120                 125

Pro Leu Gln Leu Asp Thr Gly Gln Leu Leu Lys Ile Ala Lys Arg Gly
    130                 135                 140

Gly Val Thr Ala Val Glu Ala Val His Ala Trp Arg Asn Ala Leu Thr
145                 150                 155                 160

Gly Ala Pro Leu Asn Leu Thr Pro Asp Gln Val Val Ala Ile Ala Ser
                165                 170                 175

His Asp Gly Gly Lys Gln Ala Leu Glu Thr Val Gln Arg Leu Leu Pro
            180                 185                 190

Val Leu Cys Gln Asp His Gly Leu Thr Pro Asp Gln Val Val Ala Ile
        195                 200                 205

Ala Ser His Asp Gly Gly Lys Gln Ala Leu Glu Thr Val Gln Arg Leu
    210                 215                 220

Leu Pro Val Leu Cys Gln Asp His Gly Leu Thr Pro Asp Gln Val Val
225                 230                 235                 240

Ala Ile Ala Ser Asn Gly Gly Gly Lys Gln Ala Leu Glu Thr Val Gln
                245                 250                 255
```

```
Arg Leu Leu Pro Val Leu Cys Gln Asp His Gly Leu Thr Pro Asp Gln
            260                 265                 270

Val Val Ala Ile Ala Ser His Asp Gly Gly Lys Gln Ala Leu Glu Thr
        275                 280                 285

Val Gln Arg Leu Leu Pro Val Leu Cys Gln Asp His Gly Leu Thr Pro
    290                 295                 300

Asp Gln Val Val Ala Ile Ala Ser His Asp Gly Gly Lys Gln Ala Leu
305                 310                 315                 320

Glu Thr Val Gln Arg Leu Leu Pro Val Leu Cys Gln Asp His Gly Leu
                325                 330                 335

Thr Pro Asp Gln Val Val Ala Ile Ala Ser His Asp Gly Gly Lys Gln
            340                 345                 350

Ala Leu Glu Thr Val Gln Arg Leu Leu Pro Val Leu Cys Gln Asp His
        355                 360                 365

Gly Leu Thr Pro Asp Gln Val Val Ala Ile Ala Ser Asn Asn Gly Gly
    370                 375                 380

Lys Gln Ala Leu Glu Thr Val Gln Arg Leu Leu Pro Val Leu Cys Gln
385                 390                 395                 400

Asp His Gly Leu Thr Pro Asp Gln Val Val Ala Ile Ala Ser His Asp
                405                 410                 415

Gly Gly Lys Gln Ala Leu Glu Thr Val Gln Arg Leu Leu Pro Val Leu
            420                 425                 430

Cys Gln Asp His Gly Leu Thr Pro Asp Gln Val Val Ala Ile Ala Ser
        435                 440                 445

Asn Gly Gly Lys Gln Ala Leu Glu Thr Val Gln Arg Leu Leu Pro
    450                 455                 460

Val Leu Cys Gln Asp His Gly Leu Thr Pro Asp Gln Val Val Ala Ile
465                 470                 475                 480

Ala Ser Asn Asn Gly Gly Lys Gln Ala Leu Glu Thr Val Gln Arg Leu
                485                 490                 495

Leu Pro Val Leu Cys Gln Asp His Gly Leu Thr Pro Asp Gln Val Val
            500                 505                 510

Ala Ile Ala Ser His Asp Gly Gly Lys Gln Ala Leu Glu Thr Val Gln
        515                 520                 525

Arg Leu Leu Pro Val Leu Cys Gln Asp His Gly Leu Thr Pro Asp Gln
    530                 535                 540

Val Val Ala Ile Ala Ser Asn Ile Gly Gly Lys Gln Ala Leu Glu Thr
545                 550                 555                 560

Val Gln Arg Leu Leu Pro Val Leu Cys Gln Asp His Gly Leu Thr Pro
                565                 570                 575

Asp Gln Val Val Ala Ile Ala Ser His Asp Gly Gly Lys Gln Ala Leu
            580                 585                 590

Glu Thr Val Gln Arg Leu Leu Pro Val Leu Cys Gln Asp His Gly Leu
        595                 600                 605

Thr Pro Asp Gln Val Val Ala Ile Ala Ser Asn Ile Gly Gly Lys Gln
    610                 615                 620

Ala Leu Glu Thr Val Gln Arg Leu Leu Pro Val Leu Cys Gln Asp His
625                 630                 635                 640

Gly Leu Thr Pro Asp Gln Val Val Ala Ile Ala Ser His Asp Gly Gly
                645                 650                 655

Lys Gln Ala Leu Glu Thr Val Gln Arg Leu Leu Pro Val Leu Cys Gln
            660                 665                 670

Asp His Gly Leu Thr Pro Asp Gln Val Val Ala Ile Ala Ser Asn Gly
```

```
                675                 680                 685
Gly Gly Lys Gln Ala Leu Glu Thr Val Gln Arg Leu Leu Pro Val Leu
        690                 695                 700

Cys Gln Asp His Gly Leu Thr Pro Asp Gln Val Val Ala Ile Ala Ser
705                 710                 715                 720

Asn Gly Gly Gly Lys Gln Ala Leu Glu Thr Val Gln Arg Leu Leu Pro
                725                 730                 735

Val Leu Cys Gln Asp His Gly Leu Thr Pro Asp Gln Val Val Ala Ile
            740                 745                 750

Ala Ser Asn Asn Gly Gly Lys Gln Ala Leu Glu Ser Ile Val Ala Gln
        755                 760                 765

Leu Ser Arg Pro Asp Pro Ala Leu Ala Ala Leu Thr Asn Asp His Leu
        770                 775                 780

Val Ala Leu Ala Cys Leu Gly Gly Arg Pro Ala Leu Asp Ala Val Lys
785                 790                 795                 800

Lys Gly Leu Pro His Ala Pro Ala Leu Ile Lys Arg Thr Asn Arg Arg
                805                 810                 815

Ile Pro Glu Arg Thr Ser His Arg Val Ala Gly Ser Gly Gly Gly
                820                 825                 830
```

<210> SEQ ID NO 62
<211> LENGTH: 19
<212> TYPE: DNA
<213> ORGANISM: Artificial Sequence
<220> FEATURE:
<223> OTHER INFORMATION: BCL11A gene binding site

<400> SEQUENCE: 62
tccgccctgg gtactttct                                                19

<210> SEQ ID NO 63
<211> LENGTH: 831
<212> TYPE: PRT
<213> ORGANISM: Artificial Sequence
<220> FEATURE:
<223> OTHER INFORMATION: TALE domain BCL11A #14

<400> SEQUENCE: 63

```
Met Gly Lys Pro Ile Pro Asn Pro Leu Leu Gly Leu Asp Ser Thr Gly
1               5                   10                  15

Gly Met Ala Pro Lys Lys Lys Arg Lys Val Asp Gly Val Asp Leu
            20                  25                  30

Arg Thr Leu Gly Tyr Ser Gln Gln Gln Gln Glu Lys Ile Lys Pro Lys
        35                  40                  45

Val Arg Ser Thr Val Ala Gln His His Glu Ala Leu Val Gly His Gly
    50                  55                  60

Phe Thr His Ala His Ile Val Ala Leu Ser Gln His Pro Ala Ala Leu
65                  70                  75                  80

Gly Thr Val Ala Val Lys Tyr Gln Asp Met Ile Ala Ala Leu Pro Glu
                85                  90                  95

Ala Thr His Glu Ala Ile Val Gly Val Gly Lys Gln Trp Ser Gly Ala
            100                 105                 110

Arg Ala Leu Glu Ala Leu Leu Thr Val Ala Gly Glu Leu Arg Gly Pro
        115                 120                 125

Pro Leu Gln Leu Asp Thr Gly Gln Leu Leu Lys Ile Ala Lys Arg Gly
    130                 135                 140

Gly Val Thr Ala Val Glu Ala Val His Ala Trp Arg Asn Ala Leu Thr
```

```
            145                 150                 155                 160
Gly Ala Pro Leu Asn Leu Thr Pro Asp Gln Val Val Ala Ile Ala Ser
                    165                 170                 175

Asn Ile Gly Gly Lys Gln Ala Leu Glu Thr Val Gln Arg Leu Leu Pro
                180                 185                 190

Val Leu Cys Gln Asp His Gly Leu Thr Pro Asp Gln Val Val Ala Ile
            195                 200                 205

Ala Ser Asn Asn Gly Gly Lys Gln Ala Leu Glu Thr Val Gln Arg Leu
        210                 215                 220

Leu Pro Val Leu Cys Gln Asp His Gly Leu Thr Pro Asp Gln Val Val
225                 230                 235                 240

Ala Ile Ala Ser Asn Gly Gly Lys Gln Ala Leu Glu Thr Val Gln
                    245                 250                 255

Arg Leu Leu Pro Val Leu Cys Gln Asp His Gly Leu Thr Pro Asp Gln
                260                 265                 270

Val Val Ala Ile Ala Ser His Asp Gly Gly Lys Gln Ala Leu Glu Thr
            275                 280                 285

Val Gln Arg Leu Leu Pro Val Leu Cys Gln Asp His Gly Leu Thr Pro
        290                 295                 300

Asp Gln Val Val Ala Ile Ala Ser Asn Ile Gly Gly Lys Gln Ala Leu
305                 310                 315                 320

Glu Thr Val Gln Arg Leu Leu Pro Val Leu Cys Gln Asp His Gly Leu
                    325                 330                 335

Thr Pro Asp Gln Val Val Ala Ile Ala Ser Asn Gly Gly Lys Gln
                340                 345                 350

Ala Leu Glu Thr Val Gln Arg Leu Leu Pro Val Leu Cys Gln Asp His
            355                 360                 365

Gly Leu Thr Pro Asp Gln Val Val Ala Ile Ala Ser His Asp Gly Gly
        370                 375                 380

Lys Gln Ala Leu Glu Thr Val Gln Arg Leu Leu Pro Val Leu Cys Gln
385                 390                 395                 400

Asp His Gly Leu Thr Pro Asp Gln Val Val Ala Ile Ala Ser His Asp
                    405                 410                 415

Gly Gly Lys Gln Ala Leu Glu Thr Val Gln Arg Leu Leu Pro Val Leu
                420                 425                 430

Cys Gln Asp His Gly Leu Thr Pro Asp Gln Val Val Ala Ile Ala Ser
            435                 440                 445

His Asp Gly Gly Lys Gln Ala Leu Glu Thr Val Gln Arg Leu Leu Pro
        450                 455                 460

Val Leu Cys Gln Asp His Gly Leu Thr Pro Asp Gln Val Val Ala Ile
465                 470                 475                 480

Ala Ser His Asp Gly Gly Lys Gln Ala Leu Glu Thr Val Gln Arg Leu
                    485                 490                 495

Leu Pro Val Leu Cys Gln Asp His Gly Leu Thr Pro Asp Gln Val Val
                500                 505                 510

Ala Ile Ala Ser Asn Ile Gly Gly Lys Gln Ala Leu Glu Thr Val Gln
            515                 520                 525

Arg Leu Leu Pro Val Leu Cys Gln Asp His Gly Leu Thr Pro Asp Gln
        530                 535                 540

Val Val Ala Ile Ala Ser His Asp Gly Gly Lys Gln Ala Leu Glu Thr
545                 550                 555                 560

Val Gln Arg Leu Leu Pro Val Leu Cys Gln Asp His Gly Leu Thr Pro
                    565                 570                 575
```

-continued

```
Asp Gln Val Val Ala Ile Ala Ser Asn Ile Gly Gly Lys Gln Ala Leu
                580                 585                 590
Glu Thr Val Gln Arg Leu Leu Pro Val Leu Cys Gln Asp His Gly Leu
            595                 600                 605
Thr Pro Asp Gln Val Val Ala Ile Ala Ser Asn Ile Gly Gly Lys Gln
        610                 615                 620
Ala Leu Glu Thr Val Gln Arg Leu Leu Pro Val Leu Cys Gln Asp His
625                 630                 635                 640
Gly Leu Thr Pro Asp Gln Val Val Ala Ile Ala Ser Asn Gly Gly
                645                 650                 655
Lys Gln Ala Leu Glu Thr Val Gln Arg Leu Leu Pro Val Leu Cys Gln
                660                 665                 670
Asp His Gly Leu Thr Pro Asp Gln Val Val Ala Ile Ala Ser Asn Ile
                675                 680                 685
Gly Gly Lys Gln Ala Leu Glu Thr Val Gln Arg Leu Leu Pro Val Leu
            690                 695                 700
Cys Gln Asp His Gly Leu Thr Pro Asp Gln Val Val Ala Ile Ala Ser
705                 710                 715                 720
Asn Asn Gly Gly Lys Gln Ala Leu Glu Thr Val Gln Arg Leu Leu Pro
                725                 730                 735
Val Leu Cys Gln Asp His Gly Leu Thr Pro Asp Gln Val Val Ala Ile
            740                 745                 750
Ala Ser Asn Gly Gly Gly Lys Gln Ala Leu Glu Ser Ile Val Ala Gln
        755                 760                 765
Leu Ser Arg Pro Asp Pro Ala Leu Ala Ala Leu Thr Asn Asp His Leu
        770                 775                 780
Val Ala Leu Ala Cys Leu Gly Gly Arg Pro Ala Leu Asp Ala Val Lys
785                 790                 795                 800
Lys Gly Leu Pro His Ala Pro Ala Leu Ile Lys Arg Thr Asn Arg Arg
                805                 810                 815
Ile Pro Glu Arg Thr Ser His Arg Val Ala Gly Ser Gly Gly Gly
                820                 825                 830
```

```
<210> SEQ ID NO 64
<211> LENGTH: 19
<212> TYPE: DNA
<213> ORGANISM: Artificial Sequence
<220> FEATURE:
<223> OTHER INFORMATION: BCL11A gene binding site

<400> SEQUENCE: 64
tctcttgtcc acagctcgg                                              19

<210> SEQ ID NO 65
<211> LENGTH: 831
<212> TYPE: PRT
<213> ORGANISM: Artificial Sequence
<220> FEATURE:
<223> OTHER INFORMATION: TALE domain BCL11A #15

<400> SEQUENCE: 65
```

```
Met Gly Lys Pro Ile Pro Asn Pro Leu Leu Gly Leu Asp Ser Thr Gly
1               5                   10                  15
Gly Met Ala Pro Lys Lys Lys Arg Lys Val Asp Gly Gly Val Asp Leu
            20                  25                  30
Arg Thr Leu Gly Tyr Ser Gln Gln Gln Gln Glu Lys Ile Lys Pro Lys
        35                  40                  45
```

```
Val Arg Ser Thr Val Ala Gln His His Glu Ala Leu Val Gly His Gly
    50                  55                  60

Phe Thr His Ala His Ile Val Ala Leu Ser Gln His Pro Ala Ala Leu
65                      70                  75                  80

Gly Thr Val Ala Val Lys Tyr Gln Asp Met Ile Ala Ala Leu Pro Glu
                    85                  90                  95

Ala Thr His Glu Ala Ile Val Gly Val Gly Lys Gln Trp Ser Gly Ala
                100                 105                 110

Arg Ala Leu Glu Ala Leu Leu Thr Val Ala Gly Glu Leu Arg Gly Pro
            115                 120                 125

Pro Leu Gln Leu Asp Thr Gly Gln Leu Leu Lys Ile Ala Lys Arg Gly
        130                 135                 140

Gly Val Thr Ala Val Glu Ala Val His Ala Trp Arg Asn Ala Leu Thr
145                 150                 155                 160

Gly Ala Pro Leu Asn Leu Thr Pro Asp Gln Val Val Ala Ile Ala Ser
                165                 170                 175

His Asp Gly Gly Lys Gln Ala Leu Glu Thr Val Gln Arg Leu Leu Pro
            180                 185                 190

Val Leu Cys Gln Asp His Gly Leu Thr Pro Asp Gln Val Val Ala Ile
        195                 200                 205

Ala Ser His Asp Gly Gly Lys Gln Ala Leu Glu Thr Val Gln Arg Leu
    210                 215                 220

Leu Pro Val Leu Cys Gln Asp His Gly Leu Thr Pro Asp Gln Val Val
225                 230                 235                 240

Ala Ile Ala Ser His Asp Gly Gly Lys Gln Ala Leu Glu Thr Val Gln
                245                 250                 255

Arg Leu Leu Pro Val Leu Cys Gln Asp His Gly Leu Thr Pro Asp Gln
            260                 265                 270

Val Val Ala Ile Ala Ser Asn Asn Gly Gly Lys Gln Ala Leu Glu Thr
        275                 280                 285

Val Gln Arg Leu Leu Pro Val Leu Cys Gln Asp His Gly Leu Thr Pro
    290                 295                 300

Asp Gln Val Val Ala Ile Ala Ser His Asp Gly Gly Lys Gln Ala Leu
305                 310                 315                 320

Glu Thr Val Gln Arg Leu Leu Pro Val Leu Cys Gln Asp His Gly Leu
                325                 330                 335

Thr Pro Asp Gln Val Val Ala Ile Ala Ser Asn Gly Gly Gly Lys Gln
            340                 345                 350

Ala Leu Glu Thr Val Gln Arg Leu Leu Pro Val Leu Cys Gln Asp His
        355                 360                 365

Gly Leu Thr Pro Asp Gln Val Val Ala Ile Ala Ser Asn Asn Gly Gly
    370                 375                 380

Lys Gln Ala Leu Glu Thr Val Gln Arg Leu Leu Pro Val Leu Cys Gln
385                 390                 395                 400

Asp His Gly Leu Thr Pro Asp Gln Val Val Ala Ile Ala Ser His Asp
                405                 410                 415

Gly Gly Lys Gln Ala Leu Glu Thr Val Gln Arg Leu Leu Pro Val Leu
            420                 425                 430

Cys Gln Asp His Gly Leu Thr Pro Asp Gln Val Val Ala Ile Ala Ser
        435                 440                 445

His Asp Gly Gly Lys Gln Ala Leu Glu Thr Val Gln Arg Leu Leu Pro
    450                 455                 460
```

```
Val Leu Cys Gln Asp His Gly Leu Thr Pro Asp Gln Val Val Ala Ile
465                 470                 475                 480

Ala Ser Asn Gly Gly Lys Gln Ala Leu Glu Thr Val Gln Arg Leu
            485                 490                 495

Leu Pro Val Leu Cys Gln Asp His Gly Leu Thr Pro Asp Gln Val Val
                500                 505                 510

Ala Ile Ala Ser Asn Gly Gly Gly Lys Gln Ala Leu Glu Thr Val Gln
            515                 520                 525

Arg Leu Leu Pro Val Leu Cys Gln Asp His Gly Leu Thr Pro Asp Gln
        530                 535                 540

Val Val Ala Ile Ala Ser Asn Gly Gly Gly Lys Gln Ala Leu Glu Thr
545                 550                 555                 560

Val Gln Arg Leu Leu Pro Val Leu Cys Gln Asp His Gly Leu Thr Pro
                565                 570                 575

Asp Gln Val Val Ala Ile Ala Ser Asn Gly Gly Lys Gln Ala Leu
            580                 585                 590

Glu Thr Val Gln Arg Leu Leu Pro Val Leu Cys Gln Asp His Gly Leu
        595                 600                 605

Thr Pro Asp Gln Val Val Ala Ile Ala Ser Asn Asn Gly Gly Lys Gln
610                 615                 620

Ala Leu Glu Thr Val Gln Arg Leu Leu Pro Val Leu Cys Gln Asp His
625                 630                 635                 640

Gly Leu Thr Pro Asp Gln Val Val Ala Ile Ala Ser Asn Gly Gly Gly
                645                 650                 655

Lys Gln Ala Leu Glu Thr Val Gln Arg Leu Leu Pro Val Leu Cys Gln
            660                 665                 670

Asp His Gly Leu Thr Pro Asp Gln Val Val Ala Ile Ala Ser Asn Asn
        675                 680                 685

Gly Gly Lys Gln Ala Leu Glu Thr Val Gln Arg Leu Leu Pro Val Leu
690                 695                 700

Cys Gln Asp His Gly Leu Thr Pro Asp Gln Val Val Ala Ile Ala Ser
705                 710                 715                 720

His Asp Gly Gly Lys Gln Ala Leu Glu Thr Val Gln Arg Leu Leu Pro
                725                 730                 735

Val Leu Cys Gln Asp His Gly Leu Thr Pro Asp Gln Val Val Ala Ile
            740                 745                 750

Ala Ser His Asp Gly Gly Lys Gln Ala Leu Glu Ser Ile Val Ala Gln
        755                 760                 765

Leu Ser Arg Pro Asp Pro Ala Leu Ala Ala Leu Thr Asn Asp His Leu
770                 775                 780

Val Ala Leu Ala Cys Leu Gly Gly Arg Pro Ala Leu Asp Ala Val Lys
785                 790                 795                 800

Lys Gly Leu Pro His Ala Pro Ala Leu Ile Lys Arg Thr Asn Arg Arg
                805                 810                 815

Ile Pro Glu Arg Thr Ser His Arg Val Ala Gly Ser Gly Gly Gly
            820                 825                 830

<210> SEQ ID NO 66
<211> LENGTH: 19
<212> TYPE: DNA
<213> ORGANISM: Artificial Sequence
<220> FEATURE:
<223> OTHER INFORMATION: BCL11A gene binding site

<400> SEQUENCE: 66
```
tctcccgctg actgcgcct                                                      19

<210> SEQ ID NO 67
<211> LENGTH: 831
<212> TYPE: PRT
<213> ORGANISM: Artificial Sequence
<220> FEATURE:
<223> OTHER INFORMATION: TALE domain BCL11A #16

<400> SEQUENCE: 67

Met Gly Lys Pro Ile Pro Asn Pro Leu Leu Gly Leu Asp Ser Thr Gly
1               5                   10                  15

Gly Met Ala Pro Lys Lys Lys Arg Lys Val Asp Gly Gly Val Asp Leu
            20                  25                  30

Arg Thr Leu Gly Tyr Ser Gln Gln Gln Gln Glu Lys Ile Lys Pro Lys
        35                  40                  45

Val Arg Ser Thr Val Ala Gln His His Glu Ala Leu Val Gly His Gly
    50                  55                  60

Phe Thr His Ala His Ile Val Ala Leu Ser Gln His Pro Ala Ala Leu
65                  70                  75                  80

Gly Thr Val Ala Val Lys Tyr Gln Asp Met Ile Ala Ala Leu Pro Glu
                85                  90                  95

Ala Thr His Glu Ala Ile Val Gly Val Gly Lys Gln Trp Ser Gly Ala
            100                 105                 110

Arg Ala Leu Glu Ala Leu Leu Thr Val Ala Gly Glu Leu Arg Gly Pro
        115                 120                 125

Pro Leu Gln Leu Asp Thr Gly Gln Leu Leu Lys Ile Ala Lys Arg Gly
    130                 135                 140

Gly Val Thr Ala Val Glu Ala Val His Ala Trp Arg Asn Ala Leu Thr
145                 150                 155                 160

Gly Ala Pro Leu Asn Leu Thr Pro Asp Gln Val Val Ala Ile Ala Ser
                165                 170                 175

His Asp Gly Gly Lys Gln Ala Leu Glu Thr Val Gln Arg Leu Leu Pro
            180                 185                 190

Val Leu Cys Gln Asp His Gly Leu Thr Pro Asp Gln Val Val Ala Ile
        195                 200                 205

Ala Ser His Asp Gly Gly Lys Gln Ala Leu Glu Thr Val Gln Arg Leu
    210                 215                 220

Leu Pro Val Leu Cys Gln Asp His Gly Leu Thr Pro Asp Gln Val Val
225                 230                 235                 240

Ala Ile Ala Ser Asn Gly Gly Lys Gln Ala Leu Glu Thr Val Gln
                245                 250                 255

Arg Leu Leu Pro Val Leu Cys Gln Asp His Gly Leu Thr Pro Asp Gln
            260                 265                 270

Val Val Ala Ile Ala Ser His Asp Gly Gly Lys Gln Ala Leu Glu Thr
        275                 280                 285

Val Gln Arg Leu Leu Pro Val Leu Cys Gln Asp His Gly Leu Thr Pro
    290                 295                 300

Asp Gln Val Val Ala Ile Ala Ser Asn Asn Gly Gly Lys Gln Ala Leu
305                 310                 315                 320

Glu Thr Val Gln Arg Leu Leu Pro Val Leu Cys Gln Asp His Gly Leu
                325                 330                 335

Thr Pro Asp Gln Val Val Ala Ile Ala Ser His Asp Gly Gly Lys Gln
            340                 345                 350

Ala Leu Glu Thr Val Gln Arg Leu Leu Pro Val Leu Cys Gln Asp His

```
            355                 360                 365
Gly Leu Thr Pro Asp Gln Val Ala Ile Ala Ser Asn Asn Gly Gly
        370                 375                 380
Lys Gln Ala Leu Glu Thr Val Gln Arg Leu Leu Pro Val Leu Cys Gln
385                     390                 395                 400
Asp His Gly Leu Thr Pro Asp Gln Val Val Ala Ile Ala Ser His Asp
                    405                 410                 415
Gly Gly Lys Gln Ala Leu Glu Thr Val Gln Arg Leu Leu Pro Val Leu
            420                 425                 430
Cys Gln Asp His Gly Leu Thr Pro Asp Gln Val Val Ala Ile Ala Ser
                435                 440                 445
Asn Gly Gly Lys Gln Ala Leu Glu Thr Val Gln Arg Leu Leu Pro
        450                 455                 460
Val Leu Cys Gln Asp His Gly Leu Thr Pro Asp Gln Val Val Ala Ile
465                 470                 475                 480
Ala Ser Asn Gly Gly Lys Gln Ala Leu Glu Thr Val Gln Arg Leu
                485                 490                 495
Leu Pro Val Leu Cys Gln Asp His Gly Leu Thr Pro Asp Gln Val Val
                500                 505                 510
Ala Ile Ala Ser Asn Asn Gly Gly Lys Gln Ala Leu Glu Thr Val Gln
            515                 520                 525
Arg Leu Leu Pro Val Leu Cys Gln Asp His Gly Leu Thr Pro Asp Gln
        530                 535                 540
Val Val Ala Ile Ala Ser His Asp Gly Gly Lys Gln Ala Leu Glu Thr
545                 550                 555                 560
Val Gln Arg Leu Leu Pro Val Leu Cys Gln Asp His Gly Leu Thr Pro
                565                 570                 575
Asp Gln Val Val Ala Ile Ala Ser His Asp Gly Gly Lys Gln Ala Leu
                580                 585                 590
Glu Thr Val Gln Arg Leu Leu Pro Val Leu Cys Gln Asp His Gly Leu
            595                 600                 605
Thr Pro Asp Gln Val Val Ala Ile Ala Ser His Asp Gly Gly Lys Gln
        610                 615                 620
Ala Leu Glu Thr Val Gln Arg Leu Leu Pro Val Leu Cys Gln Asp His
625                 630                 635                 640
Gly Leu Thr Pro Asp Gln Val Val Ala Ile Ala Ser Asn Gly Gly Gly
                645                 650                 655
Lys Gln Ala Leu Glu Thr Val Gln Arg Leu Leu Pro Val Leu Cys Gln
                660                 665                 670
Asp His Gly Leu Thr Pro Asp Gln Val Val Ala Ile Ala Ser His Asp
            675                 680                 685
Gly Gly Lys Gln Ala Leu Glu Thr Val Gln Arg Leu Leu Pro Val Leu
        690                 695                 700
Cys Gln Asp His Gly Leu Thr Pro Asp Gln Val Val Ala Ile Ala Ser
705                 710                 715                 720
His Asp Gly Gly Lys Gln Ala Leu Glu Thr Val Gln Arg Leu Leu Pro
                725                 730                 735
Val Leu Cys Gln Asp His Gly Leu Thr Pro Asp Gln Val Val Ala Ile
                740                 745                 750
Ala Ser His Asp Gly Gly Lys Gln Ala Leu Glu Ser Ile Val Ala Gln
            755                 760                 765
Leu Ser Arg Pro Asp Pro Ala Leu Ala Ala Leu Thr Asn Asp His Leu
        770                 775                 780
```

-continued

```
Val Ala Leu Ala Cys Leu Gly Gly Arg Pro Ala Leu Asp Ala Val Lys
785                 790                 795                 800

Lys Gly Leu Pro His Ala Pro Ala Leu Ile Lys Arg Thr Asn Arg Arg
                805                 810                 815

Ile Pro Glu Arg Thr Ser His Arg Val Ala Gly Ser Gly Gly
            820                 825                 830
```

<210> SEQ ID NO 68
<211> LENGTH: 19
<212> TYPE: DNA
<213> ORGANISM: Artificial Sequence
<220> FEATURE:
<223> OTHER INFORMATION: BCL11A gene binding site

<400> SEQUENCE: 68
tcccttgctg ccaaacttt                                              19

<210> SEQ ID NO 69
<211> LENGTH: 831
<212> TYPE: PRT
<213> ORGANISM: Artificial Sequence
<220> FEATURE:
<223> OTHER INFORMATION: TALE domain BCL11A #17

<400> SEQUENCE: 69

```
Met Gly Lys Pro Ile Pro Asn Pro Leu Leu Gly Leu Asp Ser Thr Gly
1               5                   10                  15

Gly Met Ala Pro Lys Lys Lys Arg Lys Val Asp Gly Gly Val Asp Leu
                20                  25                  30

Arg Thr Leu Gly Tyr Ser Gln Gln Gln Gln Glu Lys Ile Lys Pro Lys
            35                  40                  45

Val Arg Ser Thr Val Ala Gln His His Glu Ala Leu Val Gly His Gly
        50                  55                  60

Phe Thr His Ala His Ile Val Ala Leu Ser Gln His Pro Ala Ala Leu
65                  70                  75                  80

Gly Thr Val Ala Val Lys Tyr Gln Asp Met Ile Ala Ala Leu Pro Glu
                85                  90                  95

Ala Thr His Glu Ala Ile Val Gly Val Gly Lys Gln Trp Ser Gly Ala
            100                 105                 110

Arg Ala Leu Glu Ala Leu Leu Thr Val Ala Gly Glu Leu Arg Gly Pro
        115                 120                 125

Pro Leu Gln Leu Asp Thr Gly Gln Leu Leu Lys Ile Ala Lys Arg Gly
    130                 135                 140

Gly Val Thr Ala Val Glu Ala Val His Ala Trp Arg Asn Ala Leu Thr
145                 150                 155                 160

Gly Ala Pro Leu Asn Leu Thr Pro Asp Gln Val Val Ala Ile Ala Ser
                165                 170                 175

His Asp Gly Gly Lys Gln Ala Leu Glu Thr Val Gln Arg Leu Leu Pro
            180                 185                 190

Val Leu Cys Gln Asp His Gly Leu Thr Pro Asp Gln Val Val Ala Ile
        195                 200                 205

Ala Ser His Asp Gly Gly Lys Gln Ala Leu Glu Thr Val Gln Arg Leu
    210                 215                 220

Leu Pro Val Leu Cys Gln Asp His Gly Leu Thr Pro Asp Gln Val Val
225                 230                 235                 240

Ala Ile Ala Ser His Asp Gly Gly Lys Gln Ala Leu Glu Thr Val Gln
                245                 250                 255
```

```
Arg Leu Leu Pro Val Leu Cys Gln Asp His Gly Leu Thr Pro Asp Gln
            260                 265                 270

Val Val Ala Ile Ala Ser His Asp Gly Gly Lys Gln Ala Leu Glu Thr
            275                 280                 285

Val Gln Arg Leu Leu Pro Val Leu Cys Gln Asp His Gly Leu Thr Pro
            290                 295                 300

Asp Gln Val Val Ala Ile Ala Ser His Asp Gly Gly Lys Gln Ala Leu
305                 310                 315                 320

Glu Thr Val Gln Arg Leu Leu Pro Val Leu Cys Gln Asp His Gly Leu
                325                 330                 335

Thr Pro Asp Gln Val Val Ala Ile Ala Ser Asn Asn Gly Gly Lys Gln
            340                 345                 350

Ala Leu Glu Thr Val Gln Arg Leu Leu Pro Val Leu Cys Gln Asp His
            355                 360                 365

Gly Leu Thr Pro Asp Gln Val Val Ala Ile Ala Ser Asn Asn Gly Gly
            370                 375                 380

Lys Gln Ala Leu Glu Thr Val Gln Arg Leu Leu Pro Val Leu Cys Gln
385                 390                 395                 400

Asp His Gly Leu Thr Pro Asp Gln Val Val Ala Ile Ala Ser His Asp
                405                 410                 415

Gly Gly Lys Gln Ala Leu Glu Thr Val Gln Arg Leu Leu Pro Val Leu
            420                 425                 430

Cys Gln Asp His Gly Leu Thr Pro Asp Gln Val Val Ala Ile Ala Ser
            435                 440                 445

His Asp Gly Gly Lys Gln Ala Leu Glu Thr Val Gln Arg Leu Leu Pro
            450                 455                 460

Val Leu Cys Gln Asp His Gly Leu Thr Pro Asp Gln Val Val Ala Ile
465                 470                 475                 480

Ala Ser His Asp Gly Gly Lys Gln Ala Leu Glu Thr Val Gln Arg Leu
                485                 490                 495

Leu Pro Val Leu Cys Gln Asp His Gly Leu Thr Pro Asp Gln Val Val
            500                 505                 510

Ala Ile Ala Ser Asn Gly Gly Lys Gln Ala Leu Glu Thr Val Gln
            515                 520                 525

Arg Leu Leu Pro Val Leu Cys Gln Asp His Gly Leu Thr Pro Asp Gln
            530                 535                 540

Val Val Ala Ile Ala Ser Asn Ile Gly Gly Lys Gln Ala Leu Glu Thr
545                 550                 555                 560

Val Gln Arg Leu Leu Pro Val Leu Cys Gln Asp His Gly Leu Thr Pro
                565                 570                 575

Asp Gln Val Val Ala Ile Ala Ser Asn Asn Gly Gly Lys Gln Ala Leu
            580                 585                 590

Glu Thr Val Gln Arg Leu Leu Pro Val Leu Cys Gln Asp His Gly Leu
            595                 600                 605

Thr Pro Asp Gln Val Val Ala Ile Ala Ser His Asp Gly Gly Lys Gln
            610                 615                 620

Ala Leu Glu Thr Val Gln Arg Leu Leu Pro Val Leu Cys Gln Asp His
625                 630                 635                 640

Gly Leu Thr Pro Asp Gln Val Val Ala Ile Ala Ser Asn Gly Gly Gly
                645                 650                 655

Lys Gln Ala Leu Glu Thr Val Gln Arg Leu Leu Pro Val Leu Cys Gln
            660                 665                 670
```

```
Asp His Gly Leu Thr Pro Asp Gln Val Val Ala Ile Ala Ser His Asp
            675                 680                 685

Gly Gly Lys Gln Ala Leu Glu Thr Val Gln Arg Leu Leu Pro Val Leu
    690                 695                 700

Cys Gln Asp His Gly Leu Thr Pro Asp Gln Val Val Ala Ile Ala Ser
705                 710                 715                 720

His Asp Gly Gly Lys Gln Ala Leu Glu Thr Val Gln Arg Leu Leu Pro
                725                 730                 735

Val Leu Cys Gln Asp His Gly Leu Thr Pro Asp Gln Val Val Ala Ile
            740                 745                 750

Ala Ser Asn Gly Gly Gly Lys Gln Ala Leu Glu Ser Ile Val Ala Gln
            755                 760                 765

Leu Ser Arg Pro Asp Pro Ala Leu Ala Ala Leu Thr Asn Asp His Leu
            770                 775                 780

Val Ala Leu Ala Cys Leu Gly Gly Arg Pro Ala Leu Asp Ala Val Lys
785                 790                 795                 800

Lys Gly Leu Pro His Ala Pro Ala Leu Ile Lys Arg Thr Asn Arg Arg
                805                 810                 815

Ile Pro Glu Arg Thr Ser His Arg Val Ala Gly Ser Gly Gly Gly
            820                 825                 830
```

<210> SEQ ID NO 70
<211> LENGTH: 19
<212> TYPE: DNA
<213> ORGANISM: Artificial Sequence
<220> FEATURE:
<223> OTHER INFORMATION: BCL11A gene binding site

<400> SEQUENCE: 70
tgggccctca cgcctttct                                                    19

<210> SEQ ID NO 71
<211> LENGTH: 20
<212> TYPE: RNA
<213> ORGANISM: Artificial Sequence
<220> FEATURE:
<223> OTHER INFORMATION: gRNA #1 against CpG 105, BCL11A gene

<400> SEQUENCE: 71
gccuuucugc agacguuccc                                                   20

<210> SEQ ID NO 72
<211> LENGTH: 20
<212> TYPE: RNA
<213> ORGANISM: Artificial Sequence
<220> FEATURE:
<223> OTHER INFORMATION: gRNA #2 against CpG 105, BCL11A gene

<400> SEQUENCE: 72
ugggugugcg ccuuggccgg                                                   20

<210> SEQ ID NO 73
<211> LENGTH: 20
<212> TYPE: RNA
<213> ORGANISM: Artificial Sequence
<220> FEATURE:
<223> OTHER INFORMATION: gRNA #3 against CpG 105, BCL11A gene

<400> SEQUENCE: 73
cgguggugag augaccgccu                                                   20

```
<210> SEQ ID NO 74
<211> LENGTH: 20
<212> TYPE: RNA
<213> ORGANISM: Artificial Sequence
<220> FEATURE:
<223> OTHER INFORMATION: gRNA #4 against CpG 105, BCL11A gene

<400> SEQUENCE: 74
ggaaugugcu cacggcgccg                                                   20

<210> SEQ ID NO 75
<211> LENGTH: 20
<212> TYPE: RNA
<213> ORGANISM: Artificial Sequence
<220> FEATURE:
<223> OTHER INFORMATION: gRNA #5 against CpG 105, BCL11A gene

<400> SEQUENCE: 75
gacugcccgc gcuuuguccu                                                   20

<210> SEQ ID NO 76
<211> LENGTH: 20
<212> TYPE: RNA
<213> ORGANISM: Artificial Sequence
<220> FEATURE:
<223> OTHER INFORMATION: gRNA #6 against CpG 105, BCL11A gene

<400> SEQUENCE: 76
ccagagucug gcccccggag                                                   20

<210> SEQ ID NO 77
<211> LENGTH: 20
<212> TYPE: RNA
<213> ORGANISM: Artificial Sequence
<220> FEATURE:
<223> OTHER INFORMATION: gRNA #7 against CpG 105, BCL11A gene

<400> SEQUENCE: 77
ucugcgaccc uuaggagccg                                                   20

<210> SEQ ID NO 78
<211> LENGTH: 20
<212> TYPE: RNA
<213> ORGANISM: Artificial Sequence
<220> FEATURE:
<223> OTHER INFORMATION: gRNA #8 against CpG 105, BCL11A gene

<400> SEQUENCE: 78
gagcgccccg ccaagcgacu                                                   20

<210> SEQ ID NO 79
<211> LENGTH: 20
<212> TYPE: RNA
<213> ORGANISM: Artificial Sequence
<220> FEATURE:
<223> OTHER INFORMATION: gRNA #9 against CpG 105, BCL11A gene

<400> SEQUENCE: 79
caagucucca ggagcccgcg                                                   20

<210> SEQ ID NO 80
<211> LENGTH: 20
<212> TYPE: RNA
<213> ORGANISM: Artificial Sequence
<220> FEATURE:
<223> OTHER INFORMATION: gRNA #10 against CpG 105, BCL11A gene
```

```
<400> SEQUENCE: 80
cgcggaaucc agccuaaguu                                              20

<210> SEQ ID NO 81
<211> LENGTH: 20
<212> TYPE: RNA
<213> ORGANISM: Artificial Sequence
<220> FEATURE:
<223> OTHER INFORMATION: gRNA #11 against CpG 105, BCL11A gene

<400> SEQUENCE: 81
cccgcugcgg agcuguaacu                                              20

<210> SEQ ID NO 82
<211> LENGTH: 20
<212> TYPE: RNA
<213> ORGANISM: Artificial Sequence
<220> FEATURE:
<223> OTHER INFORMATION: gRNA #1 against CpG 31, BCL11A gene

<400> SEQUENCE: 82
cgcuccugag uccgcggagu                                              20

<210> SEQ ID NO 83
<211> LENGTH: 20
<212> TYPE: RNA
<213> ORGANISM: Artificial Sequence
<220> FEATURE:
<223> OTHER INFORMATION: gRNA #2 against CpG 31, BCL11A gene

<400> SEQUENCE: 83
cacggcucuc cccgucgccg                                              20

<210> SEQ ID NO 84
<211> LENGTH: 20
<212> TYPE: RNA
<213> ORGANISM: Artificial Sequence
<220> FEATURE:
<223> OTHER INFORMATION: gRNA #3 against CpG 31, BCL11A gene

<400> SEQUENCE: 84
ccgccuuuug uuccggccag                                              20

<210> SEQ ID NO 85
<211> LENGTH: 20
<212> TYPE: RNA
<213> ORGANISM: Artificial Sequence
<220> FEATURE:
<223> OTHER INFORMATION: gRNA #4 against CpG 31, BCL11A gene

<400> SEQUENCE: 85
gcgcgaggag ccggcacaaa                                              20

<210> SEQ ID NO 86
<211> LENGTH: 20
<212> TYPE: RNA
<213> ORGANISM: Artificial Sequence
<220> FEATURE:
<223> OTHER INFORMATION: gRNA #5 against CpG 31, BCL11A gene

<400> SEQUENCE: 86
gccacuuucu cacuauugug                                              20

<210> SEQ ID NO 87
<211> LENGTH: 20
```

```
<212> TYPE: RNA
<213> ORGANISM: Artificial Sequence
<220> FEATURE:
<223> OTHER INFORMATION: gRNA #6 against CpG 31, BCL11A gene

<400> SEQUENCE: 87
gcugccucug agguucgguc                                              20

<210> SEQ ID NO 88
<211> LENGTH: 20
<212> TYPE: RNA
<213> ORGANISM: Artificial Sequence
<220> FEATURE:
<223> OTHER INFORMATION: gRNA #7 against CpG 31, BCL11A gene

<400> SEQUENCE: 88
aagggcagga gcuagggccg                                              20

<210> SEQ ID NO 89
<211> LENGTH: 20
<212> TYPE: RNA
<213> ORGANISM: Artificial Sequence
<220> FEATURE:
<223> OTHER INFORMATION: gRNA #8 against CpG 31, BCL11A gene

<400> SEQUENCE: 89
gagcccggac ugcugccucc                                              20

<210> SEQ ID NO 90
<211> LENGTH: 20
<212> TYPE: RNA
<213> ORGANISM: Artificial Sequence
<220> FEATURE:
<223> OTHER INFORMATION: gRNA #1 against CpG 38, BCL11A gene

<400> SEQUENCE: 90
guuuacaagc accgcgugug                                              20

<210> SEQ ID NO 91
<211> LENGTH: 20
<212> TYPE: RNA
<213> ORGANISM: Artificial Sequence
<220> FEATURE:
<223> OTHER INFORMATION: gRNA #2 against CpG 38, BCL11A gene

<400> SEQUENCE: 91
aacagacaga ggaccgagcg                                              20

<210> SEQ ID NO 92
<211> LENGTH: 20
<212> TYPE: RNA
<213> ORGANISM: Artificial Sequence
<220> FEATURE:
<223> OTHER INFORMATION: gRNA #3 against CpG 38, BCL11A gene

<400> SEQUENCE: 92
ggcgccgggu gggcgauccg                                              20

<210> SEQ ID NO 93
<211> LENGTH: 20
<212> TYPE: RNA
<213> ORGANISM: Artificial Sequence
<220> FEATURE:
<223> OTHER INFORMATION: gRNA #4 against CpG 38, BCL11A gene

<400> SEQUENCE: 93
```
ggucgggcaa ggcccgggcg                          20

<210> SEQ ID NO 94
<211> LENGTH: 20
<212> TYPE: RNA
<213> ORGANISM: Artificial Sequence
<220> FEATURE:
<223> OTHER INFORMATION: gRNA #5 against CpG 38, BCL11A gene

<400> SEQUENCE: 94
aagaggucuc ggcauugugc                          20

<210> SEQ ID NO 95
<211> LENGTH: 22
<212> TYPE: RNA
<213> ORGANISM: Artificial Sequence
<220> FEATURE:
<223> OTHER INFORMATION: gRNA #6 against CpG 38, BCL11A gene

<400> SEQUENCE: 95
guuccacagc uucgggaccg cg                       22

<210> SEQ ID NO 96
<211> LENGTH: 20
<212> TYPE: RNA
<213> ORGANISM: Artificial Sequence
<220> FEATURE:
<223> OTHER INFORMATION: gRNA #7 against CpG 38, BCL11A gene

<400> SEQUENCE: 96
gaaaucggcu gggugaaacu                          20

<210> SEQ ID NO 97
<211> LENGTH: 20
<212> TYPE: RNA
<213> ORGANISM: Artificial Sequence
<220> FEATURE:
<223> OTHER INFORMATION: gRNA #8 against CpG 38, BCL11A gene

<400> SEQUENCE: 97
gcagugucuc cgcgccagcc                          20

<210> SEQ ID NO 98
<211> LENGTH: 23
<212> TYPE: RNA
<213> ORGANISM: Artificial Sequence
<220> FEATURE:
<223> OTHER INFORMATION: gRNA #9 against CpG 38, BCL11A gene

<400> SEQUENCE: 98 ccucccucc cuccgcccu ggg                        23

<210> SEQ ID NO 99
<211> LENGTH: 23
<212> TYPE: RNA
<213> ORGANISM: Artificial Sequence
<220> FEATURE:
<223> OTHER INFORMATION: gRNA #1 against CpG 115, BCL11A gene

<400> SEQUENCE: 99
uccuccuguc ccggggUuaa agg                      23

<210> SEQ ID NO 100
<211> LENGTH: 25
<212> TYPE: RNA
<213> ORGANISM: Artificial Sequence

```
<220> FEATURE:
<223> OTHER INFORMATION: gRNA #2 against CpG 115, BCL11A gene

<400> SEQUENCE: 100
caucuuuugg gacacucuag gcugg                                          25

<210> SEQ ID NO 101
<211> LENGTH: 23
<212> TYPE: RNA
<213> ORGANISM: Artificial Sequence
<220> FEATURE:
<223> OTHER INFORMATION: gRNA #3 against CpG 115, BCL11A gene

<400> SEQUENCE: 101
aagucaggcc cuucuucgga agg                                            23

<210> SEQ ID NO 102
<211> LENGTH: 23
<212> TYPE: RNA
<213> ORGANISM: Artificial Sequence
<220> FEATURE:
<223> OTHER INFORMATION: gRNA #4 against CpG 115, BCL11A gene

<400> SEQUENCE: 102
gcagccugga cugcgcgccc cgg                                            23

<210> SEQ ID NO 103
<211> LENGTH: 20
<212> TYPE: RNA
<213> ORGANISM: Artificial Sequence
<220> FEATURE:
<223> OTHER INFORMATION: gRNA #5 against CpG 115, BCL11A gene

<400> SEQUENCE: 103
ugcccggcga uucucguccg                                                20

<210> SEQ ID NO 104
<211> LENGTH: 20
<212> TYPE: RNA
<213> ORGANISM: Artificial Sequence
<220> FEATURE:
<223> OTHER INFORMATION: gRNA #6 against CpG 115, BCL11A gene

<400> SEQUENCE: 104
ugagccauuc ggucgcuagg                                                20

<210> SEQ ID NO 105
<211> LENGTH: 20
<212> TYPE: RNA
<213> ORGANISM: Artificial Sequence
<220> FEATURE:
<223> OTHER INFORMATION: gRNA #7 against CpG 115, BCL11A gene

<400> SEQUENCE: 105
ggugguacug aggaccggga                                                20

<210> SEQ ID NO 106
<211> LENGTH: 20
<212> TYPE: RNA
<213> ORGANISM: Artificial Sequence
<220> FEATURE:
<223> OTHER INFORMATION: gRNA #1 for IFNAR1 gene

<400> SEQUENCE: 106
aggaacggcg cgugcgcgga                                                20
```

<210> SEQ ID NO 107
<211> LENGTH: 20
<212> TYPE: RNA
<213> ORGANISM: Artificial Sequence
<220> FEATURE:
<223> OTHER INFORMATION: gRNA #8 against CpG 115, BCL11A gene

<400> SEQUENCE: 107
auuuucuggg ugcucagagg                                               20

<210> SEQ ID NO 108
<211> LENGTH: 20
<212> TYPE: RNA
<213> ORGANISM: Artificial Sequence
<220> FEATURE:
<223> OTHER INFORMATION: gRNA #9 against CpG 115, BCL11A gene

<400> SEQUENCE: 108
uggucucagc ucgcgcacgg                                               20

<210> SEQ ID NO 109
<211> LENGTH: 20
<212> TYPE: RNA
<213> ORGANISM: Artificial Sequence
<220> FEATURE:
<223> OTHER INFORMATION: gRNA #10 against CpG 115, BCL11A gene

<400> SEQUENCE: 109
uggucucagc ucgcgcacgg                                               20

<210> SEQ ID NO 110
<211> LENGTH: 23
<212> TYPE: DNA
<213> ORGANISM: Artificial Sequence
<220> FEATURE:
<223> OTHER INFORMATION: sequence of gRNA targeting exon 3

<400> SEQUENCE: 110
ggagctctaa tccccacgcc tgg                                           23

<210> SEQ ID NO 111
<211> LENGTH: 23
<212> TYPE: DNA
<213> ORGANISM: Artificial Sequence
<220> FEATURE:
<223> OTHER INFORMATION: sequence of gRNA for B2M

<400> SEQUENCE: 111
aggctactag ccccatcaag agg                                           23

<210> SEQ ID NO 112
<211> LENGTH: 23
<212> TYPE: DNA
<213> ORGANISM: Artificial Sequence
<220> FEATURE:
<223> OTHER INFORMATION: Primer BIS B2M #1 F

<400> SEQUENCE: 112
gttgtgtttt ttgggaagt tag                                            23

<210> SEQ ID NO 113
<211> LENGTH: 22
<212> TYPE: DNA
<213> ORGANISM: Artificial Sequence
<220> FEATURE:
<223> OTHER INFORMATION: Primer BIS B2M #1 R

```
<400> SEQUENCE: 113
aaaattcctc cctatatcct ta                                          22

<210> SEQ ID NO 114
<211> LENGTH: 27
<212> TYPE: DNA
<213> ORGANISM: Artificial Sequence
<220> FEATURE:
<223> OTHER INFORMATION: Primer BIS B2M #2 F

<400> SEQUENCE: 114
aagaatggag aaattttgta gggaatt                                     27

<210> SEQ ID NO 115
<211> LENGTH: 25
<212> TYPE: DNA
<213> ORGANISM: Artificial Sequence
<220> FEATURE:
<223> OTHER INFORMATION: Primer BIS B2M #2 R

<400> SEQUENCE: 115
accaccaaaa aaaacttaaa aaaaa                                       25

<210> SEQ ID NO 116
<211> LENGTH: 25
<212> TYPE: DNA
<213> ORGANISM: Artificial Sequence
<220> FEATURE:
<223> OTHER INFORMATION: Primer BIS B2M #3 F

<400> SEQUENCE: 116 ttttttggt ttggaggtta tttag                                        25

<210> SEQ ID NO 117
<211> LENGTH: 25
<212> TYPE: DNA
<213> ORGANISM: Artificial Sequence
<220> FEATURE:
<223> OTHER INFORMATION: Primer BIS B2M #3 R

<400> SEQUENCE: 117
caaaacacat aaaatcctta acaca                                       25

<210> SEQ ID NO 118
<211> LENGTH: 25
<212> TYPE: DNA
<213> ORGANISM: Artificial Sequence
<220> FEATURE:
<223> OTHER INFORMATION: Primer BIS B2M #4 F

<400> SEQUENCE: 118
ttttagattg gagagttgtg gattt                                       25

<210> SEQ ID NO 119
<211> LENGTH: 25
<212> TYPE: DNA
<213> ORGANISM: Artificial Sequence
<220> FEATURE:
<223> OTHER INFORMATION: Primer BIS B2M #4 R

<400> SEQUENCE: 119
aattttacaa ctccccctaac taaca                                      25

<210> SEQ ID NO 120
```

```
<211> LENGTH: 23
<212> TYPE: DNA
<213> ORGANISM: Artificial Sequence
<220> FEATURE:
<223> OTHER INFORMATION: Primer B2M -241 F

<400> SEQUENCE: 120
gcaagtcact tagcatctct ggg                                              23

<210> SEQ ID NO 121
<211> LENGTH: 20
<212> TYPE: DNA
<213> ORGANISM: Artificial Sequence
<220> FEATURE:
<223> OTHER INFORMATION: Primer B2M -241 R

<400> SEQUENCE: 121
ttgctgtctg tacatcggcg                                                  20

<210> SEQ ID NO 122
<211> LENGTH: 20
<212> TYPE: DNA
<213> ORGANISM: Artificial Sequence
<220> FEATURE:
<223> OTHER INFORMATION: Primer B2M +158 F

<400> SEQUENCE: 122
tctctcgctc cgtgacttcc                                                  20

<210> SEQ ID NO 123
<211> LENGTH: 21
<212> TYPE: DNA
<213> ORGANISM: Artificial Sequence
<220> FEATURE:
<223> OTHER INFORMATION: Primer B2M +158 R

<400> SEQUENCE: 123
cgcttccccg agatccagcc c                                                21

<210> SEQ ID NO 124
<211> LENGTH: 20
<212> TYPE: DNA
<213> ORGANISM: Artificial Sequence
<220> FEATURE:
<223> OTHER INFORMATION: Primer B2M +315 F

<400> SEQUENCE: 124
aggggagacc tttggcctac                                                  20

<210> SEQ ID NO 125
<211> LENGTH: 20
<212> TYPE: DNA
<213> ORGANISM: Artificial Sequence
<220> FEATURE:
<223> OTHER INFORMATION: Primer B2M +315 R

<400> SEQUENCE: 125
ctctgacgct tatcgacgcc                                                  20

<210> SEQ ID NO 126
<211> LENGTH: 23
<212> TYPE: DNA
<213> ORGANISM: Artificial Sequence
<220> FEATURE:
<223> OTHER INFORMATION: Primer B2M +580 F

<400> SEQUENCE: 126
```
agactggaga gctgtggact tcg                                              23

<210> SEQ ID NO 127
<211> LENGTH: 22
<212> TYPE: DNA
<213> ORGANISM: Artificial Sequence
<220> FEATURE:
<223> OTHER INFORMATION: Primer B2M +580 R

<400> SEQUENCE: 127
gccaagcatt ctacaaacgt cg                                               22

<210> SEQ ID NO 128
<211> LENGTH: 22
<212> TYPE: DNA
<213> ORGANISM: Artificial Sequence
<220> FEATURE:
<223> OTHER INFORMATION: Primer B2M +1529 F

<400> SEQUENCE: 128
cagtcagggg agctgtaaaa cc                                               22

<210> SEQ ID NO 129
<211> LENGTH: 22
<212> TYPE: DNA
<213> ORGANISM: Artificial Sequence
<220> FEATURE:
<223> OTHER INFORMATION: Primer B2M +1529 R

<400> SEQUENCE: 129
ttgccaggta cttagaaagt gc                                               22

<210> SEQ ID NO 130
<211> LENGTH: 21
<212> TYPE: DNA
<213> ORGANISM: Artificial Sequence
<220> FEATURE:
<223> OTHER INFORMATION: Primer B2M +3307 F

<400> SEQUENCE: 130
ccttgggttg atccacttag g                                                21

<210> SEQ ID NO 131
<211> LENGTH: 23
<212> TYPE: DNA
<213> ORGANISM: Artificial Sequence
<220> FEATURE:
<223> OTHER INFORMATION: Primer B2M +3307 r

<400> SEQUENCE: 131
tagtagagtg cctgggacat agc                                              23

<210> SEQ ID NO 132
<211> LENGTH: 22
<212> TYPE: DNA
<213> ORGANISM: Artificial Sequence
<220> FEATURE:
<223> OTHER INFORMATION: Primer B2M +3969 F

<400> SEQUENCE: 132
gtgtctgggt ttcatccatc cg                                               22

<210> SEQ ID NO 133
<211> LENGTH: 22
<212> TYPE: DNA

```
<213> ORGANISM: Artificial Sequence
<220> FEATURE:
<223> OTHER INFORMATION: Primer B2M +3969 R

<400> SEQUENCE: 133
gctgaaagac aagtctgaat gc                                           22

<210> SEQ ID NO 134
<211> LENGTH: 22
<212> TYPE: DNA
<213> ORGANISM: Artificial Sequence
<220> FEATURE:
<223> OTHER INFORMATION: Primer B2M +5082 F

<400> SEQUENCE: 134
aggataaagg caggtggtta cc                                           22

<210> SEQ ID NO 135
<211> LENGTH: 22
<212> TYPE: DNA
<213> ORGANISM: Artificial Sequence
<220> FEATURE:
<223> OTHER INFORMATION: Primer B2M +5082 R

<400> SEQUENCE: 135
agatgtccaa tgtggaaatg gc                                           22

<210> SEQ ID NO 136
<211> LENGTH: 23
<212> TYPE: DNA
<213> ORGANISM: Artificial Sequence
<220> FEATURE:
<223> OTHER INFORMATION: Primer CCR5 -305 F

<400> SEQUENCE: 136
agtctgacta cagaggccac tgg                                          23

<210> SEQ ID NO 137
<211> LENGTH: 23
<212> TYPE: DNA
<213> ORGANISM: Artificial Sequence
<220> FEATURE:
<223> OTHER INFORMATION: Primer CCR5 R -255

<400> SEQUENCE: 137
aggcaaatga gaccccaaac agc                                          23

<210> SEQ ID NO 138
<211> LENGTH: 23
<212> TYPE: DNA
<213> ORGANISM: Artificial Sequence
<220> FEATURE:
<223> OTHER INFORMATION: Primer PPP1R12C -861 F

<400> SEQUENCE: 138
taagaaccga ggacaagtag tgc                                          23

<210> SEQ ID NO 139
<211> LENGTH: 22
<212> TYPE: DNA
<213> ORGANISM: Artificial Sequence
<220> FEATURE:
<223> OTHER INFORMATION: Primer PPP1R12C -768R

<400> SEQUENCE: 139
tgctgggatg acgagcgtaa gc                                           22
```

<210> SEQ ID NO 140
<211> LENGTH: 149
<212> TYPE: PRT
<213> ORGANISM: Homo sapiens

<400> SEQUENCE: 140

```
Asn Val Ser Cys Lys Asn Cys Ser Ile Gln Arg Gly Ser Lys Lys His
1               5                   10                  15

Leu Leu Leu Ala Pro Ser Asp Val Ala Gly Trp Gly Ile Phe Ile Lys
            20                  25                  30

Asp Pro Val Gln Lys Asn Glu Phe Ile Ser Glu Tyr Cys Gly Glu Ile
        35                  40                  45

Ile Ser Gln Asp Glu Ala Asp Arg Arg Gly Lys Val Tyr Asp Lys Tyr
    50                  55                  60

Met Cys Ser Phe Leu Phe Asn Leu Asn Asn Asp Phe Val Val Asp Ala
65                  70                  75                  80

Thr Arg Lys Gly Asn Lys Ile Arg Phe Ala Asn His Ser Val Asn Pro
                85                  90                  95

Asn Cys Tyr Ala Lys Val Met Met Val Asn Gly Asp His Arg Ile Gly
            100                 105                 110

Ile Phe Ala Lys Arg Ala Ile Gln Thr Gly Glu Glu Leu Phe Phe Asp
        115                 120                 125

Tyr Arg Tyr Ser Gln Ala Asp Ala Leu Lys Tyr Val Gly Ile Glu Arg
    130                 135                 140

Glu Met Glu Ile Pro
145
```

<210> SEQ ID NO 141
<211> LENGTH: 250
<212> TYPE: PRT
<213> ORGANISM: Homo sapiens

<400> SEQUENCE: 141

```
Arg Leu Trp Ala Ala His Cys Arg Lys Ile Gln Leu Lys Lys Asp Gly
1               5                   10                  15

Ser Ser Asn His Val Tyr Asn Tyr Gln Pro Cys Asp His Pro Arg Gln
            20                  25                  30

Pro Cys Asp Ser Ser Cys Pro Cys Val Ile Ala Gln Asn Phe Cys Glu
        35                  40                  45

Lys Phe Cys Gln Cys Ser Ser Glu Cys Gln Asn Arg Phe Pro Gly Cys
    50                  55                  60

Arg Cys Lys Ala Gln Cys Asn Thr Lys Gln Cys Pro Cys Tyr Leu Ala
65                  70                  75                  80

Val Arg Glu Cys Asp Pro Asp Leu Cys Leu Thr Cys Gly Ala Ala Asp
                85                  90                  95

His Trp Asp Ser Lys Asn Val Ser Cys Lys Asn Cys Ser Ile Gln Arg
            100                 105                 110

Gly Ser Lys Lys His Leu Leu Leu Ala Pro Ser Asp Val Ala Gly Trp
        115                 120                 125

Gly Ile Phe Ile Lys Asp Pro Val Gln Lys Asn Glu Phe Ile Ser Glu
    130                 135                 140

Tyr Cys Gly Glu Ile Ile Ser Gln Asp Glu Ala Asp Arg Arg Gly Lys
145                 150                 155                 160

Val Tyr Asp Lys Tyr Met Cys Ser Phe Leu Phe Asn Leu Asn Asn Asp
                165                 170                 175
```

```
Phe Val Val Asp Ala Thr Arg Lys Gly Asn Lys Ile Arg Phe Ala Asn
            180                 185                 190

His Ser Val Asn Pro Asn Cys Tyr Ala Lys Val Met Met Val Asn Gly
        195                 200                 205

Asp His Arg Ile Gly Ile Phe Ala Lys Arg Ala Ile Gln Thr Gly Glu
    210                 215                 220

Glu Leu Phe Phe Asp Tyr Arg Tyr Ser Gln Ala Asp Ala Leu Lys Tyr
225                 230                 235                 240

Val Gly Ile Glu Arg Glu Met Glu Ile Pro
                245                 250

<210> SEQ ID NO 142
<211> LENGTH: 136
<212> TYPE: PRT
<213> ORGANISM: Homo sapiens

<400> SEQUENCE: 142

Met Phe Pro Gln Ser Arg His Pro Thr Pro His Gln Ala Ala Gly Gln
1               5                   10                  15

Pro Phe Lys Phe Thr Ile Pro Glu Ser Leu Asp Arg Ile Lys Glu Glu
            20                  25                  30

Phe Gln Phe Leu Gln Ala Gln Tyr His Ser Leu Lys Leu Glu Cys Glu
        35                  40                  45

Lys Leu Ala Ser Glu Lys Thr Glu Met Gln Arg His Tyr Val Met Tyr
    50                  55                  60

Tyr Glu Met Ser Tyr Gly Leu Asn Ile Glu Met His Lys Gln Thr Glu
65                  70                  75                  80

Ile Ala Lys Arg Leu Asn Thr Ile Cys Ala Gln Val Ile Pro Phe Leu
                85                  90                  95

Ser Gln Glu His Gln Gln Gln Val Ala Gln Ala Val Glu Arg Ala Lys
            100                 105                 110

Gln Val Thr Met Ala Glu Leu Asn Ala Ile Ile Gly Gln Gln Gln Leu
        115                 120                 125

Gln Ala Gln His Leu Ser His Gly
    130                 135

<210> SEQ ID NO 143
<211> LENGTH: 308
<212> TYPE: PRT
<213> ORGANISM: Homo sapiens

<400> SEQUENCE: 143

Leu Asn Arg Lys Leu Arg Leu Gly Val Gly Asn Arg Ala Ile Arg Thr
1               5                   10                  15

Glu Lys Ile Ile Cys Arg Asp Val Ala Arg Gly Tyr Glu Asn Val Pro
            20                  25                  30

Ile Pro Cys Val Asn Gly Val Asp Gly Glu Pro Cys Pro Glu Asp Tyr
        35                  40                  45

Lys Tyr Ile Ser Glu Asn Cys Glu Thr Ser Thr Met Asn Ile Asp Arg
    50                  55                  60

Asn Ile Thr His Leu Gln His Cys Thr Cys Val Asp Asp Cys Ser Ser
65                  70                  75                  80

Ser Asn Cys Leu Cys Gly Gln Leu Ser Ile Arg Cys Trp Tyr Asp Lys
                85                  90                  95

Asp Gly Arg Leu Leu Gln Glu Phe Asn Lys Ile Glu Pro Pro Leu Ile
            100                 105                 110
```

```
Phe Glu Cys Asn Gln Ala Cys Ser Cys Trp Arg Asn Cys Lys Asn Arg
            115                 120                 125

Val Val Gln Ser Gly Ile Lys Val Arg Leu Gln Leu Tyr Arg Thr Ala
        130                 135                 140

Lys Met Gly Trp Gly Val Arg Ala Leu Gln Thr Ile Pro Gln Gly Thr
145                 150                 155                 160

Phe Ile Cys Glu Tyr Val Gly Glu Leu Ile Ser Asp Ala Glu Ala Asp
                165                 170                 175

Val Arg Glu Asp Asp Ser Tyr Leu Phe Asp Leu Asp Asn Lys Asp Gly
            180                 185                 190

Glu Val Tyr Cys Ile Asp Ala Arg Tyr Tyr Gly Asn Ile Ser Arg Phe
        195                 200                 205

Ile Asn His Leu Cys Asp Pro Asn Ile Ile Pro Val Arg Val Phe Met
210                 215                 220

Leu His Gln Asp Leu Arg Phe Pro Arg Ile Ala Phe Phe Ser Ser Arg
225                 230                 235                 240

Asp Ile Arg Thr Gly Glu Glu Leu Gly Phe Asp Tyr Gly Asp Arg Phe
                245                 250                 255

Trp Asp Ile Lys Ser Lys Tyr Phe Thr Cys Gln Cys Gly Ser Glu Lys
            260                 265                 270

Cys Lys His Ser Ala Glu Ala Ile Ala Leu Glu Gln Ser Arg Leu Ala
        275                 280                 285

Arg Leu Asp Pro His Pro Glu Leu Leu Pro Glu Leu Gly Ser Leu Pro
        290                 295                 300

Pro Val Asn Thr
305

<210> SEQ ID NO 144
<211> LENGTH: 579
<212> TYPE: PRT
<213> ORGANISM: Homo sapiens

<400> SEQUENCE: 144

Leu Glu Lys Ala Leu Val Ile Gln Glu Ser Glu Arg Arg Lys Lys Leu
1               5                   10                  15

Arg Phe His Pro Arg Gln Leu Tyr Leu Ser Val Lys Gln Gly Glu Leu
            20                  25                  30

Gln Lys Val Ile Leu Met Leu Leu Asp Asn Leu Asp Pro Asn Phe Gln
        35                  40                  45

Ser Asp Gln Gln Ser Lys Arg Thr Pro Leu His Ala Ala Ala Gln Lys
    50                  55                  60

Gly Ser Val Glu Ile Cys His Val Leu Leu Gln Ala Gly Ala Asn Ile
65                  70                  75                  80

Asn Ala Val Asp Lys Gln Gln Arg Thr Pro Leu Met Glu Ala Val Val
                85                  90                  95

Asn Asn His Leu Glu Val Ala Arg Tyr Met Val Gln Arg Gly Gly Cys
            100                 105                 110

Val Tyr Ser Lys Glu Glu Asp Gly Ser Thr Cys Leu His His Ala Ala
        115                 120                 125

Lys Ile Gly Asn Leu Glu Met Val Ser Leu Leu Leu Ser Thr Gly Gln
    130                 135                 140

Val Asp Val Asn Ala Gln Asp Ser Gly Gly Trp Thr Pro Ile Ile Trp
145                 150                 155                 160

Ala Ala Glu His Lys His Ile Glu Val Ile Arg Met Leu Leu Thr Arg
```

```
                165                 170                 175
Gly Ala Asp Val Thr Leu Thr Asp Asn Glu Glu Asn Ile Cys Leu His
            180                 185                 190

Trp Ala Ser Phe Thr Gly Ser Ala Ala Ile Ala Glu Val Leu Leu Asn
            195                 200                 205

Ala Arg Cys Asp Leu His Ala Val Asn Tyr His Gly Asp Thr Pro Leu
            210                 215                 220

His Ile Ala Ala Arg Glu Ser Tyr His Asp Cys Val Leu Leu Phe Leu
225                 230                 235                 240

Ser Arg Gly Ala Asn Pro Glu Leu Arg Asn Lys Glu Gly Asp Thr Ala
                245                 250                 255

Trp Asp Leu Thr Pro Glu Arg Ser Asp Val Trp Phe Ala Leu Gln Leu
            260                 265                 270

Asn Arg Lys Leu Arg Leu Gly Val Gly Asn Arg Ala Ile Arg Thr Glu
            275                 280                 285

Lys Ile Ile Cys Arg Asp Val Ala Arg Gly Tyr Glu Asn Val Pro Ile
            290                 295                 300

Pro Cys Val Asn Gly Val Asp Gly Glu Pro Cys Pro Glu Asp Tyr Lys
305                 310                 315                 320

Tyr Ile Ser Glu Asn Cys Glu Thr Ser Thr Met Asn Ile Asp Arg Asn
                325                 330                 335

Ile Thr His Leu Gln His Cys Thr Cys Val Asp Asp Cys Ser Ser Ser
            340                 345                 350

Asn Cys Leu Cys Gly Gln Leu Ser Ile Arg Cys Trp Tyr Asp Lys Asp
            355                 360                 365

Gly Arg Leu Leu Gln Glu Phe Asn Lys Ile Glu Pro Pro Leu Ile Phe
            370                 375                 380

Glu Cys Asn Gln Ala Cys Ser Cys Trp Arg Asn Cys Lys Asn Arg Val
385                 390                 395                 400

Val Gln Ser Gly Ile Lys Val Arg Leu Gln Leu Tyr Arg Thr Ala Lys
                405                 410                 415

Met Gly Trp Gly Val Arg Ala Leu Gln Thr Ile Pro Gln Gly Thr Phe
            420                 425                 430

Ile Cys Glu Tyr Val Gly Glu Leu Ile Ser Asp Ala Glu Ala Asp Val
            435                 440                 445

Arg Glu Asp Asp Ser Tyr Leu Phe Asp Leu Asp Asn Lys Asp Gly Glu
            450                 455                 460

Val Tyr Cys Ile Asp Ala Arg Tyr Tyr Gly Asn Ile Ser Arg Phe Ile
465                 470                 475                 480

Asn His Leu Cys Asp Pro Asn Ile Ile Pro Val Arg Val Phe Met Leu
                485                 490                 495

His Gln Asp Leu Arg Phe Pro Arg Ile Ala Phe Phe Ser Ser Arg Asp
            500                 505                 510

Ile Arg Thr Gly Glu Glu Leu Gly Phe Asp Tyr Gly Asp Arg Phe Trp
            515                 520                 525

Asp Ile Lys Ser Lys Tyr Phe Thr Cys Gln Cys Gly Ser Glu Lys Cys
            530                 535                 540

Lys His Ser Ala Glu Ala Ile Ala Leu Glu Gln Ser Arg Leu Ala Arg
545                 550                 555                 560

Leu Asp Pro His Pro Glu Leu Leu Pro Glu Leu Gly Ser Leu Pro Pro
                565                 570                 575

Val Asn Thr
```

<210> SEQ ID NO 145
<211> LENGTH: 279
<212> TYPE: PRT
<213> ORGANISM: Homo sapiens

<400> SEQUENCE: 145

Met Gly Pro Asp Arg Val Thr Ala Arg Glu Leu Cys Glu Asn Asp Asp
1               5                   10                  15

Leu Ala Thr Ser Leu Val Leu Asp Pro Tyr Leu Gly Phe Arg Thr His
            20                  25                  30

Lys Met Asn Val Ser Pro Val Pro Leu Arg Arg Gln Gln His Leu
        35                  40                  45

Arg Ser Ala Leu Glu Thr Phe Leu Arg Gln Arg Asp Leu Glu Ala Ala
    50                  55                  60

Tyr Arg Ala Leu Thr Leu Gly Gly Trp Thr Ala Arg Tyr Phe Gln Ser
65                  70                  75                  80

Arg Gly Pro Arg Gln Glu Ala Ala Leu Lys Thr His Val Tyr Arg Tyr
                85                  90                  95

Leu Arg Ala Phe Leu Pro Glu Ser Gly Phe Thr Ile Leu Pro Cys Thr
            100                 105                 110

Arg Tyr Ser Met Glu Thr Asn Gly Ala Lys Ile Val Ser Thr Arg Ala
        115                 120                 125

Trp Lys Lys Asn Glu Lys Leu Glu Leu Val Gly Cys Ile Ala Glu
    130                 135                 140

Leu Arg Glu Ala Asp Glu Gly Leu Leu Arg Ala Gly Glu Asn Asp Phe
145                 150                 155                 160

Ser Ile Met Tyr Ser Thr Arg Lys Arg Ser Ala Gln Leu Trp Leu Gly
                165                 170                 175

Pro Ala Ala Phe Ile Asn His Asp Cys Lys Pro Asn Cys Lys Phe Val
            180                 185                 190

Pro Ala Asp Gly Asn Ala Ala Cys Val Lys Val Leu Arg Asp Ile Glu
        195                 200                 205

Pro Gly Asp Glu Val Thr Cys Phe Tyr Gly Glu Gly Phe Phe Gly Glu
    210                 215                 220

Lys Asn Glu His Cys Glu Cys His Thr Cys Glu Arg Lys Gly Glu Gly
225                 230                 235                 240

Ala Phe Arg Thr Arg Pro Arg Glu Pro Ala Leu Pro Pro Arg Pro Leu
                245                 250                 255

Asp Lys Tyr Gln Leu Arg Glu Thr Lys Arg Arg Leu Gln Gln Gly Leu
            260                 265                 270

Asp Ser Gly Ser Arg Gln Gly
        275

<210> SEQ ID NO 146
<211> LENGTH: 191
<212> TYPE: PRT
<213> ORGANISM: Homo sapiens

<400> SEQUENCE: 146

Met Gly Lys Lys Thr Lys Arg Thr Ala Asp Ser Ser Ser Ser Glu Asp
1               5                   10                  15

Glu Glu Glu Tyr Val Val Glu Lys Val Leu Asp Arg Arg Val Val Lys
            20                  25                  30

Gly Gln Val Glu Tyr Leu Leu Lys Trp Lys Gly Phe Ser Glu Glu His
        35                  40                  45

Asn Thr Trp Glu Pro Glu Lys Asn Leu Asp Cys Pro Glu Leu Ile Ser
        50                  55                  60

Glu Phe Met Lys Lys Tyr Lys Met Lys Glu Gly Glu Asn Asn Lys
65                  70                  75                  80

Pro Arg Glu Lys Ser Glu Ser Asn Lys Arg Lys Ser Asn Phe Ser Asn
                85                  90                  95

Ser Ala Asp Asp Ile Lys Ser Lys Lys Arg Glu Gln Ser Asn Asp
                100                 105                 110

Ile Ala Arg Gly Phe Glu Arg Gly Leu Glu Pro Glu Lys Ile Ile Gly
            115                 120                 125

Ala Thr Asp Ser Cys Gly Asp Leu Met Phe Leu Met Lys Trp Lys Asp
    130                 135                 140

Thr Asp Glu Ala Asp Leu Val Leu Ala Lys Glu Ala Asn Val Lys Cys
145                 150                 155                 160

Pro Gln Ile Val Ile Ala Phe Tyr Glu Glu Arg Leu Thr Trp His Ala
                165                 170                 175

Tyr Pro Glu Asp Ala Glu Asn Lys Glu Lys Glu Thr Ala Lys Ser
                180                 185                 190

<210> SEQ ID NO 147
<211> LENGTH: 831
<212> TYPE: PRT
<213> ORGANISM: Artificial Sequence
<220> FEATURE:
<223> OTHER INFORMATION: TALE domain

<400> SEQUENCE: 147

Met Gly Lys Pro Ile Pro Asn Pro Leu Leu Gly Leu Asp Ser Thr Gly
1               5                   10                  15

Gly Met Ala Pro Lys Lys Lys Arg Lys Val Asp Gly Gly Val Asp Leu
                20                  25                  30

Arg Thr Leu Gly Tyr Ser Gln Gln Gln Gln Glu Lys Ile Lys Pro Lys
            35                  40                  45

Val Arg Ser Thr Val Ala Gln His His Glu Ala Leu Val Gly His Gly
    50                  55                  60

Phe Thr His Ala His Ile Val Ala Leu Ser Gln His Pro Ala Ala Leu
65                  70                  75                  80

Gly Thr Val Ala Val Lys Tyr Gln Asp Met Ile Ala Ala Leu Pro Glu
                85                  90                  95

Ala Thr His Glu Ala Ile Val Gly Val Gly Lys Gln Trp Ser Gly Ala
            100                 105                 110

Arg Ala Leu Glu Ala Leu Leu Thr Val Ala Gly Glu Leu Arg Gly Pro
        115                 120                 125

Pro Leu Gln Leu Asp Thr Gly Gln Leu Leu Lys Ile Ala Lys Arg Gly
    130                 135                 140

Gly Val Thr Ala Val Glu Ala Val His Ala Trp Arg Asn Ala Leu Thr
145                 150                 155                 160

Gly Ala Pro Leu Asn Leu Thr Pro Asp Gln Val Val Ala Ile Ala Ser
                165                 170                 175

Asn Asn Gly Gly Lys Gln Ala Leu Glu Thr Val Gln Arg Leu Leu Pro
            180                 185                 190

Val Leu Cys Gln Asp His Gly Leu Thr Pro Asp Gln Val Val Ala Ile
        195                 200                 205

Ala Ser His Asp Gly Gly Lys Gln Ala Leu Glu Thr Val Gln Arg Leu
    210                 215                 220

```
Leu Pro Val Leu Cys Gln Asp His Gly Leu Thr Pro Asp Gln Val Val
225                 230                 235                 240

Ala Ile Ala Ser Asn Gly Gly Lys Gln Ala Leu Glu Thr Val Gln
            245                 250                 255

Arg Leu Leu Pro Val Leu Cys Gln Asp His Gly Leu Thr Pro Asp Gln
                260                 265                 270

Val Val Ala Ile Ala Ser His Asp Gly Gly Lys Gln Ala Leu Glu Thr
            275                 280                 285

Val Gln Arg Leu Leu Pro Val Leu Cys Gln Asp His Gly Leu Thr Pro
        290                 295                 300

Asp Gln Val Val Ala Ile Ala Ser Asn Asn Gly Gly Lys Gln Ala Leu
305                 310                 315                 320

Glu Thr Val Gln Arg Leu Leu Pro Val Leu Cys Gln Asp His Gly Leu
                325                 330                 335

Thr Pro Asp Gln Val Val Ala Ile Ala Ser His Asp Gly Gly Lys Gln
            340                 345                 350

Ala Leu Glu Thr Val Gln Arg Leu Leu Pro Val Leu Cys Gln Asp His
        355                 360                 365

Gly Leu Thr Pro Asp Gln Val Val Ala Ile Ala Ser Asn Asn Gly Gly
370                 375                 380

Lys Gln Ala Leu Glu Thr Val Gln Arg Leu Leu Pro Val Leu Cys Gln
385                 390                 395                 400

Asp His Gly Leu Thr Pro Asp Gln Val Val Ala Ile Ala Ser His Asp
                405                 410                 415

Gly Gly Lys Gln Ala Leu Glu Thr Val Gln Arg Leu Leu Pro Val Leu
            420                 425                 430

Cys Gln Asp His Gly Leu Thr Pro Asp Gln Val Val Ala Ile Ala Ser
        435                 440                 445

Asn Gly Gly Lys Gln Ala Leu Glu Thr Val Gln Arg Leu Leu Pro
450                 455                 460

Val Leu Cys Gln Asp His Gly Leu Thr Pro Asp Gln Val Val Ala Ile
465                 470                 475                 480

Ala Ser Asn Ile Gly Gly Lys Gln Ala Leu Glu Thr Val Gln Arg Leu
            485                 490                 495

Leu Pro Val Leu Cys Gln Asp His Gly Leu Thr Pro Asp Gln Val Val
                500                 505                 510

Ala Ile Ala Ser His Asp Gly Gly Lys Gln Ala Leu Glu Thr Val Gln
            515                 520                 525

Arg Leu Leu Pro Val Leu Cys Gln Asp His Gly Leu Thr Pro Asp Gln
        530                 535                 540

Val Val Ala Ile Ala Ser Asn Gly Gly Gly Lys Gln Ala Leu Glu Thr
545                 550                 555                 560

Val Gln Arg Leu Leu Pro Val Leu Cys Gln Asp His Gly Leu Thr Pro
                565                 570                 575

Asp Gln Val Val Ala Ile Ala Ser His Asp Gly Gly Lys Gln Ala Leu
            580                 585                 590

Glu Thr Val Gln Arg Leu Leu Pro Val Leu Cys Gln Asp His Gly Leu
        595                 600                 605

Thr Pro Asp Gln Val Val Ala Ile Ala Ser Asn Gly Gly Gly Lys Gln
        610                 615                 620

Ala Leu Glu Thr Val Gln Arg Leu Leu Pro Val Leu Cys Gln Asp His
625                 630                 635                 640

Gly Leu Thr Pro Asp Gln Val Val Ala Ile Ala Ser His Asp Gly Gly
```

```
            645                 650                 655
Lys Gln Ala Leu Glu Thr Val Gln Arg Leu Leu Pro Val Leu Cys Gln
            660                 665                 670

Asp His Gly Leu Thr Pro Asp Gln Val Val Ala Ile Ala Ser Asn Gly
        675                 680                 685

Gly Gly Lys Gln Ala Leu Glu Thr Val Gln Arg Leu Leu Pro Val Leu
    690                 695                 700

Cys Gln Asp His Gly Leu Thr Pro Asp Gln Val Val Ala Ile Ala Ser
705                 710                 715                 720

His Asp Gly Gly Lys Gln Ala Leu Glu Thr Val Gln Arg Leu Leu Pro
                725                 730                 735

Val Leu Cys Gln Asp His Gly Leu Thr Pro Asp Gln Val Val Ala Ile
            740                 745                 750

Ala Ser Asn Gly Gly Gly Lys Gln Ala Leu Glu Ser Ile Val Ala Gln
        755                 760                 765

Leu Ser Arg Pro Asp Pro Ala Leu Ala Ala Leu Thr Asn Asp His Leu
    770                 775                 780

Val Ala Leu Ala Cys Leu Gly Gly Arg Pro Ala Leu Asp Ala Val Lys
785                 790                 795                 800

Lys Gly Leu Pro His Ala Pro Ala Leu Ile Lys Arg Thr Asn Arg Arg
                805                 810                 815

Ile Pro Glu Arg Thr Ser His Arg Val Ala Gly Ser Gly Gly Gly
            820                 825                 830

<210> SEQ ID NO 148
<211> LENGTH: 19
<212> TYPE: DNA
<213> ORGANISM: Artificial Sequence
<220> FEATURE:
<223> OTHER INFORMATION: Binding site

<400> SEQUENCE: 148
tgctcgcgct actctctct                                                  19

<210> SEQ ID NO 149
<211> LENGTH: 20
<212> TYPE: RNA
<213> ORGANISM: Artificial Sequence
<220> FEATURE:
<223> OTHER INFORMATION: guide RNA (gRNA) #1 for beta2-microglobulin
      gene

<400> SEQUENCE: 149
uauaagugga ggcgucgcgc                                                 20

<210> SEQ ID NO 150
<211> LENGTH: 20
<212> TYPE: RNA
<213> ORGANISM: Artificial Sequence
<220> FEATURE:
<223> OTHER INFORMATION: gRNA #2 for beta2-microglobulin gene

<400> SEQUENCE: 150
gcccgaaugc ugucagcuuc                                                 20

<210> SEQ ID NO 151
<211> LENGTH: 20
<212> TYPE: RNA
<213> ORGANISM: Artificial Sequence
<220> FEATURE:
<223> OTHER INFORMATION: gRNA #3 for beta2-microglobulin gene
```

```
<400> SEQUENCE: 151
ugcgucgcug gcuuggagac                                               20

<210> SEQ ID NO 152
<211> LENGTH: 20
<212> TYPE: RNA
<213> ORGANISM: Artificial Sequence
<220> FEATURE:
<223> OTHER INFORMATION: gRNA #4 for beta2-microglobulin gene

<400> SEQUENCE: 152
ccaaucagga caaggcccgc                                               20

<210> SEQ ID NO 153
<211> LENGTH: 20
<212> TYPE: RNA
<213> ORGANISM: Artificial Sequence
<220> FEATURE:
<223> OTHER INFORMATION: gRNA #5 for beta2-microglobulin gene

<400> SEQUENCE: 153
aggguaggag agacucacgc                                               20

<210> SEQ ID NO 154
<211> LENGTH: 20
<212> TYPE: RNA
<213> ORGANISM: Artificial Sequence
<220> FEATURE:
<223> OTHER INFORMATION: gRNA #6 for beta2-microglobulin gene

<400> SEQUENCE: 154
gcgggccacc aaggagaacu                                               20

<210> SEQ ID NO 155
<211> LENGTH: 20
<212> TYPE: RNA
<213> ORGANISM: Artificial Sequence
<220> FEATURE:
<223> OTHER INFORMATION: gRNA #7 for beta2-microglobulin gene

<400> SEQUENCE: 155
gcuacucucu cuuucuggcc                                               20

<210> SEQ ID NO 156
<211> LENGTH: 20
<212> TYPE: RNA
<213> ORGANISM: Artificial Sequence
<220> FEATURE:
<223> OTHER INFORMATION: gRNA #8 for beta2-microglobulin gene

<400> SEQUENCE: 156
cucccgcucu gcacccucug                                               20

<210> SEQ ID NO 157
<211> LENGTH: 20
<212> TYPE: RNA
<213> ORGANISM: Artificial Sequence
<220> FEATURE:
<223> OTHER INFORMATION: gRNA #9 for beta2-microglobulin gene

<400> SEQUENCE: 157
uuuggccuac ggcgacggga                                               20

<210> SEQ ID NO 158
```

```
<211> LENGTH: 20
<212> TYPE: RNA
<213> ORGANISM: Artificial Sequence
<220> FEATURE:
<223> OTHER INFORMATION: gRNA #10 for beta2-microglobulin gene

<400> SEQUENCE: 158
ggggcaagua gcgcgcgucc                                                    20

<210> SEQ ID NO 159
<211> LENGTH: 20
<212> TYPE: RNA
<213> ORGANISM: Artificial Sequence
<220> FEATURE:
<223> OTHER INFORMATION: gRNA #11 for beta2-microglobulin gene

<400> SEQUENCE: 159
uaguccaggg cuggaucucg                                                    20

<210> SEQ ID NO 160
<211> LENGTH: 88
<212> TYPE: RNA
<213> ORGANISM: Artificial Sequence
<220> FEATURE:
<223> OTHER INFORMATION: gRNA scaffold

<400> SEQUENCE: 160
guuuaagagc uaugcuggaa acagcauagc aaguuuaaau aaggcuaguc cguuauucaa        60
cuugaaaaag uggcaccgag ucggugcu                                           88

<210> SEQ ID NO 161
<211> LENGTH: 20
<212> TYPE: DNA
<213> ORGANISM: Artificial Sequence
<220> FEATURE:
<223> OTHER INFORMATION: gRNA #2 for IFNAR1 gene

<400> SEQUENCE: 161
aagaggcggc gcgugcgtag                                                    20

<210> SEQ ID NO 162
<211> LENGTH: 20
<212> TYPE: RNA
<213> ORGANISM: Artificial Sequence
<220> FEATURE:
<223> OTHER INFORMATION: gRNA #3 for IFNAR1 gene

<400> SEQUENCE: 162
gggcggugug acuuaggacg                                                    20

<210> SEQ ID NO 163
<211> LENGTH: 20
<212> TYPE: RNA
<213> ORGANISM: Artificial Sequence
<220> FEATURE:
<223> OTHER INFORMATION: gRNA #4 for IFNAR1 gene

<400> SEQUENCE: 163
ccagaugaug gucguccucc                                                    20

<210> SEQ ID NO 164
<211> LENGTH: 20
<212> TYPE: RNA
<213> ORGANISM: Artificial Sequence
<220> FEATURE:
<223> OTHER INFORMATION: gRNA #5 for IFNAR1 gene
```

```
<400> SEQUENCE: 164
gacccuagug cucgucgccg                                                    20

<210> SEQ ID NO 165
<211> LENGTH: 20
<212> TYPE: RNA
<213> ORGANISM: Artificial Sequence
<220> FEATURE:
<223> OTHER INFORMATION: gRNA #6 for IFNAR1 gene

<400> SEQUENCE: 165
uggguguugu ccgcagccgc                                                    20

<210> SEQ ID NO 166
<211> LENGTH: 20
<212> TYPE: RNA
<213> ORGANISM: Artificial Sequence
<220> FEATURE:
<223> OTHER INFORMATION: gRNA #7 for IFNAR1 gene

<400> SEQUENCE: 166
acgggggcgg cgaugcuguu                                                    20

<210> SEQ ID NO 167
<211> LENGTH: 20
<212> TYPE: RNA
<213> ORGANISM: Artificial Sequence
<220> FEATURE:
<223> OTHER INFORMATION: gRNA #8 for IFNAR1 gene

<400> SEQUENCE: 167
gaccgaaggu uucccagacu                                                    20

<210> SEQ ID NO 168
<211> LENGTH: 20
<212> TYPE: RNA
<213> ORGANISM: Artificial Sequence
<220> FEATURE:
<223> OTHER INFORMATION: gRNA #9 for IFNAR1 gene

<400> SEQUENCE: 168
gucggguuua aucuuuggcg                                                    20

<210> SEQ ID NO 169
<211> LENGTH: 20
<212> TYPE: RNA
<213> ORGANISM: Artificial Sequence
<220> FEATURE:
<223> OTHER INFORMATION: gRNA #10 for IFNAR1 gene

<400> SEQUENCE: 169
cgcucccgag gacccguaca                                                    20

<210> SEQ ID NO 170
<211> LENGTH: 20
<212> TYPE: RNA
<213> ORGANISM: Artificial Sequence
<220> FEATURE:
<223> OTHER INFORMATION: gRNA #11 for IFNAR1 gene

<400> SEQUENCE: 170
cgggucccac ccccgugaaa                                                    20

<210> SEQ ID NO 171
```

```
<211> LENGTH: 20
<212> TYPE: RNA
<213> ORGANISM: Artificial Sequence
<220> FEATURE:
<223> OTHER INFORMATION: gRNA #12 for IFNAR1 gene

<400> SEQUENCE: 171
ucaaacucga cacaaagcuc                                               20

<210> SEQ ID NO 172
<211> LENGTH: 20
<212> TYPE: RNA
<213> ORGANISM: Artificial Sequence
<220> FEATURE:
<223> OTHER INFORMATION: gRNA #13 for IFNAR1 gene

<400> SEQUENCE: 172
gcggagccgc gguacuuucc                                               20

<210> SEQ ID NO 173
<211> LENGTH: 20
<212> TYPE: RNA
<213> ORGANISM: Artificial Sequence
<220> FEATURE:
<223> OTHER INFORMATION: gRNA #1 for VEGFA gene

<400> SEQUENCE: 173
ggcgcgcgcg cuagguggga                                               20

<210> SEQ ID NO 174
<211> LENGTH: 20
<212> TYPE: RNA
<213> ORGANISM: Artificial Sequence
<220> FEATURE:
<223> OTHER INFORMATION: gRNA #2 for VEGFA gene

<400> SEQUENCE: 174
agagaggcuc accgcccacg                                               20

<210> SEQ ID NO 175
<211> LENGTH: 20
<212> TYPE: RNA
<213> ORGANISM: Artificial Sequence
<220> FEATURE:
<223> OTHER INFORMATION: gRNA #3 for VEGFA gene

<400> SEQUENCE: 175
guacgugcgg ugacuccggu                                               20
```